US008309586B2

(12) United States Patent
Kim et al.

(10) Patent No.: US 8,309,586 B2
(45) Date of Patent: Nov. 13, 2012

(54) GLUCOKINASE ACTIVATORS AND PHARMACEUTICAL COMPOSITIONS CONTAINING THE SAME AS AN ACTIVE INGREDIENT

(75) Inventors: Soon Ha Kim, Daejeon (KR); Sung Bae Lee, Daejeon (KR); Seung Hyun Yoon, Daejeon (KR); Mi Kyoung Cho, Daejeon (KR); Kyoung Hee Kim, Daejeon (KR); Heui Sul Park, Daejeon (KR); Hyoung Jin Kim, Daejeon (KR)

(73) Assignee: LG Life Sciences Ltd., Seoul (KR)

( * ) Notice: Subject to any disclaimer, the term of this patent is extended or adjusted under 35 U.S.C. 154(b) by 0 days.

(21) Appl. No.: 13/329,831

(22) Filed: Dec. 19, 2011

(65) Prior Publication Data
US 2012/0088760 A1  Apr. 12, 2012

Related U.S. Application Data

(63) Continuation of application No. 12/742,991, filed as application No. PCT/KR2008/007585 on Dec. 22, 2008.

(30) Foreign Application Priority Data

Dec. 20, 2007  (KR) .................. 10-2007-0134705

(51) Int. Cl.
*A61K 31/427* (2006.01)
*C07D 417/04* (2006.01)
(52) U.S. Cl. ........................ 514/365; 548/181
(58) Field of Classification Search ......... 548/181; 514/365
See application file for complete search history.

(56) References Cited

U.S. PATENT DOCUMENTS

| 2008/0096877 | A1  | 4/2008  | Yasuma et al. |
| 2009/0247746 | A1* | 10/2009 | Yasuma et al. ............. 544/105 |
| 2010/0087360 | A1  | 4/2010  | Ogino et al. |

FOREIGN PATENT DOCUMENTS

| EP | 1 510 207 A1    | 3/2005  |
| EP | 1 873 144 A1    | 1/2008  |
| WO | WO 2005/049019 A1 | 6/2005  |
| WO | WO 2006/112549 A1 | 10/2006 |
| WO | WO 2007/007910 A1 | 1/2007  |
| WO | WO 2009/025477 A1 | 2/2009  |

OTHER PUBLICATIONS

Levin, Factors promoting and ameliorating the development of obesity, 2006, Physiology and Behavior, vol. 86, p. 633-639.*
Agius et al., "Evidence for a Role of Glucose-induced Translocation of Glucokinase in the Control of Hepatic Glycogen Synthesis.", The Journal of Biological Chemistry, 1996, vol. 271, No. 48, pp. 30479-30486.
Clinical Guidelines on the Identification, Evaluation, and Treatment of Overweight and Obesity in Adults, http://www.nhlbi.nih.gov/guidelines/obesity/ob_gdlns.pdf,accessed on Mar. 24, 2011.
Desai et al., "Phenotypic Correction of Diabetic Mice by Adenovirus-Mediated Glucokinase Expression." Diabetes, Oct. 2001, vol. 50, pp. 2287-2295.
International Search Report for Application No. PCT/KR2008/007585 dated Aug. 3, 2009.
Matschinsky et al., "Glucokinase and Glycemic Disease." Frontiers in Diabetes, 2004, vol. 16, chapters 4-7.
Matschinsky, "Assessing the potential of glucokinase activators in diabetes therapy," Nature Reviews Drug Discovery, May 2009, vol. 8, pp. 399-416.
Meglasson et al., "Pancreatic Islet Glucose Metabolism and Regulation of Insulin Secretion.", Diabetes/Metabolism Reviews, 1986, vol. 2-4, pp. 163-214.
Moller, "New drug targets for type 2 diabetes and the metabolic syndrome.", Nature, Dec. 13, 2001, vol. 414, pp. 821-827.
Nakamura et al., "Impact of Small-Molecule Glucokinase Activator on Glucose Metabolism and β-Cell Mass." Endocrinology, Mar. 2009, vol. 150(3), pp. 1147-1154.
Rossetti et al., "Abnormal regulation of HGP by hyperglycemia in mice with a disrupted glucokinase allele.", Am J Physiol Endocrinol Metab, 1997, vol. 273, pp. 743-750.
Schaftingen, "A protein from rat liver confers to glucokinase the property of being antagonistically regulated by fructose 6-phosphate and fructose 1-phospate.", Eur. J. Biochem, 1989, pp. 179-184.
Torres et al., "Restoration of Hepatic Glucokinase Expression Corrects Hepatic Glucose Flux and Normalizes Plasma Glucose in Zucker Diabetic Fatty Rats." Diabetes, Jan. 2009, vol. 58, pp. 78-86.
Zimmet et al. "Global and societal implications of the diabetes epidemic.", Nature, Dec. 13, 2001, vol. 414, pp. 782-787.

* cited by examiner

*Primary Examiner* — Golam M M Shameem
*Assistant Examiner* — Karen Cheng
(74) *Attorney, Agent, or Firm* — Birch, Stewart, Kolasch & Birch, LLP

(57) ABSTRACT

Disclosed are new compounds of formula (1) exhibiting excellent activity for glucokinase, pharmaceutical compositions having the same as an active ingredient, and a method of using the same as an active ingredient for lowering blood glucose level:

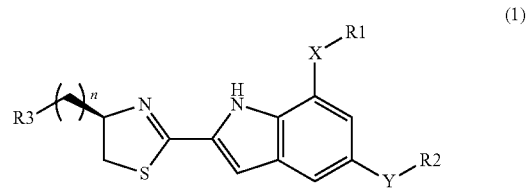

in which the substituents are as defined herein.

18 Claims, No Drawings

US 8,309,586 B2

GLUCOKINASE ACTIVATORS AND PHARMACEUTICAL COMPOSITIONS CONTAINING THE SAME AS AN ACTIVE INGREDIENT

This application is a Divisional of U.S. patent application Ser. No. 12/742,991, filed Jun. 17, 2010, which is the U.S. National Stage of PCT/KR2008/007585 filed on Dec. 22, 2008. This application also claims priority to Korean Application No. 10-2007-0134705, filed Dec. 20, 2007. The entire contents of the above mentioned applications are hereby incorporated by reference.

TECHNICAL FIELD

The present invention relates to new compounds exhibiting excellent activity for glucokinase (glucokinase activators, GKAs), and pharmaceutical compositions comprising the same as an active ingredient.

BACKGROUND ART

Diabetes affects harmful influences on human health, causing various complications. Diabetes may be classified into type 1 diabetes where insulin is not excreted due to the destruction of pancreatic cells, and type 2 diabetes where insulin is not produced due to the other conditions or the body does not response to insulin. The type 2 diabetes occupies 90% or more of the total patients suffered from diabetes. Typical complications accompanied with diabetes include hyperlipidemia, hypertension, retinosis, renal failure, etc. (Zimmer P., et al., Nature, 2001, 414, 782). As the therapeutic agents for diabetes, sulfonyl ureas (facilitating insulin secretion in the pancreatic cells), biguanides (suppressing glucose production in the liver), α-glucosidase inhibitors (suppressing glucose uptake in the bowels), etc. are used, among which peroxisome proliferator-activated receptor gamma (PPAR γ) agonists (thiazolidinediones, increased insulin sensitivity) are recently focused. However, these agents show some side effects, such as weight gain, according to the respective mechanisms of action (Moller D. E., Nature, 2001, 414, 821). Thus, there has been a need for the development of an agent for the treatment of diabetes, which does not cause such side effects.

For a normal healthy person, blood glucose is accurately controlled within a safe and narrow physiological range by means of various endocrine glucostatic systems. If such glucostatic systems do not work, glucose intolerance occurs first, which is gradually grown to the type 2 diabetes. Dysfunction of such control mechanism is resulted from (i) decrease of secretion of insulin from the pancreatic cells, (ii) increases of insulin resistance in the liver, cells of adipose tissue, and cells of skeletal muscle, and (iii) excess production of blood glucose by the liver.

According to many research outputs obtained during the past forty years, glucokinase that belongs to hexokinase IV series are involved in the first step of glucose metabolism to directly control the glucose content in the blood, whereby it plays an important role in the maintenance of glucose homeostasis in the body.

The glucokinase in the pancreatic cells can determine the thresholds of glucose-stimulated insulin release (GSIR) by acting as a glucose sensor. The glucokinase decreases blood glucose by phosphorylating glucose into glucose-6-phosphate consuming ATP, and keeping glucose-6-phosphate in the cells (Meglasson M. D. and Matschinsky F. M., Diabetes Metab Rev, 1986, 2, 163).

On the other hand, the glucokinase in hepatocytes has the feature of being short-term controlled by glucokinase regulatory protein. Glucokinase regulatory protein forms a 1:1 complex with glucokinase, and acts as a "competitive inhibitor" against glucose to confine the inactivated glucokinase within the nucleus and to protect and stabilize it from other proteins such as decomposition enzymes, etc. It has been reported that fructose-6-phosphate further stabilizes glukinase regulatory protein, whereas fructose-1-phosphate separates glucokinase from glucokinase regulatory protein and transfers it from nucleus to cytoplasm to keep its activated state (Van Schaftingen E., Eur J Biochem, 1989, 179). The glucokinase in hepatocytes appropriately controls the glucose metabolism in the liver. That is, glucose uptake and production are effectively controlled under the satiation or fast state (Agius L., et al., J Biol Chem, 1996, 271, 30479).

As explained above, glucokinase activates the two functions of (i) direct control of blood glucose in the liver, and (ii) facilitation of insulin secretion within the physiological range after detection of glucose concentration in the pancreas, and thus, plays a very important role in the maintenance of glucose homeostasis.

The experimental results in many rodent models suggested that glucokinase is a key regulator in the maintenance of glucose homeostasis. Rats lacking the glucokinase gene function in pancreatic beta cells show a significant hyperglycemic symptom, and rats lacking the glucokinase gene function in hepatocytes show depressed glucose uptake and hyperglycemic symptom. On the other hand, when the glucokinase gene is over expressed in hepatocytes of normal rats, amelioration effect of glucose tolerance is shown (Rossetti L., et al., Am J Physiol, 1997, 273, E743). And, the over expression of glucokinase in diabetic rats induces amelioration of glucose tolerance and blood glucose lowering effect under the fast state (Desai U. J., et al., Am J Diabetes, 2001, 50, 2285).

Hitherto, about 200 glucokinase gene mutants have been clinically reported for humans. Patients of MODY (maturity onset diabetes of the young)-2, a subtype of type 2 diabetes, showed some decrease of glucokinase activity due to the loss-of-function mutation and hyperglycemia due to the decrease of insulin secretion. On the contrary, patients of PNDM (permanent neonatal diabetes) and PHHI (persistent hyperinsulinemia hypoglycemia of infancy) showed serious hypoglycemia due to the glucokinase activation based on the gain-of-function mutation (Matsinsky F. M., et al., Frontiers in Daibetes, 2004, 16, chapter 4-7). Such phenotypes of glucokinase-associated diseases suggest that glucokinase plays an important role in the maintenance of glucose homeostasis in the body, which leaves a clue to develop a drug for enhancing the glucokinase activity.

According to the recent studies (Nakamura A., et al., Impact of small molecule glucokinase activator on glucose metabolism and beta cell mass, Endocrinology, 2008, Nov.), glucokinase activators facilitate pancreatic beta cell division to improve the glucose metabolism by maintaining the pancreatic cell mass. Also, it has been reported that glucose metabolism and hyperglycemia can be normalized by the restoration of hepatocellular glucokinase activity only in 20 week old ZDF (Zucker diabetic fatty) rat model (Torres T. P., et al., Restoration of hepatic glucokinase expression corrects hepatic glucose flux and normalize plasma glucose in zucker diabetic fatty rats, 2008, Endocrinology, Oct.), which suggests that hepatocyte-specific glucokinase activators may be developed as a therapeutic agent that can be used for the type 1 diabetics as well as the chronic type 2 diabetics in the future.

A lot of researches for glucokinase activators have been reported. As the recently published patents, WO2007/

007910A1, WO2006/112549A1, WO2007/031739, WO2007/037534, WO2007/043638, WO2007/028135, US20070099930, WO2007/041365, WO2007/051847, WO2007/053345, WO2007/007910, WO2006/049304, etc. may be mentioned.

The present inventors extensively studied glucokinase activators, and as a result have confirmed that the indole compounds of formula (1) are effective as glucokinase activators. Thus, they completed the present invention that relates to glucokinase activators based on indole structure.

DETAILED DESCRIPTION OF THE INVENTION

Technical Subject to be Solved

The object of the present invention is to provide glucokinase activators of the indole compounds of formula (1). It is also another object of the present invention to provide a composition for the prevention or treatment of diseases caused by the decline of glucokinase activity, which comprises said compounds as an active ingredient.

Means for Solving the Technical Subject

The present invention provides the compounds of the following formula (1):

[Formula 1]

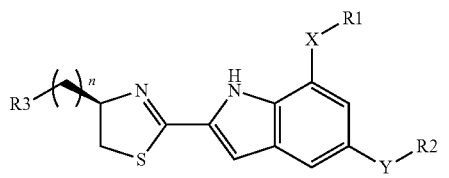

in which
X represents O or NH,
n denotes a number of 0 to 3,
Y represents a direct bond, —(CH$_2$)$_p$O—, —(CH$_2$)$_q$—, or —(CH$_2$)$_q$SO$_2$—,
P denotes a number of 0 to 2,
q denotes a number of 1 to 3,
R1 represents hydrogen, —(CR4R5)$_p$-A-R6 or —(CR4R5)$_q$-R6,
p and q are as defined above,
R4 and R5 independently of one another represent hydrogen or C$_1$-C$_5$-alkyl,
A represents 6~12 membered aryl or optionally oxo-containing C$_3$-C$_8$-cycloalkyl, or represents 3~10 membered heterocyclyl or heteroaryl each of which has 1 to 3 hetero atoms selected from O, S, and N,
R6 represents hydrogen, hydroxy, halogen, nitro, C$_1$-C$_6$-alkylcarbonyl, C$_1$-C$_6$-alkylsulfonyl, C$_1$-C$_6$-alkoxycarbonyl or carboxy,
R2 represents hydrogen, nitro, halogen, C$_1$-C$_6$-alkyl or trifluoromethyl, represents 5~12 membered heteroaryl or heterocyclyl each of which has 1 to 3 hetero atoms selected from N and O, or represents optionally C$_1$-C$_6$-alkylsulfonyl-substituted 6~12 membered aryl,
R3 represents R7-X—B—X'—,
B represents a direct bond, or represents 3~10 membered heterocyclyl or heteroaryl each of which optionally contains oxo, is optionally fused, and has 1 to 4 hetero atoms selected from N, O and S, X and X' independently of one another represent a direct bond, or are selected from the group consisting of —CO—, —(CH$_2$)$_q$—, —NR4C(O)—, —NR4-, —OC(O)—, —O—, —(CH$_2$)$_p$C(O)—, —(CH$_2$)$_p$O—, —(CH$_2$)$_p$NR4-, —C(O)NR4- and —S(O)$_r$—, wherein p and q are as defined above, r denotes a number of 0 to 2, and R4 represents hydrogen or C$_1$-C$_5$-alkyl,
R7 represents hydrogen, hydroxy, C$_1$-C$_6$-alkyl, C$_1$-C$_6$-alkoxy, halogeno-C$_1$-C$_6$-alkyl or C$_3$-C$_6$-cycloalkyl, represents 6~12 membered aryl, or represents 4~8 membered heteroaryl or heterocyclyl each of which has 1 to 4 hetero atoms selected from N and O,
where alkyl, alkoxy, aryl, cycloalkyl, heterocyclyl and heteroaryl may be optionally substituted, and the substituents are one or more selected from the group consisting of hydroxy, halogen, nitrile, amino, C$_1$-C$_6$-alkylamino, di(C$_1$-C$_6$-alkyl)amino, C$_1$-C$_6$-alkyl, halogeno-C$_1$-C$_6$-alkyl, C$_1$-C$_6$-alkylsulfonyl, aryl-C$_1$-C$_6$-alkoxy and oxo, pharmaceutically acceptable salts or isomers thereof.

In the above definitions for the compounds of formula (1), the term 'alkyl' means an aliphatic hydrocarbon radical. Alkyl may be saturated alkyl that does not comprise alkenyl or alkynyl moiety, or unsaturated alkyl that comprises at least one alkenyl or alkynyl moiety. "Alkenyl" means a group containing at least one carbon-carbon double bond, and "alkynyl" means a group containing at least one carbon-carbon triple bond. Alkyl may be branched or straight-chain when used alone or in a composite form such as alkoxy.

Alkyl group may have 1 to 20 carbon atoms unless otherwise defined. Alkyl group may be a medium sized alkyl having 1 to 10 carbon atoms. Otherwise, alkyl group may be a lower alkyl having 1 to 6 carbon atoms. Typical examples thereof include, but not limited to, methyl, ethyl, propyl, isopropyl, n-butyl, isobutyl, t-butyl, pentyl, hexyl, ethenyl, propenyl, butenyl, etc. For example, C$_1$-C$_4$-alkyl has 1 to 4 carbon atoms in the alkyl chain, and is selected from the group consisting of methyl, ethyl, propyl, isopropyl, n-butyl, isobutyl, sec-butyl and t-butyl.

The term 'alkoxy' means an alkyloxy having 1 to 10 carbon atoms unless otherwise defined.

The term 'cycloalkyl' means a saturated aliphatic 3~10 membered cycle unless otherwise defined. Typical examples thereof include, but not limited to, cyclopropyl, cyclobutyl, cyclopentyl, cyclohexyl, etc.

The term 'aryl' includes at least one ring having covalent π electron system, for example, monocyclic or fused polycyclic (i.e., cycles that share the adjacent carbon atom pairs) group. In the present specification, aryl means an aromatic 4~10 membered, preferably 6~10 membered, monocyclic or multicyclic ring including phenyl, naphthyl, etc., unless otherwise defined.

The term 'heteroaryl' means an aromatic 3~10 membered, preferably 4~8 membered, more preferably 5~6 membered cycle that has 1 to 3 hetero atoms selected from N, O and S, and may be fused with benzo or C$_3$-C$_8$ cycloalkyl, unless otherwise defined. The monocyclic heteroaryl includes, but not limited to, thiazole, oxazole, thiophene, furan, pyrrole, imidazole, isoxazole, isothiazole, pyrazole, triazole, triazine, thiadiazole, tetrazole, oxadiazole, pyridine, pyridazine, pyrimidine, pyrazine and the like. The bicyclic heteroaryl includes, but not limited to, indole, indoline, benzothiophene, benzofuran, benzimidazole, benzoxazole, benzisoxazole, benzthiazole, benzthiadiazole, benztriazole, quinoline, isoquinoline, purine, puropyridine and the like.

The term 'heterocycle' means a 3~10 membered, preferably 4~8 membered, more preferably 5~6 membered cycle that has 1 to 3 hetero atoms selected from N, O and S, may be fused with benzo or $C_3$-$C_8$ cycloalkyl, and is saturated or contains 1 or 2 double bonds, unless otherwise defined. The heterocycle includes, but not limited to, pyrroline, pyrrolidine, imidazoline, imidazolidine, pyrazoline, pyrazolidine, pyran, piperidine, morpholine, thiomorpholine, piperazine, hydrofuran and the like.

Other terms and abbreviations in the present specification may be understood to have the meaning conventionally used in this field by a skilled artisan, unless otherwise defined.

Preferred compounds among the compounds of formula (1) above are those wherein

X represents O or NH, n denotes a number of 0 to 3,

Y represents a direct bond, —$(CH_2)_pO$—, —$(CH_2)_q$—, or —$(CH_2)_qSO_2$—, p denotes a number of 0 to 2, q denotes a number of 1 to 3, R1 represents —$(CR4R5)_p$-A-R6 or —$(CR4R5)_q$-R6, p and q are as defined above, R4 and R5 independently of one another represent hydrogen or $C_1$-$C_5$-alkyl, A represents 6~12 membered aryl or optionally oxo-containing $C_3$-$C_7$-cycloalkyl, or represents 4~8 membered heterocyclyl or heteroaryl each of which has 1 to 3 hetero atoms selected from O, S, and N, R6 represents hydrogen, hydroxy, halogen, nitro, $C_1$-$C_6$-alkylcarbonyl, $C_1$-$C_6$-alkylsulfonyl, $C_1$-$C_6$-alkoxycarbonyl or carboxy, R2 represents hydrogen, halogen, $C_1$-$C_6$-alkyl or trifluoromethyl, represents 5~8 membered heteroaryl or heterocyclyl each of which has 1 to 3 hetero atoms selected from N and O, or represents optionally $C_1$-$C_6$-alkylsulfonyl-substituted 6~10 membered aryl, R3 represents R7-X—B—X'—, B represents a direct bond, or represents 4~10 membered heterocyclyl or heteroaryl each of which optionally contains oxo, is optionally fused, and has 1 to 4 hetero atoms selected from N, O and S, X and X' independently of one another represent a direct bond, or are selected from the group consisting of —CO—, —$(CH_2)_q$—, —NR4C(O)—, —NR4-, —OC(O)—, —O—, —$(CH_2)_pC(O)$—, —C(O)NR4- and —$S(O)_r$—, wherein p and q are as defined above, r denotes a number of 0 to 2, and R4 represents hydrogen or $C_1$-$C_5$-alkyl, R7 represents hydrogen, hydroxy, $C_1$-$C_6$-alkyl, halogeno-$C_1$-$C_6$-alkyl or $C_3$-$C_6$-cycloalkyl, represents 6~12 membered aryl, or represents 4~8 membered heteroaryl or heterocyclyl each of which has 1 to 4 hetero atoms selected from N and O, where alkyl, alkoxy, aryl, cycloalkyl, heterocyclyl and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, $C_1$-$C_6$-alkyl, halogeno-$C_1$-$C_6$-alkyl, $C_1$-$C_6$-alkylsulfonyl, aryl-$C_1$-$C_6$-alkoxy and oxo.

In the compounds of formula (1) of the present invention, the substituent Y more preferably represents a direct bond, —O—, —$(CH_2)O$—, —$(CH_2)$— or —$(CH_2)SO_2$—.

The substituent R1 more preferably represents —$(CH_2)_p$-A-R6 or —$(CR4R5)_q$-R6, wherein p denotes a number of 0 to 2, q denotes a number of 1 to 3, R4 and R5 independently of one another represent hydrogen or $C_1$-$C_5$-alkyl, A represents 6~12 membered aryl or optionally oxo-containing $C_3$-$C_6$-cycloalkyl or represents 5~6 membered heterocyclyl which has 1 to 2 hetero atoms selected from O, S, and N, and R6 represents hydrogen, halogen, nitro, $C_1$-$C_6$-alkylcarbonyl, $C_1$-$C_6$-alkylsulfonyl, $C_1$-$C_6$-alkoxycarbonyl or carboxy.

Most preferably, R1 is selected from the group consisting of cyclopropyl, cyclobutyl, cyclopentyl, difluorocyclohexyl, tetrahydrofuran, tetrahydropyran, (tetrahydropyran-4-yl)methyl, tetrahydrothiopyran, 4-oxo-cyclohexyl, (1-methanesulfonyl)pyrrolidine, (1-acetyl)piperidine, 4-nitrophenyl and methylpropiolate.

The substituent R2 more preferably represents hydrogen, halogen, $C_1$-$C_3$-alkyl or trifluoromethyl, represents 5~6 membered heteroaryl or heterocyclyl each of which has 1 to 3 hetero atoms selected from N and O, or represents optionally methanesulfonyl-substituted 6~10 membered aryl. Most preferably, R2 is selected from the group consisting of hydrogen, fluoro, chloro, bromo, methyl, ethyl, propyl, phenyl, methanesulfonylphenyl, pyridine, morpholine, 1,2-imidazole, 1,3-imidazole, pyrrolidine and pyrrole.

In the group R7-X—B—X'— of the substituent R3, the substituent B more preferably represents a direct bond, represents pyrazole, imidazole or oxadiazole each of which is optionally substituted by $C_1$-$C_6$-alkyl, or represents 5~9 membered heterocyclyl which optionally contains oxo, is optionally fused, and has 1 to 4 hetero atoms selected from N, S and O. Most preferably, B represents a direct bond, or may be a structure selected from the following formulae (i) to (xi)

(i)

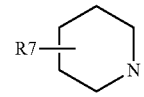

(ii)

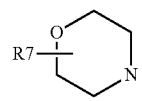

(iii)

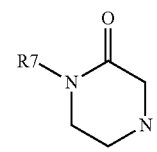

(iv)

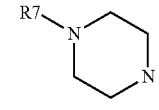

(v)

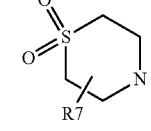

(vi)

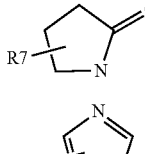

(vii)

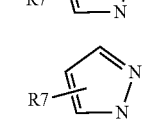

(viii)

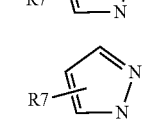

(ix)

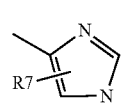

(x)

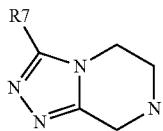

(xi)

in which R7 is as defined above.

The substituent X' more preferably represents a direct bond, or is selected from the group consisting of —CO—, —NR4CO—, —SO₂— and —O—.

The substituent X more preferably represents a direct bond, or is selected from the group consisting of —C(O)NR4-, —NR4-, —OC(O)—, —NR4C(O)—, —(CH₂)C(O)—, —S(O)₂— and —C(O)—. Most preferably, X represents a direct bond, or is selected from the group consisting of —C(O)NH—, —C(O)N(Me)-, —NH—, —N(Me)-, —OC(O)—, —N(Me)C(O)—, —(CH₂)C(O)—, —S(O)₂— and —C(O)—.

The substituent R7 more preferably represents hydrogen, hydroxy, C₁-C₆-alkyl, halogeno-C₁-C₆-alkyl or C₄-C₆-cycloalkyl, represents optionally halogen-substituted 6~10 membered aryl, or represents 5~6 membered heteroaryl or heterocyclyl each of which has 1 to 4 hetero atoms selected from N and O. Most preferably, R7 is selected from the group consisting of hydrogen, hydroxy, methyl, trifluoromethyl, ethyl, t-butyl, cyclohexyl, pyrrolidine, phenyl, 2-fluorophenyl, piperidine, pyridine, 1,3-pyrazine, 1,4-pyrazine, furan, trifluoromethyl, 1,2,3,4-tetrazole and tetrahydrofuran.

Typical compounds among the compounds of formula (1) are those selected from the following:

[(R)-2-(7-cyclopentylamino-1H-indol-2-yl)-4,5-dihydro-1,3-thiazol-4-yl]-methanol;
{(R)-2-[7-(tetrahydro-pyran-4-ylamino)-1H-indol-2-yl]-4,5-dihydro-thiazol-4-yl}-methanol;
{(R)-2-[7-(tetrahydro-furan-3-ylamino)-1H-indol-2-yl]-4,5-dihydro-thiazol-4-yl}-methanol;
{(R)-2-[7-(1-methanesulfonyl-pyrrolidin-3-ylamino)-1H-indol-2-yl]-4,5-dihydro-thiazol-4-yl}-methanol;
[(R)-2-(7-cyclopentylamino-5-fluoro-1H-indol-2-yl)-4,5-dihydro-thiazol-4-yl]-methanol;
{(R)-2-[5-fluoro-7-(tetrahydro-pyran-4-ylamino)-1H-indol-2-yl]-4,5-dihydro-thiazol-4-yl}-methanol;
[(R)-2-(5-chloro-7-cyclopentylamino-1H-indol-2-yl)-4,5-dihydro-thiazol-4-yl]-methanol;
{(R)-2-[5-chloro-7-(tetrahydro-pyran-4-ylamino)-1H-indol-2-yl]-4,5-dihydro-thiazol-4-yl}-methanol;
{(R)-2-[5-chloro-7-(tetrahydro-thiopyran-4-ylamino)-1H-indol-2-yl]-4,5-dihydro-thiazol-4-yl}-methanol;
[(R)-2-(5-bromo-7-cyclopentylamino-1H-indol-2-yl)-4,5-dihydro-thiazol-4-yl]-methanol;
{(R)-2-[5-bromo-7-(tetrahydro-pyran-4-ylamino)-1H-indol-2-yl]-4,5-dihydro-thiazol-4-yl}-methanol;
[(R)-2-(7-cyclopentylamino-5-methoxy-1H-indol-2-yl)-4,5-dihydro-thiazol-4-yl]-methanol;
{(R)-2-[7-cyclopentylamino-5-(pyridin-3-yloxy)-1H-indol-2-yl]-4,5-dihydro-thiazol-4-yl}-methanol;
{(R)-2-[5-(pyridin-3-yloxy)-7-(tetrahydro-pyran-4-ylamino)-1H-indol-2-yl]-4,5-dihydro-thiazol-4-yl}-methanol;

Cyclopentyl-[2-((R)-4-pyrrolidin-1-ylmethyl-4,5-dihydro-thiazol-2-yl)-1H-indol-7-yl]-amine;
Cyclopentyl-[2-((R)-4-morpholin-4-ylmethyl-4,5-dihydro-thiazol-2-yl)-1H-indol-7-yl]-amine;
Cyclopentyl-[2-((R)-4-dimethylaminomethyl-4,5-dihydro-thiazol-2-yl)-1H-indol-7-yl]-amine;
{(R)-2-[5-morpholin-4-ylmethyl-7-(tetrahydro-pyran-4-ylamino)-1H-indol-2-yl]-4,5-dihydro-thiazol-4-yl}-methanol;
[(R)-2-[7-cyclopentylamino-5-pyrazol-1-ylmethyl-1H-indol-2-yl]-4,5-dihydro-thiazol-4-yl]-methanol;
[(R)-2-(7-cyclopentylamino-5-imidazol-1-ylmethyl-1H-indol-2-yl)-4,5-dihydro-thiazol-4-yl]-methanol;
{(R)-2-[7-cyclopentylamino-5-(1H-pyrrol-3-ylmethyl)-1H-indol-2-yl]-4,5-dihydro-thiazol-4-yl}-methanol;
[(R)-2-(7-cyclopentylamino-5-methanesulfonylmethyl-1H-indol-2-yl)-4,5-dihydro-thiazol-4-yl]-methanol;
[7-Cyclopentylamino-2-((R)-4-hydroxymethyl-4,5-dihydro-thiazol-2-yl)-1H-indol-5-yl]-methanol;
[(R)-2-(5-chloro-7-cyclopentylamino-1H-indol-2-yl)-4,5-dihydro-thiazol-4-yl]-acetic acid methyl ester;
[(R)-2-(5-chloro-7-cyclopentylamino-1H-indol-2-yl)-4,5-dihydro-thiazol-4-yl]-acetic acid;
[(R)-2-(5-chloro-7-cyclopentylamino-1H-indol-2-yl)-4,5-dihydro-thiazol-4-yl]-acetic acid ethyl ester;
2-[(R)-2-(5-chloro-7-cyclopentylamino-1H-indol-2-yl)-4,5-dihydro-1,3-thiazol-4-yl]-ethanol;
{(R)-2-[5-chloro-7-(tetrahydro-pyran-4-ylamino)-1H-indol-2-yl]-4,5-dihydro-thiazol-4-yl}-acetic acid methyl ester;
{(R)-2-[5-chloro-7-(tetrahydro-pyran-4-ylamino)-1H-indol-2-yl]-4,5-dihydro-thiazol-4-yl}-acetic acid;
2-{(R)-2-[5-chloro-7-(tetrahydro-pyran-4-ylamino)-1H-indol-2-yl]-4,5-dihydro-thiazol-4-yl}-ethanol;
[(R)-2-(5-bromo-7-cyclopentylamino-1H-indol-2-yl)-4,5-dihydro-thiazol-4-yl]-acetic acid;
2-[(R)-2-(5-bromo-7-cyclopentylamino-1H-indol-2-yl)-4,5-dihydro-1,3-thiazol-4-yl]-ethanol;
{(R)-2-[5-bromo-7-(tetrahydro-pyran-4-ylamino)-1H-indol-2-yl]-4,5-dihydro-thiazol-4-yl}-acetic acid;
2-{(R)-2-[5-bromo-7-(tetrahydro-pyran-4-ylamino)-1H-indol-2-yl]-4,5-dihydro-thiazol-4-yl}-ethanol;
[(R)-2-(7-cyclopentylamino-5-fluoro-1H-indol-2-yl)-4,5-dihydro-thiazol-4-yl]-acetic acid;
[(R)-2-(7-cyclopentylamino-5-fluoro-1H-indol-2-yl)-4,5-dihydro-thiazol-4-yl]-acetic acid ethyl ester;
2-[(R)-2-(7-cyclopentylamino-5-fluoro-1H-indol-2-yl)-4,5-dihydro-thiazol-4-yl]-ethanol;
{(R)-2-[5-fluoro-7-(tetrahydro-pyran-4-ylamino)-1H-indol-2-yl]-4,5-dihydro-thiazol-4-yl}-acetic acid;
2-{(R)-2-[5-fluoro-7-(tetrahydro-pyran-4-ylamino)-1H-indol-2-yl]-4,5-dihydro-thiazol-4-yl}-ethanol;
[(R)-2-(7-cyclopentylamino-1H-indol-2-yl)-4,5-dihydro-thiazol-4-yl]-acetic acid;
[(R)-2-(7-cyclopentylamino-1H-indol-2-yl)-4,5-dihydro-thiazol-4-yl]-acetic acid ethyl ester;
2-[(R)-2-(7-cyclopentylamino-1H-indol-2-yl)-4,5-dihydro-thiazol-4-yl]-ethanol;
{(R)-2-[7-(tetrahydro-pyran-4-ylamino)-1H-indol-2-yl]-4,5-dihydro-thiazol-4-yl}-acetic acid;
2-{(R)-2-[7-(tetrahydro-pyran-4-ylamino)-1H-indol-2-yl]-4,5-dihydro-thiazol-4-yl}-ethanol;
[(R)-2-(7-cyclopentylamino-5-methoxy-1H-indol-2-yl)-4,5-dihydro-thiazol-4-yl]-acetic acid methyl ester;
[(R)-2-(7-cyclopentylamino-5-methoxy-1H-indol-2-yl)-4,5-dihydro-thiazol-4-yl]-acetic acid;
[(R)-2-(7-cyclopentylamino-5-methoxy-1H-indol-2-yl)-4,5-dihydro-thiazol-4-yl]-acetic acid ethyl ester;

{(R)-2-[5-methoxy-7-(tetrahydro-pyran-4-ylamino)-1H-indol-2-yl]-4,5-dihydro-thiazol-4-yl}-acetic acid methyl ester;
{(R)-2-[5-methoxy-7-(tetrahydro-pyran-4-ylamino)-1H-indol-2-yl]-4,5-dihydro-thiazol-4-yl}-acetic acid;
[(R)-2-(7-cyclopentylamino-5-ethoxy-1H-indol-2-yl)-4,5-dihydro-thiazol-4-yl]-acetic acid;
[(R)-2-(7-cyclopentylamino-5-propoxy-1H-indol-2-yl)-4,5-dihydro-thiazol-4-yl]-acetic acid;
[(R)-2-(7-cyclopentylamino-5-phenoxy-1H-indol-2-yl)-4,5-dihydro-thiazol-4-yl]-acetic acid;
{(R)-2-[5-phenoxy-7-(tetrahydro-pyran-4-ylamino)-1H-indol-2-yl]-4,5-dihydro-thiazol-4-yl}-acetic acid;
{(R)-2-[7-cyclopentylamino-5-(pyridin-3-yloxy)-1H-indol-2-yl]-4,5-dihydro-thiazol-4-yl}-acetic acid methyl ester;
{(R)-2-[7-cyclopentylamino-5-(pyridin-3-yloxy)-1H-indol-2-yl]-4,5-dihydro-thiazol-4-yl}-acetic acid;
{(R)-2-[5-(pyridin-3-yloxy)-7-(tetrahydro-pyran-4-ylamino)-1H-indol-2-yl]-4,5-dihydro-thiazol-4-yl}-acetic acid methyl ester;
{(R)-2-[5-(pyridin-3-yloxy)-7-(tetrahydro-pyran-4-ylamino)-1H-indol-2-yl]-4,5-dihydro-thiazol-4-yl}-acetic acid;
[(R)-2-(7-cyclopentylamino-5-methyl-1H-indol-2-yl)-4,5-dihydro-thiazol-4-yl]-acetic acid methyl ester;
[(R)-2-(7-cyclopentylamino-5-methyl-1H-indol-2-yl)-4,5-dihydro-thiazol-4-yl]-acetic acid;
{(R)-2-[5-methyl-7-(tetrahydro-pyran-4-ylamino)-1H-indol-2-yl]-4,5-dihydro-thiazol-4-yl}-acetic acid;
{(R)-2-[5-methyl-7-(4-oxo-cyclohexylamino)-1H-indol-2-yl]-4,5-dihydro-thiazol-4-yl}-acetic acid;
{(R)-2-[7-cyclopentylamino-5-(4-methanesulfonyl-phenoxy)-1H-indol-2-yl]-4,5-dihydro-thiazol-4-yl}-acetic acid;
[(R)-2-(7-cyclopentylamino-5-phenoxymethyl-1H-indol-2-yl)-4,5-dihydro-thiazol-4-yl]-acetic acid methyl ester;
[(R)-2-(7-cyclopentylamino-5-phenoxymethyl-1H-indol-2-yl)-4,5-dihydro-thiazol-4-yl]-acetic acid;
[(R)-2-(7-cyclopentylamino-5-pyrrolidin-1-ylmethyl-1H-indol-2-yl)-4,5-dihydro-thiazol-4-yl]-acetic acid methyl ester;
[(R)-2-(7-cyclopentylamino-5-methanesulfonylmethyl-1H-indol-2-yl)-4,5-dihydro-thiazol-4-yl]-acetic acid methyl ester;
[(R)-2-(7-cyclopentylamino-5-methanesulfonylmethyl-1H-indol-2-yl)-4,5-dihydro-thiazol-4-yl]-acetic acid;
2-[(R)-2-(7-cyclopentylamino-5-methanesulfonylmethyl-1H-indol-2-yl)-4,5-dihydro-thiazol-4-yl]-ethanol;
Cyclopentyl-{5-methanesulfonylmethyl-2-[(R)-4-(2-morpholin-4-yl-ethyl)-4,5-dihydro-thiazol-2-yl]-1H-indol-7-yl}-amine;
1-(4-{2-[(R)-2-(7-cyclopentylamino-5-methanesulfonylmethyl-1H-indol-2-yl)-4,5-dihydro-thiazol-4-yl]-ethyl}-piperazin-1-yl)-ethanone;
2-[(R)-2-(5-chloro-7-cyclopentylamino-1H-indol-2-yl)-4,5-dihydro-thiazol-4-yl]-1-morpholin-4-yl-ethanone;
2-[(R)-2-(5-chloro-7-cyclopentylamino-1H-indol-2-yl)-4,5-dihydro-thiazol-4-yl]-N-(2-morpholin-4-yl-ethyl)-acetamide;
2-[(R)-2-(5-chloro-7-cyclopentylamino-1H-indol-2-yl)-4,5-dihydro-thiazol-4-yl]-N-(3-morpholin-4-yl-propyl)-acetamide;
2-[(R)-2-(5-chloro-7-cyclopentylamino-1H-indol-2-yl)-4,5-dihydro-thiazol-4-yl]-N-methyl-acetamide;
2-[(R)-2-(5-chloro-7-cyclopentylamino-1H-indol-2-yl)-4,5-dihydro-thiazol-4-yl]-N,N-dimethyl-acetamide;
2-[(R)-2-(5-chloro-7-cyclopentylamino-1H-indol-2-yl)-4,5-dihydro-thiazol-4-yl]-1-(4-methyl-piperazin-1-yl)-ethanone;
2-[(R)-2-(5-chloro-7-cyclopentylamino-1H-indol-2-yl)-4,5-dihydro-thiazol-4-yl]-1-(3-dimethylamino-pyrrolidin-1-yl)-ethanone;
2-[(R)-2-(5-chloro-7-cyclopentylamino-1H-indol-2-yl)-4,5-dihydro-thiazol-4-yl]-1-(3-hydroxy-pyrrolidin-1-yl)-ethanone;
2-[(R)-2-(5-chloro-7-cyclopentylamino-1H-indol-2-yl)-4,5-dihydro-thiazol-4-yl]-1-piperidin-1-yl-ethanone;
2-{(R)-2-[5-chloro-7-(tetrahydro-pyran-4-ylamino)-1H-indol-2-yl]-4,5-dihydro-thiazol-4-yl}-N-methyl-acetamide;
2-{(R)-2-[5-chloro-7-(tetrahydro-pyran-4-ylamino)-1H-indol-2-yl]-4,5-dihydro-thiazol-4-yl}-1-morpholin-4-yl-ethanone;
2-[(R)-2-(7-cyclopentylamino-5-fluoro-1H-indol-2-yl)-4,5-dihydro-thiazol-4-yl]-1-(4-methyl-piperazin-1-yl)-ethanone;
2-[(R)-2-(7-cyclopentylamino-5-fluoro-1H-indol-2-yl)-4,5-dihydro-thiazol-4-yl]-N-(2-morpholin-4-yl-ethyl)-acetamide;
1-(4-Acetyl-piperazin-1-yl)-2-[(R)-2-(7-cyclopentylamino-5-fluoro-1H-indol-2-yl)-4,5-dihydro-thiazol-4-yl]-ethanone;
2-[(R)-2-(7-cyclopentylamino-5-methoxy-1H-indol-2-yl)-4,5-dihydro-thiazol-4-yl]-N-methyl-acetamide;
2-[(R)-2-(7-cyclopentylamino-5-methoxy-1H-indol-2-yl)-4,5-dihydro-thiazol-4-yl]-1-morpholin-4-yl-ethanone;
2-[(R)-2-(7-cyclopentylamino-1H-indol-2-yl)-4,5-dihydro-thiazol-4-yl]-N-ethyl-acetamide;
2-[(R)-2-(7-cyclopentylamino-1H-indol-2-yl)-4,5-dihydro-thiazol-4-yl]-N-methyl-acetamide;
2-[(R)-2-(7-cyclopentylamino-1H-indol-2-yl)-4,5-dihydro-thiazol-4-yl]-1-morpholin-4-yl-ethanone;
N-methyl-2-{(R)-2-[7-(tetrahydro-pyran-4-ylamino)-1H-indol-2-yl]-4,5-dihydro-thiazol-4-yl}-acetamide;
1-Morpholin-4-yl-2-{(R)-2-[7-(tetrahydro-pyran-4-ylamino)-1H-indol-2-yl]-4,5-dihydro-thiazol-4-yl}-ethanone;
{5-Chloro-2-[(R)-4-(2-dimethylamino-ethyl)-4,5-dihydro-thiazol-2-yl]-1H-indol-7-yl}-cyclopentyl-amine;
{5-Chloro-2-[(R)-4-(2-morpholin-4-yl-ethyl)-4,5-dihydro-thiazol-2-yl]-1H-indol-7-yl}-cyclopentyl-amine;
{5-Chloro-2-[(R)-4-(2-piperazin-1-yl-ethyl)-4,5-dihydro-thiazol-2-yl]-1H-indol-7-yl}-cyclopentyl-amine;
1-(4-{2-[(R)-2-(5-chloro-7-cyclopentylamino-1H-indol-2-yl)-4,5-dihydro-thiazol-4-yl]-ethyl}-piperazin-1-yl)-ethanone;
(5-Chloro-2-{(R)-4-[2-(4-ethanesulfonyl-piperazin-1-yl)-ethyl]-4,5-dihydro-thiazol-2-yl}-1H-indol-7-yl)-cyclopentyl-amine;
1-(4-{2-[(R)-2-(5-chloro-7-cyclopentylamino-1H-indol-2-yl)-4,5-dihydro-thiazol-4-yl]-ethyl}-piperazin-1-yl)-2-hydroxy-ethanone;
(5-Chloro-2-{(R)-4-[2-(4-methyl-piperazin-1-yl)-ethyl]-4,5-dihydro-thiazol-2-yl}-1H-indol-7-yl)-cyclopentyl-amine;
1-{2-[(R)-2-(5-chloro-7-cyclopentylamino-1H-indol-2-yl)-4,5-dihydro-thiazol-4-yl]-ethyl}-piperidin-4-ol;
(4-{2-[(R)-2-(5-chloro-7-cyclopentylamino-1H-indol-2-yl)-4,5-dihydro-thiazol-4-yl]-ethyl}-piperazin-2-one;
(5-Chloro-2-{(R)-4-[2-(3-dimethylamino-pyrrolidin-1-yl)-ethyl]-4,5-dihydro-thiazol-2-yl}-1H-indol-7-yl)-cyclopentyl-amine;
{5-Chloro-2-[(R)-4-(2-piperidin-1-yl-ethyl)-4,5-dihydro-thiazol-2-yl]-1H-indol-7-yl}-cyclopentyl-amine;

(5-Chloro-2-{(R)-4-[2-(1,1-dioxo-thiomorpholin-4-yl)-ethyl]-4,5-dihydro-thiazol-2-yl}-1H-indol-7-yl)-cyclopentyl-amine;

{5-Chloro-2-[(R)-4-(2-pyrazol-1-yl-ethyl)-4,5-dihydro-thiazol-2-yl]-1H-indol-7-yl}-cyclopentyl-amine;

(S)-1-{2-[(R)-2-(5-chloro-7-cyclopentylamino-1H-indol-2-yl)-4,5-dihydro-thiazol-4-yl]-ethyl}-pyrrolidine-2-carboxylic acid;

{5-Chloro-2-[(R)-4-(2-methanesulfonyl-ethyl)-4,5-dihydro-thiazol-2-yl]-1H-indol-7-yl}-cyclopentyl-amine;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid;

1-{2-[(R)-2-(5-chloro-7-cyclopentylamino-1H-indol-2-yl)-4,5-dihydro-thiazol-4-yl]-ethyl}-pyrrolidin-2-one;

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid;

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid dimethylamide;

[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-carbamic acid t-butyl ester;

(2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine;

N—[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-acetamide;

{5-Chloro-2-[(R)-4-(2-piperazin-1-yl-ethyl)-4,5-dihydro-thiazol-2-yl]-1H-indol-7-yl}-(tetrahydro-pyran-4-yl)-amine;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-hydroxy-ethanone;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-tetrazol-1-yl-ethanone;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-3,3,3-trifluoro-propan-1-one;

[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-furan-2-yl-methanone;

(5-Chloro-2-{(R)-4-[2-(2,3,5,6-tetrahydro-[1,2']bipyrazinyl-4-yl)-ethyl]-4,5-dihydro-thiazol-2-yl}-1H-indol-7-yl)-(tetrahydro-pyran-4-yl)-amine;

(5-Chloro-2-{(R)-4-[2-(4-pyrimidin-2-yl-piperazin-1-yl)-ethyl]-4,5-dihydro-thiazol-2-yl}-1H-indol-7-yl)-(tetrahydro-pyran-4-yl)-amine;

{2-[(R)-4-(2-amino-ethyl)-4,5-dihydro-thiazol-2-yl]-5-fluoro-1H-indol-7-yl}-cyclopentyl-amine;

1-(4-{2-[(R)-2-(7-cyclopentylamino-5-fluoro-1H-indol-2-yl)-4,5-dihydro-thiazol-4-yl]-ethyl}-piperazin-1-yl)-ethanone;

Cyclopentyl-{5-fluoro-2-[(R)-4-(2-morpholin-4-yl-ethyl)-4,5-dihydro-thiazol-2-yl]-1H-indol-7-yl}-amine;

Cyclopentyl-{2-[(R)-4-(2-dimethylamino-ethyl)-4,5-dihydro-thiazol-2-yl]-5-fluoro-1H-indol-7-yl}-amine;

Cyclopentyl-{5-fluoro-2-[(R)-4-(2-pyrrolidin-1-yl-ethyl)-4,5-dihydro-thiazol-2-yl]-1H-indol-7-yl}-amine;

Cyclopentyl-(2-{(R)-4-[2-(1,1-dioxo-thiomorpholin-4-yl)-ethyl]-4,5-dihydro-thiazol-2-yl}-5-fluoro-1H-indol-7-yl)-amine;

4-{2-[(R)-2-(7-cyclopentylamino-5-fluoro-1H-indol-2-yl)-4,5-dihydro-thiazol-4-yl]-ethyl}-piperazin-2-one;

1-(4-{2-[(R)-2-(7-cyclopentylamino-5-fluoro-1H-indol-2-yl)-4,5-dihydro-thiazol-4-yl]-ethyl}-piperazin-1-yl)-2-hydroxy-ethanone;

Cyclopentyl-{5-fluoro-2-[(R)-4-(2-methanesulfonyl-ethyl)-4,5-dihydro-thiazol-2-yl]-1H-indol-7-yl}-amine;

{2-[(R)-4-(2-dimethylamino-ethyl)-4,5-dihydro-thiazol-2-yl]-5-fluoro-1H-indol-7-yl}-(tetrahydro-pyran-4-yl)-amine;

{5-Fluoro-2-[(R)-4-(2-pyrrolidin-1-yl-ethyl)-4,5-dihydro-thiazol-2-yl]-1H-indol-7-yl}-(tetrahydro-pyran-4-yl)-amine;

{5-Fluoro-2-[(R)-4-(2-morpholin-4-yl-ethyl)-4,5-dihydro-thiazol-2-yl]-1H-indol-7-yl}-(tetrahydro-pyran-4-yl)-amine;

1-[4-(2-{(R)-2-[5-fluoro-7-(tetrahydro-pyran-4-ylamino)-1H-indol-2-yl]-4,5-dihydro-thiazol-4-yl}-ethyl-piperazin-1-yl)-ethanone;

(2-{(R)-4-[2-(1,1-dioxo-thiomorpholin-4-yl)-ethyl]-4,5-dihydro-thiazol-2-yl}-5-fluoro-1H-indol-7-yl)-(tetrahydro-pyran-4-yl)-amine;

(5-Fluoro-2-[(R)-4-(2-methanesulfonyl-ethyl)-4,5-dihydro-thiazol-2-yl]-1H-indol-7-yl)-(tetrahydro-pyran-4-yl)-amine;

4-(2-{(R)-2-[5-fluoro-7-(tetrahydro-pyran-4-ylamino)-1H-indol-2-yl]-4,5-dihydro-thiazol-4-yl}-ethyl)-piperazin-2-one;

1-[4-(2-{(R)-2-[5-fluoro-7-(tetrahydro-pyran-4-ylamino)-1H-indol-2-yl]-4,5-dihydro-thiazol-4-yl}-ethyl)-piperazin-1-yl]-2-hydroxy-ethanone;

Cyclopentyl-{2-[(R)-4-(2-methoxy-ethyl)-4,5-dihydro-thiazol-2-yl]-1H-indol-7-yl}-amine;

Cyclopentyl-{2-[(R)-4-(2-dimethylamino-ethyl)-4,5-dihydro-thiazol-2-yl]-1H-indol-7-yl}-amine;

Cyclopentyl-{2-[(R)-4-(2-morpholin-4-yl-ethyl)-4,5-dihydro-thiazol-2-yl]-1H-indol-7-yl}-amine;

Cyclopentyl-{2-[(R)-4-(2-piperidin-1-yl-ethyl)-4,5-dihydro-thiazol-2-yl]-1H-indol-7-yl}-amine;

{2-[(R)-4-(2-methanesulfonyl-ethyl)-4,5-dihydro-thiazol-2-yl]-1H-indol-7-yl}-(tetrahydro-pyran-4-yl)-amine;

1-(4-{2-[(R)-2-(7-cyclopentylamino-5-methoxy-1H-indol-2-yl)-4,5-dihydro-thiazol-4-yl]-ethyl}-piperazin-1-yl)-2-hydroxy-ethanone;

2-Hydroxy-1-[4-(2-{(R)-2-[5-methoxy-7-(tetrahydro-pyran-4-ylamino)-1H-indol-2-yl]-4,5-dihydro-thiazol-4-yl}-ethyl)-piperazin-1-yl]-ethanone;

3-[(R)-2-(5-chloro-7-cyclopentylamino-1H-indol-2-yl)-4,5-dihydro-thiazol-4-yl]-propionic acid ethyl ester;

3-[(R)-2-(5-chloro-7-cyclopentylamino-1H-indol-2-yl)-4,5-dihydro-thiazol-4-yl]-propionic acid;

3-[(R)-2-(5-chloro-7-cyclopentylamino-1H-indol-2-yl)-4,5-dihydro-thiazol-4-yl]-propan-1-ol;

3-{(R)-2-[5-chloro-7-(tetrahydro-pyran-4-ylamino)-1H-indol-2-yl]-4,5-dihydro-thiazol-4-yl}-propionic acid;

3-{(R)-2-[5-chloro-7-(tetrahydro-pyran-4-ylamino)-1H-indol-2-yl]-4,5-dihydro-thiazol-4-yl}-propan-1-ol;

3-[(R)-2-(5-chloro-7-cyclopentylamino-1H-indol-2-yl)-4,5-dihydro-thiazol-4-yl]-N-(2-morpholin-4-yl-ethyl)-propionamide;

3-[(R)-2-(5-chloro-7-cyclopentylamino-1H-indol-2-yl)-4,5-dihydro-thiazol-4-yl]-1-(4-methyl-piperazin-1-yl)-propan-1-one;

1-(4-{3-[(R)-2-(5-chloro-7-cyclopentylamino-1H-indol-2-yl)-4,5-dihydro-thiazol-4-yl]-propyl}-piperazin-1-yl)-ethanone;

{5-Chloro-2-[(R)-4-(3-morpholin-4-yl-propyl)-4,5-dihydro-thiazol-2-yl]-1H-indol-7-yl}-cyclopentyl-amine;

3-[(R)-2-(7-cyclopentylamino-5-methyl-1H-indol-2-yl)-4,5-dihydro-thiazol-4-yl]-propionic acid ethyl ester;

3-[(R)-2-(7-cyclopentylamino-5-methyl-1H-indol-2-yl)-4,5-dihydro-thiazol-4-yl]-propionic acid;

3-[(R)-2-(7-cyclopentylamino-5-phenoxy-1H-indol-2-yl)-4,5-dihydro-thiazol-4-yl]-propionic acid;

3-[(R)-2-(7-cyclopentylamino-5-fluoro-1H-indol-2-yl)-4,5-dihydro-thiazol-4-yl]-propionic acid ethyl ester;

3-[(R)-2-(7-cyclopentylamino-5-fluoro-1H-indol-2-yl)-4,5-dihydro-thiazol-4-yl]-propionic acid;

3-[(R)-2-(5-bromo-7-cyclopentylamino-1H-indol-2-yl)-4,5-dihydro-thiazol-4-yl]-propionic acid ethyl ester;

3-[(R)-2-(5-bromo-7-cyclopentylamino-1H-indol-2-yl)-4,5-dihydro-thiazol-4-yl]-propionic acid;

3-[(R)-2-(7-cyclopentylamino-1H-indol-2-yl)-4,5-dihydro-thiazol-4-yl]-propionic acid;

3-[(R)-2-(7-cyclopentylamino-5-methoxy-1H-indol-2-yl)-4,5-dihydro-thiazol-4-yl]-propionic acid;

3-[(R)-2-(7-cyclopentylamino-5-ethoxy-1H-indol-2-yl)-4,5-dihydro-thiazol-4-yl]-propionic acid ethyl ester;

3-[(R)-2-(7-cyclopentylamino-5-ethoxy-1H-indol-2-yl)-4,5-dihydro-thiazol-4-yl]-propionic acid;

3-[(R)-2-(7-cyclopentylamino-5-trifluoromethoxy-1H-indol-2-yl)-4,5-dihydro-thiazol-4-yl]-propionic acid ethyl ester;

3-[(R)-2-(7-cyclopentylamino-5-trifluoromethoxy-1H-indol-2-yl)-4,5-dihydro-thiazol-4-yl]-propionic acid;

[(R)-2-(7-cyclopentylamino-5-fluoro-1H-indol-2-yl)-4,5-dihydro-thiazol-4-ylmethoxy]-acetic acid ethyl ester;

[(R)-2-(7-cyclopentylamino-5-fluoro-1H-indol-2-yl)-4,5-dihydro-thiazol-4-ylmethoxy]-acetic acid;

Cyclopentyl-{2-[(R)-4-(3-cyclopentyl-[1,2,4]oxadiazol-5-ylmethyl)-4,5-dihydro-thiazol-2-yl]-1H-indol-7-yl}-amine;

Cyclopentyl-{2-[(R)-4-(3-piperidin-1-yl-[1,2,4]oxadiazol-5-ylmethyl)-4,5-dihydro-thiazol-2-yl]-1H-indol-7-yl}-amine;

[(R)-2-(7-phenoxy-1H-indol-2-yl)-4,5-dihydro-thiazol-4-yl]-acetic acid;

1-(4-{2-[(R)-2-(7-phenoxy-1H-indol-2-yl)-4,5-dihydro-thiazol-4-yl]-ethyl}-piperazin-1-yl)-ethanone;

2-[(R)-4-(2-morpholin-4-yl-ethyl)-4,5-dihydro-thiazol-2-yl]-7-phenoxy-1H-indole;

7-Phenoxy-2-[(R)-4-(2-pyrrolidin-1-yl-ethyl)-4,5-dihydro-thiazol-2-yl]-1H-indole;

Dimethyl-{2-[(R)-2-(7-phenoxy-1H-indol-2-yl)-4,5-dihydro-thiazol-4-yl]-ethyl}-amine;

[(S)-2-(5-chloro-7-cyclopentylamino-1H-indol-2-yl)-4,5-dihydro-thiazol-4-yl]-acetic acid;

{(S)-247-(1-acetyl-piperidin-4-ylamino)-5-methyl-1H-indol-2-yl]-4,5-dihydro-thiazol-4-yl}-acetic acid;

((S)-2-{7-[(tetrahydro-pyran-2-ylmethyl)-amino]-1H-indol-2-yl}-4,5-dihydro-thiazol-4-yl)-acetic acid;

((S)-2-{7-[(tetrahydro-pyran-4-ylmethyl)-amino]-1H-indol-2-yl}-4,5-dihydro-thiazol-4-yl)-acetic acid;

{(S)-2-[7-(tetrahydro-pyran-4-ylamino)-1H-indol-2-yl]-4,5-dihydro-thiazol-4-yl}-acetic acid;

{(S)-2-[7-(1-acetyl-pyrrolidin-3-ylamino)-5-methyl-1H-indol-2-yl]-4,5-dihydro-thiazol-4-yl}-acetic acid;

[(S)-2-(7-cyclopentylamino-1H-indol-2-yl)-4,5-dihydro-thiazol-4-yl]-acetic acid;

((S)-2-{5-phenoxy-7-[(tetrahydro-pyran-4-ylmethyl)-amino]-1H-indol-2-yl}-4,5-dihydro-thiazol-4-yl)-acetic acid;

{(S)-2-[5-phenoxy-7-(tetrahydro-pyran-4-ylamino)-1H-indol-2-yl]-4,5-dihydro-thiazol-4-yl}-acetic acid;

{(S)-2-[5-chloro-7-(tetrahydro-pyran-4-ylamino)-1H-indol-2-yl]-4,5-dihydro-thiazol-4-yl}-acetic acid;

[(S)-2-(7-cyclobutylamino-5-methyl-1H-indol-2-yl)-4,5-dihydro-thiazol-4-yl]-acetic acid;

{(S)-2-[5-methyl-7-(tetrahydro-furan-3-ylamino)-1H-indol-2-yl]-4,5-dihydro-thiazol-4-yl}-acetic acid;

{(S)-2-[7-(cyclopropylmethyl-amino)-5-methyl-1H-indol-2-yl]-4,5-dihydro-thiazol-4-yl}-acetic acid;

((S)-2-{5-methyl-7-[(tetrahydro-pyran-4-ylmethyl)-amino]-1H-indol-2-yl}-4,5-dihydro-thiazol-4-yl)-acetic acid;

{(S)-2-[5-methyl-7-(tetrahydro-pyran-4-ylamino)-1H-indol-2-yl]-4,5-dihydro-thiazol-4-yl}-acetic acid;

[(S)-2-(7-cyclopentylamino-5-methyl-1H-indol-2-yl)-4,5-dihydro-thiazol-4-yl]-acetic acid methylester;

[(S)-2-(7-cyclopentylamino-5-phenoxy-1H-indol-2-yl)-4,5-dihydro-thiazol-4-yl]-acetic acid;

{(S)-2-[7-(4,4-difluoro-cyclohexylamino)-5-methyl-1H-indol-2-yl]-4,5-dihydro-thiazol-4-yl}-acetic acid;

(2-{(S)-4-[2-((R)-3-amino-pyrrolidin-1-yl)-ethyl]-4,5-dihydro-thiazol-2-yl}-5-chloro-1H-indol-7-yl)-cyclopentyl-amine;

(5-Chloro-2-{(S)-4-[2-((R)-3-dimethylamino-pyrrolidin-1-yl)-ethyl]-4,5-dihydro-thiazol-2-yl}-1H-indol-7-yl)-cyclopentyl-amine;

1-(4-{2-[(S)-2-(5-chloro-7-cyclopentylamino-1H-indol-2-yl)-4,5-dihydro-thiazol-4-yl]-ethyl}-piperazin-1-yl)-ethanone;

1-(4-{2-[(S)-2-(7-amino-5-chloro-1H-indol-2-yl)-4,5-dihydro-thiazol-4-yl]-ethyl}-piperazin-1-yl)-ethanone;

1-(4-{2-[(S)-2-(5-methyl-7-(tetrahydro-pyran-4-ylamino)-1H-indol-2-yl)-4,5-dihydro-thiazol-4-yl]-ethyl}-piperazin-1-yl)-ethanone;

{5-Methyl-2-[(S)-4-(2-morpholin-4-yl-ethyl)-4,5-dihydro-thiazol-2-yl]-1H-indol-7-yl}-(tetrahydro-pyran-4-yl)-amine;

1-(4-{2-[(S)-2-(7-cyclopentylamino-5-phenoxy-1H-indol-2-yl)-4,5-dihydro-thiazol-4-yl]-ethyl}-piperazin-1-yl)-2-hydroxy-ethanone;

Cyclopentyl-{5-phenoxy-2-[(S)-4-(2-piperazin-1-yl-ethyl)-4,5-dihydro-thiazol-2-yl]-1H-indol-7-yl}-amine;

4-{2-[(S)-2-(7-cyclopentylamino-5-phenoxy-1H-indol-2-yl)-4,5-dihydro-thiazol-4-yl]-ethyl}-piperazine-1-carboxylic acid t-butyl ester;

Cyclopentyl-(2-{(S)-4-[2-(3-methyl-5,6-dihydro-8H-[1,2,4]triazolo[4,3-a]pyrazin-7-yl)-ethyl]-4,5-dihydro-thiazol-2-yl}-5-phenoxy-1H-indol-7-yl)-amine;

4-{2-[(S)-2-(7-cyclopentylamino-5-phenoxy-1H-indol-2-yl)-4,5-dihydro-thiazol-4-yl]-ethyl}-piperazin-2-one;

(4-{2-[(S)-2-(7-cyclopentylamino-5-phenoxy-1H-indol-2-yl)-4,5-dihydro-thiazol-4-yl]-ethyl}-piperazin-1-yl)-(tetrahydro-furan-2-yl)-methanone;

Cyclopentyl-(5-phenoxy-2-{(S)-4-[2-(4-pyridin-2-yl-piperazin-1-yl)-ethyl]-4,5-dihydro-thiazol-2-yl}-1H-indol-7-yl)-amine;

Cyclopentyl-[2-((S)-4-{2-[4-(2-fluoro-phenyl)-piperazin-1-yl]-ethyl}-4,5-dihydro-thiazol-2-yl)-5-phenoxy-1H-indol-7-yl]-amine;

1-(4-{2-[(S)-2-(7-cyclopentylamino-5-phenoxy-1H-indol-2-yl)-4,5-dihydro-thiazol-4-yl]-ethyl}-piperazin-1-yl)-ethanone;

{(R)-1-[2-[(S)-2-{5-methyl-7-[(tetrahydro-pyran-4-ylmethyl)-amino]-1H-indol-2-yl}-4,5-dihydro-thiazol-4-yl]-ethyl]-pyrrolidin-2-yl}-methanol;

N—((R)-1-{2-[(S)-2-(7-cyclopentylamino-5-phenoxy-1H-indol-2-yl)-4,5-dihydro-thiazol-4-yl]-ethyl}-pyrrolidin-3-yl)-acetamide;

(2-{(S)-4-[2-(4-benzyl-piperazin-1-yl)-ethyl]-4,5-dihydro-thiazol-2-yl}-5-phenoxy-1H-indol-7-yl)-cyclopentyl-amine;

{5-Methyl-2-[(S)-4-(2-morpholin-4-yl-ethyl)-4,5-dihydro-thiazol-2-yl]-1H-indol-7-yl}-(tetrahydro-pyran-4-ylmethyl)methyl-amine;

{2-[(S)-4-(2-morpholin-4-yl-ethyl)-4,5-dihydro-thiazol-2-yl]-5-phenoxy-1H-indol-7-yl}-(tetrahydro-pyran-4-ylmethyl)-amine;

4-[2-((S)-2-{5-phenoxy-7-[(tetrahydro-pyran-4-ylmethyl)-amino]-1H-indol-2-yl}-4,5-dihydro-thiazol-4-yl)-ethyl]-piperazin-2-one;

Cyclopentyl-{5-phenoxy-2-[(S)-4-(2-pyrrolidin-1-yl-ethyl)-4,5-dihydro-thiazol-2-yl]-1H-indol-7-yl)-amine;

(4,4-Difluoro-cyclohexyl)-{2-[(S)-4-(2-morpholin-4-yl-ethyl)-4,5-dihydro-thiazol-2-yl]-1H-indol-7-yl)-amine;

(2-{(S)-4-[2-(3-methyl-5,6-dihydro-8H-[1,2,4]triazolo[4,3-pyrazin-7-yl]-ethyl)-4,5-dihydro-thiazol-2-yl}-5-phenoxy-1H-indol-7-yl)-(tetrahydro-pyran-4-ylmethyl)-amine;

4-[2-((S)-2-{5-phenoxy-7-[(tetrahydro-pyran-4-ylmethyl)-amino]-1H-indol-2-yl}-4,5-dihydro-thiazol-4-yl)-ethyl]-piperazin-2-one; and 4-(2-{(S)-2-[7-(4,4-difluoro-cyclohexylamino)-5-phenoxy-7-1H-indol-2-yl]-4,5-dihydro-thiazol-4-yl}-ethyl)-piperazin-2-one.

Other terms and abbreviations in the present specification may be understood to have the meaning conventionally used in this field by a skilled artisan, unless otherwise defined.

The compounds of formula (1) according to the present invention can also form a pharmaceutically acceptable salt. Such a pharmaceutically acceptable salt includes non-toxic acid addition salt containing pharmaceutically acceptable anion, for example, a salt with inorganic acids such as hydrochloric acid, sulfuric acid, nitric acid, phosphoric acid, hydrobromic acid, hydriodic acid, etc.; a salt with organic acids such as tartaric acid, formic acid, citric acid, acetic acid, trichloroacetic acid, trifluoroacetic acid, gluconic acid, benzoic acid, lactic acid, fumaric acid, maleic acid, salicylic acid, etc.; or a salt with sulfonic acids such as methanesulfonic acid, ethanesulfonic acid, benzenesulfonic acid, p-toluenesulfonic acid, etc. Also, for example, the pharmaceutically acceptable carboxylic acid salt includes a salt with alkali metals or alkaline earth metals such as lithium, sodium, potassium, calcium, magnesium, etc.; a salt with amino acids such as lysine, arginine, guanidine, etc.; or an organic salt with dicyclohexylamine, N-methyl-D-glutamine, tris(hydroxymethyl)methylamine, diethanolamine, choline, triethylamine, etc. The compounds of formula (1) of the present invention may be converted to their salts according to any of the conventional methods.

The compounds of formula (1) of the present invention may have an asymmetric carbon center(s) in the structure, and so may exist in the form of R or S isomer, racemate, mixture of diastereomers, or individual diastereomer, etc. All the isomers are also covered by the present invention.

The present invention also provides processes for preparing the compounds of formula (1). Hereinafter, the processes for preparing the compounds of formula (1) are illustrated by exemplary reaction schemes for the purpose of better understanding. However, a skilled artisan in the field to which the present invention pertains may prepare the compounds of formula (1) via various routes according to their structures, and such processes should be construed to fall under the scope of the present invention. In other words, the compounds of formula (1) may be prepared by optionally combining various synthetic methods which are described in the present specification or disclosed in the prior arts. The processes for preparing the compounds of formula (1) cover even such processes, and are not limited to those explained below.

The compounds of formula (1) can be prepared according to the following Reaction Scheme (1) by reducing the nitro group of Compound (2) to give an amine Compound (3), and introducing R1 substituent to the resulting amine group. Alternatively, the compounds of formula (1) can be prepared according to the following Reaction Schemes (2) to (7) by modifying R1, R2 and R3 substituents in Compound (4).

Compound (5) can be prepared according to the following Reaction Schemes (8) and (9). Compound (7) can be prepared according to the following Reaction Scheme (10), and Compound (20) can be prepared according to the following Reaction Scheme (11).

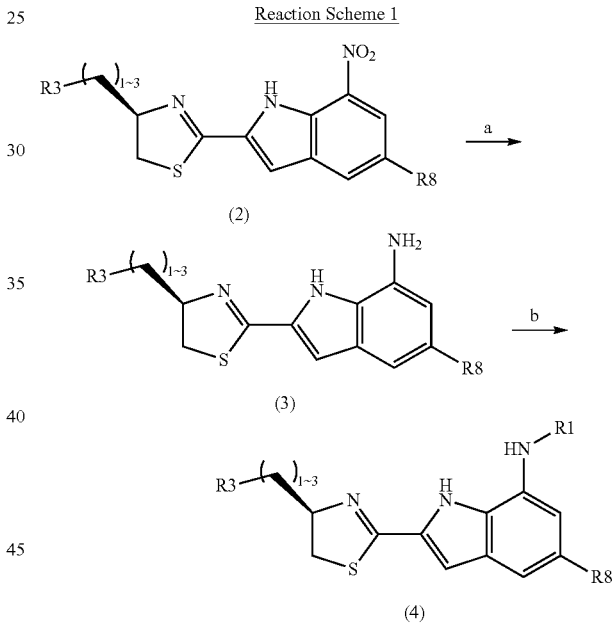

in the above Reaction Scheme (1), a represents Fe, Zn, Pd/C, etc., b represents a ketone compound in the form of R1=O, sodium triacetoxyborohydride {NaBH(OAc)$_3$}, sodium cyanoborohydride (NaBH$_3$CN), etc., R1, R2, and R3 are as defined in formula (1), and R8 represents Y—R2, wherein Y and R2 are as defined in formula (1).

Compound (2) can be prepared according to the following Reaction Schemes (2) to (9).

Compound (3) can be prepared by reducing the Compound (2). The reduction reaction may be carried out using an acid catalyst and metal, or using a metal catalyst in the presence of hydrogen gas.

The acid that can be used in the reduction reaction using an acid catalyst and metal includes, for example, inorganic acids such as hydrochloric acid, sulfuric acid, nitric acid, phosphoric acid, etc., organic carboxylic acids such as acetic acid, trifluoroacetic acid, etc., aminates such as ammonium chloride, preferably hydrochloric acid, acetic acid, ammonium chloride, etc. The acid is typically used in the amount of 0.01~10 eq., preferably 0.1~5 eq., with respect to 1 eq. of the Compound (2). The metal that can be used includes, for example, iron, zinc, lithium, sodium, tin (usually, tin chloride), etc., particularly preferably iron, zinc, tin chloride, etc. The metal is typically used in the amount of 1~20 eq., preferably 1~10 eq., with respect to 1 eq. of the Compound (2). The reaction of metal in the presence of an acid catalyst may be carried out in an inert solvent. As the inert solvent, for example, alkyl alcohols such as methanol, ethanol, etc., ethers such as tetrahydrofuran, diethylether, etc., alkyl esters such as ethyl acetate, etc., preferably methanol, ethanol, tetrahydrofuran, ethyl acetate, etc. can be mentioned. The reaction temperature is typically in the range of −10~200° C., preferably 25~120° C., and the reaction time is typically in the range of 10 min~60 h, preferably 10 min~12 h.

The metal catalyst that can be used in the reduction reaction using a metal catalyst in the presence of hydrogen gas includes palladium, nickel, platinum, ruthenium, rhodium, etc., particularly preferably palladium, nickel, etc. The metal catalyst is typically used in the amount of 0.001~2 eq., preferably 0.01~1 eq., with respect to 1 eq. of the Compound (2). The hydrogen gas pressure is typically in the range of 1~10 atm, preferably 1~3 atm. The reaction may be carried out in an inert solvent, for example, alkyl alcohols such as methanol, ethanol, etc., ethers such as tetrahydrofuran, diethylether, etc., alkyl acetates such as methyl acetate, ethyl acetate, etc., preferably methanol, ethanol, ethyl acetate, etc. The reaction temperature using the metal catalyst is typically in the range of −10~200° C., preferably 25~50° C., and the reaction time is typically in the range of 10 min~60 h, preferably 10 min~12 h.

Compound (4) can be prepared via a reductive alkylation reaction of the Compound (3).

The reductive alkylation on the amine group of the Compound (3) may be carried out with a ketone using a reducing agent, and if necessary, using an acid catalyst. The ketone is typically used in the amount of 1~10 eq., preferably 1~3 eq., with respect to 1 eq. of the Compound (3). The reducing agent that can be used includes sodium borohydride, sodium cyanoborohydride, sodium triacetoxyborohydride, etc. The reducing agent is typically used in the amount of 1~10 eq., preferably 1~3 eq., with respect to 1 eq. of the Compound (3). The acid catalyst that can be used includes, for example, inorganic acids such as hydrochloric acid, sulfuric acid, nitric acid, phosphoric acid, etc., organic carboxylic acids such as acetic acid, trifluoroacetic acid, etc., aminates such as ammonium chloride, particularly preferably hydrochloric acid, acetic acid, etc. The acid is typically used in the amount of 0.1~10 eq., preferably 1~5 eq., with respect to 1 eq. of the Compound (3). The reaction may be carried out in an inert solvent selected, for example, from ethers such as tetrahydrofuran, diethylether, etc., chloroalkanes such as dichloromethane, chloroform, dichloroethane, etc., preferably dichloroethane, chloroform, etc. The reaction temperature is typically in the range of −10~100° C., preferably −10~50° C., and the reaction time is typically in the range of 10 min~60 h, preferably 10 min~12 h.

The Compound (1) or (2) of the present invention can be prepared according to the processes that are specifically exemplified in the following Reaction Schemes (2) to (9).

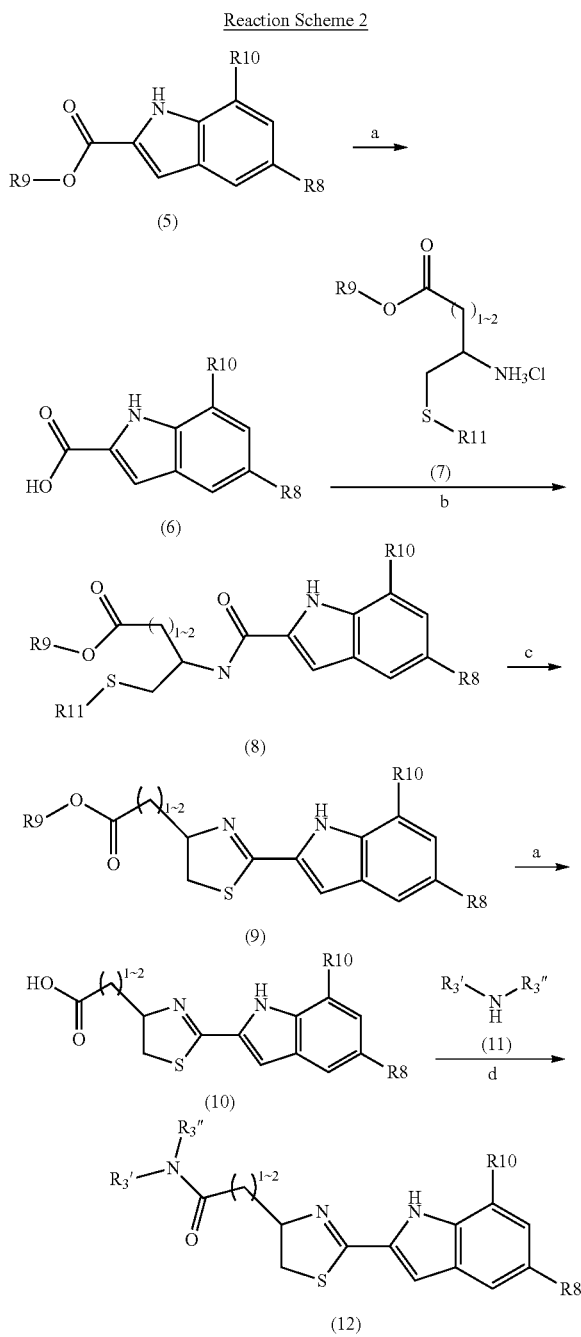

Reaction Scheme 2 in the above Reaction Scheme (2), a represents a metal hydroxide (for example, NaOH, LiOH), b represents a coupling agent (for example, EDC, CDI, BOP—Cl) and Compound (7), c represents $PCl_5$ or $Tf_2O$ and $Ph_3PO$, d represents a coupling agent (for example, EDC, CDI, BOP—Cl) and Compound (11), R8 is as defined in the Reaction Scheme (1), R9 represents $C_1$-$C_6$-alkyl, R10 represents $NO_2$ or R1-X, wherein X and R1 are as defined in formula (1), R11 represents p-MeOBn or $Ph_3C$, and R3' and R3" independently of one another represent R7-X—B—, wherein R7, X and B are as defined in formula (1).

Compound (5) can be prepared according to Reaction Schemes (8) and (9).

Compound (6) can be prepared via hydrolysis reaction of the Compound (5) using a base. The base that can be used includes lithium hydroxide, sodium hydroxide, potassium hydroxide, etc. The base is typically used in the amount of 1~10 eq., preferably 1~5 eq., with respect to 1 eq. of the Compound (5). The hydrolysis reaction may be carried out in an inert solvent selected, for example, from water, alkyl alcohols such as methanol, ethanol, etc., ethers such as tetrahydrofuran, diethylether, etc. The reaction temperature is typically in the range of −10~200° C., preferably 25~120° C., and the reaction time is typically in the range of 10 min~60 h, preferably 10 min~12 h.

Compound (7) can be prepared according to the following Reaction Schemes (10) and (11).

Compound (8) can be prepared via a coupling reaction of the carboxylic acid of Compound (6) with the amine group of the Compound (7). The known coupling agent that can be used in the coupling reaction includes, but not limited to, carboimides such as dicyclohexylcarbodiimide (DCC), 1-(3-dimethylaminopropyl)-3-ethylcarbodiimide (EDC), 1,1'-dicarbonyldiimidazole (CDI), etc. mixed with 1-hydroxy-benzotriazole (HOBT) or 1-hydroxy-7-azabenzotriazole (HOAT), or bis-(2-oxo-3-oxazolidinyl)-phosphinic acid chloride (BOP—Cl), diphenylphosphorylazide (DPPA), N-[dimethylamino-1H-1,2,3-triazole[4,5-b]-pyridin-1-ylmethylene]-N-methylmethaneaminium (HATU), etc. The coupling agent is typically used in the amount of 1~10 eq., preferably 1~3 eq., with respect to 1 eq. of the Compound (6). The amount of HOBT or HOAT used is typically in the range of 1~10 eq., preferably 1~3 eq., with respect to 1 eq. of the Compound (6). When an amine hydrochloride is used in the coupling reaction, the acid should be removed by using a base. The base that can be used includes organic bases such as triethylamine, diisopropylethylamine The base is typically used in the amount of 1~10 eq., preferably 1~3 eq., with respect to 1 eq. of the Compound (7). The coupling reaction may be carried out in an inert solvent selected from tetrahydrofuran, diethylether, N,N-dimethylformamide, etc. The reaction temperature is typically in the range of −10~200° C., preferably 25~120° C., and the reaction time is typically in the range of 10 min~60 h, preferably 10 min~12 h.

Compound (9) can be prepared by cyclizing the Compound (8) as described in Journal of Organic Chemistry, 68(24), 2003, 9506~9509, Tetrahedron, 55(34), 1999, 10271~10282, etc.

When R11 is p-methoxybenzyl (p-MeOBn) group, the cyclization reaction is carried out in dichloromethane solvent using phosphorus pentachloride ($PCl_5$). $PCl_5$ is typically used in the amount of 1~10 eq., preferably 1~3 eq., with respect to 1 eq. of the Compound (8). The reaction temperature is typically in the range of −10~50° C., preferably 0~25° C., and the reaction time is typically in the range of 10 min~60 h, preferably 10 min~12 h.

When R11 is triphenylmethyl ($Ph_3C$) group, the cyclization reaction is carried out in dichloromethane solvent using trifluoromethanesulfonic-anhydride ($Tf_2O$) and triphenylphosphineoxide ($Ph_3PO$), which are typically used in the amount of 1~10 eq., preferably 1~3 eq., with respect to 1 eq. of the Compound (8). The reaction temperature is typically in the range of −10~50° C., preferably 0~25° C., and the reaction time is typically in the range of 10 min~60 h, preferably 10 min~12 h.

Compound (11) is an amine compound that is commercially available.

Compound (12) can be prepared via a coupling reaction of the carboxylic acid of the Compound (10) with the Compound (11) according to the preparing process of the Compound (8).

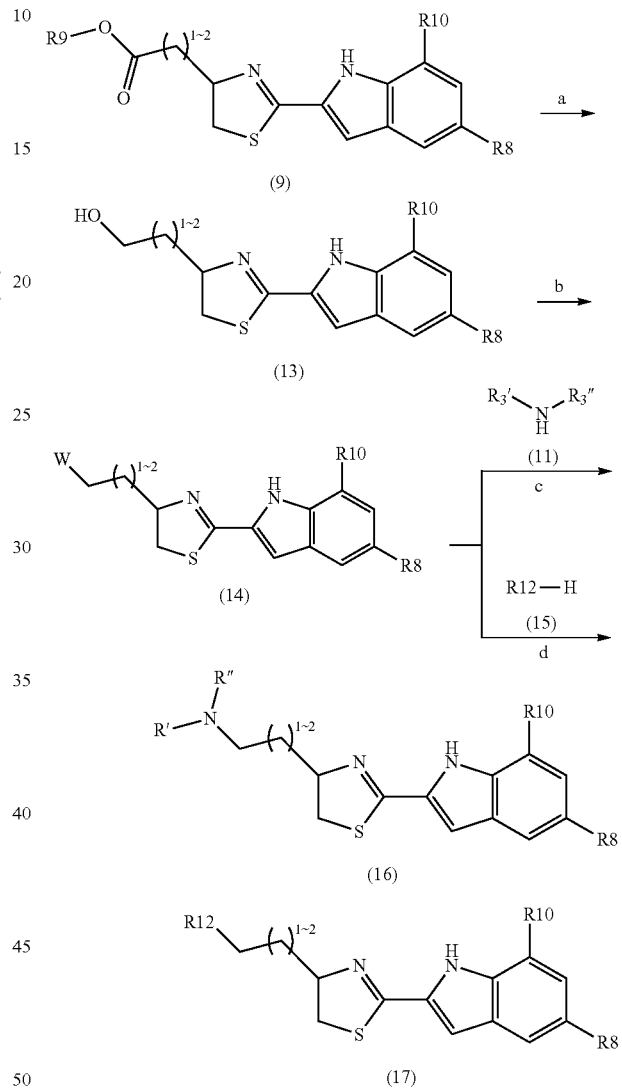

Reaction Scheme 3 in the above Reaction Scheme (3), a represents a reducing agent (for example, $NaBH_4$, $LiAlH_4$), b represents $I_2$ or MsCl, etc., c represents a base and the Compound (11), d represents a base and Compound (15), R8 is as defined in Reaction Scheme (1), R9 represents $C_1$-$C_6$-alkyl, R10 represents $NO_2$ or R1-X, wherein X and R1 are as defined in formula (1), R12 represents $C_1$-$C_6$-alkoxy, cyano or 5~6 membered heteroaryl, R' and R" are as defined in the Reaction Scheme (2), and W represents a leaving group, for example, halides such as chloride, bromide, iodide, etc., or sulfonates such as methane sulfonate, p-toluene sulfonate, etc.

Compound (13) can be prepared by converting the ester group of Compound (9) to an alcohol group. The reducing agent that can be used to reduce the ester group to the alcohol group includes, for example, sodium borohydride, lithium borohydride, borane, lithium aluminum hydride, diisobutyl aluminum hydride (DIBAL-H), etc. The reducing agent is typically used in the amount of 1~10 eq., preferably 1~3 eq., with respect to 1 eq. of the Compound (9). The reaction may be carried out in an inert solvent selected, for example, from alcohols such as methanol, ethanol, etc., ethers such as tetrahydrofuran, diethylether, etc., preferably tetrahydrofuran, diethylether, etc. The reaction temperature is typically in the range of −78~100° C., preferably −78~50° C., and the reaction time is typically in the range of 10 min~60 h, preferably 10 min~12 h.

Compound (14) can be prepared by converting the alcohol group of the Compound (13) to a leaving group W. The leaving group W can be introduced via halogenation or sulfonation reaction. The halogenation reaction may be carried out using a halogenating agent selected from iodine, bromine, N-iodosuccimide (NIS), N-bromosuccimide (NBS), carbon tetrachloride ($CCl_4$), carbon tetrabromide ($CBr_4$), etc. in the presence of a base such as imidazole, dimethylaminopyridine (DMAP), etc. and phosphines such as triphenylphosphine ($Ph_3P$), tributylphosphine ($Bu_3P$), etc. Each of the halogenating agent, base and phosphine is typically used in the amount of 1~10 eq., preferably 1~3 eq., with respect to 1 eq. of the Compound (13). This reaction may be carried out in an inert solvent selected, for example, from ethers such as tetrahydrofuran, diethylether, etc. and dichloromethane, chloroform, etc. The reaction temperature is typically in the range of −10~200° C., preferably 0~50° C., and the reaction time is typically in the range of 10 min~60 h, preferably 10 min~12 h.

The sulfonation reaction may be carried out using a sulfonating agent selected from methanesulfonyl chloride, p-toluenesulfonyl chloride, etc. in the presence of an organic base such as pyridine, triethylamine, etc. Each of the sulfonating agent and base is typically used in the amount of 1~10 eq., preferably 1~5 eq., with respect to 1 eq. of the Compound (13). This reaction may be carried out in an inert solvent selected, for example, from ethers such as tetrahydrofuran, diethylether, etc., chloroalkanes such as dichloromethane, dichloroethane, chloroform, etc., preferably dichloromethane, dichloroethane, etc. The reaction temperature is typically in the range of −10~200° C., preferably 0~50° C., and the reaction time is typically in the range of 10 min~60 h, preferably 10 min~12 h.

Compound (16) can be prepared by a coupling reaction of the Compound (11) with the Compound (14) using a base. As the base, for example, inorganic bases such as sodium carbonate, potassium carbonate, cesium carbonate, etc., organic bases such as triethylamine, diisopropylethylamine, 1,8-diazabicyclo[5,4,0]undeca-7-ene (DBU), etc. can be mentioned. The base is typically used in the amount of 1~10 eq., preferably 1~5 eq., with respect to 1 eq. of the Compound (14). This reaction may be carried out in an inert solvent selected, for example, from ethers such as tetrahydrofuran, diethylether, etc., alkyl nitriles such as acetonitrile, propionitrile, etc., amides such as N,N-dimethylformamide, etc., preferably tetrahydrofuran, acetonitrile, N,N-dimethylformamide, etc. The reaction temperature is typically in the range of −10~200° C., preferably 25~120° C., and the reaction time is typically in the range of 10 min~60 h, preferably 10 min~12 h.

Compound (17) can be prepared via a coupling reaction of the Compound (14) with the Compound (15) according to the preparing process of the Compound (16).

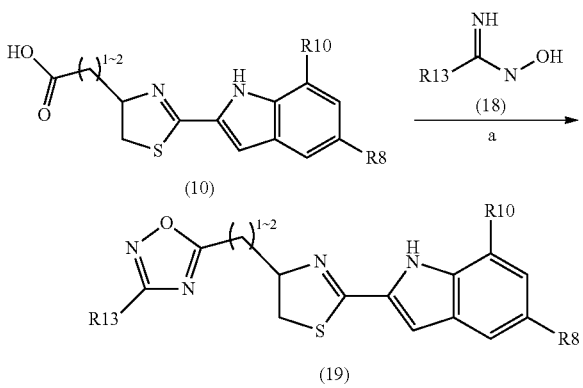

Reaction Scheme 4 in the above Reaction Scheme (4), a represents a coupling agent (for example, EDC, CDI, BOP—Cl) and Compound (18), R8 is as defined in the Reaction Scheme (1), R10 represents $NO_2$ or R1-X, wherein X and R1 are as defined in formula (1), and R13 represents $C_3$-$C_6$-cycloalkyl or piperidinyl.

Compound (18) can be prepared according to a method known in Heterocycles, 60(10), 2087, 2003 or Bioorganic & Medicinal Chemistry Letters, 11(24), 3164, 2001.

Compound (19) can be prepared via a coupling reaction of the Compound (10) with the Compound (18). As the coupling agent, dicyclohexylcarbodiimide (DCC), 1-(3-dimethylaminopropyl)-3-ethylcarbodiimide (EDC), 1,1'-dicarbonyldiimidazole (CDI), etc. can be used, but not limited thereto. The coupling agent is typically used in the amount of 1~10 eq., preferably 1~3 eq., with respect to 1 eq. of the Compound (10). This reaction may be carried out in an inert solvent selected from tetrahydrofuran, diethylether, N,N-dimethylformamide, etc. The reaction temperature is typically in the range of −10~200° C., preferably 25~120° C., and the reaction time is typically in the range of 10 min~60 h, preferably 10 min~12 h.

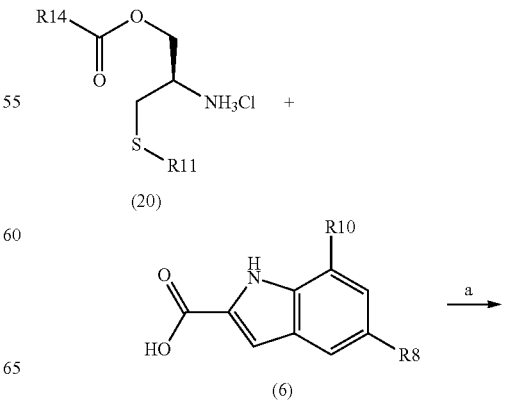

Reaction Scheme 5

Reaction Scheme 6

Compound (24) can be prepared using the Compound (23) according to the preparing process of the Compound (14) in the Reaction Scheme (3).

Compound (25) can be prepared using the Compound (24) according to the preparing process of the Compound (16) in the Reaction Scheme (3).

in the above Reaction Scheme (5), a represents a coupling agent (for example, EDC, CDI, BOP—Cl), b represents $PCl_5$ or $Tf_2O$ and $Ph_3PO$, c represents a metal hydroxide (for example, NaOH, LiOH), d represents $I_2$ or MsCl, etc., e represents a base and the Compound (11), R8 is as defined in the Reaction Scheme (1), R10 represents $NO_2$ or R1-X, wherein X and R1 are as defined in formula (1), R11 represents p-MeOBn or $Ph_3C$, R14 represents $C_1$-$C_6$-alkyl, R' and R" are as defined in the Reaction Scheme (2), and W represents a leaving group, for example, halides such as chloride, bromide, iodide, etc., or sulfonates such as methane sulfonate, p-toluene sulfonate, etc.

Compound (20) can be prepared according to the Reaction Scheme (11).

Compound (21) can be prepared using the Compounds (6) and (20) according to the preparing process of the Compound (8) in the Reaction Scheme (2).

Compound (22) can be prepared using the Compound (21) according to the preparing process of the Compound (9) in the Reaction Scheme (2).

Compound (23) can be prepared using the Compound (22) according to the preparing process of the Compound (6) in the Reaction Scheme (2).

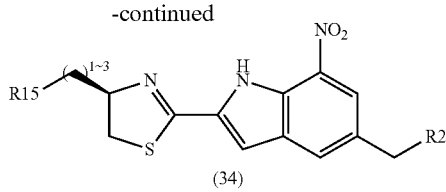

in the above Reaction Scheme (6), a represents di-t-butyloxy-dicarbonyl (Boc$_2$O), a base (for example, NaOH, K$_2$CO$_3$), b represents a brominating agent (for example, N-bromosuccinimide (NBS)), c represents sodium acetate (NaOAc), d represents an acid (for example, hydrochloric acid, trifluoroacetic acid), e represents a metal hydroxide (for example, NaOH, LiOH), f represents a coupling agent (for example, EDC, CDI, BOP—Cl) and Compound (33), g represents PCl$_5$, h represents a base and the Compound (33), R2 is as defined in formula (1), R9 represents C$_1$-C$_6$-alkyl, R11 represents p-MeOBn, and R15 represents C$_1$-C$_6$-alkoxycarbonyl or C$_1$-C$_6$-alkylcarbonyloxy.

Compound (26) can be prepared according to Reaction Scheme (9).

Compound (27) can be prepared by protecting the amine group of the Compound (26) using Boc$_2$O in the presence of a base, and converting the methyl group to bromomethyl group using a brominating agent, in the order.

Boc$_2$O used in the protection reaction of amine group is typically used in the amount of 1~10 eq., preferably 1~3 eq., with respect to 1 eq. of the Compound (26). The base is typically used in the amount of 1~10 eq., preferably 1~3 eq., with respect to 1 eq. of the Compound (26). A catalyst may be used for facilitating the reaction. The catalyst used is dimethylaminopyridine (DMAP), and typically used in the amount of 0.01~2 eq., preferably 0.1~0.3 eq., with respect to 1 eq. of the Compound (26). This reaction may be carried out in an inert solvent selected from tetrahydrofuran, diethylether, N,N-dimethylformamide, dichloromethane, etc. The reaction temperature is typically in the range of –10~200° C., preferably 25~120° C., and the reaction time is typically in the range of 10 min~60 h, preferably 10 min~12 h.

The brominating agent used in the bromomethylation reaction includes N-bromosuccinimide (NBS) and 1,3-dibromo-5,5-dimethylhydantoin, and is typically used in the amount of 1~10 eq., preferably 1~3 eq., with respect to 1 eq. of the Compound (26). A catalyst may be used for facilitating the reaction. The catalyst used is 2,2'-azidobis(2-methylpropionitrile) (AIBN) or benzoyl peroxide, and typically used in the amount of 0.001~2 eq., preferably 0.01~0.3 eq., with respect to 1 eq. of the Compound (26). This reaction may be carried out in an inert solvent selected from benzene, toluene, carbon tetrachloride, etc. The reaction temperature is typically in the range of –10~200° C., preferably 25~120° C., and the reaction time is typically in the range of 10 min~60 h, preferably 10 min~12 h.

Compound (28) can be prepared by reacting sodium acetate (NaOAc) with the Compound (27). Sodium acetate is typically used in the amount of 1~10 eq., preferably 1~5 eq., with respect to 1 eq. of the Compound (27). This reaction may be carried out in an inert solvent, for example, selected from ethers such as tetrahydrofuran, diethylether, etc., alkyl nitriles such as acetonitrile, propionitrile, etc., amides such as N,N-dimethylformamide, etc. The reaction temperature is typically in the range of –10~200° C., preferably 25~120° C., and the reaction time is typically in the range of 10 min~60 h, preferably 10 min~12 h.

Compound (29) can be prepared by removing the BOC group using an acid, and hydrolysis reaction using a base, in the order. The acid used in the removal of BOC group is hydrochloric acid, trifluoroacetic acid, etc. The acid is typically used in the amount of 1~10 eq., preferably 2~5 eq., with respect to 1 eq. of the Compound (28). This reaction may be carried out in an inert solvent, for example, selected from ethers such as tetrahydrofuran, diethylether, dioxane, etc., alkyl alcohols such as methanol, ethanol, etc., chloroalkanes such as dichloromethane, chloroform, etc. The reaction temperature is typically in the range of –10~200° C., preferably 25~120° C., and the reaction time is typically in the range of 10 min~60 h, preferably 10 min~12 h.

The base used in the hydrolysis reaction includes lithium hydroxide, sodium hydroxide, potassium hydroxide, etc. The base is typically used in the amount of 2~20 eq., preferably 2~10 eq., with respect to 1 eq. of the Compound (28). This hydrolysis reaction may be carried out in an inert solvent, for example, selected from alkyl alcohols such as methanol, ethanol, etc., ethers such as tetrahydrofuran, diethylether, etc. The reaction temperature is typically in the range of –10~200° C., preferably 25~120° C., and the reaction time is typically in the range of 10 min~60 h, preferably 10 min~12 h.

Compound (30) can be prepared according to Reaction Schemes (10) and (11).

Compound (31) can be prepared via a coupling reaction of the Compound (29) with the Compound (30) according to the preparing process of the Compound (8) in the Reaction Scheme (2).

Compound (32) can be prepared by reacting PCl$_5$ with the Compound (31). In this reaction of using PCl$_5$, cyclization and chlorination of the alcohol group occur simultaneously. PCl$_5$ is typically used in the amount of 1~10 eq., preferably 1~3 eq., with respect to 1 eq. of the Compound (31). This reaction may be carried out in a solvent selected from dichloromethane, chloroform, etc. The reaction temperature is typically in the range of –10~200° C., preferably 0~50° C., and the reaction time is typically in the range of 10 min~60 h, preferably 10 min~12 h.

Compound (33) is commercially available.

Compound (34) can be prepared via a coupling reaction of the Compound (32) with the Compound (33) according to the preparing process of the Compound (16).

Reaction Scheme 7

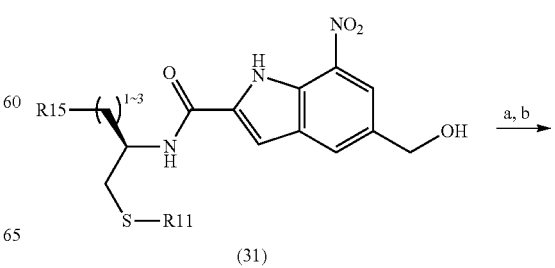

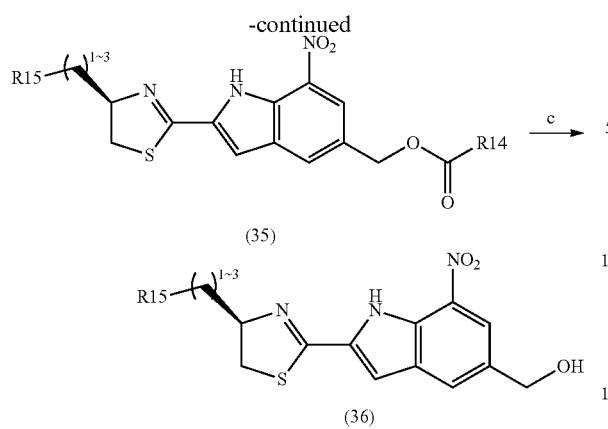

in the above Reaction Scheme (7), a represents an acylating agent [for example, R11-CO—Cl, (R11-CO)$_2$O], b represents PCl$_5$, c represents a metal hydroxide (for example, NaOH, LiOH), R11 represents p-MeOBn, R14 represents C$_1$-C$_6$-alkyl, and R15 represents C$_1$-C$_6$-alkoxycarbonyl or C$_1$-C$_6$-alkylcarbonyloxy.

Compound (35) can be prepared by protecting the alcohol group of the Compound (31) with an acyl group, and cyclizing using PCl$_5$. The protection reaction of the alcohol group is carried out using a base and an acylating agent. The base used includes organic bases such as triethylamine, diisopropylethylamine, pyridine, etc. The base is typically used in the amount of 1~10 eq., preferably 1~5 eq., with respect to 1 eq. of the Compound (31). The acylating agent used is a compound in the form of R14-CO—Cl or (R14-CO)$_2$O (R14=C$_1$~C$_6$-alkyl). The acylating agent is typically used in the amount of 1~10 eq., preferably 1~3 eq., with respect to 1 eq. of the Compound (31). This reaction may be carried out in a solvent selected from dichloromethane, chloroform, dichloroethane, etc. The reaction temperature is typically in the range of −10~200° C., preferably 0~50° C., and the reaction time is typically in the range of 10 min~60 h, preferably 10 min~12 h.

The cyclization reaction uses PCl$_5$. PCl$_5$ is typically used in the amount of 1~10 eq., preferably 2~5 eq., with respect to 1 eq. of the Compound (31). This reaction may be carried out in a solvent selected from dichloromethane, chloroform, etc. The reaction temperature is typically in the range of −10~200° C., preferably 0~50° C., and the reaction time is typically in the range of 10 min~60 h, preferably 10 min~12 h.

Compound (36) can be prepared via a deprotection reaction of the hydroxyl group of the Compound (35) using a base. The base used in the deprotection reaction includes lithium hydroxide, sodium hydroxide, potassium hydroxide, etc. The base is typically used in the amount of 1~10 eq., preferably 1~5 eq., with respect to 1 eq. of the Compound (35). This reaction may be carried out in an inert solvent, for example, selected from water, alkyl alcohols such as methanol, ethanol, etc., ethers such as tetrahydrofuran, diethylether, etc. The reaction temperature is typically in the range of −10~200° C., preferably 25~120° C., and the reaction time is typically in the range of 10 min~60 h, preferably 10 min~12 h.

Reaction Scheme 8

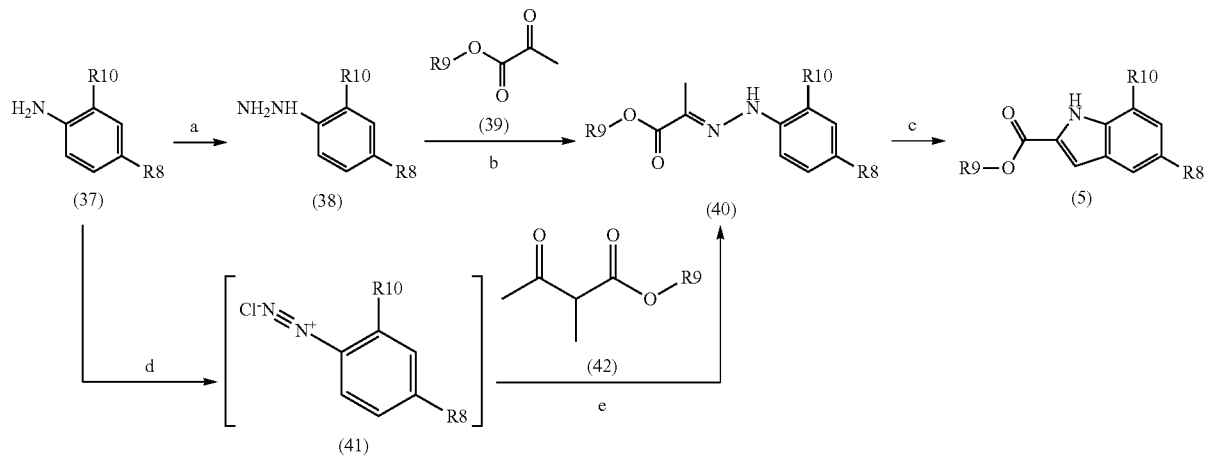

in the above Reaction Scheme (8), a represents sodium nitrite (NaNO$_2$); tin chloride (SnCl$_2$), b represents a ketone compound (39), a base (for example, NaOAc), c represents an acid (for example, polyphosphoric acid PPA), d represents NaNO$_2$, e represents Compound (42), a base (for example, NaOH), R8 is as defined in the Reaction Scheme (1), and R9 and R10 are as defined in the Reaction Scheme (2).

Compound (37) is commercially available, or can be prepared by a method known in Heterocycles, 68(11), 2285~99, 2006, or Bioorganic & Medicinal Chemistry Letters, 14(19), 4903~4906, 2004.

Compound (38) is commercially available, or can be prepared by converting the amine group of the Compound (37) to hydrazine group according to a method known in Journal of the American Chemical Society, 198(48), 15374~75, 2006.

Alternatively, the hydrazine Compound (38) can be prepared by reacting the amine group of the Compound (37) with NaNO$_2$ in the presence of hydrochloric acid to give a diazonium salt (41), which is not separated and reduced by using SnCl$_2$. NaNO$_2$ is typically used in the amount of 1~10 eq., preferably 2~5 eq., with respect to 1 eq. of the Compound (37). SnCl$_2$ is typically used in the amount of 1~10 eq., preferably 2~5 eq., with respect to 1 eq. of the Compound (37). This reaction is carried out in 1~12N, preferably 4~8N, aqueous hydrochloric acid solution. The reaction temperature is in the range of −10~50° C., and the reaction time is typically in the range of 10 min~60 h, preferably 10 min~6 h.

Compound (39) is commercially available.

Hydrazone Compound (40) can be prepared via a coupling reaction of the Compound (38) with the ketone Compound (39). A base is not used when the Compound (38) is in neutral form, but should be used when the Compound (38) is in the form of an acid salt to make the neutral form. As the base, for example, metal hydroxides such as sodium hydroxide, lithium hydroxide, etc., metal carbonates such as sodium bicarbonate, potassium carbonate, etc., metal acetates such as sodium acetate, etc., organic bases such as triethylamine, pyridine, etc., preferably sodium acetate, sodium bicarbonate, etc. can be used. The base is typically used in the amount of 1~5 eq., preferably 1~2 eq., with respect to 1 eq. of the Compound (38). This reaction may be carried out in an inert solvent selected from tetrahydrofuran, methanol, ethanol, etc. The reaction temperature is in the range of −10~100° C., and the reaction time is typically in the range of 10 min~60 h, preferably 10 min~12 h.

The Compound (40) can also be prepared by reacting the diazonium salt (41) with the Compound (42) in the presence of a base according to Japp-Klingemann rearrangement method described in Organic Process Research & Development, 2, 1988, 214~220. Hydrochloric acid is used in the preparation of the diazonium salt (41) typically in the amount of 1~10 eq., preferably 2~4 eq., with respect to 1 eq. of the Compound (37). The base used in the reaction of the Compounds (41) and (42) is sodium hydroxide, which is typically used in the amount of 1~20 eq., preferably 1~10 eq., with respect to 1 eq. of the Compound (42). 80% aqueous ethanol solution is used as the solvent, and the reaction temperature is in the range of −10~50° C. The reaction time is typically in the range of 10 min~60 h, preferably 10 min~12 h.

Compound (5) can be prepared using an acid catalyst and the Compound (40). The acid used in the synthesis is polyphosphoric acid, hydrochloric acid, p-toluenesulfonic acid, sulfuric acid, acetic acid, etc., preferably polyphosphoric acid. Polyphosphoric acid can be used alone, or as a mixture with aromatic hydrocarbons such as benzene, toluene, etc. The reaction temperature is in the range of 25~150° C., and the reaction time is typically in the range of 5 min~60 h, preferably 5 min~12 h.

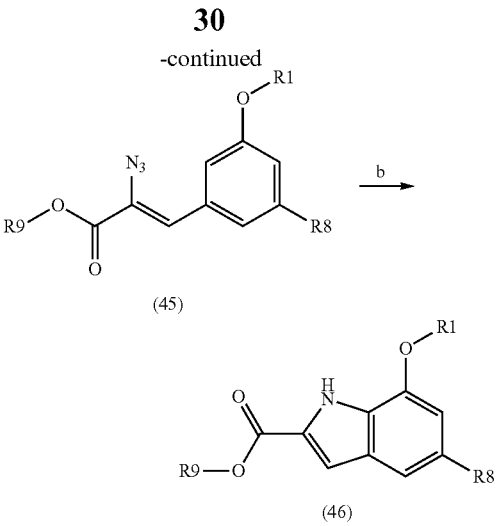

in the above Reaction Scheme (9), a represents a sodium alkoxide (for example, sodium methoxide), b represents heat, R1 is as defined in formula (1), R8 is as defined in the Reaction Scheme (1), and R9 represents $C_1$-$C_6$-alkyl.

Compound (43) is commercially available.

Compound (44) can be prepared by a method known in Journal of Medicinal Chemistry, 31(11), 2145, 1988.

Compound (45) is commercially available, or can be prepared by a method known in WO 2007040289, WO200601079 or Organic Letters 9(3), 397~400, 2007.

Alternatively, the Compound (45) can be prepared via a coupling reaction of the Compound (43) with the Compound (44) in the presence of a base. The base used is sodium methoxide, sodium ethoxide, etc. The base is typically used in the amount of 1~10 eq., preferably 1~3 eq., with respect to 1 eq. of the Compound (43). This reaction may be carried out in an inert solvent, for example, selected from alkyl alcohols such as methanol, ethanol, etc., ethers such as tetrahydrofuran, diethylether, etc. The reaction temperature is typically in the range of −10~200° C., preferably −10~25° C., and the reaction time is typically in the range of 10 min~60 h, preferably 10 min~12 h.

Compound (46) can be prepared by cyclizing the Compound (45). The cyclization reaction may be carried out by dissolving the Compound (45) in an inert solvent, and heating the solution. The inert solvent that can be used includes tetrahydrofuran, benzene, toluene, etc. The reaction temperature is typically in the range of 25~200° C., preferably 50~120° C., and the reaction time is typically in the range of 10 min~60 h, preferably 10 min~12 h.

Reaction Scheme 9

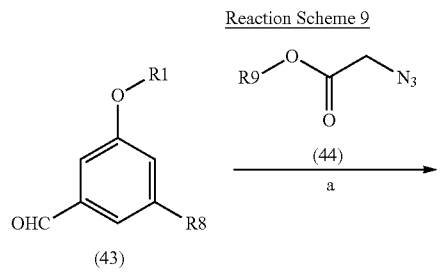

Reaction Scheme 10

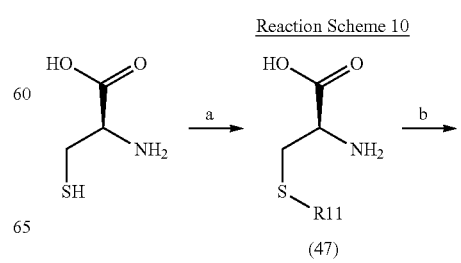

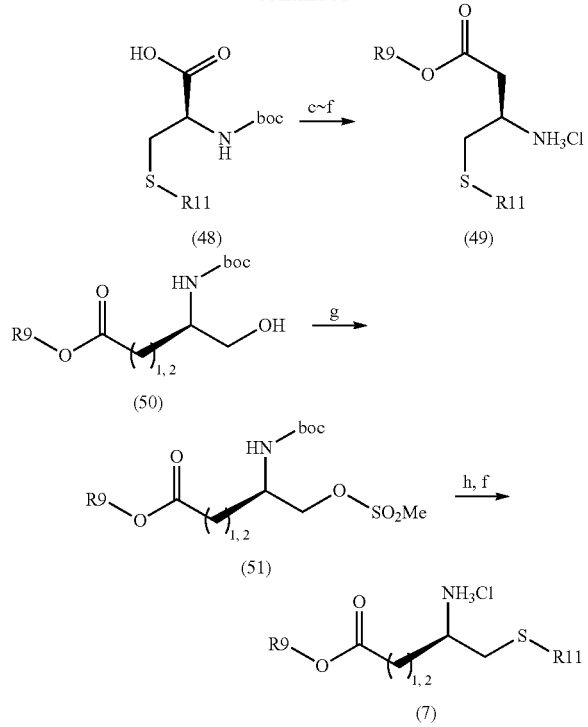

in the above Reaction Scheme (10), a represents p-methoxybenzylchloride (PMBCl) or triphenylmethyl-chloride (TrCl), a base (for example, NaOH), b represents di-t-butyloxy-dicarbonyl ($Boc_2O$), a base (for example, NaOH, $K_2CO_3$), c represents an alkylchloroformate (for example, EtOCOCl), a base (for example, N-methylmorpholine), d represents diazomethane ($CH_2N_2$), a base (for example, KOH), e represents a silver ion (for example, silver benzoate), f represents an acid, g represents MsCl, $Et_3N$, h represents p-methoxybenzylthiol (PMBSH), NaH, R9 represents $C_1$-$C_6$-alkyl, and R11 represents p-MeOBn or $Ph_3C$.

Compound (47) can be prepared by protecting the thiol group of cysteine using p-methoxybenzyl chloride (PMBCl) or triphenylmethyl chloride (TrCl) in the presence of a base.

PMBCl or TrCl used in the protection reaction of the thiol group is typically used in the amount of 1~5 eq., preferably 1~2 eq., with respect to 1 eq. of cysteine. The base used is sodium hydroxide, potassium carbonate, etc., and is typically used in the amount of 1~5 eq, preferably 1~2 eq., with respect to 1 eq. of cysteine. This reaction may be carried out in an inert solvent selected from tetrahydrofuran, methanol, ethanol, water, etc. The reaction temperature is typically in the range of –10~200° C., preferably 0~50° C., and the reaction time is typically in the range of 10 min~60 h, preferably 10 min~12 h.

Compound (48) can be prepared by protecting the amine group of the Compound (47) using BOC group.

$Boc_2O$ used in the protection reaction of the amine group is typically used in the amount of 1~5 eq., preferably 1~2 eq., with respect to 1 eq. of cysteine. The base used is selected, for example, from hydroxides such as sodium hydroxide, lithium hydroxide, etc., carbonates such as sodium carbonate, sodium bicarbonate, potassium carbonate, cesium carbonate, etc., organic bases such as diisopropylethylamine, triethylamine, etc., preferably potassium carbonate, triethylamine, etc. This reaction may be carried out in an inert solvent selected from tetrahydrofuran, methanol, ethanol, water, etc. The reaction temperature is typically in the range of –10~200° C., preferably 0~50° C., and the reaction time is typically in the range of 10 min~60 h, preferably 10 min~12 h.

Compound (49) can be prepared by a method known in Helvetica Chimica Acta, 87, 2004, 3131~3159.

1 Eq. of the Compound (48) is reacted with 1~2 eq. of ethylchloroformate (EtOCOCl) or isobutylchloroformate ($^iBuOCOCl$) in tetrahydrofuran solvent maintained at room temperature in the presence of 1~2 eq. of a base {for example, N-methylmorpholine (NMM), triethylamine, etc.} to give an anhydride compound. The resulting anhydride compound is reacted with 1~5 eq. of diazomethane and 1~5 eq. of aqueous potassium hydroxide solution in diethylether solvent maintained at 0° C., and then reacted with 0.1~2 eq. of an Ag ion (for example, silver trifluoroacetate ($CF_3CO_2Ag$), silver benzoate, etc.) and 1~10 eq. of an alkyl alcohol (for example, methanol, ethanol, etc.) under the dark condition at room temperature to give an alkyl ester.

The reaction for removing the BOC group can be made using an acid. The acid used includes hydrochloric acid, trifluoroacetic acid, etc. The acid is typically used in the amount of 1~10 eq., preferably 2~5 eq., with respect to 1 eq. of the Compound (48). This reaction may be carried out in an inert solvent, for example, selected from ethers such as tetrahydrofuran, diethylether, dioxane, etc., alkyl alcohols such as methanol, ethanol, etc., chloroalkanes such as dichloromethane, chloroform, etc. The reaction temperature is typically in the range of –10~200° C., preferably 25~120° C., and the reaction time is typically in the range of 10 min~60 h, preferably 10 min~12 h.

Compound (50) can be prepared from glutamic acid or aspartic acid by a method known in Synlett, 15, 2005, 2397~2399, Journal of Organic Chemistry, 66(5), 2001, 1919~1923, etc.

Compound (51) can be prepared by sulfonating the Compound (50). The sulfonation reaction may be carried out using methanesulfonyl chloride in the presence of an organic base such as pyridine, triethylamine, etc. The sulfonylating agent and base each are used in the amount of 1~10 eq., preferably 1~5 eq., with respect to 1 eq. of the Compound (50). This reaction may be carried out in an inert solvent selected from dichloromethane, dichloroethane, etc. The reaction temperature is typically in the range of –10~200° C., preferably 0~50° C., and the reaction time is typically in the range of 10 min~60 h, preferably 10 min~12 h.

The Compound (7) can be prepared by reacting p-methoxybenzylthiol (PMBSH) with the Compound (51) in the presence of a base, and removing the BOC group using an acid. The base used is sodium hydride, potassium carbonate, cesium carbonate, etc., preferably sodium hydride. The base is typically used in the amount of 1~10 eq., preferably 2~5 eq., with respect to 1 eq. of the Compound (51). p-Methoxybenzylthiol (PMBSH) is typically used in the amount of 1~10 eq., preferably 2~5 eq., with respect to 1 eq. of the Compound (51). This reaction may be carried out in an inert solvent selected from tetrahydrofuran, dimethylformamide, N-methylpyrrolidinone, etc. The reaction temperature is typically in the range of –10~200° C., preferably 25~100° C., and the reaction time is typically in the range of 10 min~60 h, preferably 10 min~12 h.

The reaction for removing BOC group may be carried out in the same manner as the removal of BOC group explained in the preparing process of the Compound (49).

Reaction Scheme 11

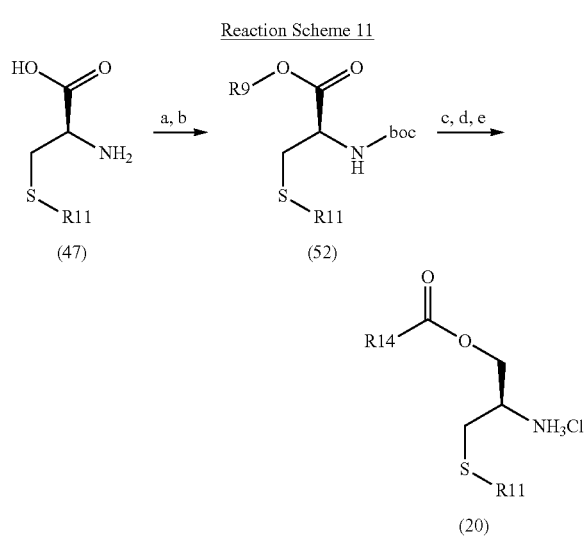

in the above Reaction Scheme (11), a represents an alkyl alcohol (for example, methanol, ethanol), acetyl chloride or thionyl chloride, b represents di-t-butyloxy-dicarbonyl ($Boc_2O$), a base (for example, NaOH, $K_2CO_3$), c represents a reducing agent (for example, $NaBH_4$), d represents an alkylcarbonyl chloride (for example, t-butylcarbonyl chloride ($^tBuCOCl$)), a base (for example, $Et_3N$), e represents an acid, R9 represents $C_1$-$C_6$-alkyl, R11 represents p-MeOBn or $Ph_3C$, and R14 represents $C_1$-$C_6$-alkyl.

Compound (52) can be prepared by esterifying the carboxylic group of the Compound (47), and protecting the amine group with BOC group. The esterification reaction may be carried out using acetyl chloride or thionyl chloride in an alkyl alcohol solvent. Acetyl chloride or thionyl chloride is used in the amount of 1~10 eq., preferably 1~5 eq., with respect to 1 eq. of the Compound (47). The reaction temperature is typically in the range of 25~200° C., preferably 25~100° C., and the reaction time is typically in the range of 10 min~60 h, preferably 10 min~12 h.

The protection reaction of the amine group may be carried out in the same manner as the preparing process of the Compound (48).

The Compound (20) can be prepared from the starting Compound (52) via reduction of the ester group, protection of the alcohol group, and removal of BOC, in the order. The reduction reaction of the ester group may be carried out by reacting with an alkylchloroformate (for example, ethylchloroformate, isobutylchloroformate) in tetrahydrofuran solvent of room temperature in the presence of 1~5 eq. of a base (for example, triethylamine, diisopropylethylamine, N-methylmorpholine, etc.) to give an anhydride, which is then reacted with 1~5 eq. of lithium borohydride or sodium borohydride in aqueous tetrahydrofuran solution of 0~25° C. for 10 min~12 h.

The protection reaction of the alcohol group may be carried out by reacting with an alkylcarbonylchloride, for example, t-BuCOCl, in dichloromethane solvent of 0~25° C. in the presence of 1~5 eq. of a base selected from triethylamine, pyridine, etc. for 10 min~12 h.

The reaction for removing BOC group may be carried out by dissolving the reactant in an inert solvent selected from tetrahydrofuran, dioxane, ethyl acetate, dichloromethane, etc. and reacting with 1~10 eq. of hydrochloric acid or trifluoroacetic acid at 0~50° C. for 10 min~12 h.

The compounds whose preparation methods are not specifically explained in the present specification are known per se, or can be prepared from a known compound according to a known process or a similar process thereto.

The compounds of formula (1) obtained by the above processes may be separated or purified from the reaction product by various methods such as recrystallization, ionophoresis, silica gel column chromatography, ion exchange chromatography, etc.

As explained above, the compounds according to the present invention, starting materials, intermediates, etc. for the preparation thereof may be obtained by various processes, and such processes for preparing the compounds of formula (1) should be construed to fall under the scope of the present invention.

[Effect]

The present invention further provides a pharmaceutical composition for the activation of glucokinase, which comprises the compounds of formula (1), pharmaceutically acceptable salts or isomers thereof as an active ingredient together with pharmaceutically acceptable carriers.

Diseases which are caused by the deactivation of glucokinase, and can be prevented or treated by the pharmaceutical composition of the present invention include, but not limited to, diabetes, complications of diabetes, obesity, etc. The pharmaceutical composition of the present invention can be used for the prevention or treatment of type 1 diabetes or type 2 diabetes, and is particularly preferable for type 2 diabetes. The complications of diabetes that can be prevented or treated by the pharmaceutical composition of the present invention include, but not limited to, hyperlipidemia, hypertension, retinosis, renal failure, etc.

The present invention further provides a hypoglycemic composition which comprises the compounds of formula (1), pharmaceutically acceptable salts or isomers thereof as an active ingredient together with pharmaceutically acceptable carriers.

The present invention further provides a process for preparing a pharmaceutical composition for the activation of glucokinase, more specifically, for the prevention or treatment of diabetes, complications of diabetes, or obesity, which comprises the step of mixing the compounds of formula (1), pharmaceutically acceptable salts or isomers thereof as an active ingredient together with pharmaceutically acceptable carriers.

The above-mentioned "pharmaceutical composition" or "hypoglycemic composition" may comprise pharmaceutically acceptable carriers, diluents, excipients, or their combinations, if needed, together with the compounds of the present invention. Pharmaceutical composition facilitates the administration of the compound into a living organism. There exist a number of techniques to administer the compound, and they include, but not limited to, oral, injectable, aerosol, parenteral and topical administration.

As used herein, "carrier" means a substance which facilitates the incorporation of the compound into the cells or tissues. For example, dimethylsulfoxide (DMSO) is a typical carrier which is used to facilitate the introduction of various organic compounds into the cells or tissues of living organisms.

As used herein, "diluent" is defined as a substance that is diluted in water which dissolves the compound, as well as stabilizes the biologically active form of the subject compound. The salts dissolved in buffer solution are utilized as diluents in the art. Typically used buffer solution is phosphate buffered saline which mimics the salt form of human solution. Buffer diluents rarely alter the biological activities of the compound, as the buffer salts can control the pH of solution at a low concentration.

As used herein, "pharmaceutically acceptable" means the property that does not impair the biological activities and physical properties of the compound.

The compounds of the present invention can be formulated as various pharmaceutical dosage forms according to the purpose. In preparing the pharmaceutical composition of the present invention, the active ingredient, specifically, the compounds of formula (1), pharmaceutically acceptable salts or isomers thereof are mixed together with various pharmaceutically acceptable carriers which can be selected according to the formulation to be prepared. For example, the pharmaceutical composition of the present invention can be formulated as injectable preparation, oral preparation, etc., according to the purpose.

The compounds of the present invention can be formulated by the methods known in the art, which utilize pharmaceutical carriers and excipients known in the art, and be incorporated into the containers of unit dose form or multi-dose form. The form of the preparation can be solutions, suspensions or emulsions in oily or aqueous media, and may contain typical dispersing agents, suspending agents or stabilizers. Further, for example, it can be a form of dry powder which is intended to be reconstituted by dissolving in sterile, pyrogen-free water prior to use. The compounds of the present invention also can be formulated into suppository forms utilizing typical suppository bases such as cocoa butter or other glycerides. As solid dosage forms for oral administration, capsules, tablets, pills, powder and granule can be prepared, and capsules and tablets are especially useful. Preferably, tablets and pills are prepared as enteric coated forms. Solid dosage forms can be prepared by mixing the compounds of the present invention together with carriers, for example, one or more inert diluents such as sucrose, lactose, starch, etc., lubricants such as magnesium stearate, disintegrant, binder, etc.

If needed, the compounds of the present invention or the pharmaceutical compositions containing the same can also be administered in combination with other active agents, for example, other agents for treating diabetes.

The dosage of the compounds of formula (1) depends on the prescription of a physician, taking into account such factors as body weight or age of a patient, specific nature of the disease, and severity of the disease, etc. However, dosage needed for the treatment of an adult is typically from about 1 to 500 mg per day, depending on the intensity and frequency of the administration. When administered to an adult via intramuscular or intravenous routes, total dosage typically from about 5 to 300 mg per day will be sufficient when separately administered in a single dosage, but for some patients a higher daily dosage may be desirable.

The present invention further provides a method for the prevention or treatment of diseases which are caused by the deactivation of glucokinase, using effective amount of the compounds of formula (1), pharmaceutically acceptable salts or isomers thereof as an active ingredient.

The present invention further provides a process for preparing a pharmaceutical composition for the prevention or treatment of diseases which are caused by the deactivation of glucokinase, which comprises the step of mixing the compounds of formula (1), pharmaceutically acceptable salts or isomers thereof as an active ingredient together with pharmaceutically acceptable carriers.

As used herein, "treatment" means the interrupting or delaying the progress of the disease when applied to the subject showing the onset of disease symptoms, and "prevention" means the interrupting or delaying the sign of the onset of disease when applied to the subject that does not show, but is at risk of, the onset of disease symptoms.

The present invention will be more specifically explained by the following preparations and examples. However, it should be understood that they are intended to illustrate the present invention but not in any manner to limit the scope of the present invention. In the following preparations and examples, M means molar concentration, and N means normal concentration.

BEST MODE FOR CARRYING OUT THE INVENTION

Preparation 1

Synthesis of 2-[(4-fluoro-2-nitro-phenyl)-hydrazono]-propionic acid ethyl ester

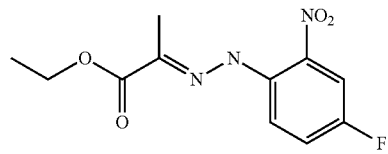

2-[(4-Fluoro-2-nitro-phenyl)-hydrazono]-propionic acid ethyl ester

4-Fluoro-2-nitroaniline (10 g, 64 mmol) was dissolved in 6N hydrochloric acid (64 ml, 0.27 mol), sodium nitrate (4.4 g, 64 mmol) dissolved in water (50 ml) was slowly added in drops thereto at 0° C., and the mixture was stirred for 30 min at 0° C.~room temperature. Simultaneously, ethyl 2-methylacetoacetate (9.2 ml, 64 mmol) and sodium hydroxide (19 g, 0.34 mol) were dissolved in 80% aqueous ethanol solution (95 ml), and stirred for 10 min at 0° C. The two solutions thus prepared were mixed, and stirred for 8 h at 0° C.~room temperature. Water was added to the reaction solution, and the insoluble solid was collected. The solid was washed with water, and dried to give the title compound (7.9 g, Yield 46%).

$^1$H-NMR (400 HMz, CDCl$_3$); δ 10.81 (br s, 1H), 8.05 (m, 1H), 7.90 (m, 1H), 7.41 (m, 1H), 4.36 (q, 2H), 2.22 (S, 3H), 1.38 (t, 3H)

Preparation 2

Synthesis of 5-fluoro-7-nitro-1H-indole-2-carboxylic acid ethyl ester

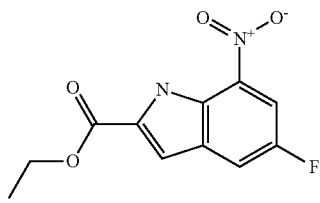

5-Fluoro-7-nitro-1H-indole-2-carboxylic acid ethyl ester

The compound (8.8 g, 33 mmol) prepared in Preparation 1 was mixed with polyphosphoric acid (50 ml), and stirred for 7 h at 60° C. Water was added to the reaction solution, and the insoluble solid was collected. The solid was washed with water, and dried to give the title compound (3.4 g, Yield 41%).

$^1$H-NMR (400 HMz, DMSO-d$_6$); δ 11.55 (br s, 1H), 8.16 (m, 1H), 8.10 (m, 1H), 7.42 (s, 1H), 4.40 (q, 2H), 1.36 (t, 3H)

Preparation 3

Synthesis of (4-chloro-2-nitro-phenyl)-hydrazine hydrochloride

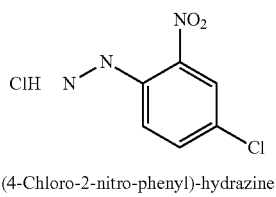

(4-Chloro-2-nitro-phenyl)-hydrazine

4-Chloro-2-nitroaniline (40 g, 0.23 mol) was dissolved in 12N hydrochloric acid (100 ml). At 0° C., sodium nitrate (16 g, 0.23 mol) dissolved in water (50 ml) was slowly added in drops thereto, and the mixture was stirred for 30 min at 0° C.~room temperature. The temperature was lowered to 0° C., and tin(II) chloride (132 g, 0.70 mol) dissolved in 12N hydrochloric acid (100 ml) was slowly added in drops thereto. The mixture was stirred for 3 h at 0° C.~room temperature. The resulting yellow solid was filtered, washed with a small quantity of 6N HCl, and dried to give the title compound (30 g, Yield 63%).

$^1$H-NMR (400 HMz, DMSO-$d_6$); δ 9.21 (s, 1H), 7.98 (d, J=2.4 Hz, 1H), 7.66 (d, J=9.6 Hz, 1H), 7.55 (dd, J=2.4, 9.6 Hz, 1H), 4.74 (br s, 2H)

Preparation 4

Synthesis of 2-[(4-chloro-2-nitro-phenyl)-hydrazono]-propionic acid methyl ester

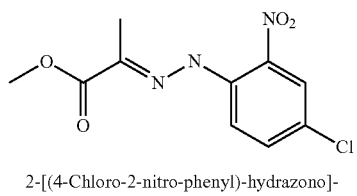

2-[(4-Chloro-2-nitro-phenyl)-hydrazono]-propionic acid methyl ester

The hydrazine (30 g, 0.14 mol) prepared in Preparation 3 and methyl pyruvate (14.4 ml, 0.16 mol) were dissolved in methanol (300 ml), and sodium acetate (14.2 g, 0.17 mol) was added thereto. The mixture was stirred for 8 h at room temperature. The resulting yellow solid was filtered, washed with water and methanol, and dried to give the title compound (30 g, Yield 82%).

$^1$H-NMR (400 HMz, CDCl$_3$); δ 10.88 (s, 1H), 8.21 (d, J=2.4 Hz, 1H), 8.01 (d, J=9.2 Hz, 1H), 7.56 (dd, J=2.4, 9.2 Hz, 1H), 3.90 (s, 3H), 2.23 (s, 3H).

Mass Spectrum (ESI, m/z): Calculated for $C_{10}H_{10}ClN_3O_4$ 271.04, Found 271.66

Preparation 5

Synthesis of 5-chloro-7-nitro-1H-indole-2-carboxylic acid methyl ester

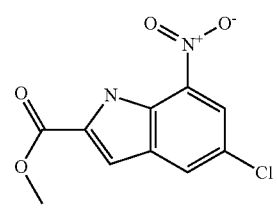

5-Chloro-7-nitro-1H-indole-2-carboxylic acid methyl ester

To the compound (13 g, 46 mmol) prepared in Preparation 4 was added polyphosphoric acid (100 ml), which was then heated at 100° C. for 4 h. After completion of the reaction, water was added to the reaction solution, and the insoluble solid was collected. The solid was washed with water, and dried to give the title compound (6.0 g, Yield 49%).

$^1$H-NMR (400 HMz, CDCl$_3$); δ 10.32 (br s, 1H), 8.29 (d, 1H), 8.03 (d, J=2.4 Hz, 1H), 7.31 (d, J=2.0 Hz, 1H), 4.01 (s, 3H)

Mass Spectrum (ESI, m/z): Calculated 254.01, Found 254.63

Preparation 6

Synthesis of 5-bromo-7-nitro-1H-indole-2-carboxylic acid methyl ester

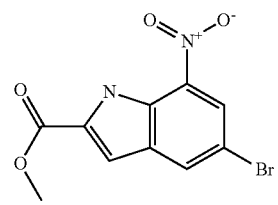

5-Bromo-7-nitro-1H-indole-2-carboxylic acid methyl ester

4-Bromo-2-nitroaniline (15.6 g, 71.9 mmol) was reacted according to the same procedures as Preparations 3 to 5 to give the title compound (7.2 g, Yield 73%).

¹H-NMR (400 HMz, CDCl₃); δ 10.33 (br s, 1H), 8.41 (s, 1H), 8.18 (s, 1H), 7.30 (d, J=4.0 Hz, 1H), 4.01 (s, 3H)

Preparation 7

Synthesis of 5-methyl-7-nitro-1H-indole-2-carboxylic acid methyl ester

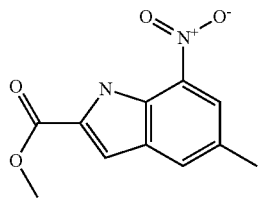

5-Methyl-7-nitro-1H-indole-2-carboxylic acid methyl ester

4-Methyl-2-nitroaniline (40 g, 0.26 mol) was reacted according to the same procedures as Preparations 3 to 5 to give the title compound (20 g, Yield 32%).
¹H-NMR (500 HMz, DMSO-d₆); δ 11.25 (br s, 1H), 8.08 (3, 1H), 7.96 (s, 1H), 7.32 (s, 1H), 3.87 (s, 3H), 2.44 (s, 3H)

Preparation 8

Synthesis of 7-nitro-1H-indole-2-carboxylic acid methyl ester

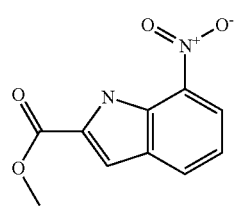

7-Nitro-1H-indole-2-carboxylic acid methyl ester

2-Nitroaniline (30 g, 0.21 mol) was reacted according to the same procedures as Preparations 3 to 5 to give the title compound (11 g, Yield 23%).
¹H-NMR (500 HMz, DMSO-d₆); δ 11.36 (br s, 1H), 8.23 (d, 1H), 8.17 (d, 1H), 7.42 (s, 1H), 7.32 (t, 1H), 3.88 (s, 3H)

Preparation 9

Synthesis of 5-methoxy-7-nitro-1H-indole-2-carboxylic acid methyl ester

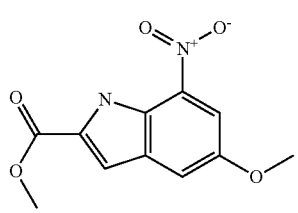

5-Methoxy-7-nitro-1H-indole-2-carboxylic acid methyl ester

4-Methoxy-2-nitrophenylamine (30 g, 0.18 mol) was reacted according to the same procedures as Preparations 3 to 5 to give the title compound (12 g, Yield 27%).

Preparation 10

Synthesis of 4-ethoxy-2-nitro-phenylamine

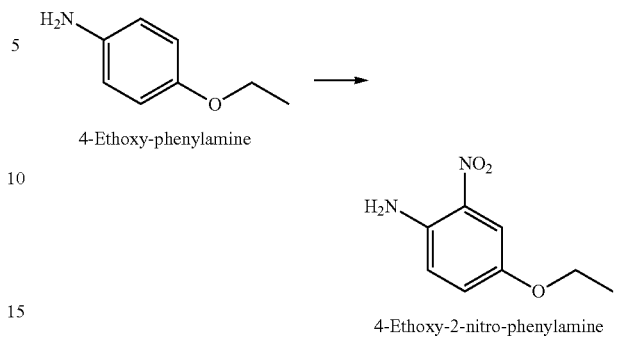

4-Ethoxyaniline (40 g, 0.29 mol) and triethylamine (61 ml, 0.44 mol) were dissolved in dichloromethane (200 ml). Acetic anhydride (30 ml, 0.32 mmol) was added in drops thereto, and the mixture was stirred for 1 h at 0° C.~room temperature. 1N hydrochloric acid solution was added thereto, and the mixture was extracted with ethyl acetate. The extract was washed with saturated sodium chloride solution, and dried over anhydrous magnesium sulfate.

The resulting acetamide compound was dissolved in dichloromethane (200 ml), and fuming nitric acid (13 ml, 0.29 mol) was added in drops thereto at 0° C. The mixture was stirred for 1 h at 0° C.~room temperature. Saturated aqueous sodium hydrogen carbonate solution was added, and the mixture was extracted with ethyl acetate. The extract was washed with saturated sodium chloride solution, and dried over anhydrous magnesium sulfate.

The resulting nitrate compound was dissolved in methanol (100 ml) and tetrahydrofuran (100 ml), and 6N sodium hydride was added in drops thereto. The mixture was stirred for 6 h at room temperature. After completion of the reaction, the reaction solution was neutralized to about pH 7 using 6N hydrochloric acid solution, and extracted with ethyl acetate. The extract was washed with saturated sodium chloride solution, and dried over anhydrous magnesium sulfate to give the title compound (44 g, Yield 83%).

Preparation 11

Synthesis of 5-ethoxy-7-nitro-1H-indole-2-carboxylic acid methyl ester

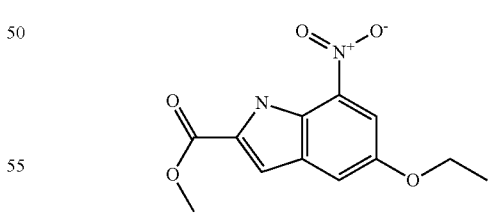

5-Ethoxy-7-nitro-1H-indole-2-carboxylic acid methyl ester

4-Ethoxy-2-nitroaniline (40 g, 0.22 mol) prepared in Preparation 10 was reacted according to the same procedures as Preparations 3 to 5 to give the title compound (13 g, Yield 22%).
¹H-NMR (400 HMz, DMSO-d₆); δ 10.20 (br s, 1H), 7.86 (s, 1H), 7.51 (s, 1H), 7.26 (s, 1H), 4.13 (m, 2H), 3.98 (s, 3H), 1.47 (m, 3H)

Preparation 12

Synthesis of 7-nitro-5-phenoxy-1H-indole-2-carboxylic acid methyl ester

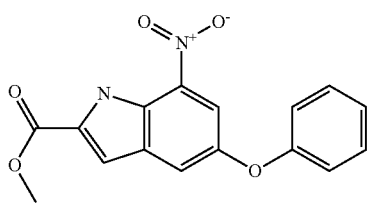

7-Nitro-5-phenoxy-1H-indole-2-carboxylic acid methyl ester

4-Aminophenyl phenyl ether (20 g, 0.11 mol) was reacted according to the same procedures as Preparation 10 and Preparations 3 to 5 in the order to give the title compound (5 g, Yield 15%).
$^1$H-NMR (400 HMz, CDCl$_3$); δ 10.26 (br s, 1H), 8.05 (s, 1H), 7.69 (s, 1H), 7.39 (m, 2H), 7.26 (s, 1H), 7.15 (m, 1H), 7.01 (m, 2H), 4.00 (s, 3H)

Preparation 13

Synthesis of 7-nitro-5-(pyridin-3-yloxy)-1H-indole-2-carboxylic acid ethyl ester

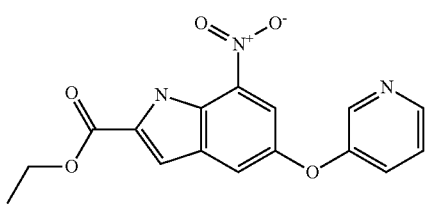

7-Nitro-5-(pyridin-3-yloxy)-1H-indole-2-carboxylic acid ethyl ester (Step 1)

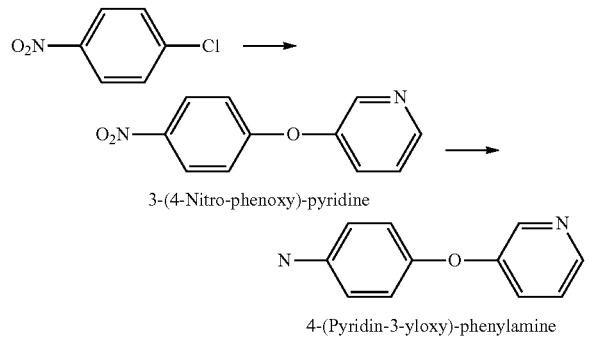

3-(4-Nitro-phenoxy)-pyridine 4-(Pyridin-3-yloxy)-phenylamine

1-Chloro-4-nitrobenzene (40 g, 0.25 mol) and 3-hydroxy-pyridine (36 g, 0.38 mol) were dissolved in N,N-dimethyl-formamide (100 ml). Potassium carbonate (52.6 g, 0.38 mol) was added thereto, and the mixture was stirred for 20 h at 100° C. Water was added to the reaction solution, which was then extracted with ethyl acetate. The extract was washed with saturated sodium chloride solution, and dried over anhydrous magnesium sulfate to give 3-(4-nitro-phenoxy)-pyridine.

The compound thus obtained was dissolved using water (100 ml), tetrahydrofuran (100 ml) and methanol (100 ml). Iron powder (103 g, 1.84 mol) and ammonium chloride (99 g, 1.84 mol) were added thereto, and the mixture was stirred using a mechanical stirrer for 3 h at 80° C. After completion of the reaction, the reaction solution was filtered through a celite, washed with methanol, and concentrated. The resulting solid was filtered, washed with ether, and dried to give 4-(pyridin-3-yloxy)-phenylamine (17 g, Yield 36%).

(Step 2)

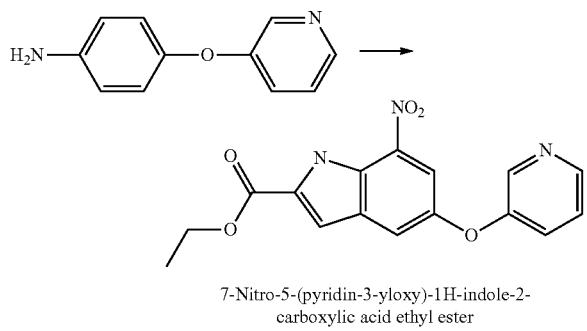

7-Nitro-5-(pyridin-3-yloxy)-1H-indole-2-carboxylic acid ethyl ester 4-(Pyridin-3-yloxy)-phenylamine (25 g, 0.13 mol) prepared in Step 1 was reacted according to the same procedures as Preparation 10 and Preparations 3 to 5 in the order to give the title compound (4.2 g, Yield 10%).
$^1$H-NMR (400 HMz, CDCl$_3$); δ 10.32 (br s, 1H), 8.51-8.47 (m, 2H), 8.05 (d, J=2.4 Hz, 1H), 7.73 (d, J=2.0 Hz, 1H), 7.42-7.35 (m, 2H), 7.31 (d, J=2.4 Hz, 1H), 4.48 (q, 2H), 1.47 (t, 3H)

Preparation 14

Synthesis of 5-(4-methanesulfonyl-phenoxy)-7-nitro-1H-indole-2-carboxylic acid methyl ester

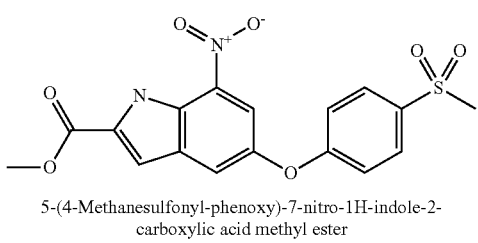

5-(4-Methanesulfonyl-phenoxy)-7-nitro-1H-indole-2-carboxylic acid methyl ester (Step 1)

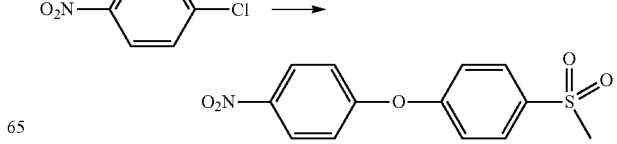

1-Chloro-4-nitrobenzene (15 g, 95 mmol) and 4-(methylmercapto)phenol (13.3 g, 95 mmol) were dissolved in dimethylsulfoxide (100 ml). Potassium carbonate (15.8 g, 134 mmol) was added thereto, and the mixture was stirred for 12 h at 100° C. After completion of the reaction, excess water was added to give precipitated solid. The solid was filtered, and dried to give 1-(4-methylsulfanylphenoxy)-4-nitrobenzene.

The compound thus obtained was dissolved in dichloromethane (500 ml). mCPBA (3-chloroperbenzoic acid) (83 g, 330 mmol) was added thereto, and the mixture was stirred for 2 h at 0° C.~room temperature. After completion of the reaction, excess 6N aqueous sodium hydroxide solution was added, and the mixture was extracted with ethyl acetate and dichloromethane. The extract was washed with saturated sodium chloride solution, and dried over anhydrous magnesium sulfate to give 1-(4-methylsulfonylphenoxy)-4-nitrobenzene (28 g, Yield 100%).

(Step 2)

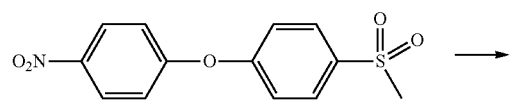

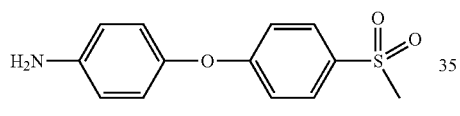

4-(4-Methanesulfonyl-phenoxy)-phenylamine 1-(4-Methylsulfonylphenoxy)-4-nitrobenzene (28 g) prepared in Step 1 was dissolved in methanol (500 ml) and ethyl acetate (500 ml). 10% Pd/C (1.0 g) was added thereto, and the mixture was stirred for 3 h under hydrogen gas of normal pressure. After completion of the reaction, the reaction solution was filtered through a celite, washed with methanol, concentrated, and dried to give 4-(4-methanesulfonylphenoxy)-phenylamine (25 g, Yield 100%).

(Step 3)

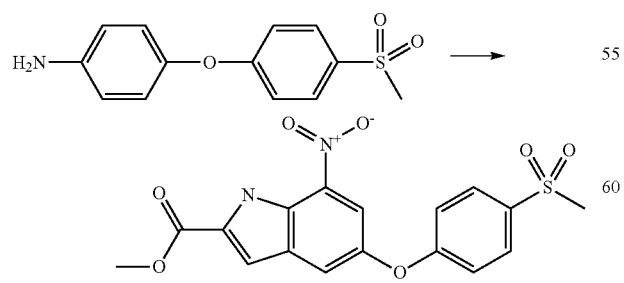

4-(4-Methanesulfonylphenoxy)-phenylamine (25 g, 95 mmol) was reacted according to the same procedures as Preparation 10 and Preparations 3 to 5 in the order to give the title compound (0.9 g, Yield 2.4%).

Preparation 15

Synthesis of (R)-3-amino-4-(4-methoxy-benzylsulfanyl)-butyric acid methyl ester hydrochloride

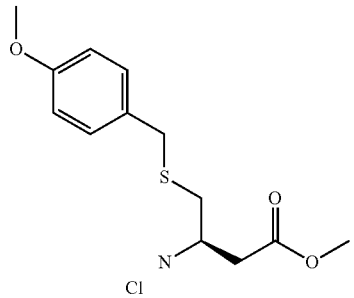

(R)-3-Amino-4-(4-methoxy-benzylsulfanyl)-butyric acid methyl ester (Step 1)

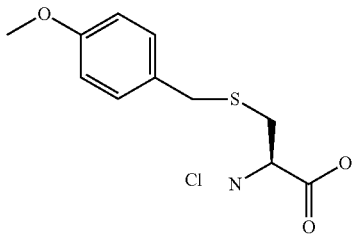

(R)-2-Amino-3-(4-methoxy-benzylsulfanyl)-propionic acid

To a solvent mixture of diethylether (400 ml) and conc. hydrochloric acid (400 ml) was added in drops 4-methoxy-benzylalcohol (280 g, 1780 mmol) dissolved in diethylether (400 ml) for 2 h, and the mixture was stirred for 1 h. The organic layer was separated, and added to a solution prepared by dissolving L-cysteine (197 g, 1625 mmol) and 2N aqueous sodium hydroxide solution (980 ml) in ethanol (1890 ml). The mixture was stirred for 2 h at room temperature. After completion of the reaction, the reaction solution was cooled to 0° C., and neutralized to pH 7 using 3N aqueous hydrochloric acid solution. The resulting solid was filtered, and dried to give (R)-2-amino-3-(4-methoxy-benzylsulfanyl)-propionic acid (250 g, 1035 mmol, Yield: 64%).

(Step 2)

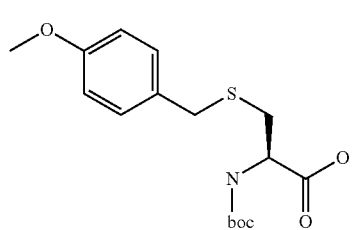

(R)-2-tert-Butoxycarbonylamino-3-(4-methoxy-benzylsulfanyl)-propionic acid

The compound (30.7 g, 127.3 mmol) prepared in Step 1 was dissolved in tetrahydrofuran (150 ml) and water (150 ml). Potassium carbonate (26.4 g, 190 mmol) and di-t-butyloxy-dicarbonyl (27.7 g, 127.3 mmol) were added thereto, and the mixture was stirred for 2 h at room temperature. After completion of the reaction, the reaction solution was distilled under reduced pressure to remove tetrahydrofuran. The residue was cooled to 0° C., and acidified to pH 3 using 3N aqueous hydrochloric acid solution. The resulting solid was washed with water, and dried to give (R)-2-t-butoxycarbony-lamino-3-(4-methoxy-benzylsulfanyl)-propionic acid (43 g, 126 mmol, Yield 99%).

(Step 3)

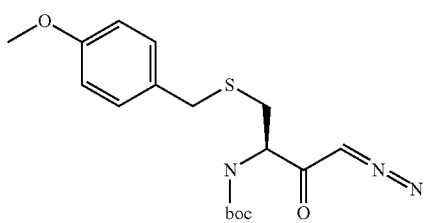

[(R)-3-Diazo-1-(4-methoxy-
benzylsulfanylmethyl)-2-oxo-propyl]-
carbamic acid tert-butyl ester The compound (43 g) prepared in Step 2, 1-methylmor-pholine (14.5 ml, 132 mmol) and ethylchloroformate (14.1 ml, 132 mmol) were dissolved in tetrahydrofuran (500 ml), and stirred for 1 h at −25° C. Simultaneously, potassium hydroxide (75 g, 1336 mmol) was dissolved in water (75 ml) and diethylether (750 ml), N-methyl-nitrosourea (26 g, 252 mmol) was added in drops thereto for 2 h at 0° C., and the mixture was stirred for 30 min. Thus prepared two solutions were mixed, and stirred for 3 h at −25° C.~room temperature. After completion of the reaction, water was added, and the mixture was washed with saturated aqueous sodium hydrogen carbonate solution and saturated aqueous ammonium chloride solution in the order. The organic layer was concentrated to give [(R)-3-diazo-1-(4-methoxy-benzylsulfanylm-ethyl)-2-oxo-propyl]-carbamic acid t-butyl ester.

$^1$H-NMR (400 HMz, CDCl$_3$); δ 7.25 (d, J=8.8 Hzm 2H), 6.86 (d, J=8.8 Hz, 2H), 5.48 (br s 1H), 5.29 (m, 1H), 4.31 (m, 1H), 3.79 (s, 3H), 3.69 (s, 2H), 2.76 (d, J=6.0 Hz, 2H), 1.45 (s, 9H)

(Step 4)

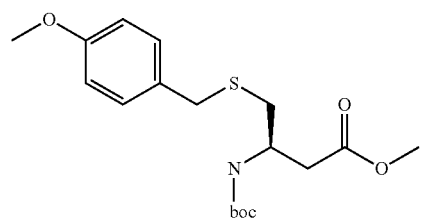

(R)-3-tert-Butoxycarbonylamino-4-(4-methoxy-
benzylsulfanyl)-butyric acid methyl ester The compound prepared in Step 3 was dissolved in methanol (1000 ml), silver benzoate (7.1 g, 31.1 mmol) was added thereto, and the mixture was sonicated for 1 h. After completion of the reaction, the reaction solution was concentrated, and separated by column chromatography to give (R)-3-t-butoxycarbonylamino-4-(4-methoxy-benzylsulfanyl)-butyric acid methyl ester (35.2 g, 95.3 mmol, Yield 76%).

$^1$H-NMR (500 HMz, CDCl$_3$); δ 7.24 (d, J=8.6 Hz, 2H), 6.83 (d, J=8.6 Hz, 2H), 5.09 (m, 1H), 4.08 (m, 1H), 3.79 (s, 3H), 3.68 (s, 2H), 3.66 (s, 3H), 2.70-2.52 (m, 4H), 1.44 (s, 9H)

(Step 5)

The compound (35.2 g) prepared in Step 4 was dissolved in dichloromethane (70 ml), 4N hydrochloric acid/1,4-dioxane solution (71 ml) was added thereto, and the mixture was stirred for 2 h at room temperature. After completion of the reaction, the reaction solution was concentrated. Dichloromethane (30 ml) and diethylether (150 ml) were added to the residue, and the resulting solid was filtered and dried to give the title compound (25.5 g, 83.3 mmol, Yield 87%).

$^1$H NMR (400 MHz, DMSO-d$_6$); δ 8.21 (br s, 3H), 7.25 (d, 2H), 6.83 (d, 2H), 3.78 (s, 3H), 3.68 (s, 2H), 3.65 (s, 3H), 3.29 (m, 1H), 2.51-2.48 (m, 2H), 2.35-2.31 (m, 2H)

Preparation 16

Synthesis of (R)-3-amino-4-(4-methoxy-benzylsulfa-nyl)-butyric acid ethyl ester hydrochloride

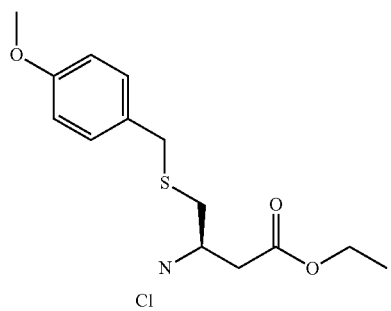

(R)-3-Amino-4-(4-methoxy-benzylsulfanyl)-
butyric acid ethyl ester

L-cysteine (50 g, 0.41 mol) was reacted according to the same procedure as Preparation 15 except that ethanol was used instead of methanol in Step 4 of Preparation 15 to give the title compound (5.2 g, Yield 40%).

$^1$H NMR (400 MHz, CDCl$_3$); δ 8.37 (br s, 3H), 7.28 (d, J=8.0 Hz, 2H), 6.87 (d, J=8.0 Hz, 2H), 4.11 (m, 2H), 3.73 (s, 3H), 3.70 (s, 2H), 2.81-2.67 (m, 4H), 1.18 (t, 3H)

Preparation 17

Synthesis of (R)-4-amino-5-(4-methoxy-benzylsulfa-nyl)-pentanoic acid ethyl ester hydrochloride

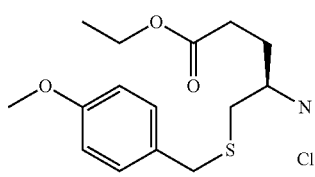

(R)-4-Amino-5-(4-methoxy-benzylsulfanyl)-
pentanoic acid ethyl ester (Step 1)

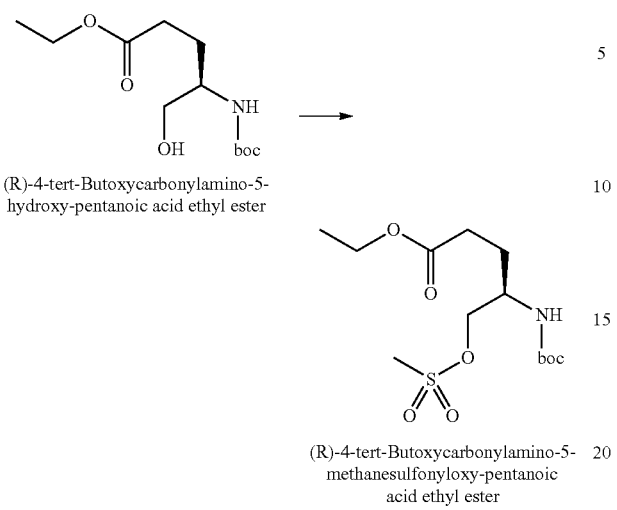

(R)-4-tert-Butoxycarbonylamino-5-hydroxy-pentanoic acid ethyl ester (R)-4-tert-Butoxycarbonylamino-5-methanesulfonyloxy-pentanoic acid ethyl ester (R)-4-t-butoxycarbonylamino-5-hydroxy-pentanoic acid ethyl ester (36 g, 137.8 mmol) that can be obtained by a known method and triethylamine (38.4 ml, 275.5 mol) were dissolved in dichloromethane (200 ml). Methanesulfonylchloride (11.7 ml, 151.5 mmol) was added in drops thereto, and the mixture was stirred for 1 h at 0° C.~room temperature. 1N hydrochloric acid solution was added thereto, and the mixture was extracted with ethyl acetate. The extract was washed with saturated sodium chloride solution, and dried over anhydrous magnesium sulfate to give (R)-4-t-butoxycarbonylamino-5-methanesulfonyloxy-pentanoic acid ethyl ester.

(Step 2)

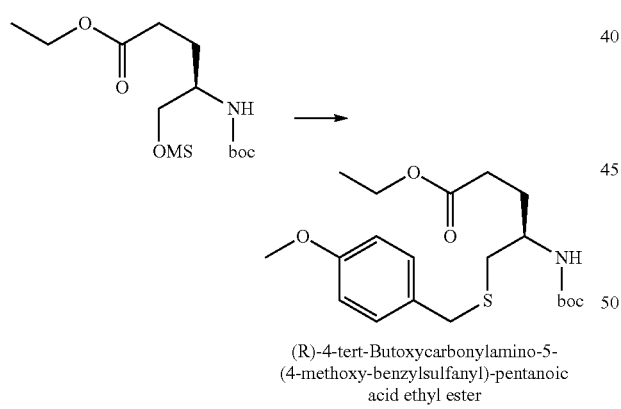

(R)-4-tert-Butoxycarbonylamino-5-(4-methoxy-benzylsulfanyl)-pentanoic acid ethyl ester Sodium hydride (5.5 g, 137.8 mmol) and 4-methoxybenzylmercaptan (15.4 ml, 110.2 mmol) were dissolved in N,N-dimethylformamide (150 ml), and stirred for 10 min at 0° C. To thus obtained solution was added in drops the methanesulfonate prepared in Step 1. The mixture was stirred for 4 h at 0° C. After completion of the reaction, water was added, and the reaction solution was extracted with ethyl acetate. The extract was washed with saturated sodium chloride solution, dried over anhydrous magnesium sulfate, and separated by column chromatography to give (R)-4-t-butoxycarbonylamino-5-(4-methoxy-benzylsulfanyl)-pentanoic acid ethyl ester (21.0 g, Yield 38%).

$^1$H-NMR (400 HMz, CDCl$_3$); δ 7.25 (d, J=8.8 Hz, 2H), 6.85 (d, J=8.8 Hz, 2H), 4.56 (m, 1H), 4.12 (m, 2H), 3.79 (s, 3H), 3.69 (s, 2H), 2.53 (m, 2H), 2.33 (t, 2H), 1.93 (m, 1H), 1.70 (m, 1H), 1.44 (s, 9H), 1.25 (t, 3H)

(Step 3)

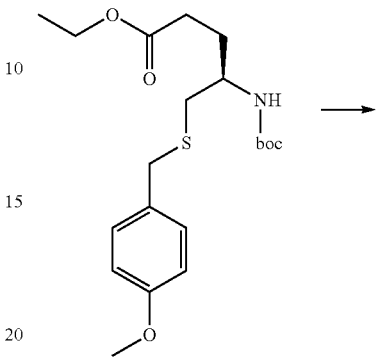

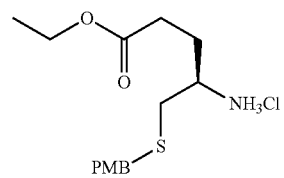

The compound (11 g, 62.7 mmol) prepared in Step 2 was dissolved in dichloromethane (200 ml), and 4N hydrochloric acid/ethyl acetate solution (20 ml) was added thereto. The mixture was stirred for 2 h at room temperature. After completion of the reaction, the reaction solution was thoroughly concentrated, and diethylether (150 ml) was added thereto. The resulting solid was filtered and dried to give the title compound (20 g, Yield 96%).

$^1$H NMR (400 MHz, DMSO-d$_6$); δ 8.69 (br s, 3H), 7.29 (d, J=8.0 Hz, 2H), 6.89 (d, J=8.0 Hz, 2H), 4.08 (m, 2H), 3.74 (m, 5H), 3.26 (m, 1H), 2.76-2.63 (m, 2H), 2.49-2.40 (m, 2H), 1.89 (m, 2H), 1.20 (t, 3H)

Preparation 18

Synthesis of 2,2-dimethyl-propionic acid (R)-2-amino-3-(4-methoxy-benzylsulfanyl)-propyl ester

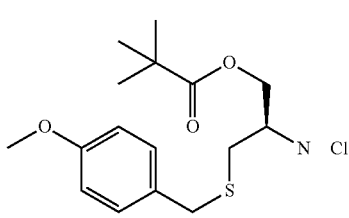

2,2-Dimethyl-propionic acid (R)-2-amino-3-(4-methoxy-benzylsulfanyl)-propyl ester (Step 1)

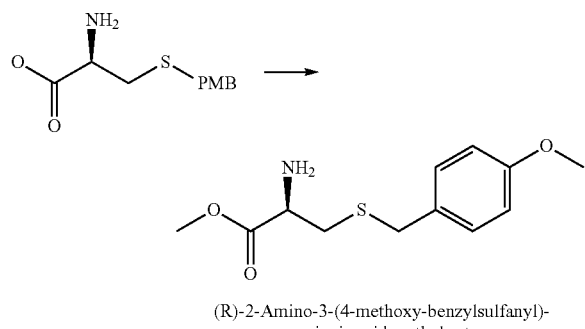

(R)-2-Amino-3-(4-methoxy-benzylsulfanyl)-
propionic acid methyl ester

The compound (50 g, 207.2 mmol) prepared in Step 1 of Preparation 15 was dissolved in methanol (300 ml). Acetyl chloride (21 ml, 207.2 mmol) was added in drops thereto, and stirred for 12 h at 50° C. After completion of the reaction, the reaction solution was thoroughly concentrated, to which was added diethylether. The resulting solid was filtered and dried to give (R)-2-amino-3-(4-methoxy-benzylsulfanyl)-propionic acid methyl ester.

$^1$H NMR (400 MHz, DMSO-$d_6$, HCl salt); δ 8.81 (br s, 3H), 7.29 (d, J=8.4 Hz, 2H), 6.91 (d, J=8.4 Hz, 2H), 4.28 (m, 1H), 3.18 (br s, 8H), 2.95 (m, 2H)

(Step 2)

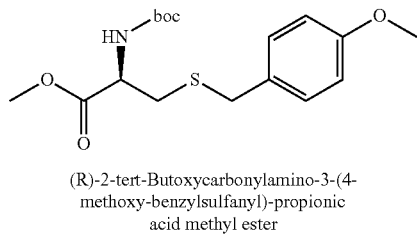

(R)-2-tert-Butoxycarbonylamino-3-(4-
methoxy-benzylsulfanyl)-propionic
acid methyl ester The compound prepared in Step 1 was dissolved in tetrahydrofuran (200 ml) and water (200 ml). Triethylamine (87 ml, 621.6 mmol) was added thereto, and di-t-butyloxy-dicarbonyl (43.0 g, 196.8 mmol) dissolved in tetrahydrofuran (100 ml) was added in drops thereto while stirring. The mixture was stirred for 8 h at room temperature. After completion of the reaction, water was added to the reaction solution, which was then extracted with ethyl acetate. The extract was washed with saturated sodium chloride solution, and dried over anhydrous magnesium sulfate to give (R)-2-t-butoxycarbonylamino-3-(4-methoxy-benzylsulfanyl)-propionic acid methyl ester.

(Step 3)

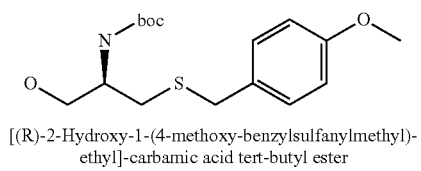

[(R)-2-Hydroxy-1-(4-methoxy-benzylsulfanylmethyl)-
ethyl]-carbamic acid tert-butyl ester The compound prepared in Step 2 was dissolved in tetrahydrofuran (300 ml). Lithium borohydride (9.0 g, 414.4 mmol) was added thereto, and the mixture was stirred for 3 h at 0° C. After completion of the reaction, water was added, and the reaction solution was extracted with ethyl acetate. The extract was washed with saturated sodium chloride solution and dried over anhydrous magnesium sulfate to give [(R)-2-hydroxy-1-(4-methoxy-benzylsulfanylmethyl)-ethyl]-carbamic acid t-butyl ester.

$^1$H NMR (500 MHz, DMSO-$d_6$); δ 7.24 (d, J=8.6 Hz, 2H), 6.84 (d, J=8.6 Hz, 2H), 4.96 (br s, 1H), 3.78 (s, 3H), 3.76 (br s, 1H), 3.70 (s, 2H), 3.7-3.66 (m, 3H), 2.58 (m, 2H), 1.44 (s, 9H)

(Step 4)

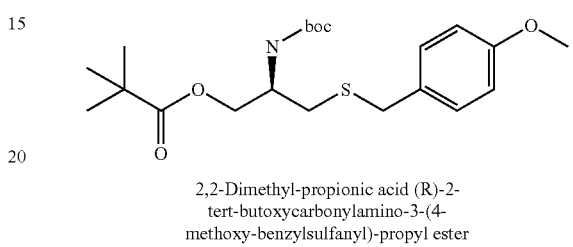

2,2-Dimethyl-propionic acid (R)-2-
tert-butoxycarbonylamino-3-(4-
methoxy-benzylsulfanyl)-propyl ester The compound prepared in Step 3 was dissolved in dichloromethane (300 ml). Triethylamine (58 ml, 414.4 mmol) and trimethylacetyl chloride (28 ml, 227.9 mmol) were added thereto, and the mixture was stirred for 6 h at 0° C. After completion of the reaction, water was added, and the reaction solution was extracted with ethyl acetate. The extract was washed with saturated sodium chloride solution, dried over anhydrous magnesium sulfate, and separated by column chromatography to give 2,2-dimethyl-propionic acid (R)-2-t-butoxycarbonylamino-3-(4-methoxy-benzylsulfanyl)-propyl ester (81.0 g, Yield 95%).

$^1$H NMR (400 MHz, CDCl$_3$); δ 7.25 (d, J=8.8 Hz, 2H), 6.85 (d, J=8.8 Hz, 2H), 4.71 (m, 1H), 4.11 (m, 2H), 3.79 (s, 3H), 3.70 (s, 2H), 2.55 (d, J=6.4 Hz, 2H), 1.52 (s, (H, 1.27 (s, 9H)

(Step 5)

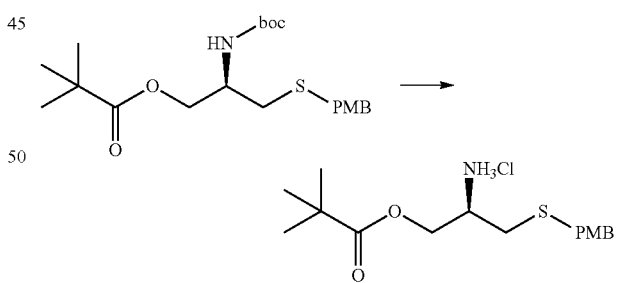

The compound (81 g, 196 mmol) prepared in Step 4 was dissolved in dichloromethane (300 ml). 4N hydrochloric acid/1,4-dioxane solution (100 ml) was added thereto, and the mixture was stirred for 8 h at room temperature. After completion of the reaction, the reaction solution was thoroughly concentrated, and diethylether was added. The resulting solid was filtered and dried to give the title compound (68 g, Yield 95%).

$^1$H NMR (400 MHz, DMSO-$d_6$, free form); δ 7.24 (d, J=12.0 Hz, 2H), 6.85 (dd, J=4.0, 8.0 Hz, 2H), 4.04 (m, 1H), 3.95 (m, 1H), 3.80 (s, 3H), 3.68 (s, 2H), 3.10 (m, 1H), 2.60 (m, 1H), 2.36 (m, 1H), 1.18 (s, 9H)

Preparation 19

Synthesis of 2,2-dimethyl-propionic acid (R)-2-(7-amino-1H-indol-2-yl)-4,5-dihydro-thiazol-4-ylmethyl ester

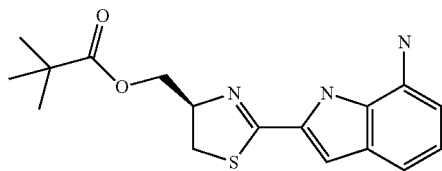

2,2-Dimethyl-propionic acid (R)-2-(7-amino-1H-indol-2-yl)-4,5-dihydrothiazol-4-ylmethyl ester (Step 1)

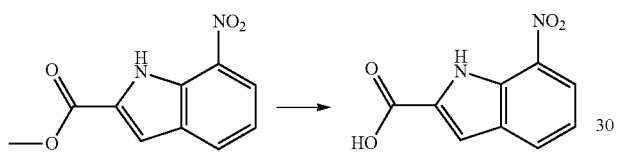

Methyl 7-nitroindole-2-carboxylate (13 g, 59 mmol) prepared in Preparation 8 was dissolved in a solvent mixture of tetrahydrofuran and water (1:1, 300 ml), and 1N aqueous sodium hydroxide solution (180 ml, 177 mmol) was added thereto. The mixture was stirred for 3 h at room temperature, excess 6N hydrochloric acid solution was added, and the mixture was extracted with ethyl acetate. The extract was washed with saturated sodium chloride solution, dried over anhydrous magnesium sulfate, and filtered. The filtrate was distilled under reduced pressure to give 7-nitro-1H-indole-2-carboxylic acid (12 g, Yield 99%).

(Step 2)

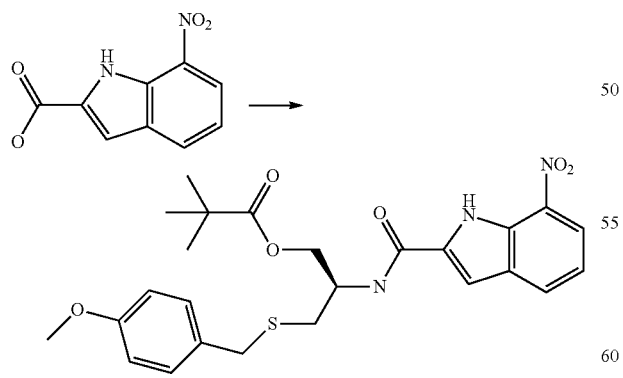

2,2-Dimethyl-propionic acid (R)-3-(4-methoxy-benzylsulfanyl)-2-[(7-nitro-1H-indole-2-carbonyl)-amino]-propyl ester 7-Nitroindole-carboxylic acid compound (8.2 g, 22.7 mmol) prepared in Step 1 and the amine compound (13.2 g, 27.2 mmol) prepared in Preparation 18 were dissolved in N,N-dimethylformamide (100 ml), and EDC (6.6 g, 25.0 mmol) and HOBT (4.6 g, 25.0 mmol) were added thereto. The mixture was stirred for 8 h at room temperature, and saturated sodium bicarbonate solution was added thereto. The mixture was extracted with ethyl acetate, dried over anhydrous magnesium sulfate, and filtered. The filtrate was distilled under reduced pressure, concentrated, and the residue was purified by column chromatography to give 2,2-dimethyl-propionic acid (R)-3-(4-methoxy-benzylsulfanyl)-2-[(7-nitro-1H-indole-2-carbonyl)-amino-propyl ester (8.1 g, Yield 71%).

$^1$H-NMR (400 HMz, CDCl$_3$); δ 10.47 (br s, 1H), 8.27 (d, J=8.0 Hz, 1H), 8.01 (d, J=8.0 Hz, 1H), 7.26 (m, 2H), 6.93 (d, J=4.0 Hz, 1H), 6.83 (m, 2H), 6.74 (d, J=8.0 Hz, 1H), 4.56 (m, 1H), 4.44 (m, 1H), 4.24 (m, 1H), 3.74 (m, 5H), 2.77 (m, 1H), 2.62 (m, 1H), 1.18 (s, 9H)

(Step 3)

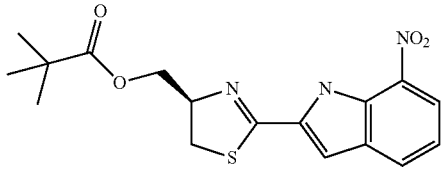

2,2-Dimethyl-propionic acid (R)-2-(7-nitro-1H-indol-2-yl)-4,5-dihydrothiazol-4-ylmethyl ester The compound (1.6 g, 3.2 mmol) prepared in Step 2 was dissolved in dichloromethane (50 ml). Phosphorus pentachloride (1.3 g, 6.4 mmol) was added thereto, and the mixture was stirred for 5 h at room temperature. After completion of the reaction, saturated sodium bicarbonate solution was added thereto. The mixture was extracted with ethyl acetate, dried over anhydrous magnesium sulfate, and filtered. The filtrate was distilled under reduced pressure, concentrated, and the residue was purified by column chromatography to give 2,2-dimethyl-propionic acid (R)-2-(7-nitro-1H-indol-2-yl)-4,5-dihydro-thiazol-4-ylmethyl ester (0.8 g, Yield 69%).

$^1$H-NMR (400 HMz, CDCl$_3$); δ 10.53 (br s, 1H), 8.26 (d, J=8.0 Hz, 1H), 7.99 (d, J=8.0 Hz, 1H), 7.04 (d, J=2.0 Hz, 1H), 6.90 (d, J=7.6 Hz, 1H), 4.78 (m, 1H), 4.46 (m, 1H), 4.30 (m, 1H), 3.59 (m, 1H), 3.36 (m, 1H), 1.20 (s, 9H)

(Step 4)

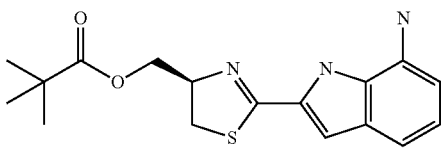

2,2-Dimethyl-propionic acid (R)-2-(7-amino-1H-indol-2-yl)-4,5-dihydro-thiazol-4-ylmethyl ester The compound (2.7 g, 7.5 mmol) prepared in Step 3 was dissolved in a solvent mixture of tetrahydrofuran, methanol and water (1:1:1, 150 ml). Iron powder (4.2 g, 74.7 mmol) and ammonium chloride (4.0 g, 74.7 mmol) were added, and the mixture was stirred for 30 min at 60° C. using a mechanical stirrer. After completion of the reaction, water was added thereto. The mixture was extracted with ethyl acetate, dried over anhydrous magnesium sulfate, and filtered. The filtrate was distilled under reduced pressure, and purified by column chromatography to give the title compound (2.0 g, Yield 81%).

$^1$H-NMR (400 HMz, CDCl$_3$); δ 9.86 (br s, 1H), 7.30 (d, J=7.6 Hz, 1H), 7.14 (d, J=8.0 Hz, 1H), 6.89 (d, J=2.0 Hz, 1H), 6.61 (dd, J=0.8, 7.2 Hz, 1H), 4.96 (m, 1H), 4.36 (m, 2H), 3.55 (m, 1H), 3.33 (m, 1H), 1.18 (s, 9H)

Preparation 20

Synthesis of 2,2-dimethyl-propionic acid (R)-2-(7-cyclopentylamino-1H-indol-2-yl)-4,5-dihydro-thiazol-4-ylmethyl ester

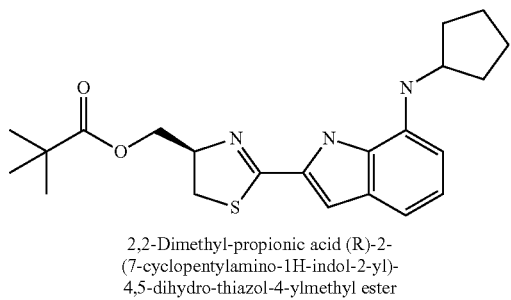

2,2-Dimethyl-propionic acid (R)-2-(7-cyclopentylamino-1H-indol-2-yl)-4,5-dihydro-thiazol-4-ylmethyl ester The compound (2.0 g, 5.0 mmol) prepared in Preparation 19 was dissolved in 1,2-dichloroethane (100 ml). Cyclopentanone (0.8 g, 7.5 mmol) and sodium triacetoxyborohydride (1.9 g, 7.5 mmol) were added thereto, and the mixture was stirred for 8 h at room temperature. After completion of the reaction, water was added thereto. The mixture was extracted with ethyl acetate, dried over anhydrous magnesium sulfate, and filtered. The filtrate was distilled under reduced pressure, and the residue was purified by column chromatography to give the title compound (1.3 g, Yield 54%).

Example 1

Synthesis of [(R)-2-(7-cyclopentylamino-1H-indol-2-yl)-4,5-dihydro-1,3-thiazol-4-yl]-methanol

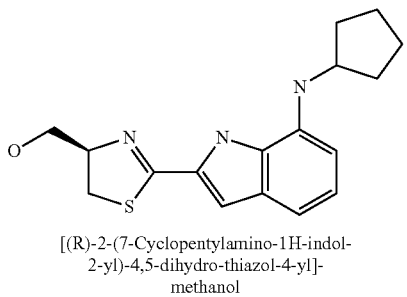

[(R)-2-(7-Cyclopentylamino-1H-indol-2-yl)-4,5-dihydro-thiazol-4-yl]-methanol

The compound (1.3 g, 3.3 mmol) prepared in Preparation 20 was dissolved in tetrahydrofuran (10 ml), methanol (10 ml) and water (10 ml). Lithium hydroxide hydrate (0.4 g, 9.8 mmol) was added thereto, and the mixture was stirred for 4 h at room temperature. The reaction solution was concentrated by distillation under reduced pressure. 1N hydrochloric acid was added to the residue, which was then extracted with ethyl acetate, dried over anhydrous magnesium sulfate, and filtered. The filtrate was distilled under reduced pressure, and purified by column chromatography to give the title compound (820 mg, Yield 80%).

$^1$H-NMR (500 HMz, CDCl$_3$); δ 11.17~11.08 (m, 1H), 7.09 (m, 1H), 6.99 (t, 1H), 6.96 (s, 1H), 6.52 (m, 1H), 4.72 (m, 1H), 4.04 (m, 1H), 3.75 (m, 1H), 3.65 (m, 1H), 3.51 (m, 1H), 3.40 (m, 1H), 1.90 (m, 2H), 1.60~1.49 (m, 4H), 1.41~1.24 (m, 2H)

Mass Spectrum (ESI, m/z): Calculated 315.14, Found 315.44

Example 2

Synthesis of {(R)-2-[7-(tetrahydro-pyran-4-ylamino)-1H-indol-2-yl]-4,5-dihydro-thiazol-4-yl}-methanol

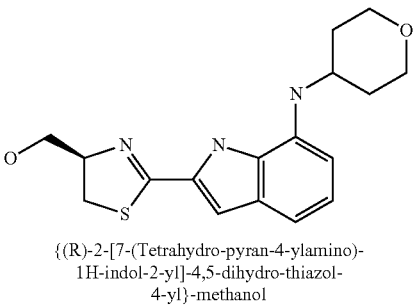

{(R)-2-[7-(Tetrahydro-pyran-4-ylamino)-1H-indol-2-yl]-4,5-dihydro-thiazol-4-yl}-methanol (Step 1)

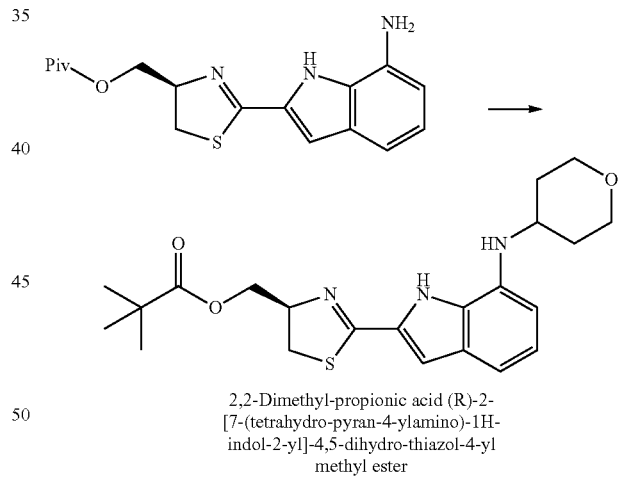

2,2-Dimethyl-propionic acid (R)-2-[7-(tetrahydro-pyran-4-ylamino)-1H-indol-2-yl]-4,5-dihydro-thiazol-4-yl methyl ester The compound (900 mg, 2.7 mmol) prepared in Preparation 19 was dissolved in 1,2-dichloroethane (100 ml). Tetrahydro-4H-pyran-4-one (0.8 ml, 8.13 mmol), sodium triacetoxyborohydride (1.72 g, 8.13 mmol) and acetic acid (0.47 ml, 8.13 mmol) were added thereto, and the mixture was stirred for 48 h at room temperature. After completion of the reaction, the reaction solution was diluted with dichloromethane, washed with saturated sodium bicarbonate solution, dried over anhydrous magnesium sulfate, and filtered. The filtrate was distilled under reduced pressure, and purified by column chromatography to give 2,2-dimethylpropionic acid (R)-2-[7-(tetrahydro-pyran-4-ylamino)-1H-indol-2-yl]-4,5-dihydro-thiazol-4-ylmethyl ester.

¹H-NMR (400 HMz, CDCl₃); δ 10.91 (br s, 1H), 7.01~6.91 (m, 3H), 6.48 (d, J=7.2 Hz, 1H), 4.86 (m, 1H), 4.34 (m 2H), 4.00 (m, 2H), 3.61 (m, 1H), 3.54 (m, 3H), 3.31 (m, 1H), 2.05 (m, 2H), 1.55 (m, 2H), 1.16 (s, 9H)

(Step 2)

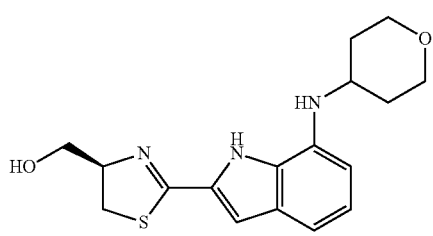

The compound prepared in Step 1 was dissolved in methanol (32 ml), tetrahydrofuran (32 ml) and water (16 ml). 1N sodium hydroxide (7 ml) was added thereto, and the mixture was stirred for 4 h at room temperature. After completion of the reaction, the reaction solution was distilled under reduced pressure, extracted with dichloromethane, washed with saturated sodium chloride solution, dried over anhydrous magnesium sulfate, and filtered. The filtrate was distilled under reduced pressure, and purified by column chromatography to give the title compound (700 mg, Yield 78%).

¹H-NMR (500 HMz, CDCl₃); δ 11.04~10.95 (m, 1H), 7.11 (m, 1H), 6.99 (t, 1H), 6.96 (s, 1H), 6.52 (m, 1H), 4.74 (m, 1H), 4.02 (m, 1H), 3.92 (m, 2H), 3.68 (m, 1H), 3.46-3.30 (m, 5H), 1.91 (m, 2H), 1.28 (m, 2H)

Mass Spectrum (ESI, m/z): Calculated 331.14, Found 331.44

Example 3

Synthesis of {(R)-2-[7-(tetrahydro-furan-3-ylamino)-1H-indol-2-yl]-4,5-dihydro-thiazol-4-yl}-methanol

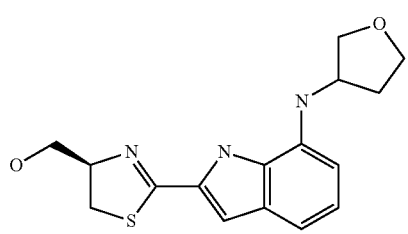

{(R)-2-[7-(Tetrahydro-furan-3-ylamino)-1H-indol-2-yl]-4,5-dihydro-thiazol-4-yl}-methanol The compound (940 mg, 2.9 mmol) prepared in Preparation 19 and tetrahydrofuran-3-one instead of tetrahydro-4H-pyran-4-one were reacted according to the same procedure as Example 2 to give the title compound (650 mg, Yield 69%).

¹H-NMR (500 HMz, CDCl₃); δ 10.58 (br s, 1H), 7.14 (d, J=7.95 Hz, 1H), 7.00 (m, 1H), 6.94 (m, 1H), 6.48 (d, J=7.35 Hz, 1H), 4.79 (m, 1H), 4.15~3.95 ((m, 3H), 3.90~3.65 (m, 4H), 3.50~3.39 (m, 2H), 2.20 (m, 1H), 1.83 (m, 1H)

Example 4

Synthesis of {(R)-2-[7-(1-methanesulfonyl-pyrrolidin-3-ylamino)-1H-indol-2-yl]-4,5-dihydro-thiazol-4-yl}-methanol

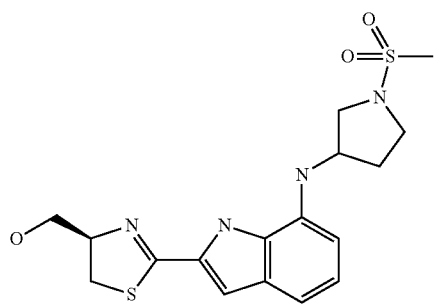

{(R)-2-[7-(1-Methanesulfonyl-pyrrolidin-3-ylamino)-1H-indol-2-yl]-4,5-dihydro-thiazol-4-yl}-methanol (Step 1)

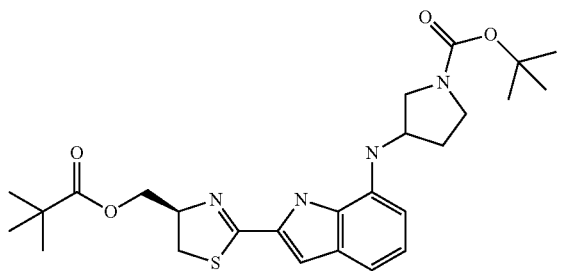

3-{2-[(R)-4-(2,2-Dimethyl-propionyl oxymethyl)-4,5-dihydro-thiazol-2-yl] 1H-indol-7-ylamino}-pyrrolidine-1-carboxylic acid tert-butyl ester The compound (1.0 mg, 3.0 mmol) prepared in Preparation 19 and 3-oxo-pyrrolidine-1-carboxylic acid t-butyl ester (1.1 g, 6.0 mmol) instead of tetrahydro-4H-pyran-4-one were reacted according to the same procedure as Step 1 of Example 2 to give a pyrrolidine compound (853 mg, Yield 57%).

(Step 2)

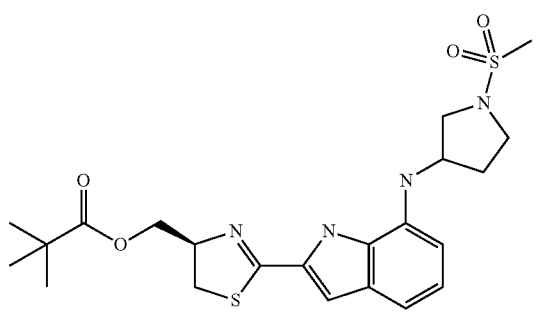

2,2-Dimethyl-propionic acid (R)-2-[7-(1-methanesulfonyl-pyrrolidin-3-ylamino)-1H-indol-2-yl]-4,5-dihydro-thiazol-4-ylmethyl ester The compound (460 mg, 0.9 mmol) prepared in Step 1 was dissolved in methanol (50 ml), and 4N hydrochloric acid solution (0.8 ml, 2.7 mmol) was added thereto. The mixture was stirred for 8 h at room temperature, distilled under reduced pressure, and purified by column chromatography.

Thus purified compound (313 mg, 0.8 mmol) was dissolved in dichloromethane (50 ml). Triethylamine (158 mg, 1.6 mmol) and methanesulfonyl chloride (90 mg, 0.8 mmol) were added, and the mixture was stirred for 30 min at 0° C.~room temperature. After completion of the reaction, water was added to the reaction solution, which was then extracted with dichloromethane, washed with saturated sodium chloride solution, dried over anhydrous magnesium sulfate, and filtered. The filtrate was distilled under reduced pressure, and purified by column chromatography to give a sulfonamide compound (223 mg, Yield 58%).

(Step 3)
The compound (223 mg, 0.47 mmol) prepared in Step 2 was reacted according to the same procedure as Example 1 to give the title compound (152 mg, Yield 82%).

$^1$H-NMR (500 HMz, CDCl$_3$); δ 10.50 (br s, 1H), 7.15 (d, J=7.95 Hz, 1H), 7.00 (dd, 1H), 6.93 (s, 1H), 6.46 (d, J=7.35 Hz, 1H), 4.77 (m, 1H), 4.18 (m, 1H), 4.08 (dd, 1H), 3.75 (dd, 1H), 3.59~3.36 (m, 6H), 3.48 (s, 3H), 2.27 (m, 1H), 1.95 (m, 1H)

Preparation 21

Synthesis of 2,2-dimethyl-propionic acid (R)-2-[7-amino-5-fluoro-1H-indol-2-yl]-4,5-dihydro-thiazol-4-ylmethyl ester

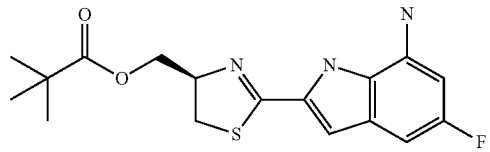

2,2-Dimethyl-propionic acid (R)-2-(7-amino-5-fluoro-1H-indol-2-yl)-4,5-dihydro-thiazol-4-ylmethyl ester Ethyl 5-fluoro-7-nitro-1H-indole-2-carboxylate (6.0 g, 23.8 mmol) prepared in Preparation 2 was reacted according to the same procedure as Preparation 19 to give the title compound (2.3 g, Yield 28%).

Example 5

Synthesis of [(R)-2-(7-cyclopentylamino-5-fluoro-1H-indol-2-yl)-4,5-dihydro-thiazol-4-yl]-methanol

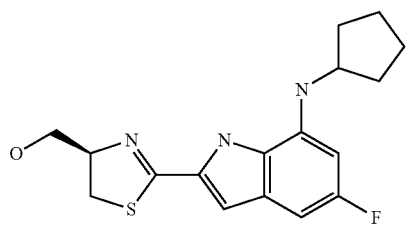

[(R)-2-(7-Cyclopentylamino-5-fluoro-1H-indol-2-yl)-4,5-dihydro-thiazol-4-yl]-methanol The amine compound (1.1 g, 3.1 mmol) prepared in Preparation 21 was reacted according to the same procedures as Preparation 20 and Example 1 to give the title compound (600 mg, Yield 58%).

$^1$H-NMR (400 HMz, CDCl$_3$); δ 10.73 (br s, 1H), 6.91 (s, 1H), 6.72 (m, 1H), 6.33 (m, 1H), 4.78 (m, 1H), 4.12 (m, 1H), 3.97 (br s, 1H), 3.79 (m, 1H), 3.75 (m, 1H), 3.49 (m, 2H), 2.01 (m, 2H), 1.62 (m, 4H), 1.41 (m, 2H)

Example 6

Synthesis of {(R)-2-[5-fluoro-7-(tetrahydro-pyran-4-ylamino)-1H-indol-2-yl]-4,5-dihydro-thiazol-4-yl}-methanol

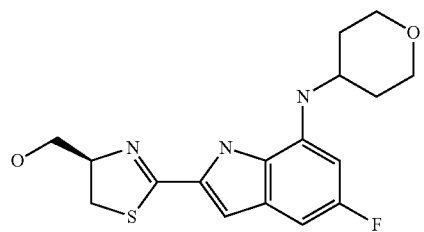

{(R)-2-[5-Fluoro-7-(tetrahydro-pyran-4-ylamino)-1H-indol-2-yl]-4,5-dihydro-thiazol-4-yl}-methanol The amine compound (1.1 g, 3.1 mmol) prepared in Preparation 21 was reacted according to the same procedure as Example 2 to give the title compound (750 mg, Yield 68%).

$^1$H-NMR (400 HMz, CDCl$_3$); δ 10.45 (br s, 1H), 6.90 (s, 1H), 6.75 (m, 1H), 6.34 (m, 1H), 4.82 (m, 1H), 4.12 (m, 1H), 4.01 (m, 2H), 3.94 (m, 1H), 3.78 (m, 1H), 3.54~3.43 (m, 5H), 2.03 (m, 2H), 1.50 (m, 2H)

Example 7

Synthesis of [(R)-2-(5-chloro-7-cyclopentylamino-1H-indol-2-yl)-4,5-dihydro-thiazol-4-yl]-methanol

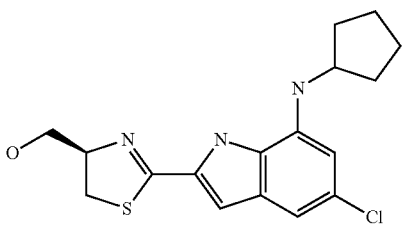

[(R)-2-(5-Chloro-7-cyclopentylamino-1H-indol-2-yl)-4,5-dihydro-thiazol-4-yl]-methanol (Step 1)

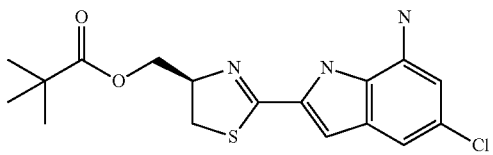

2,2-Dimethyl-propionic acid (R)-2-
(7-amino-5-chloro-1H-indol-2-yl)-4,5-
dihydro-thiazol-4-ylmethyl ester Methyl 5-chloro-7-nitro-1H-indole-2-carboxylate (3.0 g, 11.8 mmol) prepared in Preparation 5 was reacted according to the same procedure as Preparation 19 to give an amine compound (2.4 g, Yield 56%).

(Step 2)

The amine compound (150 mg, 0.4 mmol) prepared in Step 1 was reacted according to the same procedures as Preparation 20 and Example 1 to give the title compound (50 mg, Yield 36%).

$^1$H-NMR (500 HMz, CDCl$_3$); δ 10.53 (br s, 1H), 7.24 (s, 1H), 6.84 (d, 1H), 6.45 (s, 1H), 4.74 (m, 1H), 4.06 (m, 1H), 3.81 (m, 1H), 3.71 (m, 1H), 3.45 (dd, 2H), 1.99 (m, 2H), 1.60 (m, 4H), 1.37 (m, 2H)

Example 8

Synthesis of {(R)-2-[5-chloro-7-(tetrahydro-pyran-4-ylamino)-1H-indol-2-yl]-4,5-dihydro-thiazol-4-yl}-methanol

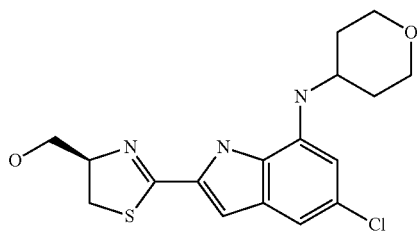

{(R)-2-[5-Chloro-7-(tetrahydro-pyran-
4-ylamino)-1H-indol-2-yl]-4,5-
dihydro-thiazol-4-yl}-methanol The amine compound (150 mg, 0.4 mmol) prepared in Step 1 of Example 7 was reacted according to the same procedure as Example 2 to give the title compound (40 mg, Yield 27%).

Example 9

Synthesis of {(R)-2-[5-chloro-7-(tetrahydro-thiopyran-4-ylamino)-1H-indol-2-yl]-4,5-dihydro-thiazol-4-yl}-methanol

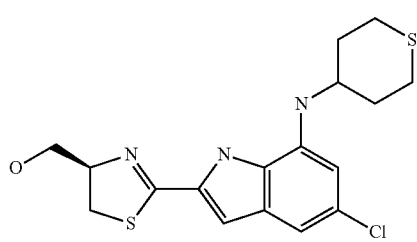

{(R)-2-[5-Chloro-7-(tetrahydro-thio
pyran-4-ylamino)-1H-indol-2-yl]-4,5-
dihydro-thiazol-4-yl}-methanol The amine compound (150 mg, 0.4 mmol) prepared in Step 1 of Example 7 and tetrahydro-thiopyran-4-one instead of tetrahydro-4H-pyran-4-one were reacted according to the same procedure as Example 2 to give the title compound (130 mg, Yield 85%).

$^1$H-NMR (400 HMz, CDCl$_3$); δ 10.87 (br s, 1H), 7.01 (s, 1H), 6.89 (s, 1H), 6.40 (s, 1H), 4.80 (m, 1H), 4.10 (m, 1H), 3.80 (m, 1H), 3.50 (m, 2H), 3.32 (m, 1H), 2.76 (m, 4H), 2.29 (m, 2H), 1.56 (m, 2H)

Example 10

Synthesis of [(R)-2-(5-bromo-7-cyclopentylamino-1H-indol-2-yl)-4,5-dihydro-thiazol-4-yl]-methanol

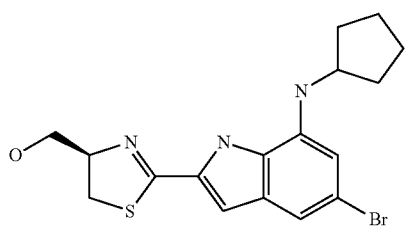

[(R)-2-(5-Bromo-7-cyclopentylamino-
1H-indol-2-yl)-4,5-dihydro-thiazol-
4-yl]-methanol Methyl 5-bromo-7-nitro-1H-indole-2-carboxylate (1.3 g, 4.3 mmol) prepared in Preparation 6 was reacted according to the same procedures as Preparation 19, Preparation 20 and Example 1 in the order to give the title compound (100 mg, Yield 6%).

$^1$H-NMR (400 HMz, CDCl$_3$); δ 10.59 (br s, 1H), 7.23 (s, 1H), 6.88 (s, 1H), 6.64 (d, 1H), 4.77 (m, 1H), 4.14 (m, 1H), 3.82 (m, 1H), 3.76 (m, 1H), 3.49 (dd, 2H), 2.04 (m, 2H), 1.65 (m, 4H), 1.41 (m, 2H)

Example 11

Synthesis of {(R)-2-[5-bromo-7-(tetrahydro-pyran-4-ylamino)-1H-indol-2-yl]-4,5-dihydro-thiazol-4-yl}-methanol

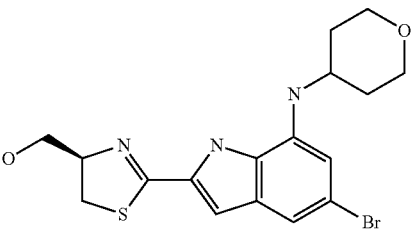

{(R)-2-[5-Bromo-7-(tetrahydro-pyran -
4-ylamino)-1H-indol-2-yl]-4,5-
dihydro-thiazol-4-yl}-methanol Methyl 5-bromo-7-nitro-1H-indole-2-carboxylate (1.3 g, 4.3 mmol) prepared in Preparation 6 was reacted according to the same procedures as Preparation 19 and Example 2 in the order to give the title compound (70 mg, Yield 4%).

¹H-NMR (400 HMz, CDCl₃); δ 10.53 (br s, 1H), 7.25 (s, 1H), 6.87 (s, 1H), 6.63 (d, 1H), 4.80 (m, 1H), 4.14 (m, 1H), 4.03 (m, 2H), 3.79 (m, 1H), 3.56-3.3.44 (m, 4H), 2.02 (m, 2H), 1.45 (m, 2H)

Example 12

Synthesis of [(R)-2-(7-cyclopentylamino-5-methoxy-1H-indol-2-yl)-4,5-dihydro-thiazol-4-yl]-methanol

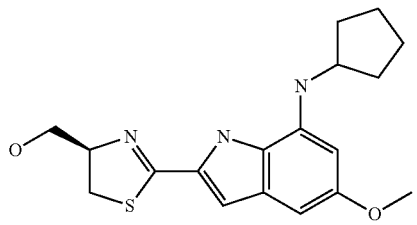

[(R)-2-(7-Cyclopentylamino-5-methoxy-1H-indol-2-yl)-4,5-dihydro-thiazol-4-yl]-methanol Methyl 5-methoxy-7-nitro-1H-indole-2-carboxylate (700 mg, 2.8 mmol) prepared in Preparation 9 was reacted according to the same procedures as Preparation 19, Preparation 20 and Example 1 in the order to give the title compound (80 mg, Yield 8%).

¹H-NMR (500 HMz, DMSO-d₆); δ 11.23 (br s, 1H), 6.60 (s, 1H), 6.23 (s, 1H), 5.89 (m, 1H), 5.84 (m, 1H), 4.96 (m, 1H), 4.65 (m, 1H), 3.77 (m, 1H), 3.70 (m, 1H), 3.45 (m, 1H), 3.33 (m, 1H), 3.29 (s, 3H), 1.91 (m, 2H), 1.67 (m, 2H), 1.53 (m, 4H)

Example 13

Synthesis of {(R)-2-[7-cyclopentylamino-5-(pyridin-3-yloxy)-1H-indol-2-yl]-4,5-dihydro-thiazol-4-yl}-methanol

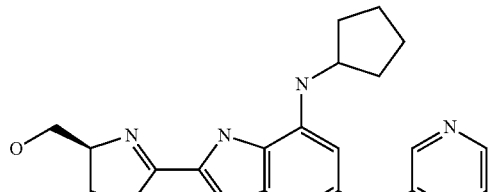

{(R)-2-[7-Cyclopentylamino-5-(pyridin-3-yloxy)-1H-indol-2-yl]-4,5-dihydro-thiazol-4-yl]-methanol 7-Nitro-5-(pyridin-3-yloxy)-1H-indole-2-carboxylic acid ethyl ester (500 mg, 1.5 mmol) prepared in Preparation 13 was reacted according to the same procedures as Preparation 19, Preparation 20 and Example 1 in the order to give the title compound (35 mg, Yield 6%).

¹H-NMR (400 HMz, CDCl₃); δ 11.16 (br s, 1H), 8.42 (d, 1H), 8.28 (m, 1H), 7.30 (m, 1H), 7.22 (m, 1H), 6.88 (s, 1H), 6.67 (d, 1H), 6.28 (d, 1H), 4.83 (m, 1H), 4.02 (m, 1H), 3.75 (m, 2H), 3.46 (m, 2H), 1.97 (m, 2H), 1.63 (m, 4H), 1.43 (m, 2H)

Example 14

Synthesis of {(R)-2-[5-(pyridin-3-yloxy)-7-(tetrahydro-pyran-4-ylamino)-1H-indol-2-yl]-4,5-dihydro-thiazol-4-yl}-methanol

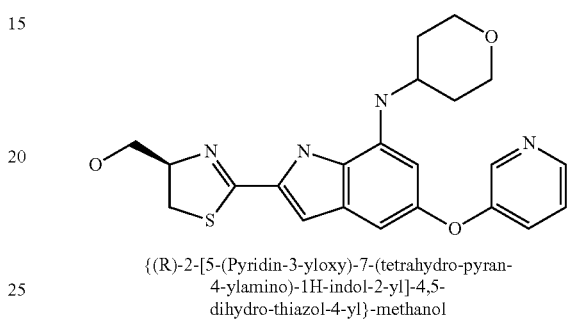

{(R)-2-[5-(Pyridin-3-yloxy)-7-(tetrahydro-pyran-4-ylamino)-1H-indol-2-yl]-4,5-dihydro-thiazol-4-yl}-methanol 7-Nitro-5-(pyridin-3-yloxy)-1H-indole-2-carboxylic acid ethyl ester (500 mg, 1.5 mmol) prepared in Preparation 13 was reacted according to the same procedures as Preparation 19 and Example 2 in the order to give the title compound (40 mg, Yield 6%).

¹H-NMR (400 HMz, CDCl₃); δ 10.96 (br s, 1H), 8.36 (d, J=2.4 Hz, 1H), 8.26 (m, 1H), 7.27 (m, 1H), 7.19 (m, 1H), 6.83 (s, 1H), 6.63 (d, J=1.6 Hz, 1H), 6.24 (d, J=1.6 Hz, 1H), 4.81 (m, 1H), 4.01~3.94 (m, 3H), 3.75 (m, 1H), 3.47 (s, 3H), 3.48~3.29 (m, 5H), 1.93 (m, 2H), 1.52 (m, 2H)

Preparation 22

Synthesis of methanesulfonic acid (R)-2-(7-cyclopentylamino-1H-indol-2-yl)-4,5-dihydro-thiazol-4-ylmethyl ester

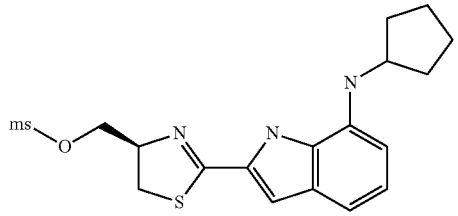

Methanesulfonic acid (R)-2-(7-cyclo pentylamino-1H-indol-2-yl)-4,5-dihydro-thiazol-4-ylmethyl ester The compound (820 mg, 2.6 mmol) prepared in Example 1 was dissolved in dichloromethane (50 ml). Methanesulfonyl chloride (0.24 ml, 3.1 mmol) and triethylamine (0.81 ml, 3.1 mmol) were added thereto, and the mixture was stirred for 30 min at 0° C. After completion of the reaction, saturated sodium bicarbonate solution was added, and the mixture was extracted with ethyl acetate, dried over anhydrous magnesium sulfate, and filtered. The filtrate was distilled under reduced pressure, and purified by column chromatography to give the title compound (600 mg, Yield 60%).

Example 15

Synthesis of cyclopentyl-[2-((R)-4-pyrrolidin-1-ylmethyl-4,5-dihydro-thiazol-2-yl)-1H-indol-7-yl]-amine

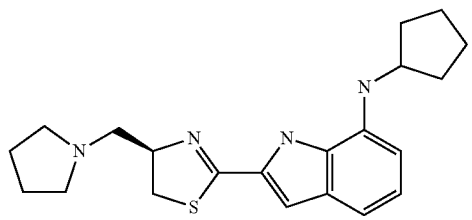

Cyclopentyl-[2-((R)-4-pyrrolidin-1-ylmethyl-4,5-dihydro-thiazol-2-yl)-1H-indol-7-yl]-amine The compound (150 mg, 0.38 mmol) prepared in Preparation 22 was dissolved in N,N-dimethylformamide (5 ml). Pyrrolidine (0.08 ml, 1.1 mmol) was added thereto, and the mixture was stirred for 4 h at 70° C. After completion of the reaction, water was added, which was then extracted with ethyl acetate, dried over anhydrous magnesium sulfate, and filtered. The filtrate was distilled under reduced pressure, and purified by column chromatography to give the title compound (20 mg, Yield 14%).

$^1$H-NMR (400 HMz, DMSO-$d_6$); δ 11.37 (br s, 1H), 6.83 (m, 1H), 6.75 (d, J=2.0 Hz, 1H), 6.29 (d, J=8.0 Hz, 1H), 5.86 (d, J=8.0 Hz, 1H), 4.80 (m, 1H), 3.87 (m, 1H), 3.52 (m, 1H), 3.43 (m, 1H), 3.33 (m, 2H), 2.78 (m, 2H), 2.61 (m, 2H), 1.99 (m, 2H), 1.72 (m, 6H), 1.60 (m, 4H)

Example 16

Synthesis of cyclopentyl-[2-((R)-4-morpholin-4-ylmethyl-4,5-dihydro-thiazol-2-yl)-1H-indol-7-yl]-amine

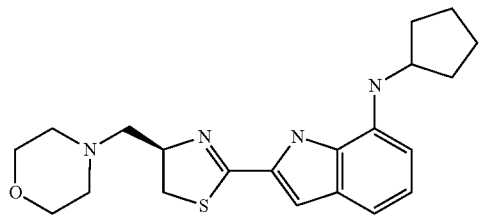

Cyclopentyl-[2-((R)-4-morpholin-4-ylmethyl-4,5-dihydro-thiazol-2-yl)-1H-indol-7-yl]-amine The compound (150 mg, 0.38 mmol) prepared in Preparation 22 and morpholine instead of pyrrolidine were reacted according to the same procedure as Example 15 to give the title compound (50 mg, Yield 34%).

$^1$H-NMR (400 HMz, DMSO-$d_6$); δ 11.37 (br s, 1H), 6.83 (m, 1H), 6.75 (m, 1H), 6.29 (d, J=8.0 Hz, 1H), 5.85 (d, J=8.0 Hz, 1H), 4.87 (m, 1H), 3.87 (m, 1H), 3.61 (m, 4H), 3.35 (m, 3H), 2.71 (m, 1H), 2.54 (m, 2H), 2.44 (m, 2H), 1.99 (m, 2H), 1.74 (m, 6H), 1.59 (m, 4H)

Example 17

Synthesis of cyclopentyl-[2-((R)-4-dimethylaminomethyl-4,5-dihydro-thiazol-2-yl)-1H-indol-7-yl]amine

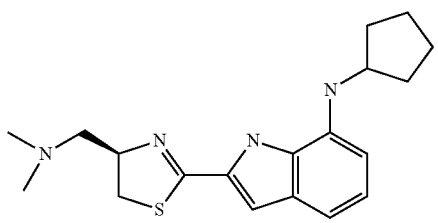

Cyclopentyl-[2-((R)-4-dimethylaminomethyl-4,5-dihydro-thiazol-2-yl)-1H-indol-7-yl]-amine The compound (150 mg, 0.38 mmol) prepared in Preparation 22 and dimethylamine instead of pyrrolidine were reacted according to the same procedure as Example 15 to give the title compound (20 mg, Yield 15%).

$^1$H-NMR (400 HMz, CDCl$_3$); δ 9.87 (br, 1H), 7.05 (d, J=8.0 Hz, 1H), 6.99 (t, 1H), 6.89 (s, 1H), 6.52 (d, J=8.0 Hz, 1H), 4.83 (m, 1H), 3.91 (m, 1H), 3.50 (t, 1H), 3.29 (t, 1H), 2.63 (m, 1H), 2.44 (m, 1H), 2.29 (s, 6H), 2.04 (m, 2H), 1.70 (m, 2H), 1.50 (m, 4H)

Example 18

Synthesis of 2-[2-((R)-4-hydroxymethyl-4,5-dihydro-thiazol-2-yl)-1H-indol-7-ylamino]-propionic acid

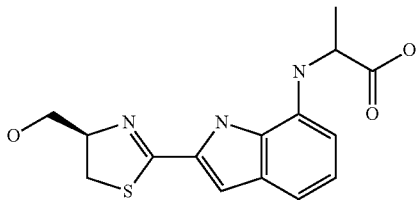

2-[2-((R)-4-Hydroxymethyl-4,5-dihydro-thiazol-2-yl)-1H-indol-7-ylamino]-propionic acid The compound prepared in Preparation 19 and methyl pyruvate were reacted according to the same procedures as Preparation 20 and Example 1 consecutively to give the title compound.

$^1$H-NMR (400 HMz, CDCl$_3$); δ 11.16 (m, 1H), 10.43 (br, 1H), 7.04 (m, 1H), 7.00 (m, 1H), 6.97 (m, 1H), 6.53 (m, 1H), 4.74 (m, 1H), 4.14 (m, 1H), 4.05 (m, 1H), 3.77 (m, 1H), 3.57 (m, 1H), 3.42 (m, 1H), 1.43 (d, 3H)

Example 19

Synthesis of {(R)-2-[7-(4-nitro-phenylamino)-1H-indol-2-yl]-4,5-dihydro-thiazol-4-yl}methanol

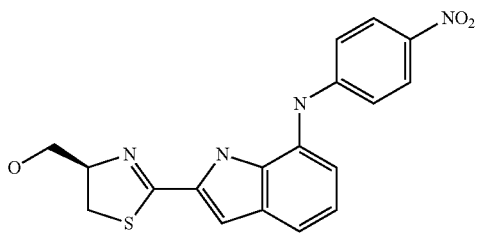

The compound prepared in Preparation 19 and 4-fluoronitrobenzene were reacted in the presence of a base $Cs_2CO_3$ according to the same procedure as Example 15 to give the title compound.

$^1$H-NMR (400 HMz, $CDCl_3$); δ 11.15 (br, 1H), 7.85 (d, 2H), 7.04 (m, 1H), 6.97 (m, 1H), 6.96 (m, 1H), 6.65 (d, 2H), 6.53 (m, 1H), 4.73 (m, 1H), 4.10 (m, 1H), 3.78 (m, 1H), 3.52 (m, 1H), 3.38 (m, 1H)

Preparation 23

Synthesis of 5-methyl-7-nitro-indole-1,2-dicarboxylic acid 1-t-butyl ester 2-methyl ester

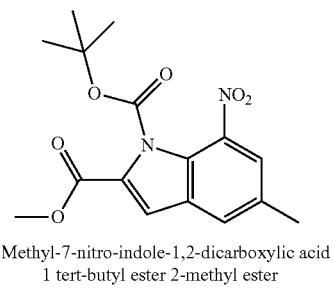

5-Methyl-7-nitro-indole-1,2-dicarboxylic acid 1 tert-butyl ester 2-methyl ester

The compound (24.0 g, 100 mmol) prepared in Preparation 7 was dissolved in dichloromethane (500 ml). Triethylamine (84 ml, 601 mmol) and 4-(dimethylamino)pyridine (600 mg, 5 mmol) were added, and di-t-butyloxy-dicarbonyl (43.7 g, 200 mmol) dissolved in dichloromethane (100 ml) was added in drops thereto. The mixture was stirred for 8 h at room temperature. After completion of the reaction, water was added. The mixture was extracted with ethyl acetate, washed with saturated sodium chloride solution, and dried over anhydrous magnesium sulfate to give the title compound (34.0 g, Yield 100%).

$^1$H-NMR (500 HMz, $CDCl_3$); δ 7.80 (s, 1H), 7.67 (s, 1H), 7.15 (s, 1H), 3.93 (s, 3H), 2.51 (s, 3H), 1.62 (s, 9H)

Preparation 24

Synthesis of 5-bromomethyl-7-nitro-indole-1,2-dicarboxylic acid 1-t-butyl ester 2-methyl ester

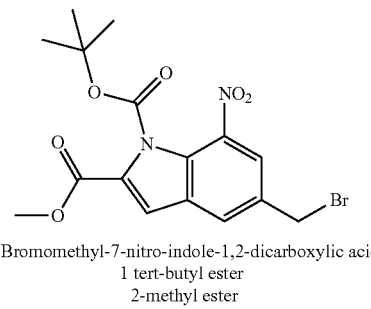

5-Bromomethyl-7-nitro-indole-1,2-dicarboxylic acid 1 tert-butyl ester 2-methyl ester The compound (34 g, 101.7 mmol) prepared in Preparation 23 was dissolved in carebon tetrachloride (100 ml). N-bromosuccinimide (27.2 g, 152.6 mmol) and AIBN (1.7 g, 10.2 mmol) were added thereto, and the mixture was stirred for 5 h at 80° C. After completion of the reaction, the reaction solution was distilled under reduced pressure, and purified by column chromatography to give the title compound (48.0 g, Yield 100%).

$^1$H-NMR (500 HMz, $CDCl_3$); δ 8.01 (s, 1H), 7.90 (s, 1H), 7.21 (s, 1H), 4.60 (s, 2H), 3.93 (s, 3H), 1.62 (s, 9H)

Preparation 25

Synthesis of 5-acetoxymethyl-7-nitro-indole-1,2-dicarboxylic acid 1-t-butyl ester 2-methyl ester

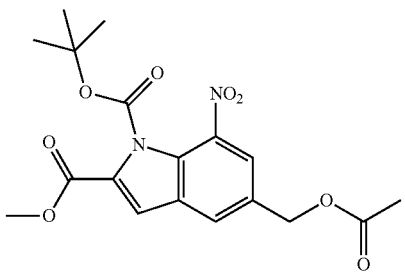

5-Acetoxymethyl-7-nitro-indole-1,2-dicarboxylic acid 1-tert-butyl ester 2-methyl ester The compound (10.0 g, 24.2 mmol) prepared in Preparation 24 was dissolved in N,N-dimethylformamide (50 ml). Sodium acetate (2.4 g, 29.0 mmol) was added thereto, and the mixture was stirred for 4 h at room temperature. After completion of the reaction, the reaction solution was distilled under reduced pressure. Water was added, and the mixture was extracted with ethyl acetate, washed with saturated sodium chloride solution, dried over anhydrous magnesium sulfate, and purified by column chromatography to give the title compound (4.7 g, Yield 50%).

¹H-NMR (500 HMz, CDCl₃); δ 7.99 (s, 1H), 7.90 (s, 1H), 7.21 (s, 1H), 5.22 (s, 2H), 3.94 (s, 3H), 2.12 (s, 3H), 1.63 (s, 9H)

Preparation 26

Synthesis of 5-acetoxymethyl-7-nitro-1H-indole-2-carboxylic acid methyl ester

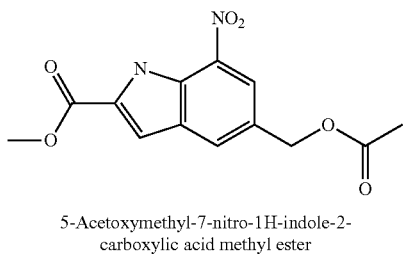

5-Acetoxymethyl-7-nitro-1H-indole-2-carboxylic acid methyl ester

The compound (4.7 g, 12.0 mmol) prepared in Preparation 25 was dissolved in dichloromethane (50 ml). 2N hydrochloric acid solution (30 ml, 60 mmol) was added thereto, and the mixture was stirred for 12 h at room temperature and distilled under reduced pressure to give the title compound (3.5 g, Yield 100%) as a solid.

¹H-NMR (500 HMz, CDCl₃); δ 10.33 (br s, 1H), 8.32 (s, 1H), 8.06 (s, 1H), 7.34 (s, 1H), 5.24 (s, 2H), 3.99 (s, 3H), 2.12 (s, 3H)

Preparation 27

Synthesis of 5-hydroxymethyl-7-nitro-1H-indole-2-carboxylic acid

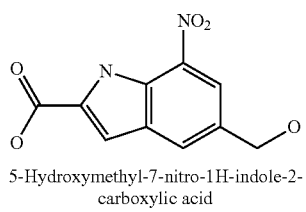

5-Hydroxymethyl-7-nitro-1H-indole-2-carboxylic acid

The compound (3.5 g, 12.0 mmol) prepared in Preparation 26 was dissolved in a solvent mixture of tetrahydrofuran, methanol and water (1:1:1, 100 ml). Lithium hydroxide hydrate (1.5 g, 35.9 mmol) was added thereto, and the mixture was stirred for 3 h at room temperature. After distillation of the mixture under reduced pressure, 1 N hydrochloric acid was added to the residue. The mixture was extracted with ethyl acetate, dried over anhydrous magnesium sulfate, and filtered. The filtrate was distilled under reduced pressure and purified by column chromatography to give the title compound (2.3 g, Yield 81%).

¹H-NMR (500 HMz, DMSO-d₆); δ 11.02 (br s, 1H), 8.21 (s, 1H), 8.10 (s, 1H), 7.34 (s, 1H), 5.43 (br s, 1H), 4.64 (s, 2H)

Preparation 28

Synthesis of 2,2-dimethyl-propionic acid (R)-2-[(5-hydroxymethyl-7-nitro-1H-indole-2-carbonyl)-amino]-3-(4-methoxy-benzylsulfanyl)-propyl ester

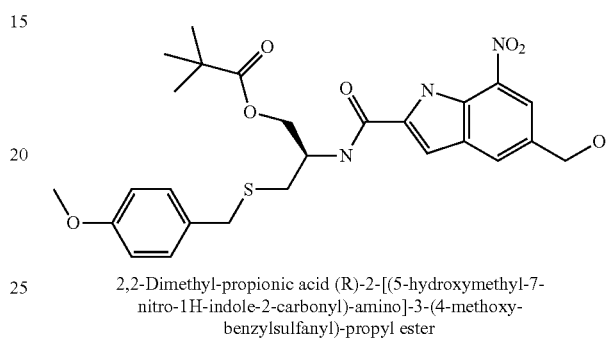

2,2-Dimethyl-propionic acid (R)-2-[(5-hydroxymethyl-7-nitro-1H-indole-2-carbonyl)-amino]-3-(4-methoxy-benzylsulfanyl)-propyl ester The compound (2.2 g, 9.3 mmol) prepared in Preparation 27 was reacted according to the same procedure as Step 2 of Preparation 19 to give the title compound (4.0 g, Yield 84%).

Preparation 29

Synthesis of 2,2-dimethyl-propionic acid (R)-2-(5-chloromethyl-7-nitro-1H-indol-2-yl)-4,5-dihydro-thiazol-4-ylmethyl ester

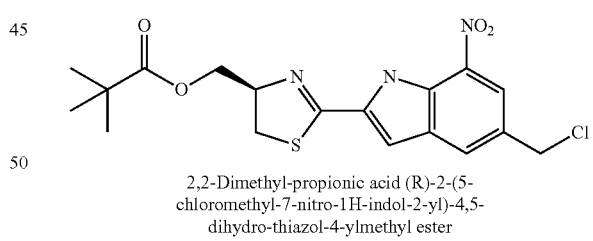

2,2-Dimethyl-propionic acid (R)-2-(5-chloromethyl-7-nitro-1H-indol-2-yl)-4,5-dihydro-thiazol-4-ylmethyl ester The compound (1.0 g, 1.9 mmol) prepared in Preparation 28 was dissolved in dichloromethane (30 ml). Phosphorus pentachloride (0.8 g, 3.9 mmol) was added thereto, and the mixture was stirred for 6 h at room temperature. After completion of the reaction, saturated sodium bicarbonate solution was added. The mixture was extracted with ethyl acetate, dried over anhydrous magnesium sulfate, and filtered. The filtrate was distilled under reduced pressure to give the title compound (0.7 g, Yield 90%).

¹H-NMR (500 HMz, CDCl₃); δ 12.89 (br s, 1H), 8.40 (s, 1H), 7.98 (s, 1H), 7.42 (s, 1H), 5.30 (m, 1H), 4.73 (s, 2H), 4.61 (m, 1H), 4.54 (m, 1H), 3.97 (m, 1H), 3.62 (m, 1H), 1.20 (s, 9H)

Example 20

Synthesis of {(R)-2-[5-morpholin-4-ylmethyl-7-(tetrahydro-pyran-4-ylamino)-1H-indol-2-yl]-4,5-dihydro-thiazol-4-yl}-methanol

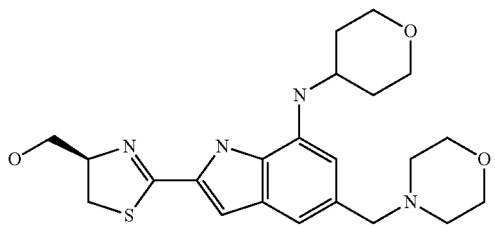

{(R)-2-[5-Morpholin-4-ylmethyl-7-(tetrahydro-pyran-4-ylamino)-1H-indol-2-yl]-4,5-dihydro-thiazol-4-yl}-methanol The compound prepared in Preparation 29, morpholine and tetrahydropyran-4-one were reacted according to the same procedures as Example 15, Preparation 20 and Example 1 in the order to give the title compound (20 mg, Yield 12%).

¹H-NMR (400 HMz, CDCl₃); δ 10.77 (br s, 1H), 7.06 (s, 1H), 6.95 (s, 1H), 6.62 (s, 1H), 4.80 (m, 1H), 4.11 (m, 1H), 3.99 (m, 2H), 3.76 (m, 1H), 3.75 (m, 4H), 3.51 (s, 2H), 3.45 (m, 5H), 2.51 (br s, 4H), 2.00 (m, 2H), 1.45 (m, 2H)

Example 21

Synthesis of [(R)-2-[7-cyclopentylamino-5-pyrazol-1-ylmethyl-1H-indol-2-yl]-4,5-dihydro-thiazol-4-yl}-methanol

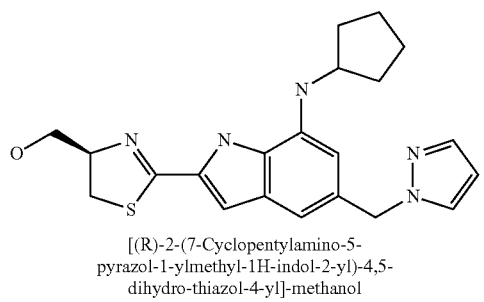

[(R)-2-(7-Cyclopentylamino-5-pyrazol-1-ylmethyl-1H-indol-2-yl)-4,5-dihydro-thiazol-4-yl]-methanol (Step 1)

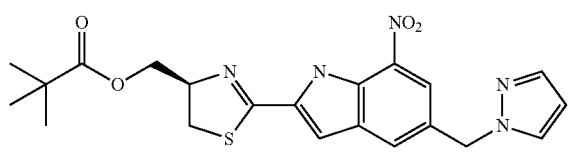

2,2-Dimethyl-propionic acid (R)-2-(7-nitro-5-pyrazol-1-ylmethyl-1H-indol-2-yl)-4,5-dihydro-thizaol-4-ylmethyl ester The compound (300 mg, 0.73 mmol) prepared in Preparation 29 was dissolved in N,N-dimethylformamide (10 ml). Potassium carbonate (300 mg, 2.2 mmol) and pyrazole (149 mg, 2.2 mmol) were added thereto, and the mixture was stirred for 1 h at room temperature. After completion of the reaction, water was added, and the mixture was extracted with ethyl acetate, dried over anhydrous magnesium sulfate, and filtered. The filtrate was distilled under reduced pressure to give a pyrazole compound (225 mg, Yield 70%).

(Step 2)

The compound (300 mg, 0.68 mmol) prepared in Step 1 was reacted according to the same procedures as Step 4 of Preparation 19, Preparation 20 and Example 1 in the order to give the title compound (42 mg, Yield 24%).

¹H-NMR (500 HMz, CDCl₃); δ 11.05 (brs, 1H), 7.52 (s, 1H), 7.34 (s, 1H), 6.93 (s, 1H), 6.87 (s, 1H), 6.34 (s, 1H), 6.23 (m, 1H), 5.30 (s, 2H), 4.71 (m, 1H), 3.99 (m, 1H), 3.66 (m, 2H), 3.42 (m, 2H), 1.86 (m, 2H), 1.52 (m, 4H), 1.26 (m, 2H)

Example 22

Synthesis of [(R)-2-(7-cyclopentylamino-5-imidazol-1-ylmethyl-1H-indol-2-yl)-4,5-dihydro-thiazol-4-yl}-methanol

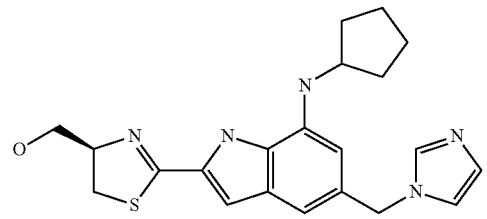

[(R)-2-(7-Cyclopentylamino-5-imidazol-1-ylmethyl-1H-indol-2-yl)-4,5-dihydro-thiazol-4-yl]-methanol The compound (300 mg, 0.73 mmol) prepared in Preparation 29 and imidazole instead of pyrazole were reacted according to the same procedure as Example 21 to give the title compound (65 mg, Yield 23%).

¹H-NMR (500 HMz, CDCl₃); δ 11.10 (brs, 1H), 8.20 (s, 1H), 7.25 (s, 1H), 7.23 (s, 1H), 6.87 (m, 2H), 6.16 (s, 1H), 5.05 (s, 2H), 4.77 (m, 1H), 3.96 (m, 1H), 3.73 (m, 2H), 3.43 (m, 2H), 1.92 (m, 2H), 1.59 (m, 4H), 1.38 (m, 2H)

Example 23

Synthesis of {(R)-2-[7-cyclopentylamino-5-(1H-pyrrol-3-ylmethyl)-1H-indol-2-yl]-4,5-dihydro-thiazol-4-yl}-methanol

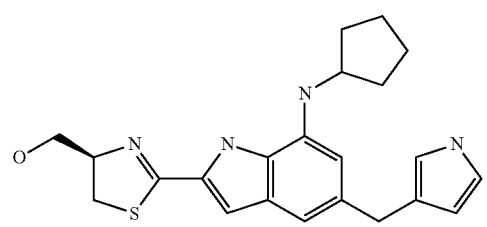

{(R)-2-[7-Cyclopentylamino-5-(1H-pyrrol-3-ylmethyl)-1H-indol-2-yl]-4,5-dihydro-thiazol-4-yl}-methanol The compound (300 mg, 0.73 mmol) prepared in Preparation 29 and pyrrole instead of pyrazole were reacted according to the same procedure as Example 21 to give the title compound (65 mg, Yield 23%).

¹H-NMR (500 HMz, CDCl₃); δ 11.04 (brs, 1H), 7.85 (s, 1H), 6.88 (m, 2H), 6.61 (s, 1H), 6.36 (s, 1H), 6.13 (m, 1H), 6.00 (s, 1H), 4.71 (m, 1H), 4.04 (m, 1H), 3.99 (s, 2H), 3.69 (m, 2H), 3.45 (m, 2H), 1.90 (m, 2H), 1.55 (m, 4H), 1.32 (m, 2H)

Example 24

Synthesis of [(R)-2-(7-cyclopentylamino-5-methanesulfonylmethyl-1H-indol-2-yl)-4,5-dihydro-thiazol-4-yl]-methanol

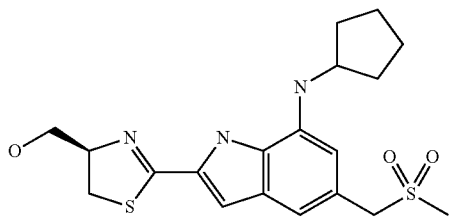

[(R)-2-(7-Cyclopentylamino-5-methanesulfonylmethyl-1H-indol-2-yl)-4,5-dihydro-thiazol-4-yl]-methanol The compound (330 mg, 0.81 mmol) prepared in Preparation 29 and sodium methanesulfinate instead of pyrazole were reacted according to the same procedure as Example 21 to give the title compound (152 mg, Yield 46%).

¹H-NMR (500 HMz, CDCl₃); δ 11.10 (brs, 1H), 7.01 (s, 1H), 6.88 (m, 1H), 6.49 (s, 1H), 4.76 (m, 1H), 4.26 (s, 2H), 3.99 (m, 1H), 3.79 (m, 1H), 3.68 (m, 1H), 3.43 (m, 2H), 2.73 (s, 3H), 1.96 (m, 2H), 1.57 (m, 4H), 1.35 (m, 2H)

Preparation 30

Synthesis of 2,2-dimethyl-propionic acid (R)-2-{[5-(2,2-dimethyl-propionyloxymethyl)-7-nitro-1H-indole-2-carbonyl]-amino}-3-(4-methoxy-benzylsulfanyl)-propyl ester

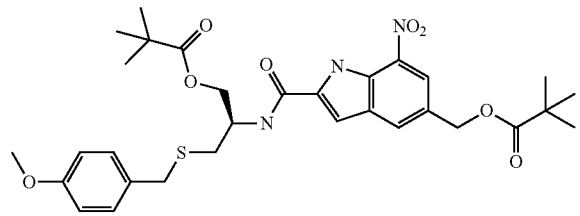

2,2-Dimethyl-propionic acid (R)-2-{[5-(2,2-dimethyl-propionyloxymethyl)-7-nitro-1H-indole-2-carbonyl]-amino}-3-(4-methoxy-benzylsulfanyl)-propyl ester The compound (3.1 g, 6.0 mmol) prepared in Preparation 28 was dissolved in dichloromethane (50 ml). Triethylamine (1.2 g, 12.0 mmol) and pivaloyl chloride (0.8 g, 6.6 mmol) were added thereto, and the mixture was stirred for 8 h at 0° C. After completion of the reaction, water was added, and the mixture was extracted with ethyl acetate, dried over anhydrous magnesium sulfate, and filtered. The filtrate was distilled under reduced pressure and purified by column chromatography to give the title compound (3.6 g, Yield 98%).

¹H-NMR (400 HMz, CDCl₃); δ 10.47 (brs, 1H), 8.27 (s, 1H), 8.01 (s, 1H), 7.27 (d, J=8.0 Hz, 2H), 6.92 (s, 1H), 6.83 (d, J=8.0 Hz, 2H), 6.76 (d, J=8.0 Hz, 1H), 5.25 (s, 2H), 4.56 (m, 1H), 4.42 (m, 1H), 4.22 (m, 1H), 3.75 (s, 3H), 3.74 (s, 2H), 2.82 (m, 1H), 2.69 (m, 1H), 1.25 (s, 9H), 1.20 (s, 9H)

Preparation 31

Synthesis of 2,2-dimethyl-propionic acid (R)-2-[5-(2,2-dimethyl-propionyloxymethyl)-7-nitro-1H-indol-2-yl]-4,5-dihydro-thiazol-4-ylmethyl ester

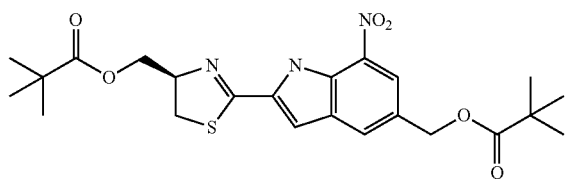

2,2-Dimethyl-propionic acid (R)-2-[5-(2,2-dimethyl-propionyloxymethyl)-7-nitro-1H-indol-2-yl]-4,5-dihydro-thiazol-4-ylmethyl ester The compound (3.6 g, 5.9 mmol) prepared in Preparation 30 was reacted according to the same procedure as Step 3 of Preparation 19 to give the title compound (2.0 g, Yield 72%).

¹H-NMR (400 HMz, CDCl₃); δ 12.91 (brs, 1H), 8.35 (s, 1H), 7.96 (s, 1H), 7.46 (s, 1H), 5.40 (m, 1H), 5.23 (s, 2H), 4.64 (m, 2H), 4.09 (m, 1H), 3.64 (m, 1H), 1.27 (s, 9H), 1.19 (s, 9H)

Preparation 32

Synthesis of 2,2-dimethyl-propionic acid (R)-2-[7-amino-5-(2,2-dimethyl-propionyloxymethyl)-1H-indol-2-yl]-4,5-dihydro-thiazol-4-ylmethyl ester

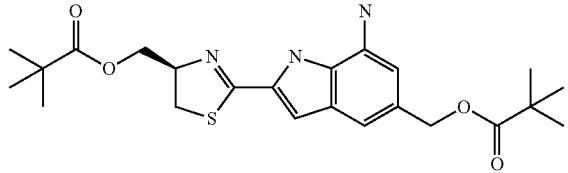

2,2-Dimethyl-propionic acid (R)-2-[7-amino-5-(2,2-dimethyl-propionyloxymethyl)-1H-indol-2-yl]-4,5-dihydro-thiazol-4-ylmethyl ester The compound (2.0 g, 4.2 mmol) prepared in Preparation 31 was reacted according to the same procedure as Step 4 of Preparation 19 to give the title compound (1.0 g, Yield 53%).

¹H-NMR (400 HMz, CDCl₃); δ 10.08 (brs, 1H), 7.26 (s, 1H), 6.87 (s, 1H), 6.60 (s, 1H), 5.09 (s, 2H), 4.95 (m, 1H), 4.40 (m, 2H), 3.58 (m, 1H), 3.35 (m, 1H), 1.20 (s, 9H), 1.12 (s, 9H)

Example 25

Synthesis of [7-cyclopentylamino-2-((R)-4-hydroxymethyl-4,5-dihydro-thiazol-2-yl)-1H-indol-5-yl]-methanol

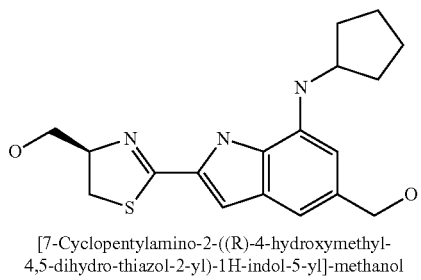

[7-Cyclopentylamino-2-((R)-4-hydroxymethyl-4,5-dihydro-thiazol-2-yl)-1H-indol-5-yl]-methanol The compound (100 mg, 0.22 mmol) prepared in Preparation 34 was reacted according to the same procedures as Preparation 20 and Example 1 to give the title compound (10 mg, Yield 13%).

$^1$H-NMR (400 HMz, CDCl$_3$); δ 9.63 (brs, 1H), 7.40 (s, 1H), 7.18 (s, 1H), 6.90 (s, 1H), 4.80 (m, 1H), 4.73 (s, 2H), 4.06 (m, 1H), 3.84 (m, 1H), 3.66 (m, 2H), 3.48 (m, 1H), 3.31 (m, 1H), 1.79 (m, 2H), 1.43 (m, 4H), 1.26 (m, 2H)

Preparation 35

Synthesis of 5-bromomethyl-7-nitro-indole-1,2-dicarboxylic acid 1-t-butyl ester 2-ethyl ester

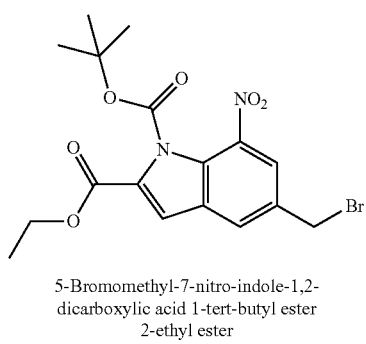

5-Bromomethyl-7-nitro-indole-1,2-dicarboxylic acid 1-tert-butyl ester 2-ethyl ester (Step 1)

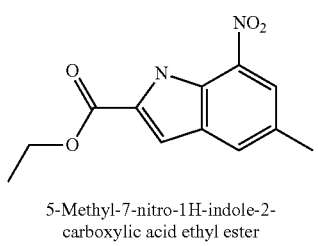

5-Methyl-7-nitro-1H-indole-2-carboxylic acid ethyl ester

4-Methyl-2-nitroaniline (20 g, 131 mmol) was reacted according to the same procedures as Preparation 1 and Preparation 2 to give 5-methyl-7-nitro-1H-indole-2-carboxylic acid ethyl ester (16 g, Yield 49%).

(Step 2)

The compound (15.1 g, 60.8 mmol) prepared in Step 1 was reacted according to the same procedures as Preparation 23 and Preparation 24 to give the title compound (6.3 g, Yield 24%).

Preparation 33

Synthesis of 5-chloro-7-nitro-1H-indole-2-carboxylic acid

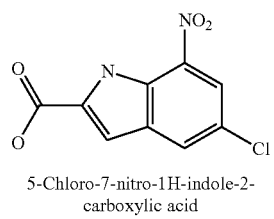

5-Chloro-7-nitro-1H-indole-2-carboxylic acid

The compound (15.0 g, 59.1 mmol) prepared in Preparation 5 was dissolved in tetrahydrofuran (300 ml) and methanol (100 ml). Lithium hydroxide monohydrate (7.43 g, 177 mmol) was dissolved in water (100 ml), and added to the reaction solution, which was then stirred for 3 h at room temperature. After completion of the reaction, the reaction solution was distilled under reduced pressure to remove tetrahydrofuran and methanol. The residue was neutralized to about pH 6 using 3N hydrochloric acid solution. The resulting solid was filtered and dried to give the title compound (13.1 g, Yield 92%).

Preparation 34

Synthesis of [(R)-2-(7-amino-5-chloro-1H-indol-2-yl)-4,5-dihydro-thiazol-4-yl]acetic acid methyl ester

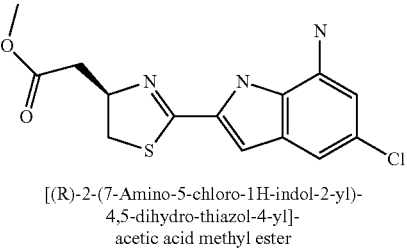

[(R)-2-(7-Amino-5-chloro-1H-indol-2-yl)-4,5-dihydro-thiazol-4-yl]-acetic acid methyl ester (Step 1)

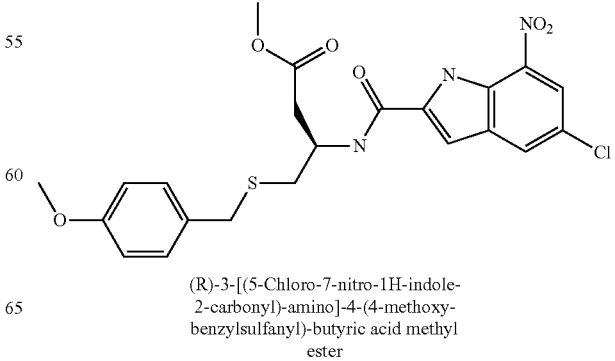

(R)-3-[(5-Chloro-7-nitro-1H-indole-2-carbonyl)-amino]-4-(4-methoxy-benzylsulfanyl)-butyric acid methyl ester The compound (12.5 g, 52.0 mmol) prepared in Preparation 33 and the compound (19.1 g, 62.4 mmol) prepared in Preparation 15 were dissolved in N,N-dimethylformamide (200 ml). Triethylamine (8.7 ml, 62.4 mmol), HOBT (14.0 g, 104 mmol) and EDC (16.9 g, 88.4 mmol) were added thereto, and the mixture was stirred for 4 h at room temperature. After completion of the reaction, the reaction solution was concentrated, extracted with ethyl acetate, and washed using saturated sodium bicarbonate solution and saturated aqueous ammonium chloride solution, respectively. The organic layer was concentrated and separated by column chromatography to give (R)-3-[(5-chloro-7-nitro-1H-indole-2-carbonyl)-amino]-4-(4-methoxy-benzylsulfanyl)-butyric acid methyl ester (20.2 g, 41.0 mmol, Yield 79%).

$^1$H-NMR (500 HMz, CDCl$_3$); δ 10.47 (br s, 1H), 8.24 (d, J=1.9 Hz, 1H), 7.96 (d, J=1.9 Hz, 1H), 7.24 (d, J=8.6 Hz, 2H), 6.89 (s, 1H), 6.81 (d, J=8.6 Hz, 2H), 4.58 (m, 1H), 3.75 (s, 3H), 3.73 (s, 2H), 3.71 (s, 3H), 2.86 (m, 1H), 2.80 (m, 1H), 2.73 (m, 1H), 2.70 (m, 1H)

(Step 2)

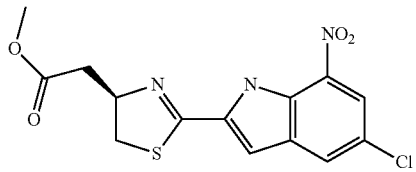

[(R)-2-(5-Chloro-7-nitro-1H-indol-2-yl)-
4,5-dihydro-thiazol-4-yl]-
acetic acid methyl ester The compound prepared in Step 1 was dissolved in dichloromethane (200 ml). Phosphorus pentachloride (17.1 g, 82 mmol) was added thereto, and the mixture was stirred for 1 h at room temperature. After completion of the reaction, the reaction solution was concentrated, and diethylether (200 ml) was added. The resulting solid was filtered and dried to give [(R)-2-(5-chloro-7-nitro-1H-indol-2-yl)-4,5-dihydro-thiazol-4-yl]-acetic acid methyl ester.

$^1$H-NMR (500 HMz, CDCl$_3$); δ 10.48 (br s, 1H), 8.22 (d, J=1.8 Hz, 1H), 7.94 (d, J=1.8 Hz, 1H), 7.29 (d, J=8.6 Hz, 2H), 6.96 (d, J=2.5 Hz, 1H), 6.89 (d, J=8.6 Hz, 2H), 5.00 (m, 1H), 3.76 (s, 3H), 3.71 (m, 1H), 3.26 (m, 1H), 2.99 (m, 1H), 2.67 (m, 1H)

(Step 3)

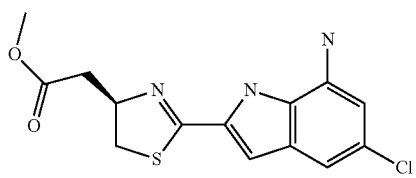

[(R)-2-(7-Amino-5-chloro-1H-indol-2-yl)-
4,5-dihydro-thiazol-4-yl]-
acetic acid methyl ester The compound prepared in Step 2 was dissolved in tetrahydrofuran (200 ml), methanol (200 ml) and water (200 ml). Iron powder (22.9 g, 410 mmol) and ammonium chloride (21.9 g, 410 mmol) were added thereto, and the mixture was stirred for 1 h at 60° C. using a mechanical stirrer. After completion of the reaction, tetrahydrofuran (300 ml) was added thereto. The mixture was filtered through a celite, washed with tetrahydrofuran (100 ml), distilled under reduced pressure, and concentrated. The residue was extracted with ethyl acetate, washed with saturated sodium chloride solution, dried over anhydrous magnesium sulfate, and filtered. The filtrate was distilled under reduced pressure, and purified by column chromatography to give the title compound (9.0 g, Yield 68%).

Example 26

Synthesis of [(R)-2-(5-chloro-7-cyclopentylamino-1H-indol-2-yl)-4,5-dihydro-thiazol-4-yl]acetic acid methyl ester

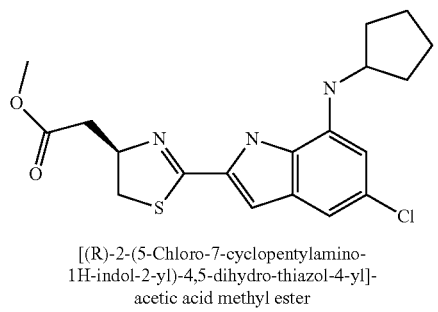

[(R)-2-(5-Chloro-7-cyclopentylamino-
1H-indol-2-yl)-4,5-dihydro-thiazol-4-yl]-
acetic acid methyl ester The compound (4.9 g, 15.1 mmol) prepared in Preparation 34 was dissolved in dichloroethane (100 ml). Cyclopentanone (2.7 ml, 30.3 mmol), acetic acid (0.86 ml, 15.1 mmol) and sodium triacetoxyborohydride (6.42 g, 30.3 mmol) were added thereto, and the mixture was stirred for 36 h at room temperature. After completion of the reaction, the reaction solution was washed with saturated aqueous sodium hydrogen carbonate solution (200 ml), concentrated, and separated by column chromatography to give the title compound (5.15 g, Yield 87%).

$^1$H NMR (DMSO-d$_6$, ppm); δ 11.51 (s, 1H), 6.79 (s, 1H), 6.79 (s, 1H), 6.16 (s, 1H), 6.13 (d, 1H), 4.85 (m, 1H), 3.80 (m, 1H), 3.62 (m, 1H), 3.58 (s, 3H), 3.19 (m, 1H), 2.71 (m, 1H), 2.63 (m, 1H), 1.93 (m, 2H), 1.69 (m, 2H), 1.56 (m, 4H)

FAB MS (m/e)=392

Example 27

Synthesis of [(R)-2-(5-chloro-7-cyclopentylamino-1H-indol-2-yl)-4,5-dihydro-thiazol-4-yl]acetic acid

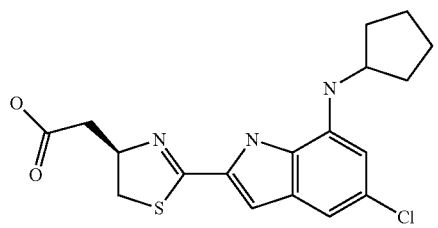

[(R)-2-(5-Chloro-7-cyclopentylamino-
1H-indol-2-yl)-4,5-dihydro-thiazol-4-yl]-
acetic acid The compound (1.5 g, 3.83 mmol) prepared in Example 26 was dissolved in tetrahydrofuran (100 ml) and methanol (50 ml). Lithium hydroxide monohydrate (640 mg, 15.3 mmol) was dissolved in water (50 ml) and added to the reaction solution, which was then stirred for 4 h at room temperature. After completion of the reaction, the reaction solution was distilled under reduced pressure to remove tetrahydrofuran and methanol. 1N hydrochloric acid solution was added to the residue, and the mixture was extracted with ethyl acetate, washed with saturated sodium chloride solution, dried over anhydrous magnesium sulfate, and filtered. The filtrate was distilled under reduced pressure and separated by column chromatography to give the title compound (13.1 g, Yield 92%).

$^1$H NMR (DMSO-$d_6$, ppm); δ 12.51 (br s, 1H), 11.51 (s, 1H), 6.79 (s, 1H), 6.79 (s, 1H), 6.16 (s, 1H), 6.14 (d, 1H), 4.87 (m, 1H), 3.80 (m, 1H), 3.61 (m, 1H), 3.19 (m, 1H), 2.72 (m, 1H), 2.64 (m, 1H), 1.93 (m, 2H), 1.69 (m, 2H), 1.56 (m, 4H)

FAB MS (m/e)=378

Example 28

Synthesis of [(R)-2-(5-chloro-7-cyclopentylamino-1H-indol-2-yl)-4,5-dihydro-thiazol-4-yl]acetic acid ethyl ester

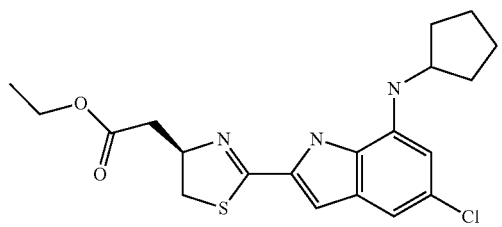

[(R)-2-(5-Chloro-7-cyclopentylamino-1H-indol-2-yl)-4,5-dihydro-thiazol-4-yl]-acetic acid ethyl ester The compound (4.5 g, 18.7 mmol) prepared in Preparation 33 and the compound (6.3 g, 19.7 mmol) prepared in Preparation 16 were reacted according to the same procedures as Preparation 34 and Example 26 to give the title compound (840 mg, Yield 11%).

$^1$H-NMR (500 HMz, CDCl$_3$); δ 10.01 (brs, 1H), 6.99 (s, 1H), 6.80 (s, 2H), 6.43 (s, 1H), 5.03 (m, 1H), 4.07 (q, 2H), 3.81 (m, 1H), 3.64 (m, 1H), 3.21 (m, 1H), 2.81 (m, 1H), 2.67 (m, 1H), 2.04 (m, 2H), 1.64 (m, 4H), 1.49 (m, 2H), 1.20 (t, 3H)

Example 29

Synthesis of 2-[(R)-2-(5-chloro-7-cyclopentylamino-1H-indol-2-yl)-4,5-dihydro-1,3-thiazol-4-yl]-ethanol

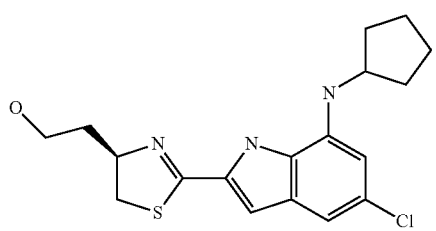

2-[(R)-2-(5-Chloro-7-cyclopentylamino-1H-indol-2-yl)-4,5-dihydro-thiazol-4-yl]-ethanol The compound (550 mg, 1.4 mmol) prepared in Example 26 was dissolved in tetrahydrofuran (50 ml). 1 M lithium borohydride tetrahydrofuran solution (2.11 ml, 2.11 mmol) was added thereto, and the mixture was stirred for 1 h while raising the reaction temperature from −60° C. to 0° C. After completion of the reaction, water was added. The mixture was extracted with ethyl acetate, washed with saturated sodium chloride solution, dried over anhydrous magnesium sulfate, and filtered. The filtrate was distilled under reduced pressure, and separated by column chromatography to give the title compound (510 mg, Yield 100%).

$^1$H NMR (DMSO-$d_6$, ppm); δ 11.47 (1H, s), 6.79 (1H, s), 6.67 (1H, s), 6.11 (1H, s), 6.09 (1H, m), 4.65 (1H, t), 4.54 (1H, m), 3.80 (2H, m), 3.61 (2H, m), 3.52 (1H, m), 3.15 (1H, m), 2.47 (1H, m), 1.97 (2H, m), 1.68 (2H, m), 1.54 (4H, m)

FAB MS (m/e)=364

Example 30

Synthesis of {(R)-2-[5-chloro-7-(tetrahydro-pyran-4-ylamino)-1H-indol-2-yl]-4,5-dihydro-thiazol-4-yl}acetic acid methyl ester

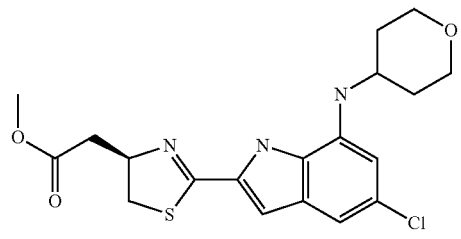

{(R)-2-[5-Chloro-7-(tetrahydro-pyran-4-ylamino)-1H-indol-2-yl]-4,5-dihydro-thiazol-4-yl}-acetic acid methyl ester The compound (1.0 g, 3.1 mmol) prepared in Preparation 34 was dissolved in 1,2-dichloroethane (100 ml). Tetrahydro-4H-pyran-4-one (0.57 ml, 6.18 mmol), sodium triacetoxyborohydride (1.31 g, 6.18 mmol) and acetic acid (0.18 ml, 3.09 mmol) were added thereto, and the mixture was stirred for 24 h at room temperature. After completion of the reaction, the reaction solution was diluted with dichloromethane, washed with saturated sodium bicarbonate solution, dried over anhydrous magnesium sulfate, and filtered. The filtrate was distilled under reduced pressure, and purified by column chromatography to give the title compound (0.5 g, Yield 40%).

$^1$H NMR (DMSO-$d_6$, ppm); δ 11.52 (1H, s), 6.81 (1H, s), 6.71 (1H, s), 6.28 (1H, s), 6.07 (1H, d), 4.90 (1H, m), 3.86 (2H, m), 3.64 (3H, s), 3.62 (2H, m), 3.44 (2H, t), 2.82-2.71 (2H, m), 1.94 (2H, m), 1.40 (2H, m)

FAB MS (m/e)=408

Example 31

Synthesis of {(R)-2-[5-chloro-7-(tetrahydro-pyran-4-ylamino)-1H-indol-2-yl]-4,5-dihydro-thiazol-4-yl}-acetic acid

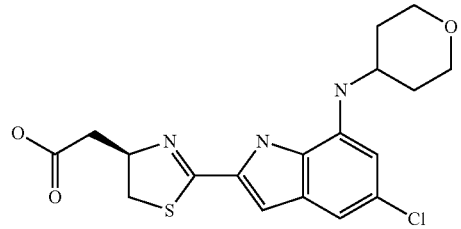

{(R)-2-[5-Chloro-7-(tetrahydro-pyran-4-ylamino)-1H-indol-2-yl]-4,5-dihydro-thiazol-4-yl}-acetic acid The compound (400 mg, 1.0 mmol) prepared in Example 30 was reacted according to the same procedure as Example 27 to give the title compound (360 mg, Yield 92%).

$^1$H NMR (DMSO-d$_6$, ppm); δ 12.43 (1H, s, br), 11.53 (1H, s), 6.81 (1H, s), 6.71 (1H, s), 6.28 (1H, s), 6.06 (1H, d), 4.87 (1H, m), 3.87 (2H, m), 3.62 (2H, m), 3.44 (2H, t), 3.19 (1H, m), 3.74 (1H, m), 2.63 (1H, m), 1.94 (2H, m), 1.41 (2H, m)

FAB MS (m/e)=394

Example 32

Synthesis of 2-{(R)-2-[5-chloro-7-(tetrahydro-pyran-4-ylamino)-1H-indol-2-yl]-4,5-dihydro-thiazol-4-yl}-ethanol

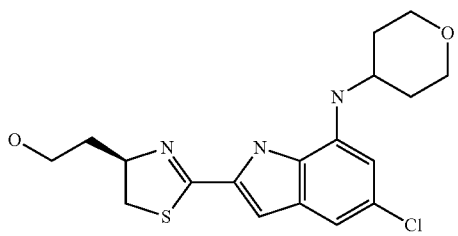

2-{(R)-2-[5-Chloro-7-(tetrahydro-pyran-4-ylamino)-1H-indol-2-yl]-4,5-dihydro-thiazol-4-yl}-ethanol The compound (2.5 g, 6.12 mmol) prepared in Example 30 was reacted according to the same procedure as Example 29 to give the title compound (2.19 g, 5.76 mmol, Yield 94%).

$^1$H NMR (DMSO-d$_6$, ppm); δ 11.48 (1H, s), 6.81 (1H, s), 6.68 (1H, s), 6.28 (1H, s), 6.05 (1H, d), 4.66 (1H, quin), 4.54 (1H, t), 3.87 (2H, m), 3.61-3.54 (3H, m), 3.44 (2H, t), 3.15 (1H, m), 1.99-1.93 (3H, m), 1.73 (1H, m), 1.40 (2H, m), 1.20 (1H, m)

FAB MS (m/e)=380

Preparation 35

Synthesis of [(R)-2-(7-amino-5-bromo-1H-indol-2-yl)-4,5-dihydro-thiazol-4-yl]-acetic acid methyl ester

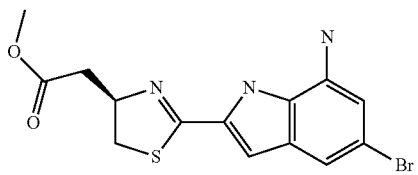

[(R)-2-(7-Amino-5-bromo-1H-indol-2-yl)-4,5-dihydro-thiazol-4-yl]-acetic acid methyl ester Methyl 5-bromo-7-nitro-1H-indole-2-carboxylate (2.7 g, 9.0 mmol) prepared in Preparation 6 was reacted according to the same procedures as Preparation 33 and Preparation 34 to give the title compound (585 mg, Yield 18%).

Example 33

Synthesis of [(R)-2-(5-bromo-7-cyclopentylamino-1H-indol-2-yl)-4,5-dihydro-thiazol-4-yl]acetic acid

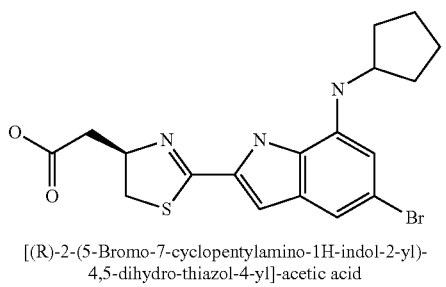

[(R)-2-(5-Bromo-7-cyclopentylamino-1H-indol-2-yl)-4,5-dihydro-thiazol-4-yl]-acetic acid The compound (340 mg, 0.9 mmol) prepared in Preparation 35 was reacted according to the same procedures as Example 26 and Example 27 to give the title compound (250 mg, Yield 66%).

$^1$H-NMR (400 HMz, CDCl$_3$); δ 12.50 (br s, 1H), 7.10 (sm 1H), 7.06 (s, 1H), 6.56 (s, 1H), 5.31 (m, 1H), 3.89 (m, 2H), 3.40 (m, 1H), 2.99 (m, 1H), 2.83 (m, 1H), 2.08 (m, 2H), 1.86 (m, 2H), 1.66 (m, 4H)

Example 34

Synthesis of 2-[(R)-2-(5-bromo-7-cyclopentylamino-1H-indol-2-yl)-4,5-dihydro-1,3-thiazol-4-yl]-ethanol

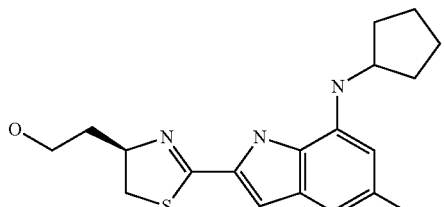

2-[(R)-2-(5-Bromo-7-cyclopentylamino-1H-indol-2-yl)-4,5-dihydro-thiazol-4-yl]-ethanol (Step 1)

The compound (582 mg, 1.58 mmol) prepared in Preparation 35 was reacted according to the same procedure as Example 26 to give a cyclopentylamine compound (430 mg, Yield 62%).

(Step 2)

The compound (150 mg, 0.34 mmol) prepared in Step 1 was dissolved in tetrahydrofuran (8 ml). Lithium borohydride (15 mg, 0.69 mmol) was added thereto, and the mixture was stirred for 1 h at room temperature. After completion of the reaction, water was added. The mixture was extracted with ethyl acetate, washed with saturated sodium chloride solution, dried over anhydrous magnesium sulfate, and filtered. The filtrate was distilled under reduced pressure, and separated by column chromatography to give the title compound (135 mg, Yield 96%).

¹H-NMR (400 HMz, CDCl₃); δ 10.42 (br s, 1H), 7.18 (s, 1H), 6.87 (s, 1H), 6.59 (d, 1H), 4.67 (m, 2H), 4.02 (m, 2H), 3.91 (m, 1H), 3.63 (m, 1H), 3.16 (t, 1H), 2.10 (m, 4H), 1.74 (m, 2H), 1.4 (m, 4H)

Example 35

Synthesis of {(R)-2-[5-bromo-7-(tetrahydro-pyran-4-ylamino)-1H-indol-2-yl]-4,5-dihydro-thiazol-4-yl}-acetic acid

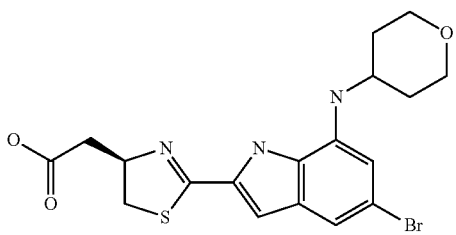

{(R)-2-[5-Bromo-7-(tetrahydro-pyran-4-ylamino)-1H-indol-2-yl]-4,5-dihydro-thiazol-4-yl}-acetic acid The compound (50 mg, 0.14 mmol) prepared in Preparation 44 was reacted according to the same procedures as Example 30 and Example 27 to give the title compound (54 mg, Yield 88%).

¹H-NMR (400 HMz, CDCl₃); δ 7.07 (m, 2H), 6.50 (s, 1H), 5.10 (m, 1H), 4.03 (m, 2H), 3.91 (m, 1H), 3.70-3.41 (m, 4H), 3.11 (m, 1H), 2.83 (m, 2H), 2.52 (m, 1H), 2.04 (m, 2H), 1.69 (m, 2H)

Example 36

Synthesis of 2-{(R)-2-[5-bromo-7-(tetrahydro-pyran-4-ylamino)-1H-indol-2-yl]-4,5-dihydro-thiazol-4-yl}-ethanol

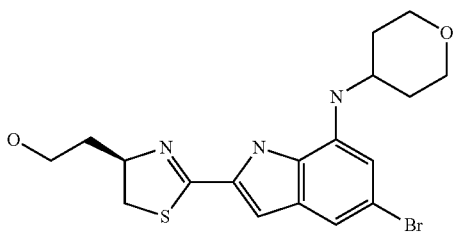

2-{(R)-2-[5-Bromo-7-(tetrahydro-pyran-4-ylamino)-1H-indol-2-yl]-4,5-dihydro-thiazol-4-yl}-ethanol The compound (50 mg, 0.14 mmol) prepared in Preparation 35 was reacted according to the same procedures as Example 30 and Step 2 of Example 34 to give the title compound (35 mg, Yield 59%).

¹H-NMR (400 HMz, CDCl₃); δ 10.50 (br s, 1H), 7.19 (s, 1H), 6.89 (s, 1H), 6.59 (d, 1H), 4.67 (m, 2H), 4.05 (m, 4H), 3.63 (m, 4H), 3.18 (t, 1H), 2.12 (m, 4H), 1.64 (m, 4H)

Preparation 36

Synthesis of [(R)-2-(7-amino-5-fluoro-1H-indol-2-yl)-4,5-dihydro-thiazol-4-yl]-acetic acid methyl ester

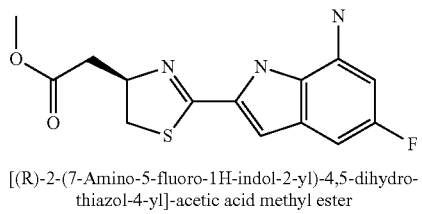

[(R)-2-(7-Amino-5-fluoro-1H-indol-2-yl)-4,5-dihydro-thiazol-4-yl]-acetic acid methyl ester Ethyl 5-fluoro-7-nitro-1H-indole-2-carboxylate (2.3 g, 9.1 mmol) prepared in Preparation 2 was reacted according to the same procedures as Preparation 33 and Preparation 34 to give the title compound (650 mg, Yield 23%).

Example 37

Synthesis of [(R)-2-(7-cyclopentylamino-5-fluoro-1H-indol-2-yl)-4,5-dihydro-thiazol-4-yl]acetic acid

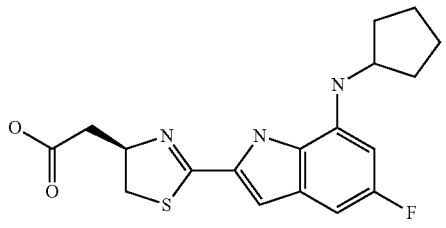

[(R)-2-(7-Cyclopentylamino-5-fluoro-1H-indol-2-yl)-4,5-dihydro-thiazol-4-yl]-acetic acid The compound (361 mg, 1.2 mmol) prepared in Preparation 36 was reacted according to the same procedures as Example 26 and Example 27 to give the title compound (189 mg, Yield 44%).

¹H-NMR (400 HMz, CDCl₃); δ 11.09 (br s, 1H), 6.73 (s, 1H), 6.45 (dd, 1H), 6.07 (dd, 1H), 4.98 (m, 1H), 3.79 (m, 1H), 3.59 (m, 1H), 3.16 (m, 1H), 2.79 (m, 1H), 2.60 (m, 1H), 1.96 (m, 2H), 1.71 (m, 2H), 1.58 (m, 4H)

Example 38

Synthesis of [(R)-2-(7-cyclopentylamino-5-fluoro-1H-indol-2-yl)-4,5-dihydro-thiazol-4-yl]acetic acid ethyl ester

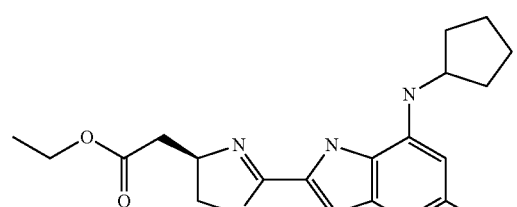

[(R)-2-(7-Cyclopentylamino-5-fluoro-1H-indol-2-yl)-4,5-dihydro-thiazol-4-yl]-acetic acid ethyl ester The compound (80 mg, 0.22 mmol) prepared in Example 37 was dissolved in ethanol (2 ml). Acetyl chloride (0.1 ml) was added thereto, and the mixture was stirred for 8 h at room temperature. After completion of the reaction, the reaction solution was diluted with ethyl acetate, washed with saturated sodium bicarbonate solution, dried over anhydrous magnesium sulfate, and filtered. The filtrate was distilled under reduced pressure, and purified by column chromatography to give the title compound (50 mg, Yield 58%).

$^1$H-NMR (400 HMz, CDCl$_3$); δ 10.71 (br s, 1H), 6.86 (s, 1H), 6.64 (dd, 1H), 6.23 (dd, 1H), 5.07 (m, 1H), 3.99 (q, 2H), 3.91 (m, 1H), 3.76 (m, 1H), 3.64 (m, 1H), 3.22 (m, 1H), 2.88 (m, 1H), 2.65 (m, 1H), 2.00 (m, 2H), 1.63 (m, 4H), 1.40 (m, 2H), 1.12 (t, 3H)

Example 39

Synthesis of 2-[(R)-2-(7-cyclopentylamino-5-fluoro-1H-indol-2-yl)-4,5-dihydro-thiazol-4-yl]-ethanol

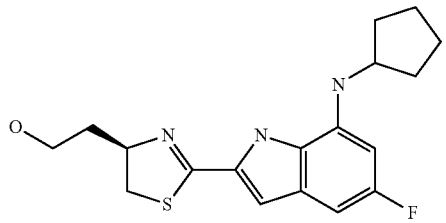

2-[(R)-2-(7-Cyclopentylamino-5-fluoro-1H-indol-2-yl)-4,5-dihydro-thiazol-4-yl]-ethanol The compound (90 mg, 0.29 mmol) prepared in Preparation 36 was reacted according to the same procedures as Example 26 and Step 2 of Example 34 to give the title compound (46 mg, Yield 46%).

$^1$H-NMR (400 HMz, CDCl$_3$); δ 10.90 (br s, 1H), 6.91 (s, 1H), 6.65 (dd, 1H), 6.26 (dd, 1H), 4.68 (m, 1H), 4.08 (m, 2H), 3.88 (m, 1H), 3.62 (m, 1H), 3.15 (t, 1H), 2.10 (m, 4H), 1.74 (m, 2H), 1.62 (m, 4H)

Example 40

Synthesis of {(R)-2-[5-fluoro-7-(tetrahydro-pyran-4-ylamino)-1H-indol-2-yl]-4,5-dihydro-thiazol-4-yl}-acetic acid

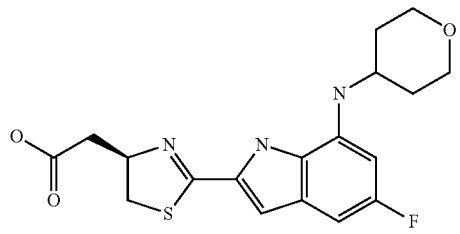

{(R)-2-[5-Fluoro-7-(tetrahydro-pyran-4-ylamino)-1H-indol-2-yl]-4,5-dihydro-thiazol-4-yl}-acetic acid The compound (852 mg, 2.8 mmol) prepared in Preparation 36 was reacted according to the same procedures as Example 30 and Example 27 to give the title compound (970 mg, Yield 92%).

$^1$H-NMR (400 HMz, DMSO-d$_6$); δ 11.45 (s, 1H), 6.75 (d, 1H), 6.22 (dd, 1H), 6.16 (d, J=6.8 Hz, 1H), 4.91 (m, 1H), 3.88 (m, 2H), 3.66 (m, 1H), 3.61 (m, 1H), 3.48 (m, 2H), 3.22 (m, 1H), 2.80 (m, 1H), 2.65 (m, 1H), 2.99 (m, 2H), 1.40 (m, 2H)

Example 41

Synthesis of 2-{(R)-2-[5-fluoro-7-(tetrahydro-pyran-4-ylamino)-1H-indol-2-yl]-4,5-dihydro-thiazol-4-yl}-ethanol

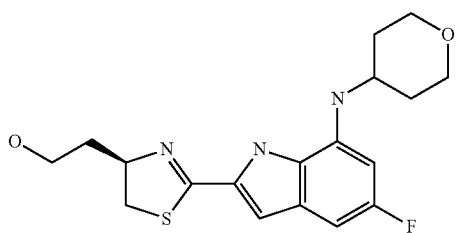

2-{(R)-2-[5-Fluoro-7-(tetrahydro-pyran-4-ylamino)-1H-indol-2-yl]-4,5-dihydro-thiazol-4-yl}-ethanol The compound (1.24 g, 4.0 mmol) prepared in Preparation 36 was reacted according to the same procedures as Example 30 and Step 2 of Example 34 to give the title compound (810 mg, Yield 55%).

$^1$H-NMR (400 HMz, CDCl$_3$); δ 10.69 (br s, 1H), 6.87 (s, 1H), 6.63 (d, 1H), 6.22 (d, 1H), 4.87 (m, 1H), 4.66 (m, 1H), 4.02 (m, 4H), 3.55 (m, 4H), 3.15 (m, 1H), 2.04 (m, 4H), 1.54 (m, 2H)

Preparation 37

Synthesis of [(R)-2-(7-amino-1H-indol-2-yl)-4,5-dihydro-thiazol-4-yl]-acetic acid methyl ester

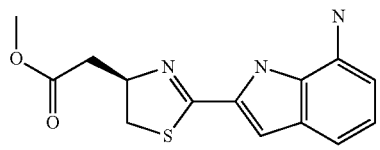

[(R)-2-(7-Amino-1H-indol-2-yl)-4,5-dihydro-thiazol-4-yl]-acetic acid methyl ester Methyl 7-nitro-1H-indole-2-carboxylate (14.0 g, 63.6 mmol) prepared in Preparation 8 was reacted according to the same procedures as Preparation 33 and Preparation 34 to give the title compound (6.5 g, Yield 35%).

Example 42

Synthesis of [(R)-2-(7-cyclopentylamino-1H-indol-2-yl)-4,5-dihydro-thiazol-4-yl]acetic acid

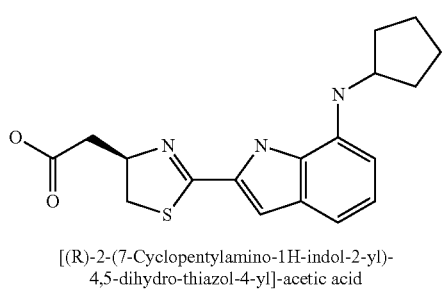

[(R)-2-(7-Cyclopentylamino-1H-indol-2-yl)-
4,5-dihydro-thiazol-4-yl]-acetic acid (Step 1)

The compound (5.0 g, 17.3 mmol) prepared in Preparation 37 was reacted according to the same procedure as Example 26 to give a methyl ester compound.

(Step 2)

The compound prepared in Step 1 was reacted according to the same procedure as Example 27 to give the title compound (5.44 g, 2 steps, Yield 91%).

$^1$H-NMR (400 HMz, CDCl$_3$); δ 11.77 (br s, 1H), 7.04 (d, 1H), 6.97 (m, 2H), 6.43 (d, 1H), 5.34 (m, 1H), 3.88 (m, 1H), 3.69 (m, 1H), 3.19 (m, 1H), 2.72 (m, 1H), 2.60 (m, 1H), 2.01 (m, 2H), 1.74 (m, 2H), 1.59 (m, 4H)

Example 43

Synthesis of [(R)-2-(7-cyclopentylamino-1H-indol-2-yl)-4,5-dihydro-thiazol-4-yl]acetic acid ethyl ester

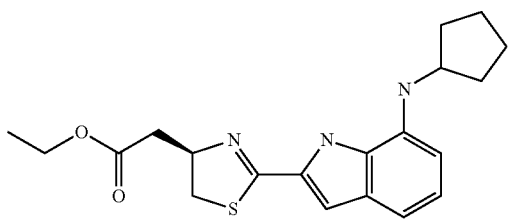

[(R)-2-(7-Cyclopentylamino-1H-indol-2-yl)-
4,5-dihydro-thiazol-4-yl]-acetic acid ethyl ester The compound (500 mg, 1.46 mmol) prepared in Example 42 was reacted according to the same procedure as Example 38 to give the title compound (420 mg, Yield 78%).

$^1$H-NMR (400 HMz, CDCl$_3$); δ 10.12 (br s, 1H), 7.05 (m, 1H), 6.99 (m, 1H), 6.91 (d, 1H), 6.51 (d, 1H), 5.07 (m, 1H), 4.09 (q, 2H), 3.87 (m, 1H), 3.65 (m, 1H), 3.21 (m, 1H), 2.86 (m, 1H), 2.65 (m, 1H), 2.01 (m, 2H), 1.74 (m, 2H), 1.62 (m, 4H), 1.46 (m, 2H), 1.81 (t, 3H)

Example 44

Synthesis of 2-[(R)-2-(7-cyclopentylamino-1H-indol-2-yl)-4,5-dihydro-thiazol-4-yl]ethanol

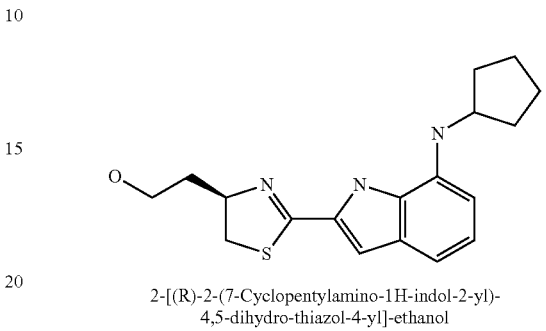

2-[(R)-2-(7-Cyclopentylamino-1H-indol-2-yl)-
4,5-dihydro-thiazol-4-yl]-ethanol

The compound (1.46 g, 5.06 mmol) prepared in Preparation 37 was reacted according to the same procedures as Example 26 and Step 2 of Example 34 to give the title compound (1.44 g, Yield 78%).

$^1$H NMR (DMSO-d$_6$, ppm); δ 11.28 (1H, s), 6.77-6.74 (2H, m), 6.69 (1H, s), 6.25 (1H, d), 5.78 (1H, d), 4.65 (1H, quin), 4.53 (1H, t), 3.82 (1H, m), 3.60 (2H, m), 3.51 (1H, m), 3.11 (1H, m), 1.99-1.91 (3H, m), 1.75-1.67 (3H, m), 1.56-1.54 (4H, m)

FAB MS (m/e)=330

Example 45

Synthesis of {(R)-2-[7-(tetrahydro-pyran-4-ylamino)-1H-indol-2-yl]-4,5-dihydro-thiazol-4-yl}-acetic acid

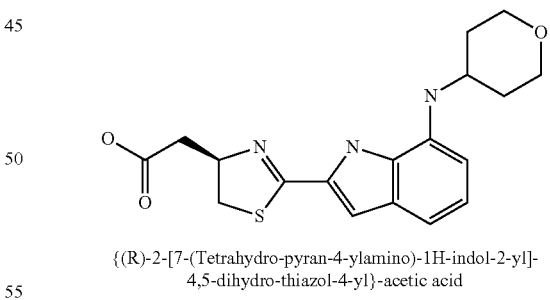

{(R)-2-[7-(Tetrahydro-pyran-4-ylamino)-1H-indol-2-yl]-
4,5-dihydro-thiazol-4-yl}-acetic acid The compound (1.32 g, 4.58 mmol) prepared in Preparation 37 was reacted according to the same procedures as Example 30 and Example 27 to give the title compound (1.25 g, Yield 76%).

$^1$H NMR (DMSO-d$_6$, ppm); δ 12.42 (1H, s, br), 11.34 (1H, s), 6.80 (1H, d), 6.72 (1H, s), 6.33 (1H, d), 5.79 (1H, d), 4.86 (1H, quin), 3.88 (2H, m), 3.60-3.52 (2H, m), 3.42 (2H, t), 3.17 (1H, m), 2.74 (1H, m), 2.59 (1H, m), 1.94 (2H, m), 1.39 (2H, m)

FAB MS (m/e)=360

Example 46

Synthesis of 2-{(R)-2-[7-(tetrahydro-pyran-4-ylamino)-1H-indol-2-yl]-4,5-dihydro-thiazol-4-yl}-ethanol

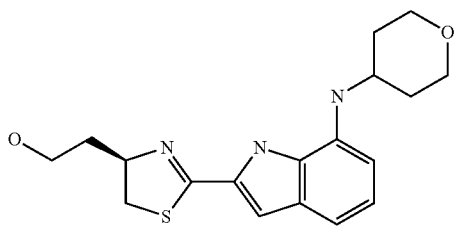

2-{(R)-2-[7-(Tetrahydro-pyran-4-ylamino)-
1H-indol-2-yl]-4,5-dihyrdro-thiazol-4-yl}-
ethanol The compound (529 mg, 1.83 mmol) prepared in Preparation 37 was reacted according to the same procedures as Example 30 and Step 1 of Example 34 to give the title compound (340 mg, Yield 54%).

$^1$H NMR (DMSO-$d_6$, ppm); δ 11.29 (1H, s), 6.79 (2H, m), 6.70 (1H, s), 6.33 (1H, d), 5.76 (1H, d), 4.66 (1H, quin), 4.54 (1H, t), 3.88 (2H, m), 3.62-3.59 (3H, m), 3.53 (1H, t), 3.43 (2H, m), 3.12 (1H, m), 1.96 (3H, m), 1.75 (1H, m), 1.40 (2H, m)

FAB MS (m/e)=346

Preparation 38

Synthesis of [(R)-2-(7-amino-5-methoxy-1H-indol-2-yl)-4,5-dihydro-thiazol-4-yl]acetic acid methyl ester

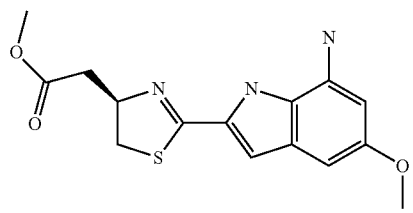

[(R)-2-(7-Amino-5-methoxy-1H-indol-2-yl)-
4,5-dihydro-thiazol-4-yl]-
acetic acid methyl ester Methyl 5-methoxy-7-nitro-1H-indole-2-carboxylate (2.5 g, 6.0 mmol) prepared in Preparation 9 was reacted according to the same procedures as Preparation 33 and Preparation 34 to give the title compound (1.0 g, Yield 52%).

Example 47

Synthesis of [(R)-2-(7-cyclopentylamino-5-methoxy-1H-indol-2-yl)-4,5-dihydro-thiazol-4-yl]-acetic acid methyl ester

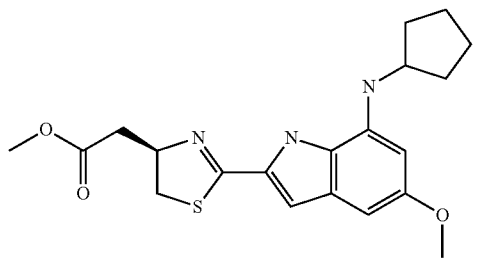

[(R)-2-(7-Cyclopentylamino-5-methoxy-
1H-indol-2-yl)-4,5-dihydro-thiazol-4-yl]-
acetic acid methyl ester The compound (1.0 g, 3.13 mmol) prepared in Preparation 38 was reacted according to the same procedure as Example 26 to give the title compound (490 g, Yield 40%).

$^1$H NMR (DMSO-$d_6$, ppm); δ 11.24 (1H, s), 6.62 (1H, s), 6.22 (1H, s), 5.89 (1H, d), 5.84 (1H, s), 4.83 (1H, quin), 3.77 (1H, m), 3.64 (3H, s), 3.59 (3H, s), 3.56 (1H, m), 3.15 (1H, m), 2.69 (1H, m), 2.58 (1H, m), 1.90 (2H, m), 1.67 (2H, m), 1.51 (4H, m)

FAB MS (m/e)=388

Example 48

Synthesis of [(R)-2-(7-cyclopentylamino-5-methoxy-1H-indol-2-yl)-4,5-dihydro-thiazol-4-yl]-acetic acid

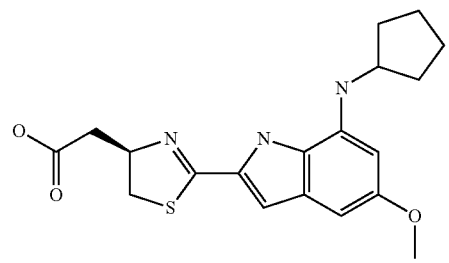

[(R)-2-(7-Cyclopentylamino-5-methoxy-
1H-indol-2-yl)-4,5-dihydro-thiazol-4-yl]-
acetic acid The compound (300 mg, 0.78 mmol) prepared in Example 47 was reacted according to the same procedure as Example 27 to give the title compound (240 mg, Yield 82%).

$^1$H NMR (DMSO-$d_6$, ppm); δ 12.54 (1H, s, br), 11.21 (1H, s), 6.63 (1H, s), 6.23 (1H, s), 5.89 (1H, d), 5.84 (1H, s), 4.84 (1H, quin), 3.77 (1H, m), 3.64 (3H, s), 3.56 (1H, m), 3.15 (1H, m), 2.69 (1H, m), 2.58 (1H, m), 1.90 (2H, m), 1.67 (2H, m), 1.52 (4H, m)

FAB MS (m/e)=374

Example 49

Synthesis of [(R)-2-(7-cyclopentylamino-5-methoxy-1H-indol-2-yl)-4,5-dihydro-thiazol-4-yl]-acetic acid ethyl ester

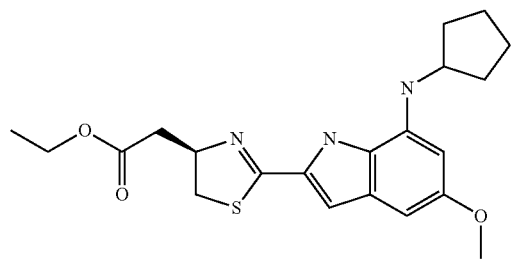

[(R)-2-(7-Cyclopentylamino-5-methoxy-
1H-indol-2-yl)-4,5-dihydro-thiazol-4-yl]-
acetic acid ethyl ester The compound (200 mg, 0.54 mmol) prepared in Example 48 was reacted according to the same procedure as Example 38 to give the title compound (124 mg, Yield 57%).

¹H-NMR (400 HMz, CDCl₃); δ 10.73 (br s, 1H), 6.83 (s, 1H), 6.43 (s, 1H), 6.16 (s, 1H), 5.07 (m, 1H), 4.00-3.88 (m, 3H), 3.80 (s, 3H), 3.76 (m, 1H), 3.62 (m, 1H), 3.20 (m, 1H), 2.83 (m, 1H), 2.63 (m, 1H), 1.98 (m, 2H), 1.61 (m, 4H), 1.40 (m, 2H), 1.12 (t, 3H)

Example 50

Synthesis of {(R)-2-[5-methoxy-7-(tetrahydro-pyran-4-ylamino)-1H-indol-2-yl]-4,5-dihydro-thiazol-4-yl}-acetic acid methyl ester

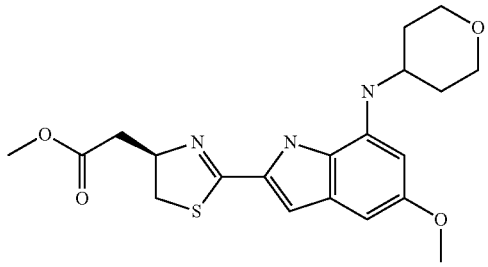

{(R)-2-[5-Methoxy-7-(tetrahydro-pyran-4-ylamino)-1H-indol-2-yl]-4,5-dihydro-thiazol-4yl}-acetic acid methyl ester The compound (4.8 g, 14.8 mmol) prepared in Preparation 38 was reacted according to the same procedure as Example 30 to give the title compound (2.5 g, Yield 42%).

Example 51

Synthesis of {(R)-2-[5-methoxy-7-(tetrahydro-pyran-4-ylamino)-1H-indol-2-yl]-4,5-dihydro-thiazol-4-yl}-acetic acid

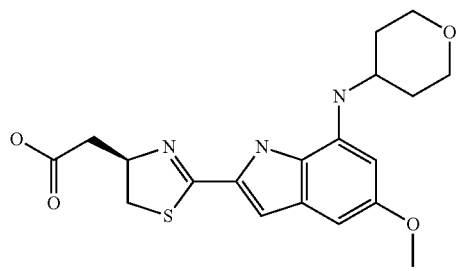

{(R)-2-[5-Methoxy-7-(tetrahydro-pyran-4-ylamino)-1H-indol-2-yl]-4,5-dihydro-thiazol-4-yl}-acetic acid The compound (30 mg, 0.07 mmol) prepared in Example 50 was reacted according to the same procedure as Example 27 to give the title compound (8.7 g, Yield 30%).

¹H-NMR (500 HMz, DMSO-d₆); δ 11.21 (br s, 1H), 6.64 (m, 1H), 6.26 (m, 1H), 5.95 (m, 1H), 5.84 (m, 1H), 4.85 (m, 1H), 3.85 (m, 1H), 3.64 (s, 3H), 3.63-3.49 (m, 2H), 3.43 (m, 2H), 3.17 (m, 1H), 2.73 (m, 1H), 2.62 (m, 1H), 1.94 (m, 2H), 1.72 (m, 1H), 1.38 (m, 2H)

Example 52

Synthesis of [(R)-2-(7-cyclopentylamino-5-ethoxy-1H-indol-2-yl)-4,5-dihydro-thiazol-4-yl]acetic acid

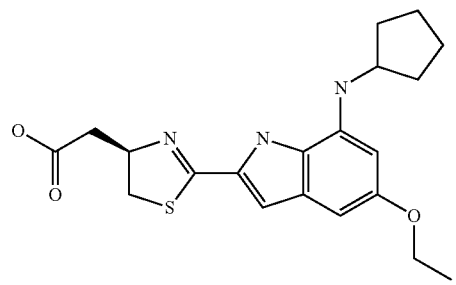

[(R)-2-(7-Cyclopentylamino-5-ethoxy-1H-indol-2-yl)-4,5-dihydro-thiazol-4-yl]-acetic acid Methyl 5-ethoxy-7-nitro-1H-indole-2-carboxylate (1.5 g, 5.7 mmol) prepared in Preparation 11 was reacted according to the same procedures as Preparation 33, Preparation 34, Example 26 and Example 27 in the order to give the title compound (150 mg, Yield 7%).

¹H-NMR (400 HMz, DMSO-d₆); δ 11.24 (br s, 1H), 6.65 (d, J=2.0 Hz, 1H), 6.26 (d, J=2.0 Hz, 1H), 5.92 (d, J=6.0 Hz, 1H), 5.88 (d, J=2.0 Hz, 1H), 4.89 (m, 1H), 3.94 (q, 2H), 3.81 (m, 1H), 3.65 (m, 1H), 3.20 (m, 1H), 2.74 (m, 1H), 2.62 (m, 1H), 1.94 (m, 2H), 1.72 (m, 2H), 1.61 (m, 4H), 1.31 (t, 3H)

Preparation 39

Synthesis of 7-nitro-5-propoxy-1H-indole-2-carboxylic acid ethyl ester

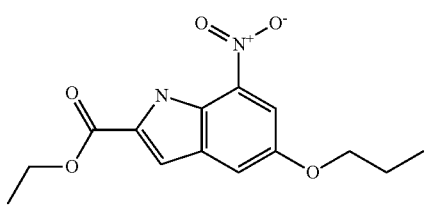

7-Nitro-5-propoxy-1H-indole-2-carboxylic acid ethyl ester

2-Nitro-4-propoxy-phenylamine (20 g, 102 mmol) was reacted according to the same procedures as Preparation 1 and Preparation 2 to give the title compound (1.5 g, Yield 5%).

Example 53

Synthesis of [(R)-2-(7-cyclopentylamino-5-propoxy-1H-indol-2-yl)-4,5-dihydro-thiazol-4-yl]-acetic acid

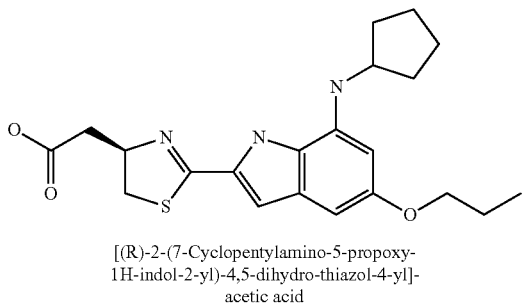

[(R)-2-(7-Cyclopentylamino-5-propoxy-1H-indol-2-yl)-4,5-dihydro-thiazol-4-yl]-acetic acid Ethyl 5-propoxy-7-nitro-1H-indole-2-carboxylate (1.4 g, 4.82 mmol) prepared in Preparation 39 was reacted according to the same procedures as Preparation 33, Preparation 34, Example 26 and Example 27 in the order to give the title compound (70 mg, Yield 4%).

$^1$H-NMR (500 HMz, CDCl$_3$); δ 12.79 (br s, 1H), 7.05 (s, 1H), 6.26 (s, 1H), 6.22 (s, 1H), 5.14 (br s, 1H), 3.88 (m, 3H), 3.41 (m, 2H), 3.07 (m, 1H), 2.83 (m, 1H), 2.03 (m, 2H), 1.82 (m, 3H), 1.69 (m, 2H), 1.60 (m, 2H), 1.04 (t, 3H)

Preparation 40

Synthesis of [(R)-2-(7-amino-5-phenoxy-1H-indol-2-yl)-4,5-dihydro-thiazol-4-yl]acetic acid methyl ester

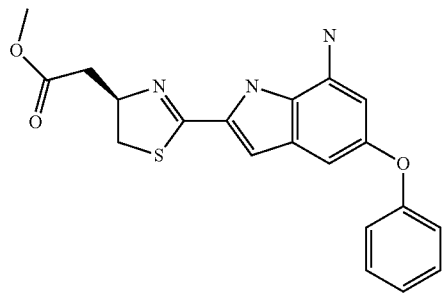

[(R)-2-(7-Amino-5-phenoxy-1H-indol-2-yl)-4,5-dihydro-thiazol-4-yl]-acetic acid methyl ester Methyl 5-phenoxy-7-nitro-1H-indole-2-carboxylate (550 mg, 1.84 mmol) prepared in Preparation 12 was reacted according to the same procedures as Preparation 33 and Preparation 34 to give the title compound (150 mg, Yield 16%).

Example 54

Synthesis of [(R)-2-(7-cyclopentylamino-5-phenoxy-1H-indol-2-yl)-4,5-dihydro-thiazol-4-yl]-acetic acid

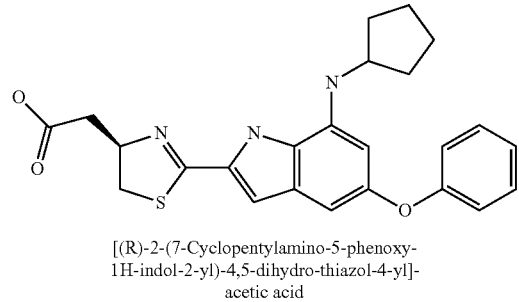

[(R)-2-(7-Cyclopentylamino-5-phenoxy-1H-indol-2-yl)-4,5-dihydro-thiazol-4-yl]-acetic acid The compound (65 mg, 0.13 mmol) prepared in Preparation 40 was reacted according to the same procedures as Example 26 and Example 27 to give the title compound (20 mg, Yield 35%).

$^1$H-NMR (400 HMz, CDCl$_3$); δ 11.92 (br s, 1H), 7.28 (m, 2H), 7.00 (m, 4H), 6.56 (s, 1H), 6.22 (s, 1H), 5.34 (br s, 1H), 3.81 (br s, 1H), 3.70 (m, 1H), 3.22 (d, J=12.0 Hz, 1H), 2.76-2.62 (m, 2H), 1.96 (m, 2H), 1.73 (m, 2H), 1.58 (m, 4H)

Example 55

Synthesis of {(R)-2-[5-phenoxy-7-(tetrahydro-pyran-4-ylamino)-1H-indol-2-yl]-4,5-dihydro-thiazol-4-yl}-acetic acid

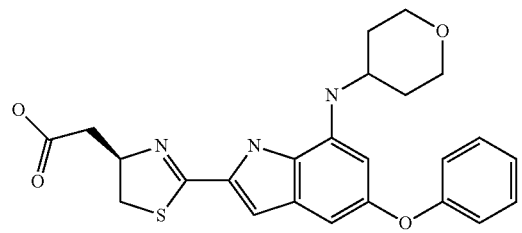

{(R)-2-[5-(Phenoxy-7-(tetrahydro-pyran-4-ylamino)-1H-indol-2-yl]-4,5-dihydro-thiazol-4-yl}-acetic acid The compound (65 mg, 0.13 mmol) prepared in Preparation 40 was reacted according to the same procedures as Example 30 and Example 27 to give the title compound (13 mg, Yield 22%).

$^1$H-NMR (400 HMz, CDCl$_3$); δ 11.98 (br s, 1H), 7.28 (m, 2H), 7.00 (m, 4H), 6.58 (s, 1H), 6.22 (s, 1H), 5.34 (br s, 1H), 3.98 (br s, 2H), 3.70 (m, 1H), 3.50 (m, 3H), 3.21 (m, 2H), 2.74 (m, 1H), 2.66 (m, 1H), 2.05 (m, 2H), 1.58 (m, 2H)

Preparation 41

Synthesis of {(R)-2-[7-amino-5-(pyridin-3-yloxy)-1H-indol-2-yl]-4,5-dihydro-thiazol-4-yl}-acetic acid methyl ester

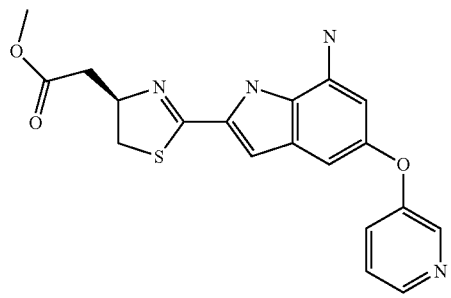

{(R)-2-[7-(Amino-5-(pyridin-3-yloxy)-1H-indol-2-yl]-4,5-dihydro-thiazol-4-yl}-acetic acid methyl ester 7-Nitro-5-(pyridin-3-yloxy)-1H-indole-2-carboxylic acid ethyl ester (1.0 g, 3.1 mmol) prepared in Preparation 13 was reacted according to the same procedures as Preparation 33 and Preparation 34 to give the title compound (160 mg, Yield 14%).

Example 56

Synthesis of {(R)-2-[7-cyclopentylamino-5-(pyridin-3-yloxy)-1H-indol-2-yl]-4,5-dihydro-thiazol-4-yl}-acetic acid methyl ester

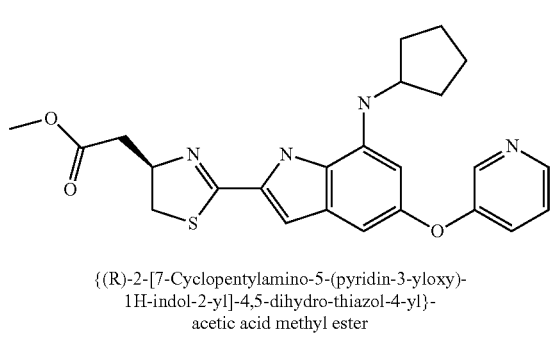

{(R)-2-[7-Cyclopentylamino-5-(pyridin-3-yloxy)-1H-indol-2-yl]-4,5-dihydro-thiazol-4-yl}-acetic acid methyl ester The compound (80 mg, 0.21 mmol) prepared in Preparation 41 was reacted according to the same procedure as Example 26 to give the title compound (45 mg, Yield 48%).

$^1$H-NMR (400 HMz, CDCl$_3$); δ 10.89 (br s, 1H), 8.41 (d, 1H), 8.26 (m, 1H), 7.27 (m, 1H), 7.19 (m, 1H), 6.85 (s, 1H), 6.62 (d, 1H), 6.22 (m, 1H), 5.04 (m, 1H), 4.13 (br s, 1H), 3.78 (m, 1H), 3.65 (m, 1H), 3.59 (s, 3H), 3.20 (m, 1H), 2.83 (m, 1H), 2.67 (m, 1H), 1.98 (m, 2H), 1.61 (m, 4H), 1.46 (m, 2H)

Example 57

Synthesis of {(R)-2-[7-cyclopentylamino-5-(pyridin-3-yloxy)-1H-indol-2-yl]-4,5-dihydro-thiazol-4-yl}-acetic acid

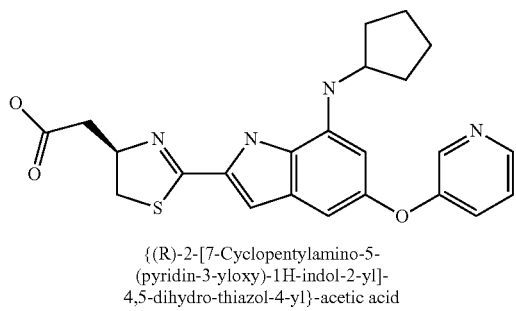

{(R)-2-[7-Cyclopentylamino-5-(pyridin-3-yloxy)-1H-indol-2-yl]-4,5-dihydro-thiazol-4-yl}-acetic acid The compound (35 mg, 0.08 mmol) prepared in Example 56 was reacted according to the same procedure as Example 27 to give the title compound (15 mg, Yield 44%).

$^1$H-NMR (400 HMz, CDCl$_3$); δ 11.86 (br s, 1H), 8.40 (d, 1H), 8.26 (m, 1H), 7.25 (m, 1H), 7.17 (m, 1H), 6.96 (s, 1H), 6.57 (d, 1H), 6.18 (d, 1H), 5.33 (br s, 1H), 3.80 (br s, 1H), 3.70 (m, 1H), 3.21 (m, 1H), 2.73 (m, 1H), 2.65 (m, 1H), 1.96 (m, 2H), 1.72 (m, 2H), 1.58 (m, 4H)

Example 58

Synthesis of {(R)-2-[5-(pyridin-3-yloxy)-7-(tetrahydro-pyran-4-ylamino)-1H-indol-2-yl]-4,5-dihydro-thiazol-4-yl}-acetic acid methyl ester

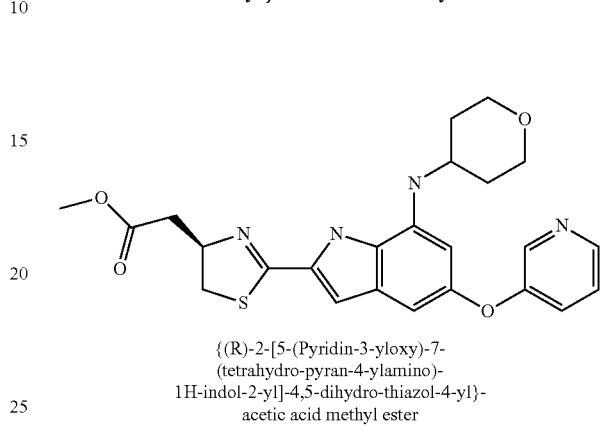

{(R)-2-[5-(Pyridin-3-yloxy)-7-(tetrahydro-pyran-4-ylamino)-1H-indol-2-yl]-4,5-dihydro-thiazol-4-yl}-acetic acid methyl ester The compound (480 g, 0.21 mmol) prepared in Preparation 41 was reacted according to the same procedure as Example 30 to give the title compound (35 mg, Yield 36%).

$^1$H-NMR (400 HMz, DMSO-d$_6$); δ 11.48 (br s, 1H), 8.30 (d, 1H), 8.25 (m, 1H), 7.34 (m, 1H), 7.29 (m, 1H), 6.76 (d, 1H), 6.46 (d, 1H), 6.18 (d, 1H), 4.93 (m, 1H), 3.87 (m, 3H), 3.66 (s, 3H), 3.59 (m, 1H), 3.44 (m, 2H), 3.23 (m, 1H), 2.81 (m, 2H), 1.95 (m, 2H), 1.43 (m, 2H)

Example 59

Synthesis of {(R)-2-[5-(pyridin-3-yloxy)-7-(tetrahydro-pyran-4-ylamino)-1H-indol-2-yl]-4,5-dihydro-thiazol-4-yl}-acetic acid

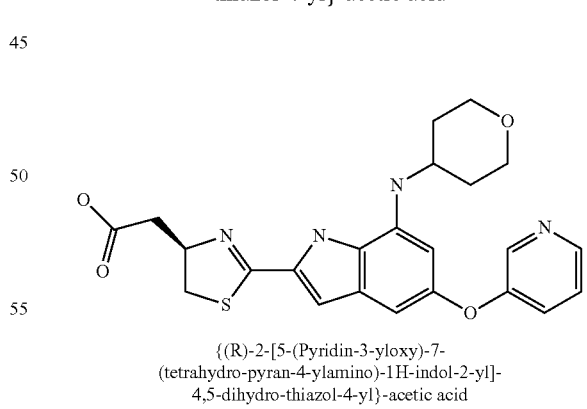

{(R)-2-[5-(Pyridin-3-yloxy)-7-(tetrahydro-pyran-4-ylamino)-1H-indol-2-yl]-4,5-dihydro-thiazol-4-yl}-acetic acid The compound (25 mg, 0.05 mmol) prepared in Example 58 was reacted according to the same procedure as Example 27 to give the title compound (15 mg, Yield 58%).

$^1$H-NMR (400 HMz, MeOH-d$_4$); δ 8.14 (s, 1H), 8.07 (s, 1H), 7.25 (m, 2H), 6.76 (s, 1H), 6.45 (s, 1H), 6.12 (d, 1H), 4.84 (m, 1H), 3.85 (m, 1H), 3.83 (m, 1H), 3.53 (m, 1H), 3.40

Preparation 42

Synthesis of [(R)-2-(7-amino-5-methyl-1H-indol-2-yl)-4,5-dihydro-thiazol-4-yl]acetic acid methyl ester

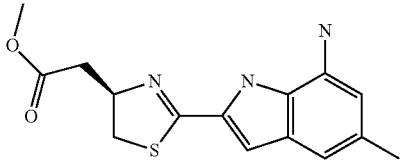

[(R)-2-(7-Amino-5-methyl-1H-indol-2-yl)-
4,5-dihydro-thiazol-4-yl)-
acetic acid methyl ester Methyl 5-methyl-7-nitro-1H-indole-2-carboxylate (3.4 g, 14.5 mmol) prepared in Preparation 7 was reacted according to the same procedures as Preparation 33 and Preparation 34 to give the title compound (1.7 g, Yield 39%).

Example 60

Synthesis of [(R)-2-(7-cyclopentylamino-5-methyl-1H-indol-2-yl)-4,5-dihydro-thiazol-4-yl]acetic acid methyl ester

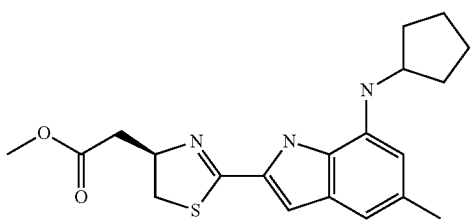

[(R)-2-(7-Cyclopentylamino-5-methyl-
1H-indol-2-yl)-4,5-dihydro-thiazol-4-yl]-
acetic acid methyl ester The compound (1.7 g, 5.67 mmol) prepared in Preparation 42 was reacted according to the same procedure as Example 26 to give the title compound (1.2 g, Yield 58%).

$^1$H NMR (DMSO-$d_6$, ppm); δ 11.19 (1H, s), 6.62 (1H, s), 6.55 (1H, s), 6.07 (1H, s), 5.75 (1H, d), 4.88 (1H, quin), 3.79 (1H, m), 3.63-3.57 (5H, m), 3.17 (1H, m), 2.82-2.73 (2H, m), 2.23 (3H, s), 1.94 (2H, m), 1.68 (2H, m), 1.55 (3H, m)
FAB MS (m/e)=372

Example 61

Synthesis of [(R)-2-(7-cyclopentylamino-5-methyl-1H-indol-2-yl)-4,5-dihydro-thiazol-4-yl]-acetic acid

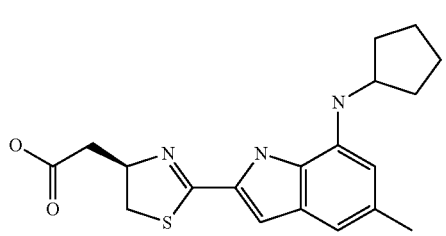

[(R)-2-(7-Cyclopentylamino-5-methyl-
1H-indol-2-yl)-4,5-dihydro-thiazol-4-yl]-
acetic acid The compound (12 mg, 0.03 mmol) prepared in Example 60 was reacted according to the same procedure as Example 27 to give the title compound (5 mg, Yield 43%).

$^1$H NMR (DMSO-$d_6$, ppm); δ 12.42 (1H, s, br), 11.21 (1H, s), 6.61 (1H, s), 6.54 (1H, s), 6.02 (1H, s), 5.76 (1H, d), 4.87 (1H, quin), 3.77 (1H, m), 3.62 (2H, t), 3.16 (1H, m), 2.81-2.72 (2H, m), 2.23 (3H, s), 1.94 (2H, m), 1.68 (2H, m), 1.55 (3H, m)
FAB MS (m/e)=358

Example 62

Synthesis of {(R)-2-[5-methyl-7-(tetrahydro-pyran-4-ylamino)-1H-indol-2-yl]-4,5-dihydro-thiazol-4-yl}-acetic acid

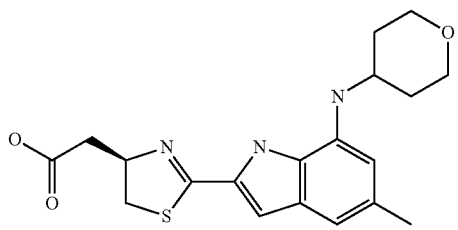

{(R)-2-[5-Methyl-7-(tetrahydro-pyran-4-ylamino)-
1H-indol-2-yl]-4,5-dihydro-thiazol-4-yl}-
acetic acid The compound (55 mg, 0.18 mmol) prepared in Preparation 42 was reacted according to the same procedures as Example 30 and Example 27 to give the title compound (47 mg, Yield 70%).

$^1$H-NMR (500 HMz, CDCl$_3$); δ 11.85 (br s, 1H), 6.97 (d, 1H), 6.76 (s, 1H), 6.26 (s, 1H), 5.32 (m, 1H), 3.99 (m, 2H), 3.71 (m, 1H), 3.65 (m, 1H), 3.54 (m, 2H), 3.23 (m, 1H), 2.76 (m, 1H), 2.64 (m, 1H), 2.31 (s, 3H), 2.06 (m, 2H), 1.58 (m, 2H)

Preparation 43

Synthesis of {(R)-2-[7-(1,4-dioxa-spiro[4,5]dec-8-ylamino)-5-methyl-1H-indol-2-yl]-4,5-dihydro-thiazol-4-yl}-acetic acid methyl ester

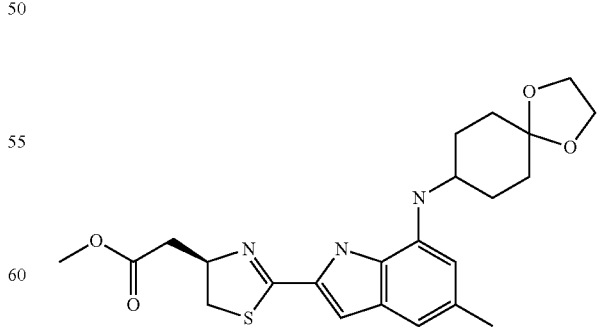

{(R)-2-[7-(1,4-Dioxa-spiro[4.5]dec-8-ylamino)-
5-methyl-1H-indol-2-yl]-4,5-dihydro-thiazol-4-yl}-
acetic acid methyl ester The compound (98 mg, 0.32 mmol) prepared in Preparation 42 and 1,4-cyclohexandione monoethylene acetal instead of cyclopentanone were reacted according to the same procedure as Example 26 to give the title compound (31 mg, Yield 23%).

$^1$H-NMR (500 HMz, CDCl$_3$); δ 10.62 (br s, 1H), 6.85 (s, 1H), 6.77 (s, 1H), 6.31 (s, 1H), 4.98 (m, 1H), 3.96 (m, 4H), 3.72 (s, 3H), 3.64 (m, 1H), 3.55 (m, 1H), 3.21 (m, 1H), 2.89 (m, 1H), 2.66 (m, 1H), 2.37 (s, 3H), 2.08 (m, 2H), 1.99 (m, 2H), 1.69 (m, 4H)

Example 63

Synthesis of {(R)-2-[5-methyl-7-(4-oxo-cyclohexylamino)-1H-indol-2-yl]-4,5-dihydro-thiazol-4-yl}-acetic acid

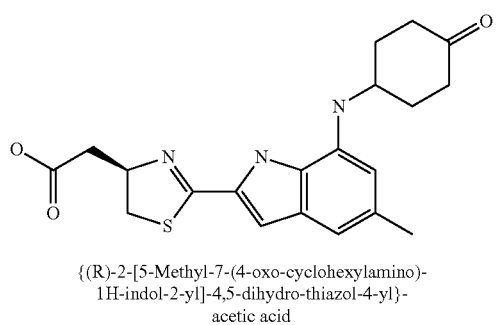

{(R)-2-[5-Methyl-7-(4-oxo-cyclohexylamino)-
1H-indol-2-yl]-4,5-dihydro-thiazol-4-yl}-
acetic acid The compound (40 mg, 0.09 mmol) prepared in Preparation 43 was dissolved in tetrahydrofuran (2 ml), methanol (2 ml) and water (2 ml). Lithium hydroxide monohydrate (8 mg, 0.18 mmol) was added thereto, and the mixture was stirred for 4 h at room temperature. After completion of the reaction, 1N hydrochloric acid solution was added. The mixture was extracted with ethyl acetate, washed with saturated sodium chloride solution, dried over anhydrous magnesium sulfate, and filtered. The filtrate was distilled under reduced pressure, and purified by column chromatography.

Thus purified compound was dissolved in acetone (5 ml). p-Toluenesulfonic acid (5 mg) was added thereto, and the mixture was stirred for 8 h at room temperature. After completion of the reaction, water was added. The mixture was extracted with ethyl acetate, washed with saturated sodium chloride solution, dried over anhydrous magnesium sulfate, and filtered. The filtrate was distilled under reduced pressure, and separated by column chromatography to give the title compound (7 mg, Yield 20%).

$^1$H-NMR (500 HMz, CDCl$_3$); δ 11.99 (br s, 1H), 7.00 (s, 1H), 6.79 (s, 1H), 6.30 (s, 1H), 5.34 (m, 1H), 3.89 (m, 1H), 3.71 (m, 1H), 3.21 (m, 1H), 2.66 (m, 2H), 2.59 (m, 2H), 2.43-2.35 (m, 5H), 2.26 (m, 2H), 1.97 (m, 2H)

Preparation 44

Synthesis of {(R)-2-[7-amino-5-(4-methanesulfonyl-phenoxy)-1H-indol-2-yl]-4,5-dihydro-thiazol-4-yl}-acetic acid methyl ester

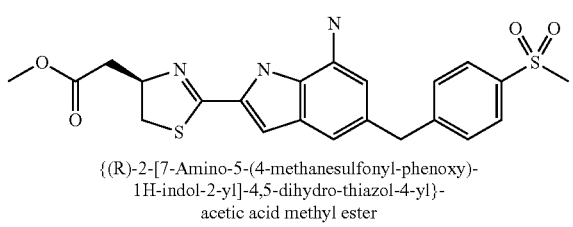

{(R)-2-[7-Amino-5-(4-methanesulfonyl-phenoxy)-
1H-indol-2-yl]-4,5-dihydro-thiazol-4-yl}-
acetic acid methyl ester The compound (900 mg, 2.30 mmol) prepared in Preparation 14 was reacted according to the same procedures as Preparation 33 and Preparation 34 to give the title compound (328 mg, Yield 31%).

Example 64

Synthesis of {(R)-2-[7-cyclopentylamino-5-(4-methanesulfonyl-phenoxy)-1H-indol-2-yl]-4,5-dihydro-thiazol-4-yl}-acetic acid

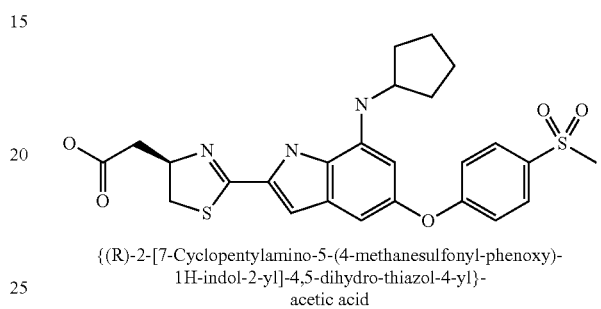

{(R)-2-[7-Cyclopentylamino-5-(4-methanesulfonyl-phenoxy)-
1H-indol-2-yl]-4,5-dihydro-thiazol-4-yl}-
acetic acid The compound (320 mg, 0.7 mmol) prepared in Preparation 44 was reacted according to the same procedures as Example 26 and Example 27 to give the title compound (45 mg, Yield 13%).

$^1$H-NMR (500 HMz, DMSO-d$_6$); δ 11.71 (br s, 1H), 7.81 (d, 2H), 7.05 (m, 2H), 6.65 (s, 1H), 6.49 (s, 1H), 6.35 (m, 1H), 5.96 (s, 1H), 4.86 (m, 1H), 3.75 (m, 1H), 3.52 (m, 1H), 3.17 (m, 1H), 3.12 (s, 3H), 1.87 (m, 2H), 1.67 (m, 2H), 1.53 (m, 4H)

Preparation 45

Synthesis of (R)-3-[(5-hydroxymethyl-7-nitro-1H-indole-2-carbonyl)-amino]-4-(4-methoxy-benzylsulfanyl)-butyric acid methyl ester

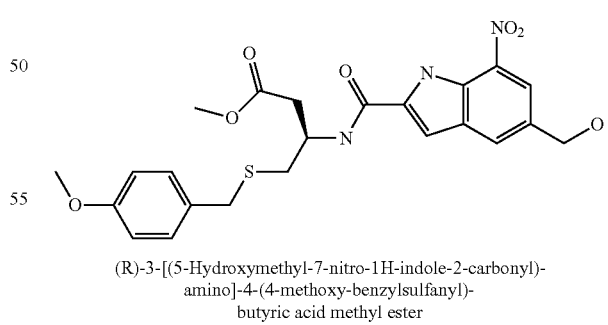

(R)-3-[(5-Hydroxymethyl-7-nitro-1H-indole-2-carbonyl)-
amino]-4-(4-methoxy-benzylsulfanyl)-
butyric acid methyl ester The compound (12.9 g, 54.8 mmol) prepared in Preparation 27 was reacted according to the same procedure as Step 1 of Preparation 34 to give the title compound (15.3 g, Yield 57%).

¹H-NMR (500 HMz, CDCl₃); δ 10.43 (br s, 1H), 8.28 (s, 1H), 8.00 (s, 1H), 7.25 (m, 2H), 6.92 (d, 1H), 6.84 (s, 1H), 6.82 (s, 1H), 4.86 (m, 2H), 4.59 (m, 1H), 3.76 (s, 3H), 3.73 (s, 2H), 3.69 (s, 3H), 2.88 (m, 1H), 2.82 (m, 2H), 2.73 (m, 1H), 2.69 (m, 1H)

Preparation 46

Synthesis of [(R)-2-(5-chloromethyl-7-nitro-1H-indol-2-yl)-4,5-dihydro-thiazol-4-yl]-acetic acid methyl ester

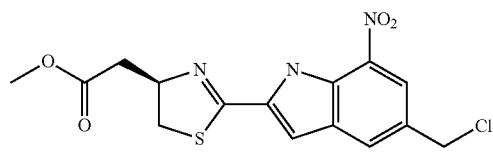

[(R)-2-(5-Choloromethyl-7-nitro-1H-indol-2-yl)-4,5-dihydro-thiazol-4-yl]-acetic acid methyl ester The compound (4.8 g, 0.8 mmol) prepared in Preparation 45 was reacted according to the same procedure as Preparation 29 to give the title compound (3.2 g, Yield 88%).

¹H-NMR (500 HMz, CDCl₃); δ 12.82 (br s, 1H), 8.43 (s, 1H), 8.04 (s, 1H), 7.49 (s, 1H), 5.25 (m, 1H), 4.74 (s, 2H), 4.03 (m, 1H), 3.57 (m, 1H), 3.45 (m, 1H), 2.99 (m, 1H)

Preparation 47

Synthesis of [(R)-2-(7-nitro-5-phenoxymethyl-1H-indol-2-yl)-4,5-dihydro-thiazol-4-yl]acetic acid methyl ester

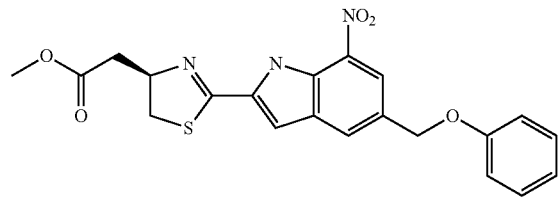

[(R)-2-(7-Nitro-5-phenoxymethyl-1H-indol-2-yl)-4,5-dihydro-thiazol-4-yl]-acetic acid methyl ester The compound (500 mg, 1.4 mmol) prepared in Preparation 46 was dissolved in N,N-dimethylformamide (10 ml). Potassium hydride (82 mg, 2.0 mmol) and phenol (192 mg, 2.0 mmol) were added thereto, and the mixture was stirred for 8 h at 0° C.~room temperature. After completion of the reaction, water was added. The mixture was extracted with ethyl acetate, dried over anhydrous magnesium sulfate, and filtered. The filtrate was distilled under reduced pressure to give the title compound (55 mg, Yield 6%).

¹H-NMR (500 HMz, CDCl₃); δ 10.46 (br s, 1H), 8.34 (s, 1H), 8.06 (s, 1H), 7.31 (m, 2H), 7.25 (s, 1H), 7.00 (m, 3H), 5.19 (s, 2H), 5.06 (m, 1H), 3.77 (s, 3H), 3.71 (m, 1H), 3.26 (m, 1H), 2.97 (m, 1H), 2.69 (m, 1H)

Example 65

Synthesis of [(R)-2-(7-cyclopentylamino-5-phenoxymethyl-1H-indol-2-yl)-4,5-dihydro-thiazol-4-yl]-acetic acid methyl ester

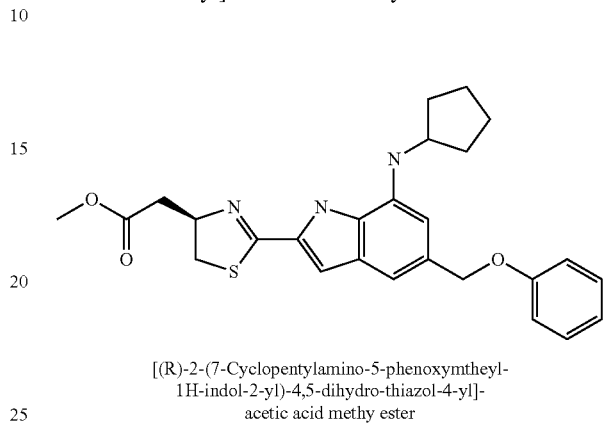

[(R)-2-(7-Cyclopentylamino-5-phenoxymtheyl-1H-indol-2-yl)-4,5-dihydro-thiazol-4-yl]-acetic acid methy ester The compound (33 mg, 0.08 mmol) prepared in Preparation 47 was reacted according to the same procedures as Step 3 of Preparation 34 and Example 26 to give the title compound (16 mg, Yield 43%).

¹H-NMR (500 HMz, CDCl₃); δ 9.49 (br s, 1H), 7.27 (m, 2H), 7.10 (s, 1H), 7.01 (m, 2H), 6.93 (m, 1H), 6.89 (s, 1H), 6.59 (s, 1H), 5.07 (s, 2H), 5.02 (m, 1H), 3.93 (m, 1H), 3.71 (s, 3H), 3.65 (m, 1H), 3.21 (m, 1H), 2.88 (m, 1H), 2.68 (m, 1H), 2.04 (m, 2H), 1.75 (m, 2H), 1.58 (m, 4H)

Example 66

Synthesis of [(R)-2-(7-cyclopentylamino-5-phenoxymethyl-1H-indol-2-yl)-4,5-dihydro-thiazol-4-yl]-acetic acid

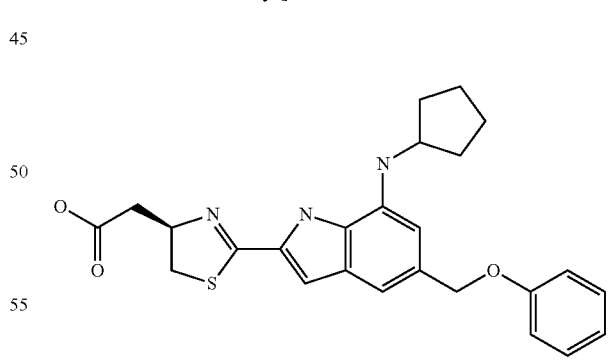

[(R)-2-(7-Cyclopentylamino-5-phenoxymethyl-1H-indol-2-yl)-4,5-dihydro-thiazol-4-yl]-acetic acid The compound (11 mg, 0.02 mmol) prepared in Example 65 was reacted according to the same procedure as Example 27 to give the title compound (5 mg, Yield 45%).

¹H-NMR (500 HMz, CDCl₃); δ 11.79 (br s, 1H), 7.26 (m, 2H), 7.02 (m, 2H), 6.99 (m, 1H), 6.92 (m, 1H), 6.48 (s, 1H), 5.35 (m, 1H), 5.07 (s, 2H), 3.89 (m, 1H), 3.71 (m, 1H), 3.21

(m, 1H), 2.75 (m, 1H), 2.63 (m, 1H), 2.00 (m, 2H), 1.73 (m, 2H), 1.59 (m, 4H), 1.75 (m, 2H)

Preparation 48

Synthesis of [(R)-2-(7-nitro-5-pyrrolidin-1-ylmethyl-1H-indol-2-yl)-4,5-dihydro-thiazol-4-yl]-acetic acid methyl ester

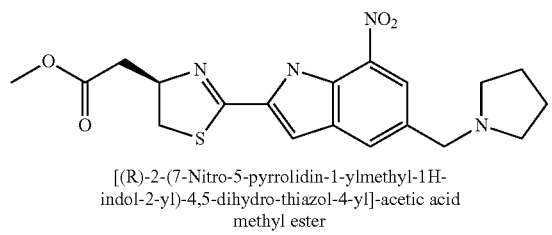

[(R)-2-(7-Nitro-5-pyrrolidin-1-ylmethyl-1H-indol-2-yl)-4,5-dihydro-thiazol-4-yl]-acetic acid methyl ester The compound (87 mg, 0.24 mmol) prepared in Preparation 46 and pyrrolidine instead of dimethylamine were reacted according to the same procedure as Example 15 to give the title compound (56 mg, Yield 58%).

$^1$H-NMR (500 HMz, CDCl$_3$); δ 8.28 (s, 1H), 8.26 (s, 1H), 7.00 (s, 1H), 5.03 (m, 1H), 4.10 (s, 2H), 3.74 (s, 3H), 3.68 (m, 1H), 2.94 (m, 1H), 2.92 (m, 4H), 2.66 (m, 1H), 1.98 (m, 4H)

Example 67

Synthesis of [(R)-2-(7-cyclopentylamino-5-pyrrolidin-1-ylmethyl-1H-indol-2-yl)-4,5-dihydro-thiazol-4-yl]acetic acid methyl ester

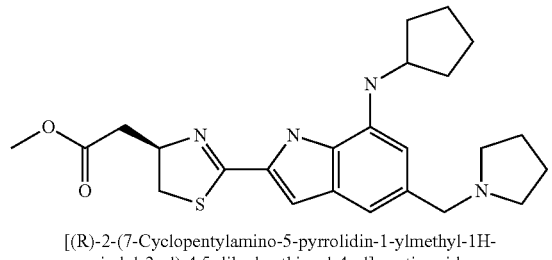

[(R)-2-(7-Cyclopentylamino-5-pyrrolidin-1-ylmethyl-1H-indol-2-yl)-4,5-dihydro-thiazol-4-yl]-acetic acid methyl ester The compound (56 mg, 0.14 mmol) prepared in Preparation 48 was reacted according to the same procedures as Step 3 of Preparation 34 and Example 26 to give the title compound (13 mg, Yield 21%).

$^1$H-NMR (400 HMz, CDCl$_3$); δ 10.20 (br s, 1H), 6.97 (s, 1H), 6.88 (s, 1H), 6.73 (s, 1H), 5.01 (m, 1H), 4.04 (s, 2H), 4.02

(m, 1H), 3.73 (s, 3H), 3.65 (m, 1H), 3.22 (m, 1H), 3.10 (m, 4H), 2.87 (m, 1H), 2.68 (m, 1H), 2.06 (m, 3H), 1.95 (m, 4H), 1.65 (m, 3H), 1.47 (m, 2H)

Preparation 49

Synthesis of [(R)-2-(5-methanesulfonylmethyl-7-nitro-1H-indol-2-yl)-4,5-dihydro-thiazol-4-yl]-acetic acid methyl ester

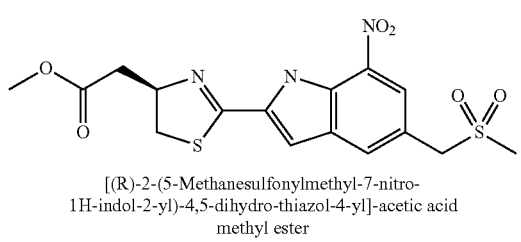

[(R)-2-(5-Methanesulfonylmethyl-7-nitro-1H-indol-2-yl)-4,5-dihydro-thiazol-4-yl]-acetic acid methyl ester The compound (110 mg, 0.30 mmol) prepared in Preparation 55 and sodium methanesulfinate instead of dimethylamine were reacted according to the same procedure as Example 15 to give the title compound (92 mg, Yield 74%).

$^1$H-NMR (500 HMz, CDCl$_3$); δ 10.55 (br s, 1H), 8.26 (s, 1H), 8.08 (s, 1H), 7.04 (s, 1H), 5.06 (m, 1H), 4.40 (s, 2H), 3.77 (s, 3H), 3.48 (m, 1H), 3.27 (m, 1H), 2.99 (m, 1H), 2.86 (s, 3H), 2.71 (m, 1H)

Example 68

Synthesis of [(R)-2-(7-cyclopentylamino-5-methanesulfonylmethyl-1H-indol-2-yl)-4,5-dihydro-thiazol-4-yl]-acetic acid methyl ester

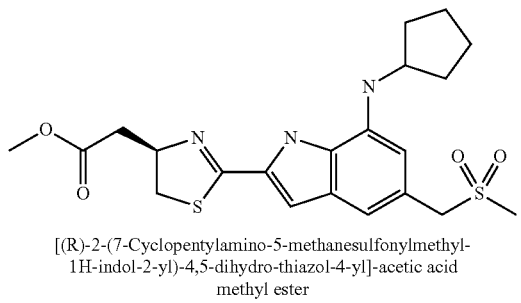

[(R)-2-(7-Cyclopentylamino-5-methanesulfonylmethyl-1H-indol-2-yl)-4,5-dihydro-thiazol-4-yl]-acetic acid methyl ester The compound (92 mg, 0.22 mmol) prepared in Preparation 49 was reacted according to the same procedures as Step 3 of Preparation 34 and Example 26 to give the title compound (31 mg, Yield 31%).

$^1$H-NMR (500 HMz, CDCl$_3$); δ 10.22 (br s, 1H), 7.00 (s, 1H), 6.87 (s, 1H), 6.50 (s, 1H), 5.05 (m, 1H), 4.27 (s, 2H), 3.87

(m, 1H), 3.61 (s, 3H), 3.22 (m, 1H), 2.83 (m, 1H), 2.72 (s, 3H), 2.66 (m, 1H), 2.03 (m, 2H), 1.64 (m, 4H), 1.46 (m, 2H)

Example 69

Synthesis of [(R)-2-(7-cyclopentylamino-5-methanesulfonylmethyl-1H-indol-2-yl)-4,5-dihydro-thiazol-4-yl]-acetic acid

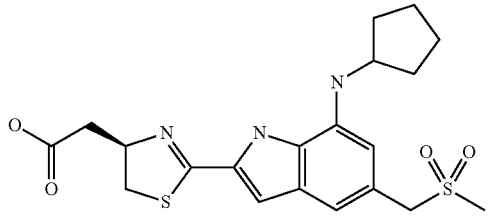

[(R)-2-(7-Cyclopentylamino-5-methanesulfonylmethyl-1H-indol-2-yl)-4,5-dihydro-thiazol-4-yl]-acetic acid The compound (29 mg, 0.07 mmol) prepared in Example 68 was reacted according to the same procedure as Example 27 to give the title compound (19 mg, Yield 67%).

$^1$H-NMR (400 HMz, DMSO-d$_6$); δ 11.68 (br s, 1H), 6.85 (s, 1H), 6.71 (s, 1H), 6.33 (s, 1H), 6.18 (m, 1H), 4.88 (m, 1H), 4.35 (s, 2H), 3.84 (m, 1H), 3.56 (m, 1H), 3.20 (m, 1H), 2.84 (s, 3H), 2.55 (m, 1H), 2.09 (m, 1H), 1.97 (m, 2H), 1.73 (m, 2H), 1.58 (m, 4H)

Example 70

Synthesis of 2-[(R)-2-(7-cyclopentylamino-5-methanesulfonylmethyl-1H-indol-2-yl)-4,5-dihydro-thiazol-4-yl]-ethanol

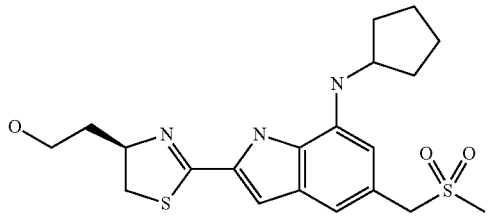

2-[(R)-2-(7-Cyclopentylamino-5-methanesulfonylmethyl-1H-indol-2-yl)-4,5-dihydro-thiazol-4-yl]-ethanol The compound (720 mg, 1.60 mmol) prepared in Example 68 was dissolved in tetrahydrofuran (20 ml). 2 M lithium borohydride tetrahydrofuran solution (1.6 ml, 3.2 mmol) was added thereto, and the mixture was stirred for 3 h at room temperature. After completion of the reaction, water was added. The mixture was extracted with ethyl acetate, washed with saturated sodium chloride solution, dried over anhydrous magnesium sulfate, and filtered. The filtrate was distilled under reduced pressure, and separated by column chromatography to give the title compound (292 mg, Yield 43%).

$^1$H-NMR (500 HMz, CDCl$_3$); δ 10.41 (br s, 1H), 6.98 (s, 1H), 6.90 (s, 1H), 6.49 (s, 1H), 4.68 (m, 1H), 4.28 (s, 2H), 3.96 (m, 3H), 3.59 (m, 1H), 3.13 (m, 1H), 2.05 (m, 4H), 1.72 (m, 2H), 1.60 (m, 4H)

Preparation 50

Synthesis of cyclopentyl-{2-[(R)-4-(2-iodo-ethyl)-4,5-dihydro-thiazol-2-yl]-5-methanesulfonylmethyl-1H-indol-7-yl}-amine

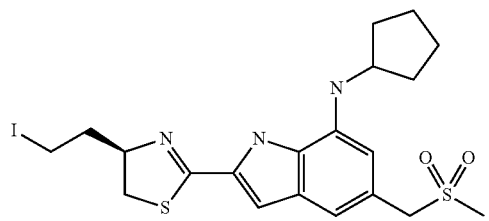

Cyclopentyl-{2-[(R)-4-(2-iodo-ethyl)-4,5-dihydro-thiazol-2-yl]-5-methanesulfonylmethyl-1H-indol-7-yl}-amine The compound (178 mg, 0.42 mmol) prepared in Example 70 was dissolved in tetrahydrofuran (10 ml). Iodine (161 mg, 0.63 mmol), triphenylphosphine (166 mg, 0.63 mmol) and imidazole (86 mg, 1.23 mmol) were added thereto, and the mixture was stirred for 8 h at room temperature. After completion of the reaction, water was added. The mixture was extracted with ethyl acetate, washed with saturated sodium chloride solution, dried over anhydrous magnesium sulfate, and filtered. The filtrate was distilled under reduced pressure, and separated by column chromatography to give the title compound (120 mg, Yield 54%).

Example 71

Synthesis of cyclopentyl-{5-methanesulfonylmethyl-2-[(R)-4-(2-morpholin-4-yl-ethyl)-4,5-dihydro-thiazol-2-yl]-1H-indol-7-yl}-amine

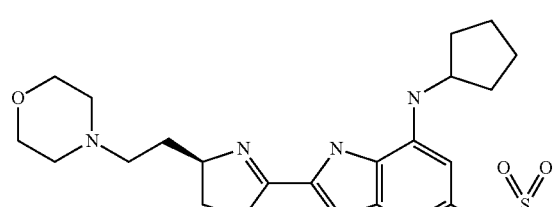

Cyclopentyl-{5-methanesulfonylmethyl-2-[(R)-4-(2-morpholin-4-yl-ethyl)-4,5-dihydro-thiazol-2-yl]-1H-indol-7-yl}-amine The compound (116 mg, 0.22 mmol) prepared in Preparation 50 was dissolved in N,N-dimethylformamide (4 ml). Morpholine (57 mg, 0.66 mmol) was added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure to give the title compound (68 mg, Yield 64%).

¹H-NMR (500 HMz, CDCl₃); δ 10.60 (br s, 1H), 6.99 (s, 1H), 6.89 (s, 1H), 6.49 (s, 1H), 4.79 (m, 1H), 4.26 (s, 2H), 3.86 (m, 1H), 3.57 (m, 5H), 3.19 (m, 1H), 2.72 (s, 3H), 2.45 (m, 2H), 2.32 (m, 2H), 2.26 (m, 2H), 2.04 (m, 2H), 1.80 (m, 2H), 1.66 (m, 4H), 1.41 (m, 2H)

Example 72

Synthesis of 1-(4-{2-[(R)-2-(7-cyclopentylamino-5-methanesulfonylmethyl-1H-indol-2-yl)-4,5-dihydro-thiazol-4-yl]-ethyl}-piperazin-1-yl)-ethanone

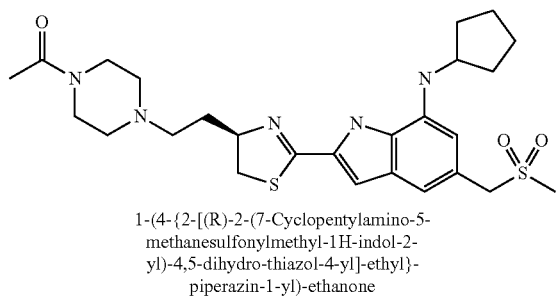

1-(4-{2-[(R)-2-(7-Cyclopentylamino-5-methanesulfonylmethyl-1H-indol-2-yl)-4,5-dihydro-thiazol-4-yl]-ethyl}-piperazin-1-yl)-ethanone The compound (129 mg, 0.24 mmol) prepared in Preparation 50 and 1-acetylpiperazine instead of morpholine were reacted according to the same procedure as Example 71 to give the title compound (54 mg, Yield 42%).

¹H-NMR (500 HMz, CDCl₃); δ 10.62 (br s, 1H), 6.99 (s, 1H), 6.89 (s, 1H), 6.46 (s, 1H), 4.77 (m, 1H), 4.26 (s, 2H), 3.87 (m, 1H), 3.57 (m, 1H), 3.30 (m, 2H), 3.16 (m, 1H), 2.72 (s, 3H), 2.46 (m, 2H), 2.31 (m, 2H), 2.21 (m, 2H), 2.04 (s, 3H), 2.03 (m, 2H), 1.79 (m, 2H), 1.64 (m, 4H), 1.45 (m, 2H)

Example 73

Synthesis of 2-[(R)-2-(5-chloro-7-cyclopentylamino-1H-indol-2-yl)-4,5-dihydro-thiazol-4-yl]-1-morpholin-4-yl-ethanone

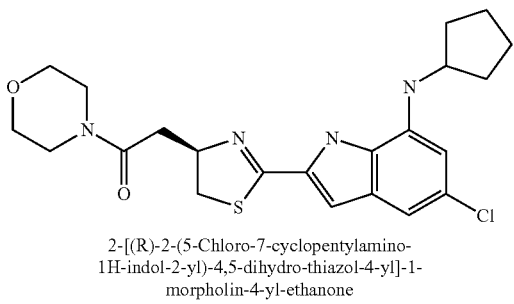

2-[(R)-2-(5-Chloro-7-cyclopentylamino-1H-indol-2-yl)-4,5-dihydro-thiazol-4-yl]-1-morpholin-4-yl-ethanone The compound (50 mg, 0.13 mmol) prepared in Example 27 was dissolved in N,N-dimethylformamide (2 ml). Morpholine (17 mg, 0.20 mmol), EDC (43 mg, 0.23 mmol) and HOBT (36 mg, 0.26 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (22 mg, Yield 37%).

¹H-NMR (500 HMz, DMSO-d₆); δ 11.52 (br s, 1H), 6.80 (s, 1H), 6.69 (s, 1H), 6.16 (s, 1H), 6.12 (m, 1H), 4.95 (m, 1H), 3.81 (m, 1H), 3.63 (m, 1H), 3.41 (m, 8H), 3.12 (m, 1H), 2.85 (m, 1H), 2.69 (m, 1H), 1.93 (m, 2H), 1.68 (m, 2H), 1.56 (m, 4H)

Example 74

Synthesis of 2-[(R)-2-(5-chloro-7-cyclopentylamino-1H-indol-2-yl)-4,5-dihydro-thiazol-4-yl]-N-(2-morpholin-4-yl-ethyl)-acetamide

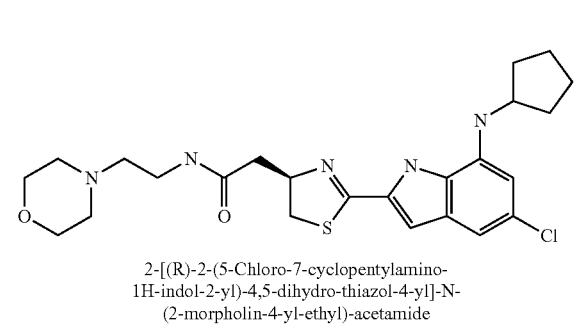

2-[(R)-2-(5-Chloro-7-cyclopentylamino-1H-indol-2-yl)-4,5-dihydro-thiazol-4-yl]-N-(2-morpholin-4-yl-ethyl)-acetamide The compound (50 mg, 0.13 mmol) prepared in Example 27 and 4-(2-aminoethyl)morpholine instead of morpholine were reacted according to the same procedure as Example 73 to give the title compound (22 mg, Yield 34%).

¹H-NMR (500 HMz, DMSO-d₆); δ 11.53 (br s, 1H), 7.91 (m, 1H), 6.80 (s, 1H), 6.70 (s, 1H), 6.16 (s, 1H), 6.12 (m, 1H), 4.93 (m, 1H), 3.80 (m, 1H), 3.53 (m, 5H), 3.20 (m, 3H), 2.60 (m, 1H), 2.32 (m, 7H), 1.93 (m, 2H), 1.68 (m, 2H), 1.53 (m, 4H)

Example 75

Synthesis of 2-[(R)-2-(5-chloro-7-cyclopentylamino-1H-indol-2-yl)-4,5-dihydro-thiazol-4-yl]-N-(3-morpholin-4-yl-propyl)-acetamide

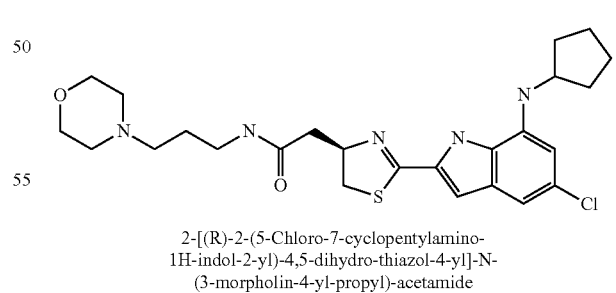

2-[(R)-2-(5-Chloro-7-cyclopentylamino-1H-indol-2-yl)-4,5-dihydro-thiazol-4-yl]-N-(3-morpholin-4-yl-propyl)-acetamide The compound (50 mg, 0.13 mmol) prepared in Example 27 and 4-(3-aminopropyl)morpholine instead of morpholine were reacted according to the same procedure as Example 73 to give the title compound (23 mg, Yield 35%).

¹H-NMR (500 HMz, DMSO-d₆); δ 11.52 (br s, 1H), 7.94 (m, 1H), 6.79 (s, 1H), 6.70 (s, 1H), 6.16 (s, 1H), 6.12 (m, 1H), 4.93 (m, 1H), 3.80 (m, 1H), 3.51 (m, 5H), 3.10 (m, 3H), 2.59 (m, 1H), 2.37 (m, 1H), 2.25 (m, 6H), 1.93 (m, 2H), 1.68 (m, 2H), 1.53 (m, 6H)

Example 76

Synthesis of 2-[(R)-2-(5-chloro-7-cyclopentylamino-1H-indol-2-yl)-4,5-dihydro-thiazol-4-yl]-N-methyl-acetamide

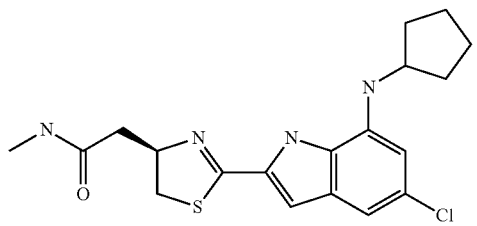

2-[(R)-2-(5-Chloro-7-cyclopentylamino-1H-indol-2-yl)-4,5-dihydro-thiazol-4-yl]-N-methyl-acetamide The compound (50 mg, 0.13 mmol) prepared in Example 27 and methylamine instead of morpholine were reacted according to the same procedure as Example 73 to give the title compound (45 mg, Yield 87%).

$^1$H-NMR (500 HMz, DMSO-d$_6$); δ 11.52 (br s, 1H), 7.90 (m, 1H), 6.80 (s, 1H), 6.69 (s, 1H), 6.16 (s, 1H), 6.13 (m, 1H), 4.93 (m, 1H), 3.80 (m, 1H), 3.55 (m, 1H), 3.15 (m, 1H), 2.58 (m, 4H), 2.39 (m, 1H), 1.93 (m, 2H), 1.68 (m, 2H), 1.56 (m, 4H)

Example 77

Synthesis of 2-[(R)-2-(5-chloro-7-cyclopentylamino-1H-indol-2-yl)-4,5-dihydro-thiazol-4-yl]-N,N-dimethyl-acetamide

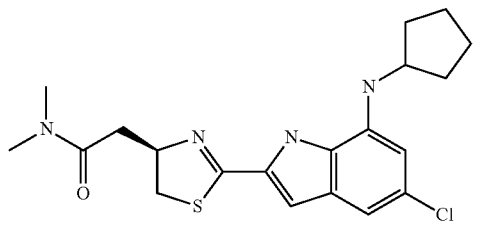

2-[(R)-2-(5-Chloro-7-cyclopentylamino-1H-indol-2-yl)-4,5-dihydro-thiazol-4-yl]-N,N-dimethyl-acetamide The compound (50 mg, 0.13 mmol) prepared in Example 27 and dimethylamine instead of morpholine were reacted according to the same procedure as Example 73 to give the title compound (26 mg, Yield 49%).

$^1$H-NMR (500 HMz, DMSO-d$_6$); δ 11.53 (br s, 1H), 6.79 (s, 1H), 6.69 (s, 1H), 6.16 (s, 1H), 6.12 (m, 1H), 4.93 (m, 1H), 3.81 (m, 1H), 3.63 (m, 1H), 3.15 (m, 1H), 2.95 (s, 3H), 2.87 (m, 1H), 2.83 (s, 3H), 2.65 (m, 1H), 1.93 (m, 2H), 1.69 (m, 2H), 1.53 (m, 4H)

Example 78

Synthesis of 2-[(R)-2-(5-chloro-7-cyclopentylamino-1H-indol-2-yl)-4,5-dihydro-thiazol-4-yl]-1-(4-methyl-piperazin-1-yl)-ethanone

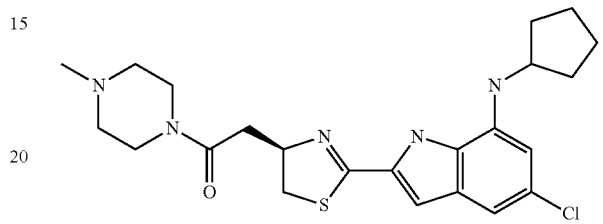

2-[(R)-2-(5-Chloro-7-cyclopentylamino-1H-indol-2-yl)-4,5-dihydro-thiazol-4-yl]-1-(4-methyl-piperazin-1-yl)-ethanone The compound (40 mg, 0.11 mmol) prepared in Example 27 and 1-methylpiperazine instead of morpholine were reacted according to the same procedure as Example 73 to give the title compound (21 mg, Yield 43%).

$^1$H-NMR (500 HMz, DMSO-d$_6$); δ 11.52 (br s, 1H), 6.80 (s, 1H), 6.69 (s, 1H), 6.16 (s, 1H), 6.12 (m, 1H), 4.94 (m, 1H), 3.80 (m, 1H), 3.62 (m, 1H), 3.42 (m, 4H), 3.35 (m, 1H), 3.15 (m, 1H), 2.85 (m, 1H), 2.66 (m, 1H), 2.24 (m, 4H), 2.13 (s, 3H), 1.93 (m, 2H), 1.68 (m, 2H), 1.55 (m, 4H)

Example 79

Synthesis of 2-[(R)-2-(5-chloro-7-cyclopentylamino-1H-indol-2-yl)-4,5-dihydro-thiazol-4-yl]-1-(3-dimethylamino-pyrrolidin-1-yl)-ethanone

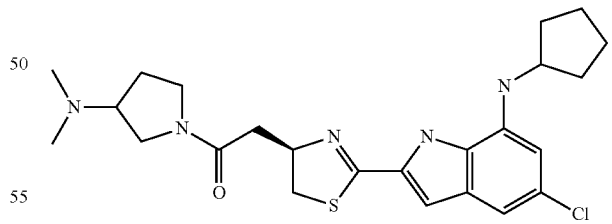

2-[(R)-2-(5-Chloro-7-cyclopentylamino-1H-indol-2-yl)-4,5-dihydro-thiazol-4-yl]-1-(3-dimethylamino-pyrrolidin-1-yl)-ethanone The compound (40 mg, 0.11 mmol) prepared in Example 27 and 3-dimethylaminopyrrolidine instead of morpholine were reacted according to the same procedure as Example 73 to give the title compound (24 mg, Yield 48%).

$^1$H-NMR (500 HMz, DMSO-d$_6$); δ 11.53 (br s, 1H), 6.80 (s, 1H), 6.69 (s, 1H), 6.16 (s, 1H), 6.12 (m, 1H), 4.94 (m, 1H), 3.81 (m, 1H), 3.62 (m, 3H), 3.30 (m, 1H), 3.17 (m, 2H), 2.78 (m, 1H), 2.53 (m, 2H), 2.11 (s, 3H), 2.07 (s, 3H), 1.93 (m, 2H), 1.69 (m, 3H), 1.59 (m, 5H)

Example 80

Synthesis of 2-[(R)-2-(5-chloro-7-cyclopentylamino-1H-indol-2-yl)-4,5-dihydro-thiazol-4-yl]-1-(3-hydroxy-pyrrolidin-1-yl)-ethanone

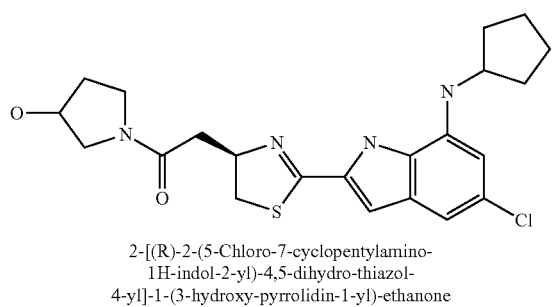

2-[(R)-2-(5-Chloro-7-cyclopentylamino-
1H-indol-2-yl)-4,5-dihydro-thiazol-
4-yl]-1-(3-hydroxy-pyrrolidin-1-yl)-ethanone The compound (40 mg, 0.11 mmol) prepared in Example 27 and 3-pyrrolidinol instead of morpholine were reacted according to the same procedure as Example 73 to give the title compound (19 mg, Yield 40%).

$^1$H-NMR (500 HMz, DMSO-d$_6$); δ 11.54 (br s, 1H), 6.80 (s, 1H), 6.69 (s, 1H), 6.16 (s, 1H), 6.12 (m, 1H), 4.93 (m, 1H), 4.25 (m, 1H), 3.81 (m, 1H), 3.63 (m, 3H), 3.47 (m, 2H), 3.32 (m, 2H), 3.17 (m, 1H), 2.79 (m, 1H), 2.59 (m, 1H), 1.93 (m, 3H), 1.80 (m, 1H), 1.68 (m, 2H), 1.53 (m, 4H)

Example 81

Synthesis of 2-[(R)-2-(5-chloro-7-cyclopentylamino-1H-indol-2-yl)-4,5-dihydro-thiazol-4-yl]-1-piperidin-1-yl-ethanone

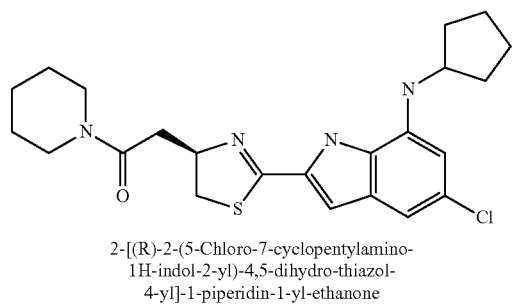

2-[(R)-2-(5-Chloro-7-cyclopentylamino-
1H-indol-2-yl)-4,5-dihydro-thiazol-
4-yl]-1-piperidin-1-yl-ethanone The compound (40 mg, 0.11 mmol) prepared in Example 27 and piperidine instead of morpholine were reacted according to the same procedure as Example 73 to give the title compound (27 mg, Yield 57%).

$^1$H-NMR (500 HMz, DMSO-d$_6$); δ 11.52 (br s, 1H), 6.80 (s, 1H), 6.69 (s, 1H), 6.16 (s, 1H), 6.12 (m, 1H), 4.94 (m, 1H), 3.81 (m, 1H), 3.63 (m, 1H), 3.45 (m, 1H), 3.38 (m, 3H), 3.14 (m, 1H), 2.85 (m, 1H), 1.93 (m, 2H), 1.68 (m, 2H), 1.48 (m, 10H)

Example 82

Synthesis of 2-{(R)-2-[5-chloro-7-(tetrahydro-pyran-4-ylamino)-1H-indol-2-yl]-4,5-dihydro-thiazol-4-yl}-N-methyl-acetamide

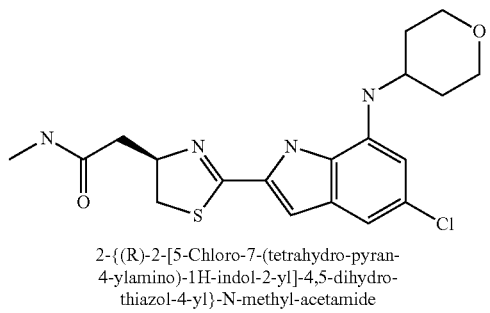

2-{(R)-2-[5-Chloro-7-(tetrahydro-pyran-
4-ylamino)-1H-indol-2-yl]-4,5-dihydro-
thiazol-4-yl}-N-methyl-acetamide The compound (44 mg, 0.11 mmol) prepared in Example 31 was dissolved in N,N-dimethylformamide (2 ml). Methylamine (0.08 ml, 2M in THF, 0.17 mmol), EDC (36 mg, 0.19 mmol) and HOBT (30 mg, 0.22 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (18 mg, Yield 37%).

$^1$H-NMR (500 HMz, DMSO-d$_6$); δ 11.54 (br s, 1H), 7.91 (m, 1H), 6.81 (s, 1H), 6.70 (s, 1H), 6.28 (s, 1H), 6.08 (m, 1H), 4.93 (m, 1H), 3.85 (m, 2H), 3.56 (m, 2H), 3.44 (m, 2H), 3.15 (m, 1H), 2.06 (m, 4H), 2.37 (m, 1H), 1.93 (m, 2H), 1.39 (m, 2H)

Example 83

Synthesis of 2-{(R)-2-[5-chloro-7-(tetrahydro-pyran-4-ylamino)-1H-indol-2-yl]-4,5-dihydro-thiazol-4-yl}-1-morpholin-4-yl-ethanone

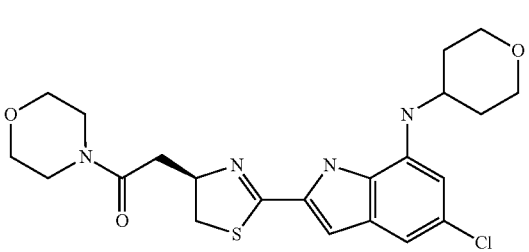

2-{(R)-2-[5-Chloro-7-(tetrahydro-pyran-
4-ylamino)-1H-indol-2-yl]-4,5-dihydro-
thiazol-4-yl}-1-morpholin-4-yl-ethanone The compound (44 mg, 0.11 mmol) prepared in Example 31 and morpholine instead of methylamine were reacted according to the same procedure as Example 82 to give the title compound (35 mg, Yield 68%).

¹H-NMR (500 HMz, DMSO-d₆); δ 11.53 (br s, 1H), 6.81 (s, 1H), 6.70 (s, 1H), 6.28 (s, 1H), 6.08 (m, 1H), 4.96 (m, 1H), 3.86 (m, 2H), 3.47 (m, 12H), 3.15 (m, 1H), 2.85 (m, 1H), 2.69 (m, 1H), 1.94 (m, 2H), 1.39 (m, 2H)

Example 84

Synthesis of 2-[(R)-2-(7-cyclopentylamino-5-fluoro-1H-indol-2-yl)-4,5-dihydro-thiazol-4-yl]-1-(4-methyl-piperazin-1-yl)-ethanone

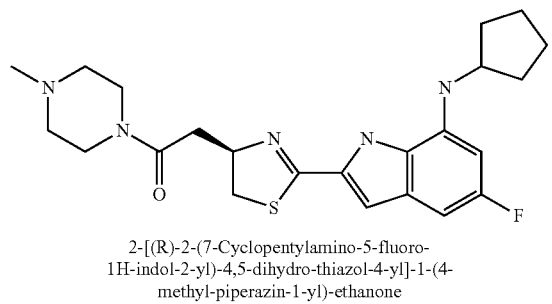

2-[(R)-2-(7-Cyclopentylamino-5-fluoro-1H-indol-2-yl)-4,5-dihydro-thiazol-4-yl]-1-(4-methyl-piperazin-1-yl)-ethanone The compound (100 mg, 0.28 mmol) prepared in Example 37 was dissolved in N,N-dimethylformamide (3 ml). 1-Methylpiperazine (36 mg, 0.36 mmol), EDC (90 mg, 0.47 mmol) and HOBT (75 mg, 0.55 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (78 mg, Yield 64%).

¹H-NMR (400 HMz, DMSO-d₆); δ 11.44 (br s, 1H), 6.73 (s, 1H), 6.52 (dd, 1H), 6.19 (d, J=1.2 Hz, 1H), 6.07 (dd, 1H), 4.99 (m, 1H), 3.84 (m, 2H), 3.65 (m, 1H), 3.49 (m, 4H), 3.20 (m, 1H), 2.88 (m, 1H), 2.71 (m, 1H), 2.28 (m, 4H), 2.17 (s, 3H), 1.98 (m, 2H), 1.72 (m, 2H), 1.58 (m, 4H)

Example 85

Synthesis of 2-[(R)-2-(7-cyclopentylamino-5-fluoro-1H-indol-2-yl)-4,5-dihydro-thiazol-4-yl]-N-(2-morpholin-4-yl-ethyl)-acetamide

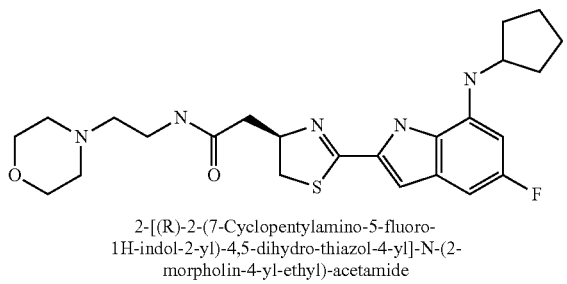

2-[(R)-2-(7-Cyclopentylamino-5-fluoro-1H-indol-2-yl)-4,5-dihydro-thiazol-4-yl]-N-(2-morpholin-4-yl-ethyl)-acetamide The compound (100 mg, 0.28 mmol) prepared in Example 37 and 4-(2-aminoethyl)morpholine instead of 1-methylpiperazine were reacted according to the same procedure as Example 84 to give the title compound (80 mg, Yield 60%).

¹H-NMR (400 HMz, DMSO-d₆); δ 11.46 (br s, 1H), 7.95 (m, 1H), 6.75 (s, 1H), 6.73 (dd, 1H), 6.18 (d, J=4.0 Hz, 1H), 6.07 (dd, 1H), 5.00 (m, 1H), 3.84 (m, 1H), 3.58 (m, 1H), 3.53 (m, 4H), 3.20 (m, 3H), 2.73 (m, 1H), 2.45 (m, 3H), 2.34 (m, 4H), 1.98 (m, 2H), 1.72 (m, 2H), 1.59 (m, 4H)

Example 86

Synthesis of 1-(4-acetyl-piperazin-1-yl)-2-[(R)-2-(7-cyclopentylamino-5-fluoro-1H-indol-2-yl)-4,5-dihydro-thiazol-4-yl]-ethanone

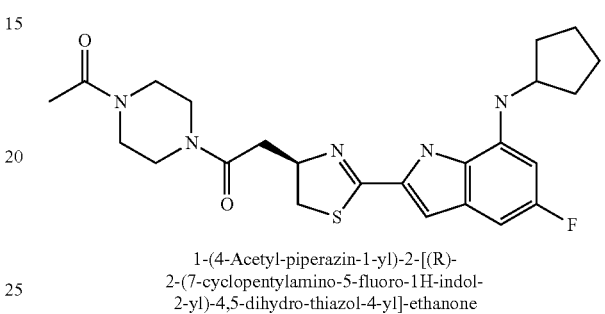

1-(4-Acetyl-piperazin-1-yl)-2-[(R)-2-(7-cyclopentylamino-5-fluoro-1H-indol-2-yl)-4,5-dihydro-thiazol-4-yl]-ethanone The compound (100 mg, 0.28 mmol) prepared in Example 37 and 1-acetylpiperazine instead of 1-methylpiperazine were reacted according to the same procedure as Example 84 to give the title compound (60 mg, Yield 55%).

Example 87

Synthesis of 2-[(R)-2-(7-cyclopentylamino-5-methoxy-1H-indol-2-yl)-4,5-dihydro-thiazol-4-yl]-N-methyl-acetamide

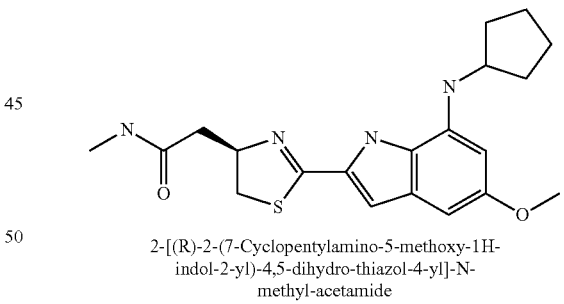

2-[(R)-2-(7-Cyclopentylamino-5-methoxy-1H-indol-2-yl)-4,5-dihydro-thiazol-4-yl]-N-methyl-acetamide The compound (83 mg, 0.22 mmol) prepared in Example 48 was dissolved in N,N-dimethylformamide (3 ml). Methylamine (0.17 ml, 2M in THF, 0.33 mmol), EDC (72 mg, 0.38 mmol) and HOBT (60 mg, 0.44 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (39 mg, Yield 46%).

¹H-NMR (500 HMz, DMSO-d₆); δ 11.22 (br s, 1H), 7.90 (m, 1H), 6.61 (s, 1H), 6.23 (s, 1H), 5.87 (m, 1H), 5.85 (s, 1H), 4.90 (m, 1H), 3.76 (m, 1H), 3.64 (s, 3H), 3.52 (m, 1H), 3.12 (m, 1H), 2.58 (m, 4H), 2.35 (m, 1H), 1.91 (m, 2H), 1.67 (m, 2H), 1.53 (m, 4H)

Example 88

Synthesis of 2-[(R)-2-(7-cyclopentylamino-5-methoxy-1H-indol-2-yl)-4,5-dihydro-thiazol-4-yl]-1-morpholin-4-yl-ethanone

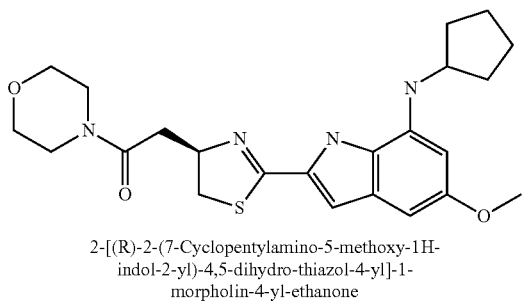

2-[(R)-2-(7-Cyclopentylamino-5-methoxy-1H-indol-2-yl)-4,5-dihydro-thiazol-4-yl]-1-morpholin-4-yl-ethanone The compound (83 mg, 0.22 mmol) prepared in Example 48 and morpholine instead of methylamine were reacted according to the same procedure as Example 87 to give the title compound (24 mg, Yield 24%).

$^1$H-NMR (500 HMz, DMSO-$d_6$); δ 11.21 (br s, 1H), 6.62 (s, 1H), 6.24 (s, 1H), 5.87 (m, 1H), 5.85 (s, 1H), 4.92 (m, 1H), 3.77 (m, 1H), 3.65 (s, 3H), 3.60 (m, 1H), 3.58-3.33 (m, 8H), 3.13 (m, 1H), 2.84 (m, 1H), 2.66 (m, 1H), 1.91 (m, 2H), 1.67 (m, 2H), 1.53 (m, 4H)

Example 89

Synthesis of 2-[(R)-2-(7-cyclopentylamino-1H-indol-2-yl)-4,5-dihydro-thiazol-4-yl]-N-ethyl-acetamide

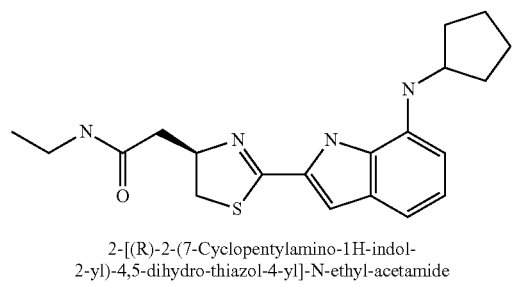

2-[(R)-2-(7-Cyclopentylamino-1H-indol-2-yl)-4,5-dihydro-thiazol-4-yl]-N-ethyl-acetamide The compound (9 mg, 0.03 mmol) prepared in Example 42 was dissolved in N,N-dimethylformamide (1 ml). Ethylamine hydrochloride (3 mg, 0.03 mmol), EDC (8 mg, 0.04 mmol), HOBT (5 mg, 0.04 mmol) and triethylamine (8 mg, 0.08 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (4 mg, Yield 41%).

$^1$H-NMR (400 HMz, CDCl$_3$); δ 9.66, 7.08~6.99 (m, 2H), 6.92 (d, 1H), 6.55 (d, J=7.2 Hz, 1H), 5.88 (m, 1H), 5.02 (m, 1H), 4.13 (m, 1H), 3.61 (m, 1H), 3.32~3.18 (m, 3H), 2.67 (1H, m), 2.52 (m, 1H), 2.04 (m, 1H), 1.72~1.53 (m, 6H), 1.08 (m, 3H)

Example 90

Synthesis of 2-[(R)-2-(7-cyclopentylamino-1H-indol-2-yl)-4,5-dihydro-thiazol-4-yl]-N-methyl-acetamide

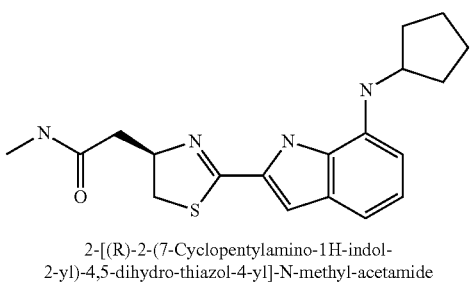

2-[(R)-2-(7-Cyclopentylamino-1H-indol-2-yl)-4,5-dihydro-thiazol-4-yl]-N-methyl-acetamide The compound (97 mg, 0.28 mmol) prepared in Example 42 and methylamine instead of ethylamine were reacted according to the same procedure as Example 89 to give the title compound (34 mg, Yield 34%).

$^1$H-NMR (500 HMz, DMSO-$d_6$); δ 11.33 (br s, 1H), 7.90 (m, 1H), 6.78 (m, 1H), 6.71 (s, 1H), 6.24 (s, 1H), 5.80 (m, 1H), 4.93 (m, 1H), 3.81 (m, 1H), 3.54 (m, 1H), 3.14 (m, 1H), 2.62 (m, 1H), 2.58 (m, 3H), 2.38 (m, 1H), 1.93 (m, 2H), 1.69 (m, 2H), 1.54 (m, 4H)

Example 91

Synthesis of 2-[(R)-2-(7-cyclopentylamino-1H-indol-2-yl)-4,5-dihydro-thiazol-4-yl]-1-morpholin-4-yl-ethanone

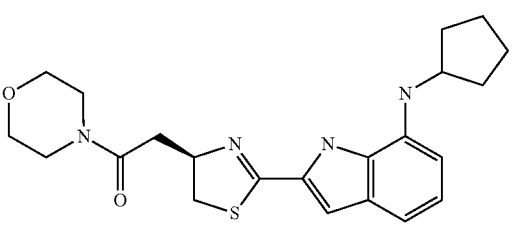

2-[(R)-2-(7-Cyclopentylamino-1H-indol-2-yl)-4,5-dihydro-thiazol-4-yl]-1-morpholin-4-yl-ethanone The compound (97 mg, 0.28 mmol) prepared in Example 42 and morpholine instead of ethylamine were reacted according to the same procedure as Example 89 to give the title compound (19 mg, Yield 16%).

$^1$H-NMR (500 HMz, DMSO-$d_6$); δ 11.32 (br s, 1H), 6.78 (m, 1H), 6.71 (s, 1H), 6.24 (s, 1H), 5.81 (m, 1H), 4.95 (m, 1H), 3.81 (m, 1H), 3.61 (m, 1H), 3.59-3.39 (m, 8H), 3.15 (m, 1H), 2.87 (m, 1H), 2.68 (m, 1H), 1.93 (m, 2H), 1.68 (m, 2H), 1.54 (m, 4H)

Example 92

Synthesis of N-methyl-2-{(R)-2-[7-(tetrahydro-pyran-4-ylamino)-1H-indol-2-yl]-4,5-dihydro-thiazol-4-yl}-acetamide

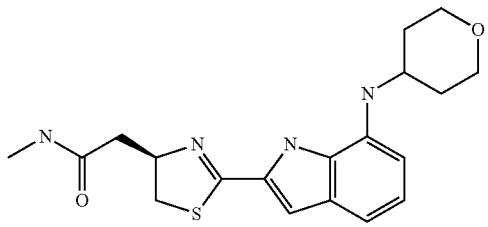

N-Methyl-2-{(R)-2-[7-(tetrahydro-pyran-4-ylamino)-1H-indol-2-yl]-4,5-dihydro-thiazol-4-yl}-acetamide The compound (80 mg, 0.22 mmol) prepared in Example 45 instead of the compound prepared in Example 48 was reacted according to the same procedure as Example 87 to give the title compound (17 mg, Yield 20%).

$^1$H-NMR (500 HMz, DMSO-d$_6$); δ 11.34 (br s, 1H), 7.90 (m, 1H), 6.79 (m, 1H), 6.72 (s, 1H), 6.33 (m, 1H), 5.76 (m, 1H), 4.93 (m, 1H), 3.86 (m, 1H), 3.54 (m, 2H), 3.43 (m, 2H), 3.14 (m, 1H), 2.61 (m, 1H), 2.59 (m, 3H), 2.38 (m, 1H), 1.95 (m, 2H), 1.40 (m, 2H)

Example 93

Synthesis of 1-morpholin-4-yl-2-{(R)-2-[7-(tetrahydro-pyran-4-ylamino)-1H-indol-2-yl]-4,5-dihydro-thiazol-4-yl}-ethanone

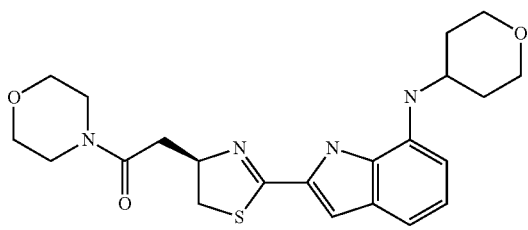

1-Morpholin-4-yl-2-{(R)-2-[7-(tetrahydro-pyran-4-ylamino)-1H-indol-2-yl]-4,5-dihydro-thiazol-4-yl}-ethanone The compound (80 mg, 0.22 mmol) prepared in Example 45 instead of the compound prepared in Example 42 was reacted according to the same procedure as Example 91 to give the title compound (12 mg, Yield 13%).

$^1$H-NMR (500 HMz, DMSO-d$_6$); δ 11.34 (br s, 1H), 6.79 (m, 1H), 6.72 (s, 1H), 6.33 (m, 1H), 5.77 (m, 1H), 4.95 (m, 1H), 3.87 (m, 1H), 3.61 (m, 1H), 3.57-3.38 (m, 11H), 3.15 (m, 1H), 2.87 (m, 1H), 2.68 (m, 1H), 1.95 (m, 2H), 1.40 (m, 2H)

Preparation 51

Synthesis of {5-chloro-2-[(R)-4-(2-iodo-ethyl)-4,5-dihydro-thiazol-2-yl]-1H-indol-7-yl}-cyclopentyl-amine

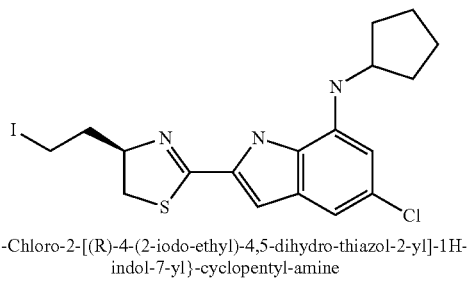

{5-Chloro-2-[(R)-4-(2-iodo-ethyl)-4,5-dihydro-thiazol-2-yl]-1H-indol-7-yl}-cyclopentyl-amine The compound (520 mg, 1.43 mmol) prepared in Example 28 was reacted according to the same procedure as Preparation 50 to give the title compound (524 mg, Yield 77%).

Example 94

Synthesis of {5-chloro-2-[(R)-4-(2-dimethylamino-ethyl)-4,5-dihydro-thiazol-2-yl]-1H-indol-7-yl}-cyclopentyl-amine

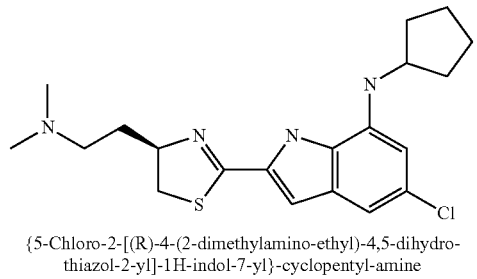

{5-Chloro-2-[(R)-4-(2-dimethylamino-ethyl)-4,5-dihydro-thiazol-2-yl]-1H-indol-7-yl}-cyclopentyl-amine The compound (52 mg, 0.11 mmol) prepared in Preparation 51 was dissolved in N,N-dimethylformamide (4 ml). Dimethylamine (1.1 ml, 2M in THF, 2.2 mmol) and potassium carbonate (300 mg, 2.17 mmol) were added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and concentrated. The residue was purified by column chromatography to give the title compound (29 mg, Yield 68%).

$^1$H-NMR (500 HMz, CDCl$_3$); δ 10.07 (br s, 1H), 6.99 (s, 1H), 6.80 (s, 1H), 6.42 (s, 1H), 4.67 (m, 1H), 3.54 (m, 1H), 3.16 (m, 1H), 2.46 (m, 1H), 2.37 (m, 1H), 2.19 (s, 6H), 2.02 (m, 3H), 1.81 (m, 4H), 1.69 (m, 4H)

Example 95

Synthesis of {5-chloro-2-[(R)-4-(2-morpholin-4-yl-ethyl)-4,5-dihydro-thiazol-2-yl]-1H-indol-7-yl}-cyclopentyl-amine

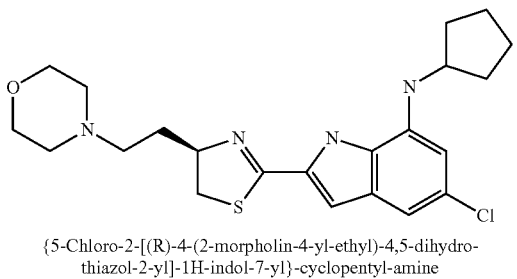

{5-Chloro-2-[(R)-4-(2-morpholin-4-yl-ethyl)-4,5-dihydro-thiazol-2-yl]-1H-indol-7-yl}-cyclopentyl-amine The compound (52 mg, 0.11 mmol) prepared in Preparation 51 and morpholine instead of dimethylamine were reacted according to the same procedure as Example 94 to give the title compound (18 mg, Yield 38%).

$^1$H NMR (DMSO-$d_6$, ppm); δ 11.46 (1H, s), 6.79 (1H, s), 6.68 (1H, s), 6.11 (1H, s), 6.09 (1H, d), 4.61 (1H, quin), 3.81 (1H, m), 3.57 (4H, m), 3.15 (1H, m), 2.50-2.43 (3H, m), 2.35 (4H, m), 1.95 (2H, m), 1.80 (1H, m), 1.68 (2H, m), 1.57-1.49 (4H, m), 1.21 (1H, m)

FAB MS (m/e)=434

Example 96

Synthesis of {5-chloro-2-[(R)-4-(2-piperazin-1-yl-ethyl)-4,5-dihydro-thiazol-2-yl]-1H-indol-7-yl}-cyclopentyl-amine

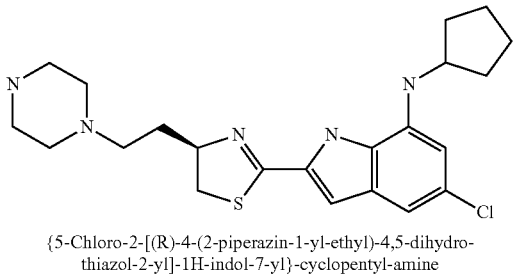

{5-Chloro-2-[(R)-4-(2-piperazin-1-yl-ethyl)-4,5-dihydro-thiazol-2-yl]-1H-indol-7-yl}-cyclopentyl-amine The compound (250 mg, 0.53 mmol) prepared in Preparation 51 was dissolved in tetrahydrofuran (10 ml). 1-t-Butoxycarbonylpiperazine (980 mg, 5.28 mmol) and potassium carbonate (730 mg, 5.28 mmol) were added thereto, and the mixture was stirred for 8 h at 80° C. After completion of the reaction, water was added. The mixture was extracted with ethyl acetate, dried over anhydrous magnesium sulfate, and filtered. The filtrate was distilled under reduced pressure.

Thus obtained compound was dissolved in dichloromethane (50 ml), and 4N hydrochloric acid ethyl acetate solution (1.3 ml, 5.28 mmol) was added thereto. The mixture was stirred for 4 h at room temperature. After completion of the reaction, the reaction solution was distilled under reduced pressure to give a solid. The solid was washed with ethylether, and dried to give the title compound (125 mg, Yield 55%).

$^1$H NMR (DMSO-$d_6$, ppm); δ 11.48 (1H, s), 6.79 (1H, s), 6.67 (1H, s), 6.11 (1H, s), 6.10 (1H, d), 4.61 (1H, m), 3.80 (1H, m), 3.54 (1H, m), 3.15 (1H, m), 2.93 (2H, m), 2.50-2.41 (2H, m), 2.31 (3H, m), 1.95 (4H, m), 1.79 (1H, m), 1.68 (3H, m), 1.57-1.50 (4H, m), 1.20 (1H, m)

FAB MS (m/e)=432

Example 97

Synthesis of 1-(4-{2-[(R)-2-(5-chloro-7-cyclopentylamino-1H-indol-2-yl)-4,5-dihydro-thiazol-4-yl]-ethyl}-piperazin-1-yl)-ethanone

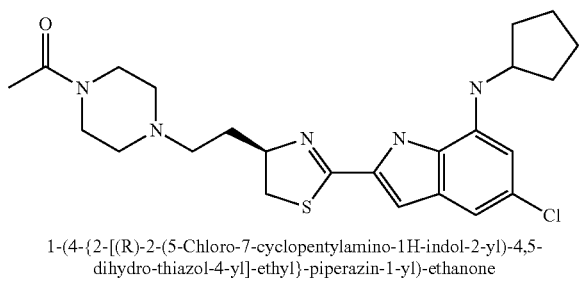

1-(4-{2-[(R)-2-(5-Chloro-7-cyclopentylamino-1H-indol-2-yl)-4,5-dihydro-thiazol-4-yl]-ethyl}-piperazin-1-yl)-ethanone The compound (80 mg, 0.22 mmol) prepared in Preparation 51 and 1-acetylpiperazine instead of dimethylamine were reacted according to the same procedure as Example 94 to give the title compound (26 mg, Yield 33%).

$^1$H-NMR (500 HMz, DMSO-$d_6$); δ 11.47 (br s, 1H), 6.79 (s, 1H), 6.68 (s, 1H), 6.16 (s, 1H), 6.11 (m, 1H), 4.62 (m, 1H), 3.80 (m, 1H), 3.55 (m, 1H), 3.39 (m, 4H), 3.15 (m, 1H), 2.46 (m, 1H), 2.32 (m, 4H), 1.95 (m, 4H), 1.80 (m, 1H), 1.68 (m, 2H), 1.53 (m, 4H)

Example 98

Synthesis of (5-chloro-2-{(R)-4-[2-(4-ethanesulfonyl-piperazin-1-yl)-ethyl]-4,5-dihydro-thiazol-2-yl}-1H-indol-7-yl)-cyclopentyl-amine

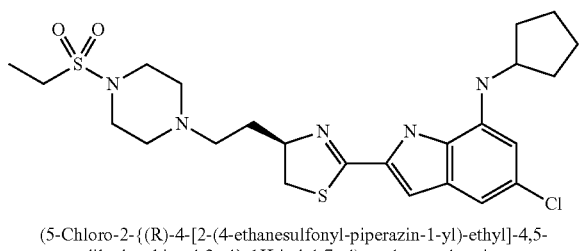

(5-Chloro-2-{(R)-4-[2-(4-ethanesulfonyl-piperazin-1-yl)-ethyl]-4,5-dihydro-thiazol-2-yl}-1H-indol-7-yl)-cyclopentyl-amine The compound (40 mg, 0.11 mmol) prepared in Preparation 51 and 1-ethylsulfonylpiperazine instead of dimethylamine were reacted according to the same procedure as Example 94 to give the title compound (17 mg, Yield 39%).

$^1$H-NMR (500 HMz, CDCl$_3$); δ 11.29 (br s, 1H), 6.97 (s, 1H), 6.86 (s, 1H), 6.37 (s, 1H), 4.93 (m, 1H), 3.92 (br s, 1H), 3.77 (m, 1H), 3.57 (m, 1H), 3.16 (m, 1H), 2.95 (m, 2H), 2.80

(m, 4H), 2.42-2.28 (m, 4H), 2.03 (m, 4H), 1.74 (m, 3H), 1.63 (m, 4H), 1.43 (m, 1H), 1.32 (t, 3H)

Example 99

Synthesis of 1-(4-{2-[(R)-2-(5-chloro-7-cyclopentylamino-1H-indol-2-yl)-4,5-dihydro-thiazol-4-yl]-ethyl}-piperazin-1-yl)-2-hydroxy-ethanone

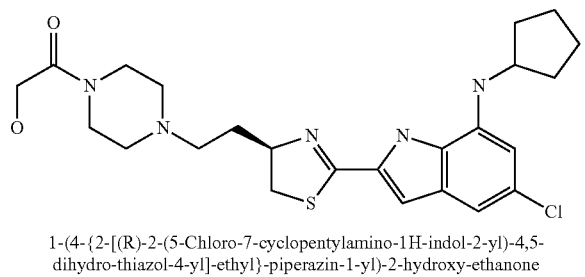

1-(4-{2-[(R)-2-(5-Chloro-7-cyclopentylamino-1H-indol-2-yl)-4,5-dihydro-thiazol-4-yl]-ethyl}-piperazin-1-yl)-2-hydroxy-ethanone The compound (85 mg, 0.20 mmol) prepared in Example 96 was dissolved in N,N-dimethylformamide (1 ml). Glycolic acid (22 mg, 0.30 mmol), EDC (64 mg, 0.33 mmol) and HOBT (53 mg, 0.39 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (41 mg, Yield 44%).

$^1$H-NMR (500 HMz, DMSO-$d_6$); δ 11.47 (br s, 1H), 6.79 (s, 1H), 6.68 (s, 1H), 6.16 (s, 1H), 6.10 (m, 1H), 4.63 (m, 1H), 4.50 (m, 1H), 4.04 (m, 2H), 3.81 (m, 1H), 3.55 (m, 1H), 3.43 (m, 2H), 3.16 (m, 1H), 2.52 (m, 2H), 2.35 (m, 4H), 1.95 (m, 3H), 1.81 (m, 1H), 1.68 (m, 2H), 1.53 (m, 4H)

Example 100

Synthesis of (5-chloro-2-{(R)-4-[2-(4-methyl-piperazin-1-yl)-ethyl]-4,5-dihydro-thiazol-2-yl}-1H-indol-7-yl)-cyclopentyl-amine

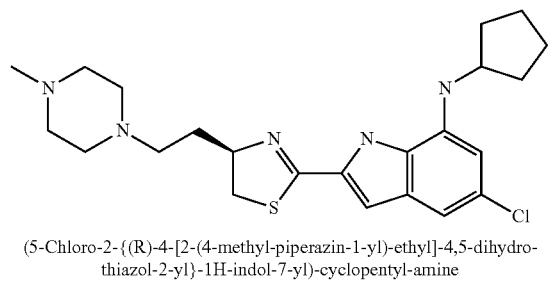

(5-Chloro-2-{(R)-4-[2-(4-methyl-piperazin-1-yl)-ethyl]-4,5-dihydro-thiazol-2-yl}-1H-indol-7-yl)-cyclopentyl-amine The compound (80 mg, 0.22 mmol) prepared in Preparation 51 and 1-methylpiperazine instead of dimethylamine were reacted according to the same procedure as Example 94 to give the title compound (24 mg, Yield 32%).

$^1$H-NMR (500 HMz, DMSO-$d_6$); δ 11.47 (br s, 1H), 6.79 (s, 1H), 6.67 (s, 1H), 6.16 (s, 1H), 6.10 (m, 1H), 4.59 (m, 1H), 3.80 (m, 1H), 3.54 (m, 1H), 3.15 (m, 1H), 2.40 (m, 10H), 2.13 (s, 3H), 1.95 (m, 3H), 1.78 (m, 1H), 1.68 (m, 2H), 1.53 (m, 4H)

Example 101

Synthesis of 1-{2-[(R)-2-(5-chloro-7-cyclopentylamino-1H-indol-2-yl)-4,5-dihydro-thiazol-4-yl]-ethyl}-piperidin-4-ol

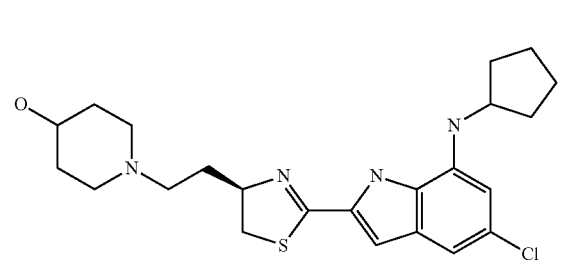

1-{2-[(R)-2-(5-Chloro-7-cyclopentylamino-1H-indol-2-yl)-4,5-dihydro-thiazol-4-yl]-ethyl}-piperidin-4-ol The compound (80 mg, 0.22 mmol) prepared in Preparation 51 and 4-hydroxypiperidine instead of dimethylamine were reacted according to the same procedure as Example 94 to give the title compound (28 mg, Yield 37%).

$^1$H-NMR (500 HMz, DMSO-$d_6$); δ 11.48 (br s, 1H), 6.79 (s, 1H), 6.68 (s, 1H), 6.16 (s, 1H), 6.10 (m, 1H), 4.60 (m, 1H), 3.80 (m, 1H), 3.54 (m, 1H), 3.32 (m, 4H), 3.16 (m, 1H), 2.71 (m 1H), 2.60 (m, 1H), 2.32 (m, 5H), 1.71 (m, 5H), 1.57 (m, 5H)

Example 102

Synthesis of (4-{2-[(R)-2-(5-chloro-7-cyclopentylamino-1H-indol-2-yl)-4,5-dihydro-thiazol-4-yl]-ethyl}-piperazin-2-one

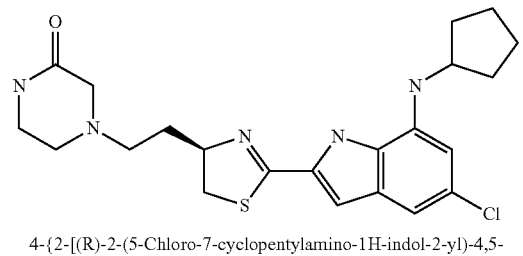

4-{2-[(R)-2-(5-Chloro-7-cyclopentylamino-1H-indol-2-yl)-4,5-dihydro-thiazol-4-yl]-ethyl}-piperazin-2-one The compound (80 mg, 0.22 mmol) prepared in Preparation 51 and 2-oxopiperazine instead of dimethylamine were reacted according to the same procedure as Example 94 to give the title compound (38 mg, Yield 51%).

$^1$H-NMR (500 HMz, DMSO-$d_6$); δ 11.48 (br s, 1H), 7.71 (s, 1H), 6.79 (s, 1H), 6.68 (s, 1H), 6.16 (s, 1H), 6.10 (m, 1H), 4.61 (m, 1H), 3.81 (m, 1H), 3.55 (m, 1H), 3.13 (m, 3H), 2.92 (m, 2H), 2.56 (m 3H), 1.96 (m, 3H), 1.80 (m, 1H), 1.68 (m, 2H), 1.53 (m, 4H)

Example 103

Synthesis of (5-chloro-2-{(R)-4-[2-(3-dimethylamino-pyrrolidin-1-yl)-ethyl]-4,5-dihydro-thiazol-2-yl}-1H-indol-7-yl)-cyclopentyl-amine

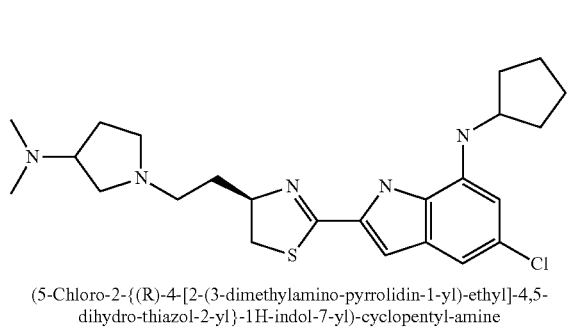

(5-Chloro-2-{(R)-4-[2-(3-dimethylamino-pyrrolidin-1-yl)-ethyl]-4,5-dihydro-thiazol-2-yl}-1H-indol-7-yl)-cyclopentyl-amine The compound (80 mg, 0.22 mmol) prepared in Preparation 51 and 3-dimethylaminopyrrolidine instead of dimethylamine were reacted according to the same procedure as Example 94 to give the title compound (21 mg, Yield 27%).

$^1$H-NMR (500 HMz, DMSO-$d_6$); δ 11.47 (br s, 1H), 6.79 (s, 1H), 6.67 (s, 1H), 6.16 (s, 1H), 6.11 (m, 1H), 4.62 (m, 1H), 3.80 (m, 1H), 3.52 (m, 1H), 3.15 (m, 1H), 2.66 (m, 2H), 2.56 (m 2H), 2.41 (m, 2H), 2.27 (m, 1H), 1.93 (m, 3H), 1.71 (m, 4H), 1.53 (m, 4H)

Example 104

Synthesis of {5-chloro-2-[(R)-4-(2-piperidin-1-yl-ethyl)-4,5-dihydro-thiazol-2-yl]-1H-indol-7-yl}-cyclopentyl-amine

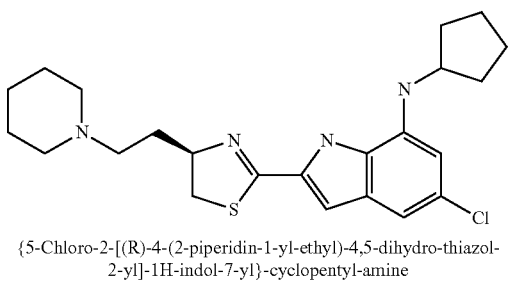

{5-Chloro-2-[(R)-4-(2-piperidin-1-yl-ethyl)-4,5-dihydro-thiazol-2-yl]-1H-indol-7-yl}-cyclopentyl-amine The compound (80 mg, 0.22 mmol) prepared in Preparation 51 and piperidine instead of dimethylamine were reacted according to the same procedure as Example 94 to give the title compound (30 mg, Yield 41%).

$^1$H-NMR (500 HMz, DMSO-$d_6$); δ 11.52 (br s, 1H), 6.80 (s, 1H), 6.70 (s, 1H), 6.16 (s, 1H), 6.12 (m, 1H), 4.63 (m, 1H), 3.80 (m, 1H), 3.57 (m, 1H), 3.29 (m, 4H), 3.17 (m, 1H), 2.60 (m, 4H), 1.95 (m, 3H), 1.68 (m, 2H), 1.58 (m, 9H)

Example 105

Synthesis of (5-chloro-2-{(R)-4-[2-(1,1-dioxo-thiomorpholin-4-yl)-ethyl]-4,5-dihydro-thiazol-2-yl}-1H-indol-7-yl)-cyclopentyl-amine

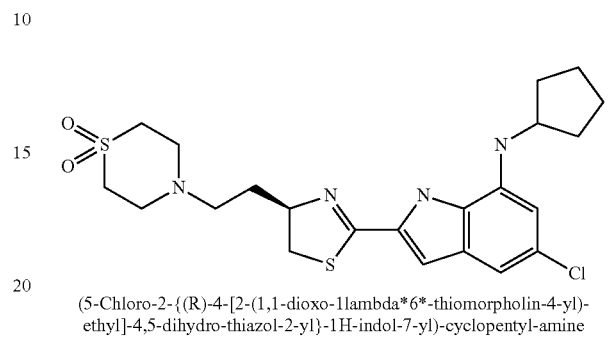

(5-Chloro-2-{(R)-4-[2-(1,1-dioxo-1lambda*6*-thiomorpholin-4-yl)-ethyl]-4,5-dihydro-thiazol-2-yl}-1H-indol-7-yl)-cyclopentyl-amine The compound (80 mg, 0.22 mmol) prepared in Preparation 51 and thiomorpholine-1,1-dioxide instead of dimethylamine were reacted according to the same procedure as Example 94 to give the title compound (31 mg, Yield 38%).

$^1$H-NMR (500 HMz, DMSO-$d_6$); δ 11.48 (br s, 1H), 6.79 (s, 1H), 6.68 (s, 1H), 6.16 (s, 1H), 6.09 (m, 1H), 4.61 (m, 1H), 3.80 (m, 1H), 3.56 (m, 1H), 3.16 (m, 1H), 3.07 (m, 4H), 2.89 (m, 4H), 2.67 (m, 2H), 1.94 (m, 3H), 1.81 (m, 1H), 1.68 (m, 2H), 1.53 (m, 4H)

Example 106

Synthesis of {5-chloro-2-[(R)-4-(2-pyrazol-1-yl-ethyl)-4,5-dihydro-thiazol-2-yl]-1H-indol-7-yl}-cyclopentyl-amine

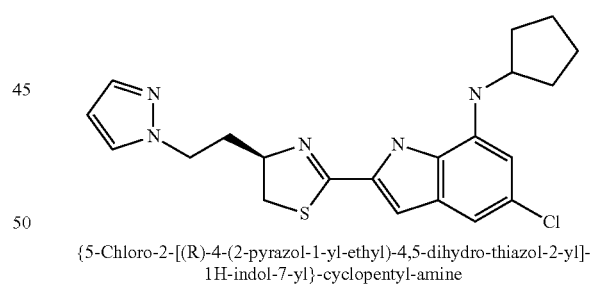

{5-Chloro-2-[(R)-4-(2-pyrazol-1-yl-ethyl)-4,5-dihydro-thiazol-2-yl]-1H-indol-7-yl}-cyclopentyl-amine The compound (81 mg, 0.11 mmol) prepared in Preparation 51 was dissolved in tetrahydrofuran (4 ml). Pyrazole (58 mg, 0.85 mmol) and sodium hydride (21 mg, 60%, 0.85 mmol) were added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and concentrated. The residue was purified by column chromatography to give the title compound (24 mg, Yield 34%).

$^1$H NMR (DMSO-$d_6$, ppm); δ 11.50 (1H, s), 7.76 (1H, s), 7.42 (1H, s), 6.80 (1H, s), 6.70 (1H, s), 6.22 (1H, s), 6.17 (1H, s), 6.11 (1H, d), 4.49 (1H, quin), 4.32 (2H, m), 3.80 (1H, m), 3.53 (1H, t), 3.12 (1H, t), 2.38 (1H, m), 2.14 (1H, m), 1.92 (2H, m), 1.68 (2H, m), 1.59-1.50 (4H, m)
FAB MS (m/e)=414

Example 107

Synthesis of (S)-1-{2-[(R)-2-(5-chloro-7-cyclopentylamino-1H-indol-2-yl)-4,5-dihydro-thiazol-4-yl]-ethyl}-pyrrolidine-2-carboxylic acid

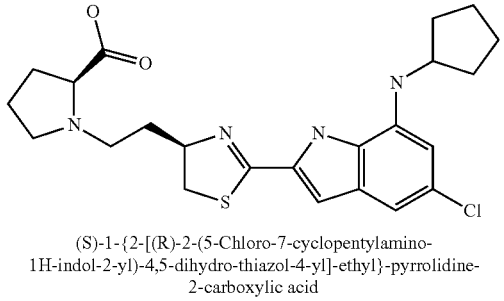

(S)-1-{2-[(R)-2-(5-Chloro-7-cyclopentylamino-1H-indol-2-yl)-4,5-dihydro-thiazol-4-yl]-ethyl}-pyrrolidine-2-carboxylic acid The compound (200 mg, 0.42 mmol) prepared in Preparation 51 was dissolved in tetrahydrofuran (20 ml). Pyrrolidine-2-carboxylic acid methyl ester hydrochloride (700 mg, 4.22 mmol) and potassium carbonate (1.2 g, 8.44 mmol) were added thereto, and the mixture was stirred for 8 h at 80° C. After completion of the reaction, water was added. The mixture was extracted with ethyl acetate, dried over anhydrous magnesium sulfate, and filtered. The filtrate was distilled under reduced pressure.

Thus obtained compound was dissolved in tetrahydrofuran (10 ml), methanol (10 ml) and water (10 ml). Lithium hydroxide monohydrate (71 mg, 1.70 mmol) was added thereto, and the mixture was stirred for 4 h at room temperature. After completion of the reaction, 1N hydrochloric acid solution was added. The mixture was extracted with ethyl acetate, washed with saturated sodium chloride solution, dried over anhydrous magnesium sulfate, and filtered. The filtrate was distilled under reduced pressure, and purified by column chromatography to give the title compound (34 mg, Yield 18%).

$^1$H NMR (CDCl$_3$, ppm); δ 12.04 (1H, s), 11.02 (1H, s), 6.85 (1H, s), 6.69 (1H, s), 6.31 (1H, s), 6.24 (1H, m), 4.37 (1H, m), 4.10 (1H, m), 3.86 (1H, m), 3.79 (1H, m), 3.59 (1H, m), 3.28 (1H, m), 3.17 (1H, m), 2.88 (2H, m), 2.59 (1H, m), 2.21 (1H, m), 2.06-1.59 (11H, m), 1.23 (1H, m)
FAB MS (m/e)=461

Example 108

Synthesis of {5-chloro-2-[(R)-4-(2-methanesulfonyl-ethyl)-4,5-dihydro-thiazol-2-yl]-1H-indol-7-yl}-cyclopentyl-amine

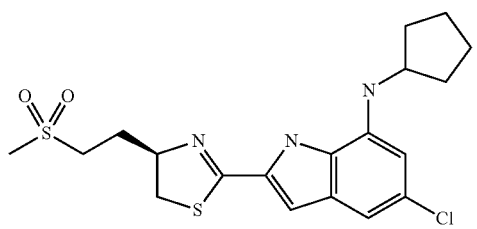

{5-Chloro-2-[(R)-4-(2-methanesulfonyl-ethyl)-4,5-dihydro-thiazol-2-yl]-1H-indol-7-yl}-cyclopentyl-amine The compound (50 mg, 0.11 mmol) prepared in Preparation 51 was dissolved in N,N-dimethylformamide (2 ml). Sodium methanesulfinate (54 mg, 0.55 mmol) was added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and concentrated. The residue was purified by column chromatography to give the title compound (19 mg, Yield 45%).

$^1$H-NMR (400 HMz, CDCl$_3$); δ 10.39 (br s, 1H), 7.03 (s, 1H), 6.89 (s, 1H), 6.48 (s, 1H), 6.17 (s, 1H), 4.77 (m, 1H), 3.87 (m, 1H), 3.59 (m, 1H), 3.29 (m, 1H), 3.17 (m, 2H), 2.86 (s, 3H), 2.26 (m, 2H), 2.10 (m, 2H), 1.70 (m, 4H), 1.51 (m, 2H)

Example 109

Synthesis of 3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester

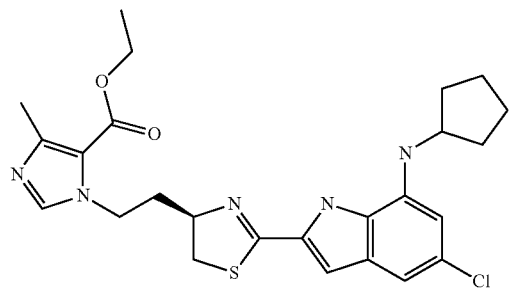

3-{2-[(R)-2-(5-Chloro-7-cyclopentylamino-1H-indol-2-yl)-4,5-dihydro-thiazol-4-yl]-ethyl}-5-methyl-3H-imidazole-4-carboxylic acid ethyl ester The compound (150 mg, 0.31 mmol) prepared in Preparation 51 and 5-methyl-3H-imidazole-4-carboxylic acid ethyl ester instead of pyrazole were reacted according to the same procedure as Example 106 to give the title compound (74 mg, Yield 47%).

$^1$H-NMR (500 HMz, DMSO-d$_6$); δ 11.49 (br s, 1H), 7.71 (s, 1H), 6.80 (s, 1H), 6.72 (s, 1H), 6.17 (s, 1H), 6.08 (m, 1H), 4.56 (m, 1H), 4.16 (m, 4H), 3.81 (m, 1H), 3.58 (m, 1H), 3.18 (m, 1H), 2.46 (s, 3H), 2.11 (m, 2H), 1.95 (m, 2H), 1.68 (m, 2H), 1.53 (m, 4H), 1.22 (m, 3H)

Example 110

Synthesis of 3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid

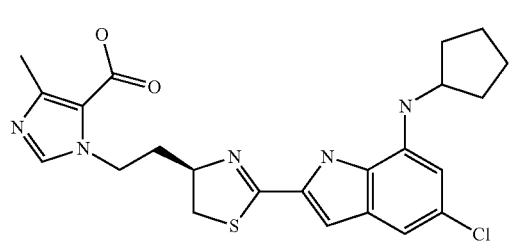

3-{2-[(R)-2-(5-Chloro-7-cyclopentylamino-1H-indol-2-yl)-4,5-dihydro-thiazol-4-yl]-ethyl}-5-methyl-3H-imidazole-4-carboxylic acid The compound (35 mg, 0.07 mmol) prepared in Example 109 was dissolved in tetrahydrofuran (10 ml), methanol (10 ml) and water (10 ml). Lithium hydroxide monohydrate (29 mg, 0.70 mmol) was added thereto, and the mixture was stirred for 8 h at room temperature. After completion of the reaction, 1N hydrochloric acid solution was added. The mixture was extracted with ethyl acetate, washed with saturated sodium chloride solution, dried over anhydrous magnesium sulfate, and filtered. The filtrate was distilled under reduced pressure, and purified by column chromatography to give the title compound (17 mg, Yield 52%).

$^1$H NMR (DMSO-$d_6$, ppm); δ 11.50 (1H, s), 7.71 (1H, s), 6.80 (1H, s), 6.72 (1H, s), 6.17 (1H, s), 6.08 (1H, m), 4.55 (1H, m), 4.13 (2H, m), 3.80 (1H, m), 3.55 (2H, m), 2.19-2.15 (2H, m), 1.95 (3H, m), 1.68 (3H, m), 1.51 (5H, m)

FAB MS (m/e)=472

Example 111

Synthesis of 1-{2-[(R)-2-(5-chloro-7-cyclopentylamino-1H-indol-2-yl)-4,5-dihydro-thiazol-4-yl]-ethyl}-pyrrolidin-2-one

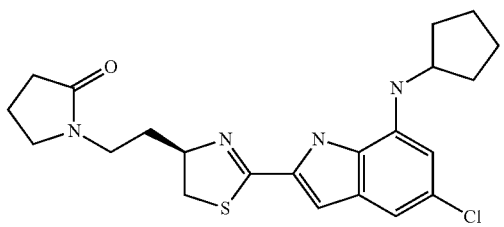

1-{2-[(R)-2-(5-Chloro-7-cyclopentylamino-1H-indol-2-yl]-4,5-dihydro-thiazol-4-yl]-ethyl}-pyrrolidine-2-one The compound (80 mg, 0.22 mmol) prepared in Preparation 51 and pyrrolidinone instead of dimethylamine were reacted according to the same procedure as Example 94 to give the title compound (17 mg, Yield 36%).

$^1$H-NMR (500 HMz, DMSO-$d_6$); δ 11.49 (br s, 1H), 6.80 (s, 1H), 6.69 (s, 1H), 6.16 (s, 1H), 4.51 (m, 1H), 3.80 (m, 1H), 3.57 (m, 1H), 3.46 (m, 1H), 3.32 (m, 1H), 3.15 (m, 1H), 2.18 (m, 2H), 1.91 (m, 5H), 1.80 (m, 1H), 1.68 (m, 2H), 1.53 (m, 4H)

Preparation 52

Synthesis of {5-chloro-2-[(R)-4-(2-iodo-ethyl)-4,5-dihydro-thiazol-2-yl]-1H-indol-7-yl}-(tetrahydro-pyran-4-yl)-amine

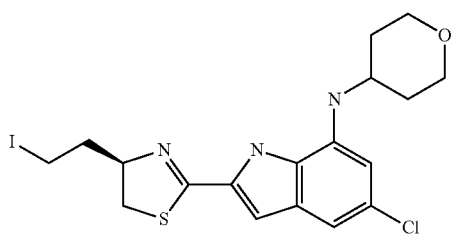

{5-Chloro-2-[(R)-4-(2-iodo-ethyl)-4,5-dihydro-thiazol-2-yl]-1H-indol-7-yl}-(tetrahydro-pyran-4-yl)-amine The compound (3.7 g, 10.2 mmol) prepared in Example 32 was dissolved in tetrahydrofuran (100 ml). Imidazole (2.1 g, 30.6 mmol), triphenylphosphine (4.0 g, 15.3 mmol), and iodine (3.9 g, 15.3 mmol) were added thereto, and the mixture was stirred for 8 h at 0° C.~room temperature. After completion of the reaction, ethyl acetate (100 ml) was added, and the mixture was washed with water (2×100 ml). The organic layer was concentrated, and the residue was separated by column chromatography to give the title compound (2.0 g, 4.07 mmol, Yield 40%).

Preparation 53

Synthesis of 1-(2-{(R)-2-[5-chloro-7-(tetrahydropyran-4-ylamino)-1H-indol-2-yl]-4,5-dihydro-thiazol-4-yl}-ethyl)-piperidine-3-carboxylic acid ethyl ester

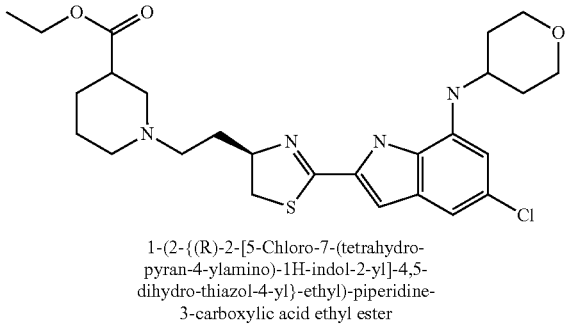

1-(2-{(R)-2-[5-Chloro-7-(tetrahydropyran-4-ylamino)-1H-indol-2-yl]-4,5-dihydro-thiazol-4-yl}-ethyl)-piperidine-3-carboxylic acid ethyl ester The compound (300 mg, 0.63 mmol) prepared in Preparation 52 was dissolved in N,N-dimethylformamide (20 ml). Piperidine-3-carboxylic acid ethyl ester (1.97 ml, 12.7 mmol) and potassium carbonate (1.75 g, 12.7 mmol) were added thereto, and the mixture was stirred for 4 h at room temperature. After completion of the reaction, 1N hydrochloric acid solution was added. The mixture was extracted with ethyl acetate, washed with saturated sodium chloride solution, dried over anhydrous magnesium sulfate, and filtered. The filtrate was distilled under reduced pressure, and purified by column chromatography to give the title compound (150 mg, Yield 46%).

$^1$H NMR (DMSO-$d_6$, ppm); δ 11.48 (1H, s), 6.82 (1H, s), 6.67 (1H, s), 6.29 (1H, s), 6.04 (1H, d), 4.61 (1H, quin), 4.47 (1H, m), 3.87 (2H, m), 3.62 (2H, q), 3.56 (2H, m), 3.44-3.39 (4H, m), 3.14 (2H, m), 2.52 (1H, m), 2.37-2.30 (6H, m), 1.96-1.92 (3H, m), 1.81 (1H, m), 1.42 (2H, m), 1.28 (3H, t)

FAB MS (m/e)=519

Example 112

Synthesis of 1-(2-{(R)-2-[5-chloro-7-(tetrahydropyran-4-ylamino)-1H-indol-2-yl]-4,5-dihydro-thiazol-4-yl}-ethyl)-piperidine-3-carboxylic acid

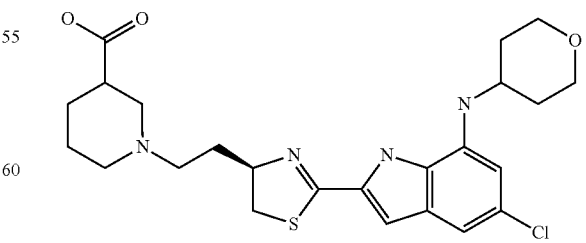

1-(2-{(R)-2-[5-Chloro-7-(tetrahydropyran-4-ylamino)-1H-indol-2-yl]-4,5-dihydro-thiazol-4-yl}-ethyl)-piperidine-3-carboxylic acid The compound (135 mg, 0.28 mmol) prepared in Preparation 53 was reacted according to the same procedure as Example 110 to give the title compound (90 mg, Yield 58%).

$^1$H NMR (DMSO-d$_6$, ppm); δ 13.17 (1H, s), 11.94 (1H, s), 6.80 (1H, s), 6.68 (1H, s), 6.28 (1H, s), 6.04 (1H, d), 4.62 (1H, quin), 4.47 (1H, m), 3.87 (2H, m), 3.56 (2H, m), 3.44-3.39 (4H, m), 3.14 (2H, m), 2.52 (1H, m), 2.37-2.30 (6H, m), 1.96-1.92 (3H, m), 1.80 (1H, m), 1.40 (2H, m)

FAB MS (m/e)=491

Example 113

Synthesis of 1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid dimethylamide

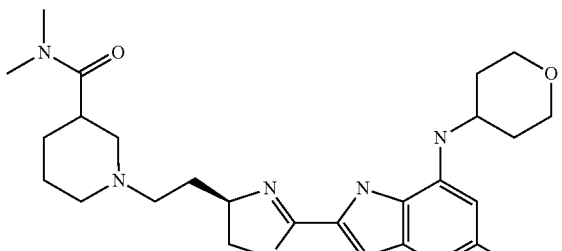

1-(2-{(R)-2-[5-Chloro-7-(tetrahydro-pyran-4-ylamino)-1H-indol-2-yl]-4,5-dihydro-thiazol-4-yl}-ethyl)-piperidine-3-carboxylic acid dimethylamide The compound (84 mg, 0.18 mmol) prepared in Example 112 was dissolved in N,N-dimethylformamide (4 ml). Dimethylamine (0.13 ml, 2M in THF, 0.27 mmol), EDC (58 mg, 0.30 mmol) and HOBT (48 mg, 0.35 mmol) were added thereto, and the mixture was stirred for 8 h at room temperature. After completion of the reaction, saturated sodium bicarbonate solution was added. The mixture was extracted with ethyl acetate, dried over anhydrous magnesium sulfate, and filtered. The filtrate was distilled under reduced pressure, and concentrated. The residue was purified by column chromatography to give the title compound (18 mg, Yield 20%).

$^1$H NMR (DMSO-d$_6$, ppm); δ 11.48 (1H, s), 6.81 (1H, s), 6.69 (1H, s), 6.28 (1H, s), 6.04 (1H, d), 4.60 (1H, quin), 3.87 (2H, m), 3.56 (2H, m), 3.44 (2H, t), 3.16 (1H, m), 2.97 (3H, s), 2.95 (1H, m), 2.88-2.76 (2H, m), 2.74 (5H, m), 1.96 (4H, m), 1.80 (2H, m), 1.66 (2H, m), 1.50-1.37 (3H, m), 1.23 (1H, m)

FAB MS (m/e)=518

Example 114

Synthesis of [(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-carbamic acid t-butyl ester

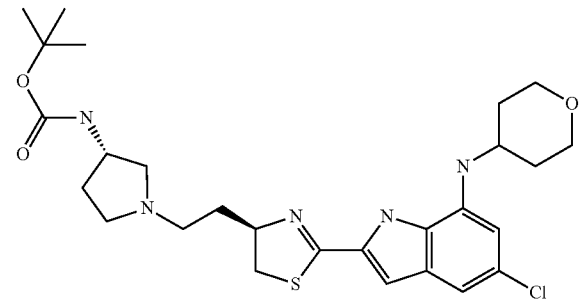

[(S)-1-(2-{(R)-2-[5-Chloro-7-(tetrahydro-pyran-4-ylamino)-1H-indol-2-yl]-4,5-dihydro-thiazol-4-yl}-ethyl)-pyrrolidin-3-yl]-carbamic acid tert-butyl ester The compound (300 mg, 0.63 mmol) prepared in Preparation 52 and (S)-pyrrolidin-3-yl-carbamic acid t-butyl ester instead of piperidine-3-carboxylic acid ethyl ester were reacted according to the same procedure as Preparation 53 to give the title compound (210 mg, Yield 61%).

$^1$H-NMR (500 HMz, DMSO-d$_6$); δ 11.48 (br s, 1H), 6.92 (m, 1H), 6.81 (s, 1H), 6.68 (s, 1H), 6.28 (m, 1H), 6.05 (m, 1H), 4.63 (m, 1H), 3.86 (m, 3H), 3.59 (m, 1H), 3.54 (m, 1H), 3.44 (m, 2H), 3.14 (m, 1H), 2.71-2.58 (m, 2H), 2.25 (m, 1H), 1.95 (m, 4H), 1.75 (m, 1H), 1.52 (m, 1H), 1.39 (m, 2H), 1.37-1.32 (m, 11H)

Example 115

Synthesis of (2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine

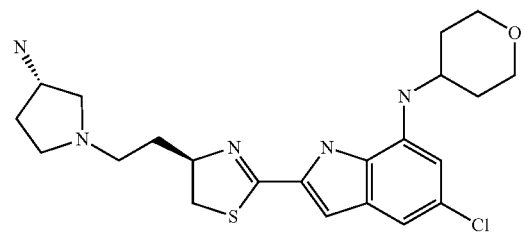

(2-{(R)-4-[2-((S)-3-Amino-pyrrolidin-1-yl)-ethyl]-4,5-dihydro-thiazol-2-yl}-5-chloro-1H-indol-7-yl)-(tetrahydro-pyran-4-yl)-amine The compound (150 mg, 0.27 mmol) prepared in Example 114 was dissolved in dichloromethane (30 ml). 4N hydrochloric acid dioxane solution (0.34 ml, 1.35 mmol) was added thereto, and the mixture was stirred for 4 h at room temperature. After completion of the reaction, the reaction solution was distilled under reduced pressure to give a solid. The solid was washed with ethylether, and dried to give the title compound (92 mg, Yield 75%).

$^1$H NMR (DMSO-d$_6$, ppm); δ 10.92 (1H, s), 8.63 (2H, s, br), 6.86 (1H, s), 6.83 (1H, s), 6.43 (1H, s), 6.11 (1H, m), 4.72 (1H, m), 3.65 (5H, m), 3.45 (5H, m), 3.22 (3H, m), 2.37 (2H, m), 2.19 (3H, m), 1.90 (2H, m), 1.49 (2H, m)

FAB MS (m/e)=448

Example 116

Synthesis of N—[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-acetamide

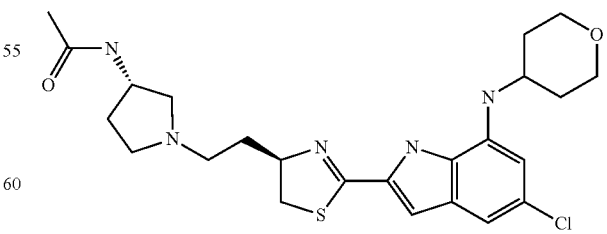

N-[(S)-1-(2-{(R)-2-[5-Chloro-7-(tetrahydro-pyran-4-ylamino)-1H-indol-2-yl]-4,5-dihydro-thiazol-4-yl}-ethyl)-pyrrolidin-3-yl]-acetamide The compound (85 mg, 0.19 mmol) prepared in Example 115 was dissolved in dichloromethane (10 ml). Diisopropylethylamine (0.13 ml, 0.75 mmol) and acetyl chloride (0.013 ml, 0.19 mmol) were added thereto, and the mixture was stirred for 30 min at room temperature. After completion of the reaction, water was added. The mixture was extracted with ethyl acetate, dried over anhydrous magnesium sulfate, and filtered. The filtrate was distilled under reduced pressure, and concentrated. The residue was purified by column chromatography to give the title compound (39 mg, Yield 42%).

$^1$H NMR (DMSO-d$_6$, ppm); δ 11.49 (1H, s), 7.97 (1H, s), 6.81 (1H, s), 6.69 (1H, s), 6.28 (1H, s), 6.05 (1H, d), 4.64 (1H, quin), 4.12 (1H, m), 3.85 (2H, m), 3.53 (2H, m), 3.44 (2H, t), 3.34 (2H, m), 3.15 (1H, t), 2.72-2.60 (3H, m), 2.39 (1H, m), 2.05-1.87 (4H, m), 1.80-1.72 (4H, m), 1.53 (1H, m), 1.37 (2H, m), FAB MS (m/e)=490

Example 117

Synthesis of {5-chloro-2-[(R)-4-(2-piperazin-1-yl-ethyl)-4,5-dihydro-thiazol-2-yl]-1H-indol-7-yl}-(tetrahydro-pyran-4-yl)-amine

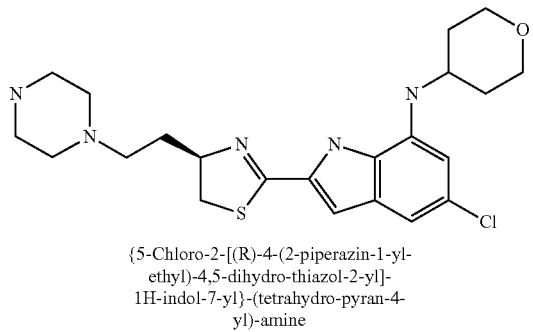

{5-Chloro-2-[(R)-4-(2-piperazin-1-yl-ethyl)-4,5-dihydro-thiazol-2-yl]-1H-indol-7-yl}-(tetrahydro-pyran-4-yl)-amine The compound (100 mg, 0.2 mmol) prepared in Preparation 52 was reacted according to the same procedure as Example 96 to give the title compound (25 mg, Yield 30%).

$^1$H NMR (DMSO-d$_6$, ppm); δ 11.42 (1H, s), 6.83 (1H, s), 6.74 (1H, s), 6.30 (1H, s), 6.02 (1H, d), 4.69 (1H, m), 3.85 (1H, m), 3.52-3.42 (6H, m), 3.35 (3H, m), 3.20 (2H, m), 2.16 (2H, m), 1.92 (3H, m), 1.42 (3H, m)

FAB MS (m/e)=448

Example 118

Synthesis of 1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-hydroxy-ethanone

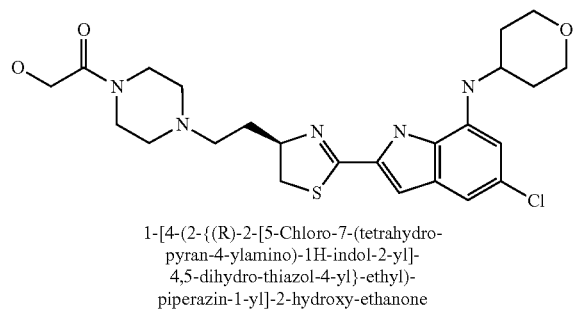

1-[4-(2-{(R)-2-[5-Chloro-7-(tetrahydro-pyran-4-ylamino)-1H-indol-2-yl]-4,5-dihydro-thiazol-4-yl}-ethyl)-piperazin-1-yl]-2-hydroxy-ethanone The compound (23 mg, 0.05 mmol) prepared in Example 117 was dissolved in N,N-dimethylformamide (5 ml). Glycolic acid (15.1 mg, 0.2 mmol), triethylamine (28 ul, 0.2 mmol), EDC (45 mg, 0.23 mmol) and HOBT (40 mg, 0.29 mmol) were added thereto, and the mixture was stirred for 8 h at room temperature. After completion of the reaction, 1N hydrochloric acid solution was added. The mixture was extracted with ethyl acetate, dried over anhydrous magnesium sulfate, and filtered. The filtrate was distilled under reduced pressure, and purified by column chromatography to give the title compound (5 mg, Yield 19%).

$^1$H-NMR (500 HMz, DMSO-d$_6$); δ 11.48 (br s, 1H), 6.81 (s, 1H), 6.69 (d, J=1.8 Hz, 1H), 6.29 (s, 1H), 6.05 (d, J=7.4 Hz, 1H), 4.62 (m, 1H), 4.49 (t, 1H), 4.04 (m, 2H), 3.87 (m, 2H), 3.56 (m, 1H), 3.45 (m, 4H), 3.29 (m, 4H), 3.16 (m, 1H), 2.36 (m, 4H), 1.96 (m, 3H), 1.80 (m, 1H), 1.40 (m, 2H)

Example 119

Synthesis of 1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-tetrazol-1-yl-ethanone

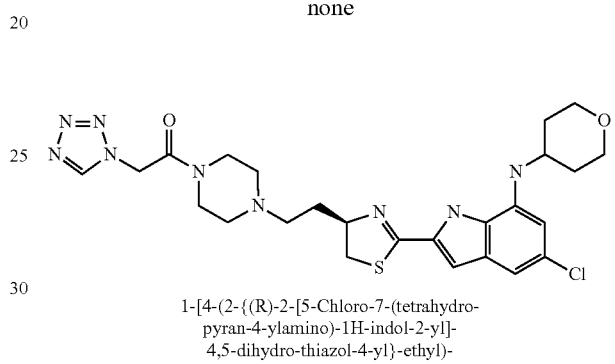

1-[4-(2-{(R)-2-[5-Chloro-7-(tetrahydro-pyran-4-ylamino)-1H-indol-2-yl]-4,5-dihydro-thiazol-4-yl}-ethyl)-piperazin-1-yl]-2-tetrazol-1-yl-ethanone The compound (61 mg, 0.14 mmol) prepared in Example 117 and 1H-tetrazole-1-acetic acid instead of glycolic acid were reacted according to the same procedure as Example 118 to give the title compound (31 mg, Yield 48%).

$^1$H NMR (DMSO-d$_6$, ppm); δ 11.48 (1H, s), 9.26 (1H, s), 6.81 (1H, s), 6.70 (1H, s), 6.29 (1H, s), 6.04 (1H, d), 5.60 (2H, s), 4.64 (1H, quin), 3.87 (2H, m), 3.57 (2H, m), 3.47-3.41 (7H, m), 3.17 (2H, m), 2.58 (1H, m), 2.39 (2H, m), 1.99-1.93 (4H, m), 1.81 (1H, m), 1.40 (2H, m)

FAB MS (m/e)=558

Example 120

Synthesis of 1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-3,3,3-trifluoro-propan-1-one

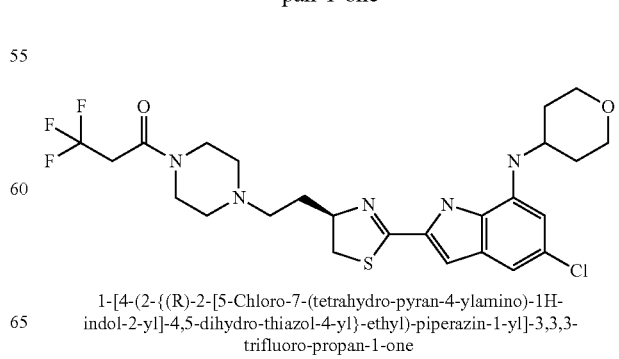

1-[4-(2-{(R)-2-[5-Chloro-7-(tetrahydro-pyran-4-ylamino)-1H-indol-2-yl]-4,5-dihydro-thiazol-4-yl}-ethyl)-piperazin-1-yl]-3,3,3-trifluoro-propan-1-one The compound (66 mg, 0.15 mmol) prepared in Example 117 was dissolved in dichloromethane (10 ml). Diisopropylethylamine (0.08 ml, 0.44 mmol) and 3,3,3-trifluoropropionic acid 2,5-dioxo-pyrrolidin-1-yl ester (29 mg, 0.13 mmol) were added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and purified by column chromatography to give the title compound (6 mg, Yield 9%).

$^1$H NMR (DMSO-$d_6$, ppm); δ 11.47 (1H, s), 6.81 (1H, s), 6.69 (1H, s), 6.28 (1H, s), 6.09 (1H, d), 4.62 (1H, quin), 3.87 (2H, m), 3.56 (4H, m), 3.47-3.38 (7H, m), 3.16 (1H, m), 2.53 (1H, m), 2.37-2.30 (4H, m), 1.94 (3H, m), 1.81 (1H, m), 1.40 (2H, m)

FAB MS (m/e)=558

Example 121

Synthesis of [4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-furan-2-yl-methanone

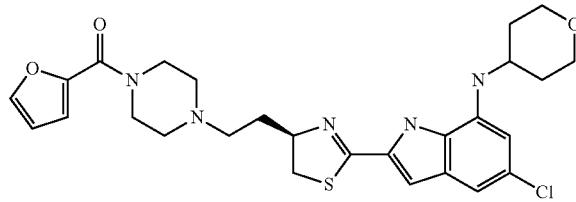

[4-(2-{(R)-2-[5-Chloro-7-(tetrahydro-pyran-4-ylamino)-1H-indol-2-yl]-4,5-dihydro-thiazol-4-yl}-ethyl)-piperazin-1-yl]-furan-2-yl-methanone The compound (100 mg, 0.20 mmol) prepared in Preparation 52 and furanoylpiperazine instead of piperidine-3-carboxylic acid ethyl ester were reacted according to the same procedure as Preparation 53 to give the title compound (19 mg, Yield 17%).

$^1$H-NMR (500 HMz, DMSO-$d_6$); δ 11.48 (br s, 1H), 7.79 (s, 1H), 6.81 (s, 1H), 6.69 (s, 1H), 6.59 (m, 1H), 6.28 (s, 1H), 6.05 (m, 1H), 4.63 (m, 1H), 3.86 (m, 2H), 3.57 (m, 6H), 3.44 (m, 2H), 3.16 (m, 2H), 2.56 (m, 1H), 1.96 (m, 3H), 1.83 (m, 1H), 1.41 (m, 2H)

Example 122

Synthesis of (5-chloro-2-{(R)-4-[2-(2,3,5,6-tetrahydro-[1,2']bipyrazinyl-4-yl)-ethyl]-4,5-dihydro-thiazol-2-yl}-1H-indol-7-yl)-(tetrahydropyran-4-yl)-amine

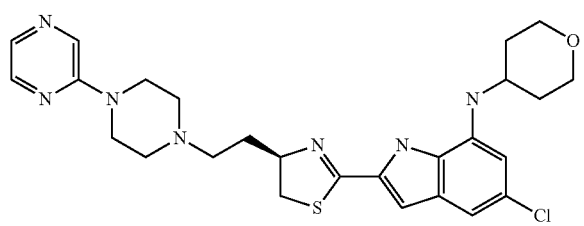

(5-Chloro-2-{(R)-4-[2-(2,3,5,6-tetrahydro-[1,2']bipyrazinyl-4-yl)-ethyl]-4,5-dihydro-thiazol-2-yl}-1H-indol-7-yl)-(tetrahydro-pyran-4-yl)-amine The compound (100 mg, 0.20 mmol) prepared in Preparation 52 and 1-(2-pyrazinyl)piperazine instead of piperidine-3-carboxylic acid ethyl ester were reacted according to the same procedure as Preparation 53 to give the title compound (13 mg, Yield 12%).

$^1$H-NMR (500 HMz, DMSO-$d_6$); δ 11.48 (br s, 1H), 8.27 (s, 1H), 8.04 (s, 1H), 7.80 (s, 1H), 6.81 (s, 1H), 6.69 (s, 1H), 6.29 (s, 1H), 6.05 (m, 1H), 4.64 (m, 1H), 3.86 (m, 2H), 3.57 (m, 2H), 3.53 (m, 4H), 3.18 (m, 1H), 2.57 (m, 1H). 1.99 (m, 1H), 1.95 (m, 2H), 1.83 (m, 1H), 1.40 (m, 2H)

Example 123

Synthesis of (5-chloro-2-{(R)-4-[2-(4-pyrimidin-2-yl-piperazin-1-yl)-ethyl]-4,5-dihydro-thiazol-2-yl}-1H-indol-7-yl)-(tetrahydro-pyran-4-yl)-amine

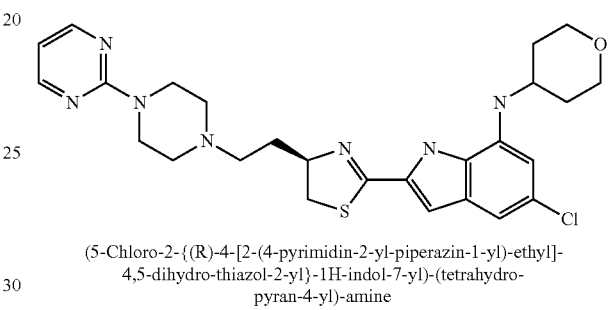

(5-Chloro-2-{(R)-4-[2-(4-pyrimidin-2-yl-piperazin-1-yl)-ethyl]-4,5-dihydro-thiazol-2-yl}-1H-indol-7-yl)-(tetrahydro-pyran-4-yl)-amine The compound (100 mg, 0.20 mmol) prepared in Preparation 52 and 1-(2-pyrimidyl)piperazine instead of piperidine-3-carboxylic acid ethyl ester were reacted according to the same procedure as Preparation 53 to give the title compound (10 mg, Yield 9%).

$^1$H-NMR (500 HMz, DMSO-$d_6$); δ 11.49 (br s, 1H), 8.31 (m, 1H), 6.81 (s, 1H), 6.69 (s, 1H), 6.58 (m, 1H), 6.28 (s, 1H), 6.06 (m, 1H), 4.65 (m, 1H), 3.86 (m, 2H), 3.69 (m, 4H), 3.58 (m, 2H), 3.45 (m, 2H), 3.35 (m, 1H), 3.18 (m, 1H), 2.56 (m, 1H). 2.43 (m, 3H), 2.00 (m, 1H), 1.96 (m, 2H), 1.40 (m, 2H)

Preparation 54

Synthesis of cyclopentyl-{5-fluoro-2-[(R)-4-(2-iodo-ethyl)-4,5-dihydro-thiazol-2-yl]-1H-indol-7-yl}-amine

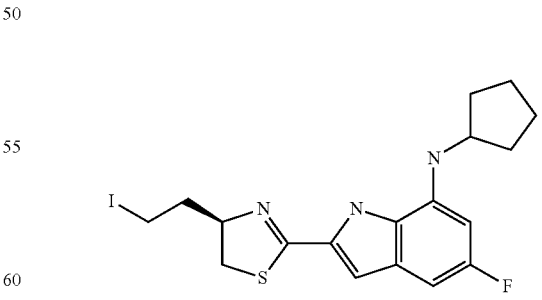

Cyclopentyl-{5-fluoro-2-[(R)-4-(2-iodo-ethyl)-4,5-dihydro-thiazol-2-yl]-1H-indol-7-yl}-amine The compound (120 mg, 0.35 mmol) prepared in Example 39 was reacted according to the same procedure as Preparation 50 to give the title compound (110 mg, Yield 70%).

Example 124

Synthesis of {2-[(R)-4-(2-amino-ethyl)-4,5-dihydro-thiazol-2-yl]-5-fluoro-1H-indol-7-yl}-cyclopentyl-amine

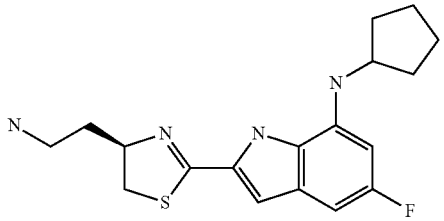

{2-[(R)-4-(2-Amino-ethyl)-4,5-dihydro-thiazol-2-yl]-5-fluoro-1H-indol-7-yl}-cyclopentyl-amine (Step 1)

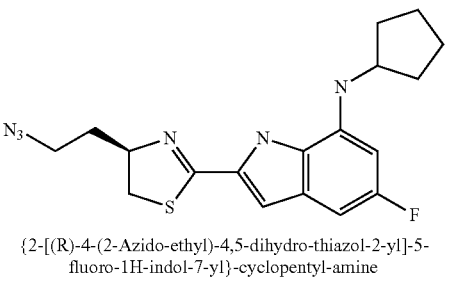

{2-[(R)-4-(2-Azido-ethyl)-4,5-dihydro-thiazol-2-yl]-5-fluoro-1H-indol-7-yl}-cyclopentyl-amine The compound (100 mg, 0.22 mmol) prepared in Preparation 54 was dissolved in N,N-dimethylformamide (2 ml). Sodium azide (43 mg, 0.66 mmol) was added thereto, and the mixture was stirred for 1 h at 70° C. After completion of the reaction, water was added. The mixture was extracted with ethyl acetate, dried over anhydrous magnesium sulfate, and filtered. The filtrate was distilled under reduced pressure, and purified by column chromatography to give an azido compound (75 mg, Yield 9%).

(Step 2)
The compound (70 mg, 0.19 mmol) prepared in Step 1 was dissolvd in tetrahydrofuran (3 ml). Water (4 ul, 0.2 mmol) and triphenylphosphine (55 mg, 0.31 mmol) were added thereto, and the mixture was stirred for 2 h at 80° C. After completion of the reaction, the reaction solution was distilled under reduced pressure, and purified by column chromatography to give the title compound (45 mg, Yield 69%).

$^1$H-NMR (400 HMz, CDCl$_3$/DMSO-d$_6$); δ 11.28 (br s, 1H), 6.80 (br s, 2H), 6.80 (d, J=2.0 Hz), 6.50 (dd, 1H), 6.16 (dd, 1H), 4.58 (m, 1H), 3.81 (m, 1H), 3.54 (m, 1H), 3.24 (m, 2H), 3.02 (m, 1H), 2.13~1.55 (m, 10H)

Preparation 55

Synthesis of methanesulfonic acid 2-[(R)-2-(7-cyclopentylamino-5-fluoro-1H-indol-2-yl)-4,5-dihydro-thiazol-4-yl]-ethyl ester

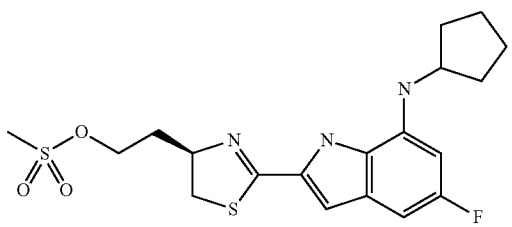

Methanesulfonic acid 2-[(R)-2-(7-cyclopentylamino-5-fluoro-1H-indol-2-yl)-4,5-dihydro-thiazol-4-yl]-ethyl ester The compound (1.0 g, 2.87 mmol) prepared in Example 39 was reacted according to the same procedure as Preparation 22 to give the title compound (1.1 g, Yield 90%).

Example 125

Synthesis of 1-(4-{2-[(R)-2-(7-cyclopentylamino-5-fluoro-1H-indol-2-yl)-4,5-dihydro-thiazol-4-yl]-ethyl}-piperazin-1-yl)-ethanone

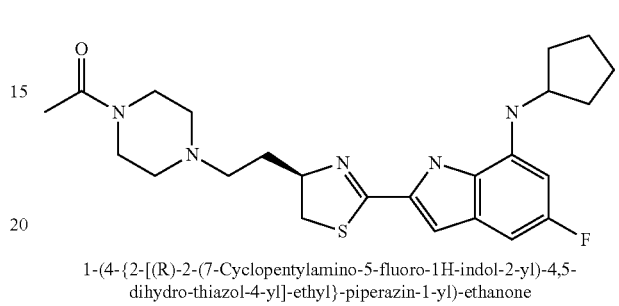

1-(4-{2-[(R)-2-(7-Cyclopentylamino-5-fluoro-1H-indol-2-yl)-4,5-dihydro-thiazol-4-yl]-ethyl}-piperazin-1-yl)-ethanone The compound (100 mg, 0.23 mmol) prepared in Preparation 55 was dissolved in N,N-dimethylformamide (10 ml). Triethylamine (48 mg, 0.47 mmol) and 1-acetylpiperazine (92 mg, 0.70 mmol) were added thereto, and the mixture was stirred for 8 h at 50° C. After completion of the reaction, water was added. The mixture was extracted with ethyl acetate, dried over anhydrous magnesium sulfate, and filtered. The filtrate was distilled under reduced pressure, and purified by column chromatography to give the title compound (60 mg, Yield 56%).

$^1$H-NMR (400 HMz, CDCl$_3$); δ 10.47 (br s, 1H), 6.87 (s, 1H), 6.66 (d, J=8.0 Hz, 1H), 6.26 (d, J=12.0 Hz, 1H), 4.80 (m, 1H), 3.92 (m, 1H), 3.81 (m, 1H), 3.59 (m, 2H), 3.49 (m, 1H), 3.28 (m, 1H), 3.18 (m, 1H), 2.44 (m, 2H), 2.34 (m, 1H), 2.23 (m, 2H), 2.14 (m, 1H), 2.05 (s, 3H), 1.93 (m, 1H), 1.81 (m, 1H), 1.71 (m, 5H), 1.48 (m, 2H)

Example 126

Synthesis of cyclopentyl-{5-fluoro-2-[(R)-4-(2-morpholin-4-yl-ethyl)-4,5-dihydro-thiazol-2-yl]-1H-indol-7-yl}-amine

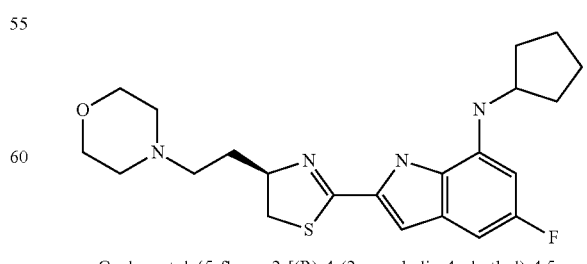

Cyclopentyl-{5-fluoro-2-[(R)-4-(2-morpholin-4-yl-ethyl)-4,5-dihydro-thiazol-2-yl]-1H-indol-7-yl}-amine The compound (100 mg, 0.23 mmol) prepared in Preparation 55 and morpholine instead of 1-acetylpiperazine were reacted according to the same procedure as Example 125 to give the title compound (50 mg, Yield 52%).

¹H-NMR (400 HMz, CDCl₃); δ 10.92 (br s, 1H), 6.87 (s, 1H), 6.64 (d, J=8.0 Hz, 1H), 6.24 (d, J=12.0 Hz, 1H), 4.83 (m, 1H), 3.93 (m, 1H), 3.77 (m, 1H), 3.54 (m, 4H), 3.47 (m, 1H), 3.17 (m, 1H), 2.38 (m, 1H), 2.33 (m, 2H), 2.16 (m, 2H), 2.04 (m, 3H), 1.77 (m, 1H), 1.65 (m, 4H), 1.47 (m, 1H), 1.35 (m, 1H)

Example 127

Synthesis of cyclopentyl-{2-[(R)-4-(2-dimethylamino-ethyl)-4,5-dihydro-thiazol-2-yl]-5-fluoro-1H-indol-7-yl}-amine

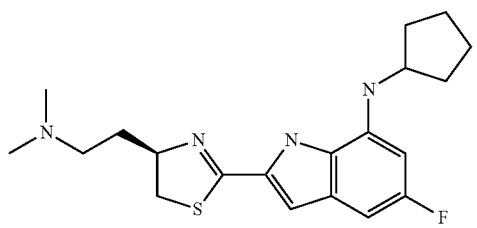

Cyclopentyl-{2-[(R)-4-(2-dimethylamino-ethyl)-4,5-dihydro-thiazol-2-yl]-5-fluoro-1H-indol-7-yl}-amine The compound (100 mg, 0.23 mmol) prepared in Preparation 55 and dimethylamine instead of 1-acetylpiperazine were reacted according to the same procedure as Example 125 to give the title compound (40 mg, Yield 47%).

¹H-NMR (400 HMz, CDCl₃); δ 10.99 (br s, 1H), 6.80 (s, 1H), 6.60 (d, J=8.0 Hz, 1H), 6.22 (d, J=12.0 Hz, 1H), 4.59 (m, 1H), 4.13 (m, 1H), 3.47 (m, 1H), 3.03 (m, 1H), 2.90 (m, 1H), 2.55 (m, 1H), 2.42 (s, 6H), 2.01 (m, 3H), 1.81 (m, 1H), 1.62 (m, 2H), 1.55 (m, 4H)

Example 128

Synthesis of cyclopentyl-{5-fluoro-2-[(R)-4-(2-pyrrolidin-1-yl-ethyl)-4,5-dihydro-thiazol-2-yl]-1H-indol-7-yl}-amine

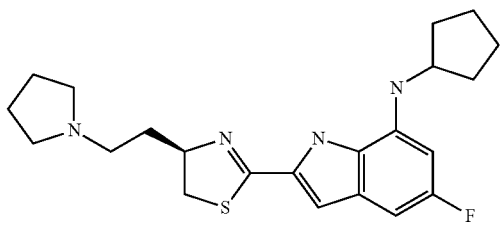

Cyclopentyl-{5-fluoro-2-[(R)-4-(2-pyrrolidin-1-yl-ethyl)-4,5-dihydro-thiazol-2-yl]-1H-indol-7-yl}-amine The compound (100 mg, 0.23 mmol) prepared in Preparation 55 and pyrrolidine instead of 1-acetylpiperazine were reacted according to the same procedure as Example 125 to give the title compound (30 mg, Yield 33%).

¹H-NMR (400 HMz, CDCl₃); δ 11.39 (br s, 1H), 6.81 (s, 1H), 6.63 (dd, 1H), 6.25 (dd, 1H), 4.59 (m, 1H), 4.17 (m, 1H), 3.89 (m, 1H), 3.32 (m, 1H), 3.07 (m, 3H), 2.71 (m, 1H), 2.09 (m, 2H), 1.95 (m, 4H), 1.77 (m, 2H), 1.65 (m, 4H)

Example 129

Synthesis of cyclopentyl-(2-{(R)-4-[2-(1,1-dioxo-thiomorpholin-4-yl)-ethyl]-4,5-dihydro-thiazol-2-yl}-5-fluoro-1H-indol-7-yl)-amine

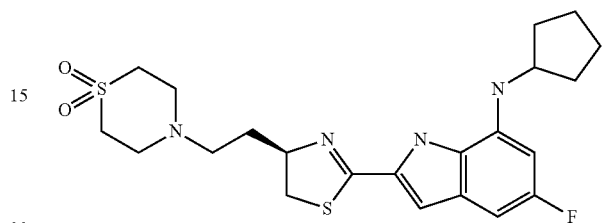

Cyclopentyl-(2-{(R)-4-[2-(1,1-dioxo-1lambda*6*-thiomorpholin-4-yl)-ethyl]-4,5-dihydro-thiazol-2-yl}-5-fluoro-1H-indol-7-yl)-amine The compound (100 mg, 0.23 mmol) prepared in Preparation 55 and thiomorpholine-1,1-dioxide instead of 1-acetylpiperazine were reacted according to the same procedure as Example 125 to give the title compound (10 mg, Yield 9%).

¹H-NMR (400 HMz, CDCl₃); δ 11.05 (br s, 1H), 6.94 (s, 1H), 6.60 (d, J=8.0 Hz, 1H), 6.26 (d, J=12.0 Hz, 1H), 4.74 (m, 1H), 3.85 (m, 1H), 3.62 (t, 1H), 3.49 (q, 1H), 3.18 (q, 1H), 3.00 (m, 8H), 2.74 (m, 2H), 2.05 (m, 3H), 1.79 (m, 2H), 1.63 (m, 4H)

Example 130

Synthesis of 4-{2-[(R)-2-(7-cyclopentylamino-5-fluoro-1H-indol-2-yl)-4,5-dihydro-thiazol-4-yl]-ethyl}-piperazin-2-one

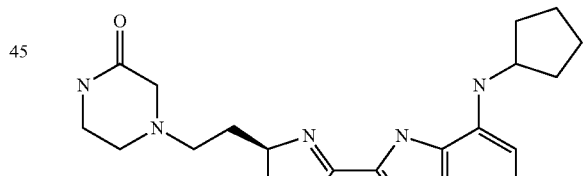

4-{2-[(R)-2-(7-Cyclopentylamino-5-fluoro-1H-indol-2-yl)-4,5-dihydro-thiazol-4-yl]-ethyl}-piperazin-2-one The compound (200 mg, 0.44 mmol) prepared in Preparation 55 was dissolved in tetrahydrofuran (5 ml). 2-Oxopiperazine (87 mg, 0.88 mmol) and potassium carbonate (118 mg, 0.88 mmol) were added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and purified by column chromatography to give the title compound (650 mg, Yield 27%).

¹H-NMR (400 HMz, CDCl₃); δ 11.26 (br s, 1H), 7.26 (br s, 1H), 6.87 (s, 1H), 6.58 (d, J=8.0 Hz, 1H), 6.22 (d, J=12.0 Hz,

1H), 4.73 (m, 1H), 3.84 (m, 1H), 3.53 (t, 1H), 3.19 (m, 5H), 2.57 (m, 4H), 2.04 (m, 3H), 1.95 (m, 1H), 1.74 (m, 2H), 1.62 (m, 2H)

Example 131

Synthesis of 1-(4-{2-[(R)-2-(7-cyclopentylamino-5-fluoro-1H-indol-2-yl)-4,5-dihydro-thiazol-4-yl]-ethyl}-piperazin-1-yl)-2-hydroxy-ethanone

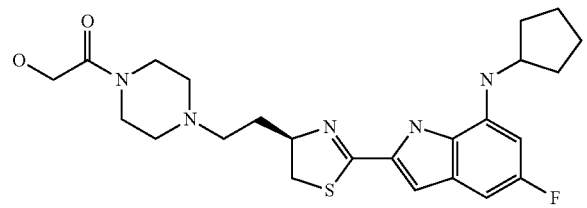

1-(4-{2-[(R)-2-(7-Cyclopentylamino-5-fluoro-1H-indol-2-yl)-4,5-dihydro-thiazol-4-yl]-ethyl}-piperazin-1-yl)-2-hydroxy-ethanone The compound (500 mg, 1.09 mmol) prepared in Preparation 55 was reacted according to the same procedures as Example 96 and Example 99 to give the title compound (100 mg, Yield 19%).

$^1$H-NMR (400 HMz, CDCl$_3$); δ 11.26 (br s, 1H), 6.89 (s, 1H), 6.63 (d, J=8.0 Hz, 1H), 6.22 (d, J=12.0 Hz, 1H), 4.85 (m, 1H), 4.10 (s, 2H), 3.77 (m, 1H), 3.57 (m, 2H), 3.41 (m, 1H), 3.14 (q, 1H), 3.00 (m, 1H), 2.91 (m, 1H), 2.38 (m, 3H), 2.12 (m, 2H), 2.02 (m, 4H), 1.85 (m, 1H), 1.77 (m, 1H), 1.63 (m, 4H), 1.36 (m, 1H), 1.26 (m, 1H)

Example 132

Synthesis of cyclopentyl-{5-fluoro-2-[(R)-4-(2-methanesulfonyl-ethyl)-4,5-dihydro-thiazol-2-yl]-1H-indol-7-yl}-amine

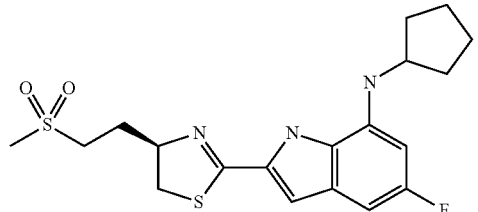

Cyclopentyl-{5-fluoro-2-[(R)-4-(2-methanesulfonyl-ethyl)-4,5-dihydro-thiazol-2-yl]-1H-indol-7-yl}-amine The compound (50 mg, 0.12 mmol) prepared in Preparation 55 and sodium iodide (88 mg, 0.59 mmol) were dissolvd in N,N-dimethylformamide (5 ml), and stirred for 6 h at 50° C. Sodium methanesulfinate (60 mg, 0.59 mmol) was added thereto, and the mixture was stirred for 8 h at room temperature. After completion of the reaction, water was added. The mixture was extracted with ethyl acetate, dried over anhydrous magnesium sulfate, and filtered. The filtrate was distilled under reduced pressure, and purified by column chromatography to give the title compound (14 mg, Yield 29%).

$^1$H-NMR (400 HMz, CDCl$_3$); δ 9.89 (br s, 1H), 6.87 (s, 1H), 6.67 (dd, 1H), 6.28 (dd, 1H), 4.77 (m, 1H), 3.83 (t, 1H), 3.59 (m, 1H), 3.31 (m, 1H), 3.13 (m, 2H), 2.84 (s, 3H), 2.27 (m, 2H), 2.04 (m, 2H), 1.68 (m, 6H), 1.51 (m, 2H)

Preparation 56

Synthesis of methanesulfonic acid 2-{(R)-2-[5-fluoro-7-(tetrahydro-pyran-4-ylamino)-1H-indol-2-yl]-4,5-dihydro-thiazol-4-yl}-ethyl ester

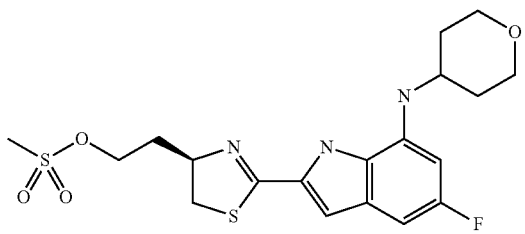

Methanesulfonic acid 2-{(R)-2-[5-fluoro-7-(tetrahydro-pyran-4-ylamino)-1H-indol-2-yl]-4,5-dihydro-thiazol-4-yl}-ethyl ester The compound (740 mg, 2.03 mol) prepared in Example 44 was reacted according to the same procedure as Preparation 22 to give the title compound (750 mg, Yield 84%).

Example 133

Synthesis of {2-[(R)-4-(2-dimethylamino-ethyl)-4,5-dihydro-thiazol-2-yl]-5-fluoro-1H-indol-7-yl}-(tetrahydro-pyran-4-yl)-amine

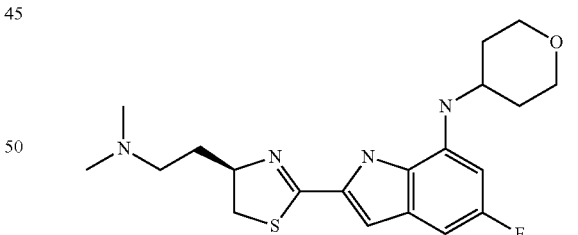

{2-[(R)-4-(2-Dimethylamino-ethyl)-4,5-dihydro-thiazol-2-yl]-5-fluoro-1H-indol-7-yl}-(tetrahydro-pyran-4-yl)-amine The compound (100 mg, 0.23 mmol) prepared in Preparation 56 and dimethylamine instead of 1-acetylpiperazine were reacted according to the same procedure as Example 125 to give the title compound (21 mg, Yield 23%).

$^1$H-NMR (400 HMz, CDCl$_3$); δ 11.27 (br s, 1H), 6.79 (s, 1H), 6.60 (d, J=8.0 Hz, 1H), 6.22 (d, J=12.0 Hz, 1H), 4.61 (m,

1H), 4.13 (m, 2H), 3.59 (m, 4H), 3.04 (m, 1H), 2.55 (s, 4H), 2.04 (m, 6H), 1.65 (m, 2H), 1.26 (m, 2H)

Example 134

Synthesis of {5-fluoro-2-[(R)-4-(2-pyrrolidin-1-yl-ethyl)-4,5-dihydro-thiazol-2-yl]-1H-indol-7-yl}-(tetrahydro-pyran-4-yl)-amine

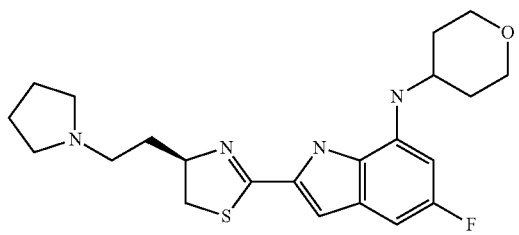

{5-Fluoro-2-[(R)-4-(2-pyrrolidin-1-yl-ethyl)-4,5-dihydro-thiazol-2-yl]-1H-indol-7-yl}-(tetrahydro-pyran-4-yl)-amine The compound (100 mg, 0.23 mmol) prepared in Preparation 56 and pyrrolidine instead of 1-acetylpiperazine were reacted according to the same procedure as Example 125 to give the title compound (29 mg, Yield 30%).

$^1$H-NMR (400 HMz, CDCl$_3$); δ 11.16 (br s, 1H), 6.87 (s, 1H), 6.68 (d, J=8.0 Hz, 1H), 6.26 (d, J=12.0 Hz, 1H), 4.69 (m, 1H), 4.17 (d, J=8.0 Hz, 2H), 3.60 (m, 5H), 3.17 (m, 1H), 2.90 (m, 1H), 2.67 (m, 5H), 2.09 (m, 3H), 1.90 (m, 4H), 1.57 (m, 2H)

Example 135

Synthesis of {5-fluoro-2-[(R)-4-(2-morpholin-4-yl-ethyl)-4,5-dihydro-thiazol-2-yl]-1H-indol-7-yl}-(tetrahydro-pyran-4-yl)-amine

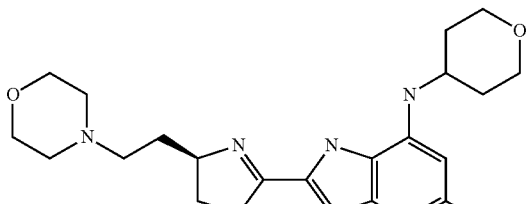

{5-Fluoro-2-[(R)-4-(2-morpholin-4-yl-ethyl)-4,5-dihydro-thiazol-2-yl]-1H-indol-7-yl}-(tetrahydro-pyran-4-yl)-amine The compound (100 mg, 0.23 mmol) prepared in Preparation 56 and morpholine instead of 1-acetylpiperazine were reacted according to the same procedure as Example 125 to give the title compound (16 mg, Yield 16%).

$^1$H-NMR (400 HMz, CDCl$_3$); δ 11.16 (br s, 1H), 6.86 (s, 1H), 6.64 (d, J=8.0 Hz, 1H), 6.23 (d, J=12.0 Hz, 1H), 4.75 (m, 1H), 4.02 (m, 1H), 3.66 (m, 4H), 3.51 (m, 4H), 3.18 (m, 1H), 2.60 (m, 1H), 2.49 (m, 4H), 2.07 (m, 4H), 1.80 (m, 1H), 1.54 (m, 2H)

Example 136

Synthesis of 1-[4-(2-{(R)-2-[5-fluoro-7-(tetrahydro-pyran-4-ylamino)-1H-indol-2-yl]-4,5-dihydro-thiazol-4-yl}-ethyl-piperazin-1-yl)-ethanone

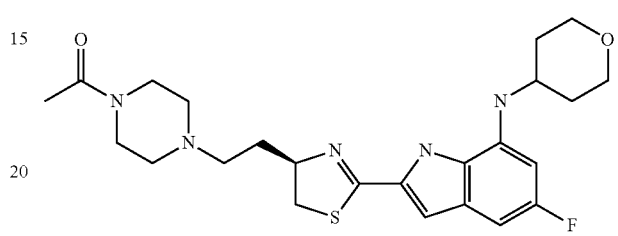

1-[4-(2-{(R)-2-[5-Fluoro-7-(tetrahydro-pyran-4-ylamino)-1H-indol-2-yl]-4,5-dihydro-thiazol-4-yl}-ethyl)-piperazin-1-yl]-ethanone The compound (100 mg, 0.23 mmol) prepared in Preparation 56 and 1-acetylpiperazine were reacted according to the same procedure as Example 125 to give the title compound (24 mg, Yield 22%).

$^1$H-NMR (400 HMz, CDCl$_3$); δ 10.20 (br s, 1H), 6.87 (s, 1H), 6.68 (d, J=8.0 Hz, 1H), 6.27 (d, J=12.0 Hz, 1H), 4.76 (m, 1H), 4.01 (m, 3H), 3.61 (m, 4H), 3.30 (m, 2H), 3.20 (m, 1H), 2.51 (m, 2H), 2.33 (m, 4H), 2.06 (m, 7H), 1.99 (m, 1H), 1.49 (m, 2H)

Example 137

Synthesis of (2-{(R)-4-[2-(1,1-dioxo-thiomorpholin-4-yl)-ethyl]-4,5-dihydro-thiazol-2-yl}-5-fluoro-1H-indol-7-yl)-(tetrahydropyran-4-yl)-amine

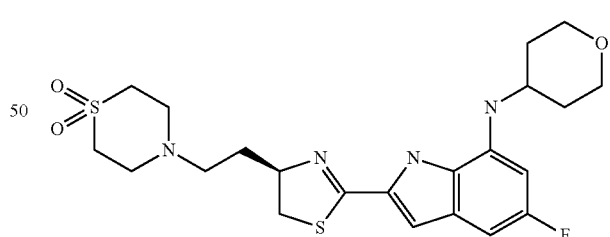

(2-{(R)-4-[2-(1,1-Dioxo-1lambda*6*-thiomorpholin-4-yl)-ethyl]-4,5-dihydro-thiazol-2-yl}-5-fluoro-1H-indol-7-yl)-(tetrahydro-pyran-4-yl)-amine The compound (100 mg, 0.23 mmol) prepared in Preparation 56 and thiomorpholine-1,1-dioxide instead of 1-acetylpiperazine were reacted according to the same procedure as Example 125 to give the title compound (28 mg, Yield 25%).

$^1$H-NMR (400 HMz, CDCl$_3$); δ 6.93 (s, 1H), 6.64 (d, J=8.0 Hz, 1H), 6.28 (d, J=12.0 Hz, 1H), 4.68 (m, 1H), 4.03 (m, 2H), 3.55 (m, 3H), 3.26 (m, 2H), 3.17 (m, 3H), 3.05 (m, 4H), 2.95 (m, 1H), 2.82 (m, 1H), 2.09 (m, 4H), 1.82 (m, 1H), 1.65 (m, 2H)

Example 138

Synthesis of (5-fluoro-2-[(R)-4-(2-methanesulfonyl-ethyl)-4,5-dihydro-thiazol-2-yl]-1H-indol-7-yl)-(tetrahydro-pyran-4-yl)-amine

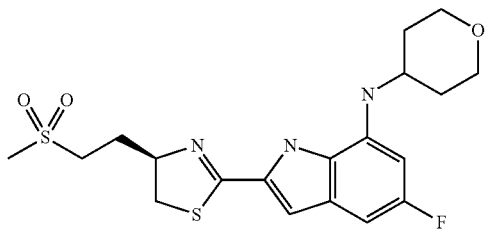

{5-Fluoro-2-[(R)-4-(2-methanesulfonyl-ethyl)-4,5-dihydro-thiazol-2-yl]-1H-indol-7-yl}-(tetrahydro-pyran-4-yl)-amine The compound (50 mg, 0.11 mmol) prepared in Preparation 56 was reacted according to the same procedure as Example 132 to give the title compound (18 mg, Yield 38%).
$^1$H-NMR (400 HMz, CDCl$_3$); δ 10.15 (br s, 1H), 6.86 (s, 1H), 6.65 (dd, 1H), 6.26 (dd, 1H), 4.77 (m, 1H), 4.05 (m, 1H), 3.56 (m, 4H), 3.36 (m, 1H), 3.24 (m, 2H), 3.12 (m, 1H), 2.91 (s, 3H), 2.32 (m, 1H), 2.22 (m, 1H), 2.13 (m, 1H), 2.02 (m, 1H), 1.54 (m, 2H)

Preparation 57

Synthesis of {5-fluoro-2-[(R)-4-(2-iodo-ethyl)-4,5-dihydro-thiazol-2-yl]-1H-indol-7-yl}-(tetrahydro-pyran-4-yl)-amine

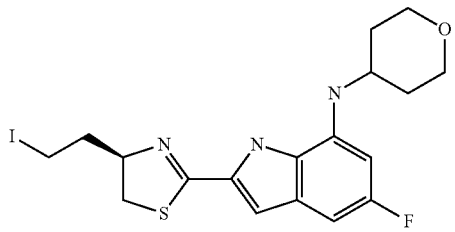

{5-Fluoro-2-[(R)-4-(2-iodo-ethyl)-4,5-dihydro-thiazol-2-yl]-1H-indol-7-yl}-(tetrahydro-pyran-4-yl)-amine The compound (3.2 g, 8.82 mol) prepared in Example 41 was reacted according to the same procedure as Preparation 50 to give the title compound (1.9 g, Yield 46%).

Example 139

Synthesis of 4-(2-{(R)-2-[5-fluoro-7-(tetrahydro-pyran-4-ylamino)-1H-indol-2-yl]-4,5-dihydro-thiazol-4-yl}-ethyl)-piperazin-2-one

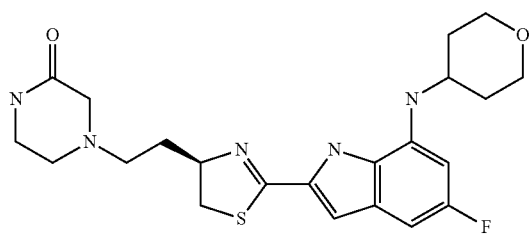

4-(2-{(R)-2-[5-Fluoro-7-(tetrahydro-pyran-4-ylamino)-1H-indol-2-yl]-4,5-dihydro-thiazol-4-yl}-ethyl)-piperazin-2-one The compound (200 mg, 0.44 mmol) prepared in Preparation 57 was reacted according to the same procedure as Example 130 to give the title compound (50 mg, Yield 51%).
$^1$H-NMR (400 HMz, CDCl$_3$); δ 11.07 (br s, 1H), 7.70 (br s, 1H), 6.83 (s, 1H), 6.61 (d, J=8.0 Hz, 1H), 6.22 (d, J=12.0 Hz, 1H), 5.19 (m, 1H), 4.71 (m, 1H), 4.05 (d, J=12.0 Hz, 2H), 3.55 (m, 4H), 3.33 (m, 3H), 3.14 (m, 1H), 2.73 (m, 4H), 2.10 (m, 2H), 1.98 (m, 2H), 1.58 (m, 4H)

Example 140

Synthesis of 1-[4-(2-{(R)-2-[5-fluoro-7-(tetrahydro-pyran-4-ylamino)-1H-indol-2-yl]-4,5-dihydro-thiazol-4-yl}-ethyl)-piperazin-1-yl]-2-hydroxy-ethanone

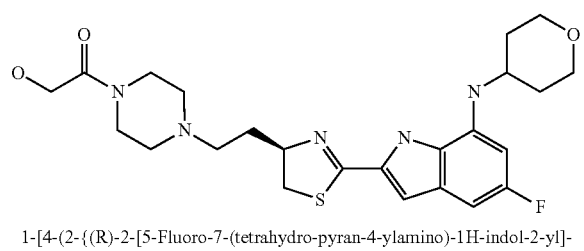

1-[4-(2-{(R)-2-[5-Fluoro-7-(tetrahydro-pyran-4-ylamino)-1H-indol-2-yl]-4,5-dihydro-thiazol-4-yl}-ethyl)-piperazin-1-yl]-2-hydroxy-ethanone The compound (500 mg, 1.06 mmol) prepared in Preparation 57 was reacted according to the same procedures as Example 96 and Example 97 to give the title compound (100 mg, Yield 19%).
$^1$H-NMR (400 HMz, CDCl$_3$); δ 11.19 (br s, 1H), 6.89 (s, 1H), 6.65 (d, J=8.0 Hz, 1H), 6.23 (d, J=12.0 Hz, 1H), 4.82 (m, 1H), 4.20 (m, 1H), 4.18 (s, 2H), 3.98 (m, 2H), 3.61 (m, 2H), 3.47 (m, 4H), 3.16 (m, 3H), 2.42 (m, 3H), 2.17 (m, 5H), 1.90 (m, 2H), 1.40 (m, 2H)

Preparation 58

Synthesis of cyclopentyl-{2-[(R)-4-(2-iodo-ethyl)-4,5-dihydro-thiazol-2-yl]-1H-indol-7-yl}-amine

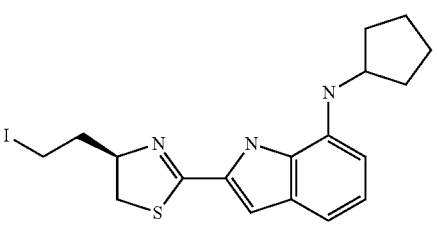

Cyclopentyl-{2-[(R)-4-(2-iodo-ethyl)-4,5-dihydro-thiazol-2-yl]-1H-indol-7-yl}-amine The compound (1.68 g, 5.10 mol) prepared in Example 44 was reacted according to the same procedure as Preparation 50 to give the title compound (1.75 g, Yield 78%).

Example 141

Synthesis of cyclopentyl-{2-[(R)-4-(2-methoxy-ethyl)-4,5-dihydro-thiazol-2-yl]-1H-indol-7-yl}-amine

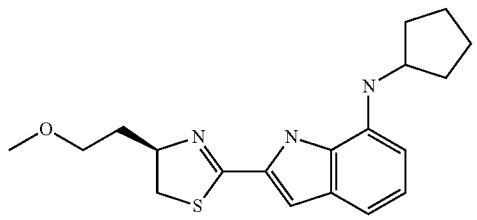

Cyclopentyl-{2-[(R)-4-(2-methoxy-ethyl)-4,5-dihydro-thiazol-2-yl]-1H-indol-7-yl}-amine The compound (100 mg, 0.23 mmol) prepared in Preparation 58 was dissolved in tetrahydrofuran (20 ml). Sodium methoxide (61 mg, 1.15 mmol) was added thereto, and the mixture was stirred for 8 h at 80° C. After completion of the reaction, water was added. The mixture was extracted with ethyl acetate, dried over anhydrous magnesium sulfate, and filtered. The filtrate was distilled under reduced pressure, and purified by column chromatography to give the title compound (15 mg, Yield 19%).

$^1$H-NMR (500 HMz, DMSO-d$_6$); δ 10.62 (br s, 1H), 7.03 (d, J=7.95 Hz, 1H), 6.99 (t, 1H), 6.93 (s, 1H), 6.48 (d, J=7.35 Hz, 1H), 4.83 (m, 1H), 3.83 (m, 1H), 3.56 (m, 1H), 3.46 (m, 2H), 3.20 (m, 4H), 2.05~1.87 (m, 4H), 1.70~1.38 (m, 6H)

Example 142

Synthesis of cyclopentyl-{2-[(R)-4-(2-dimethylamino-ethyl)-4,5-dihydro-thiazol-2-yl]-1H-indol-7-yl}-amine

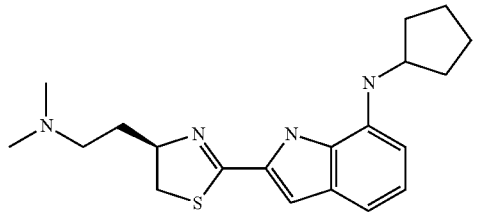

Cyclopentyl-{2-[(R)-4-(2-dimethylamino-ethyl)-4,5-dihydro-thiazol-2-yl]-1H-indol-7-yl}-amine The compound (150 mg, 0.34 mmol) prepared in Preparation 58 and dimethylamine instead of 2-oxopiperazine were reacted according to the same procedure as Example 130 to give the title compound (38 mg, Yield 31%).

$^1$H-NMR (500 HMz, DMSO-d$_6$); δ 11.28 (br s, 1H), 6.78 (m, 2H), 6.24 (m, 2H), 5.80 (m, 1H), 4.59 (m, 1H), 3.81 (m, 1H), 3.51 (m, 1H), 3.13 (m, 1H), 2.50 (m, 1H), 2.37 (m, 1H), 2.17 (s, 6H), 1.93 (m, 3H). 1.79-1.65 (m, 3H), 1.54 (m, 4H)

Example 143

Synthesis of cyclopentyl-{2-[(R)-4-(2-morpholin-4-yl-ethyl)-4,5-dihydro-thiazol-2-yl]-1H-indol-7-yl}-amine

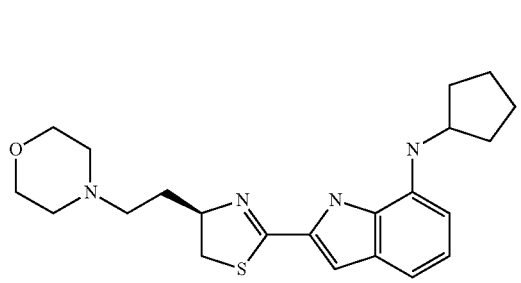

Cyclopentyl-{2-[(R)-4-(2-morpholin-4-yl-ethyl)-4,5-dihydro-thiazol-2-yl]-1H-indol-7-yl}-amine The compound (150 mg, 0.34 mmol) prepared in Preparation 58 and morpholine instead of 2-oxopiperazine were reacted according to the same procedure as Example 130 to give the title compound (48 mg, Yield 35%).

$^1$H-NMR (500 HMz, DMSO-d$_6$); δ 11.27 (br s, 1H), 6.78 (m, 2H), 6.70 (m, 1H), 6.24 (m, 1H), 5.80 (m, 1H), 4.60 (m, 1H), 3.81 (m, 1H), 3.55-3.49 (m, 4H), 3.13 (m, 1H), 2.46 (m, 1H), 2.36 (m, 4H), 1.96 (m, 3H). 1.80 (m, 1H), 1.68 (m, 2H), 1.54 (m, 4H)

Example 144

Synthesis of cyclopentyl-{2-[(R)-4-(2-piperidin-1-yl-ethyl)-4,5-dihydro-thiazol-2-yl]-1H-indol-7-yl}-amine

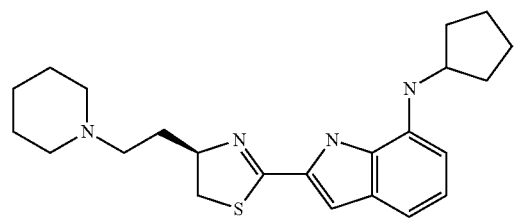

Cyclopentyl-{2-[(R)-4-(2-piperidin-1-yl-ethyl)-4,5-dihydro-thiazol-2-yl]-1H-indol-7-yl}-amine (Step 1)

Methyl ester compound (68 mg, 0.19 mmol) prepared from the compound of Step 1 of Example 42 was dissolved in dichloromethane (4 ml). Diisobutylaluminum hydridie (0.13 ml, 1.5M in CH$_2$Cl$_2$, 0.21 mmol) was added at −78° C., and the mixture was stirred for 2 h. After completion of the reaction, potassium sodium tartrate solution was added. The mixture was extracted with ethyl acetate, dried over anhydrous magnesium sulfate, and filtered. The filtrate was distilled under reduced pressure to give an aldehyde compound (62 mg, Yield 100%).

(Step 2)

The aldehyde compound (23 mg, 0.07 mmol) prepared in Step 1 was dissolved in dichloroethane (2 ml). Piperidine (9 mg, 0.11 mmol) and sodium triacetoxyborohydride (19 mg, 0.09 mmol) were added thereto, and the mixture was stirred for 30 min at room temperature. After completion of the reaction, water was added. The mixture was extracted with ethyl acetate, dried over anhydrous magnesium sulfate, and filtered. The filtrate was distilled under reduced pressure, and purified by column chromatography to give the title compound (10 mg, Yield 36%).

$^1$H-NMR (400 HMz, CDCl$_3$); δ 10.34 (br s, 1H), 7.04 (d, 1H), 6.99 (t, 1H), 6.49 (d, 1H), 4.72 (m, 1H), 3.86 (m, 1H), 3.51 (m, 1H), 3.15 (m, 1H), 2.30~2.00 (m, 8H), 2.69~1.40 (m, 14H)

Preparation 59

Synthesis of {2-[(R)-4-(2-iodo-ethyl)-4,5-dihydro-thiazol-2-yl]-1H-indol-7-yl}-(tetrahydro-pyran-4-yl)-amine

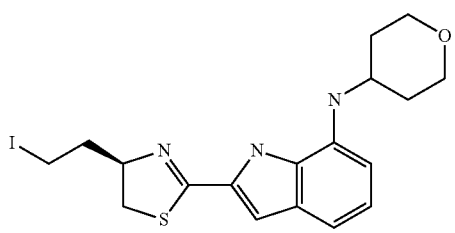

{2-[(R)-4-(2-Iodo-ethyl)-4,5-dihydro-thiazol-2-yl]-1H-indol-7-yl}-(tetrahydro-pyran-4-yl)-amine The compound (340 mg, 0.98 mol) prepared in Example 46 was reacted according to the same procedure as Preparation 50 to give the title compound (370 mg, Yield 83%).

Example 145

Synthesis of {2-[(R)-4-(2-methanesulfonyl-ethyl)-4,5-dihydro-thiazol-2-yl]-1H-indol-7-yl}-(tetrahydro-pyran-4-yl)-amine

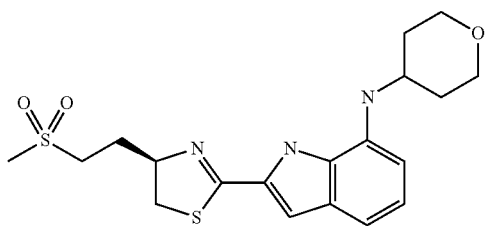

{2-[(R)-4-(2-Methanesulfonyl-ethyl)-4,5-dihydro-thiazol-2-yl]-1H-indol-7-yl}-(tetrahydro-pyran-4-yl)-amine The compound (50 mg, 0.11 mmol) prepared in Preparation 59 was reacted according to the same procedure as Example 108 to give the title compound (18 mg, Yield %).

$^1$H-NMR (400 HMz, CDCl$_3$); δ 10.02 (br s, 1H), 7.08 (d, 1H), 7.00 (t, 1H), 6.95 (s, 1H), 6.54 (d, 1H), 4.78 (m, 1H), 4.01 (m, 2H), 3.61-3.47 (m, 4H), 3.33 (m, 1H), 3.15 (m, 2H), 2.85 (s, 3H), 2.25 (m, 2H). 2.05 (m, 2H), 1.51 (m, 2H)

Preparation 60

Synthesis of 2-[(R)-2-(7-cyclopentylamino-5-methoxy-1H-indol-2-yl]-4,5-dihydro-thiazol-4-yl]ethanol

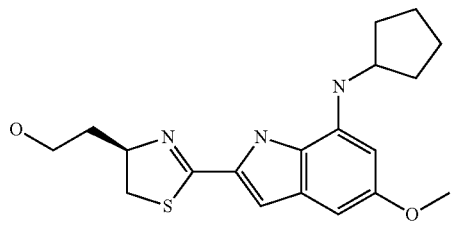

2-[(R)-2-(7-Cyclopentylamino-5-methoxy-1H-indol-2-yl)-4,5-dihydro-thiazol-4-yl]-ethanol The compound (2.40 g, 6.19 mmol) prepared in Example 47 was reacted according to the same procedure as Example 70 to give the title compound (1.20 g, Yield 54%).

Preparation 61

Synthesis of cyclopentyl-{2-[(R)-4-(2-iodo-ethyl)-4,5-dihydro-thiazol-2-yl]-5-methoxy-1H-indol-7-yl}-amine

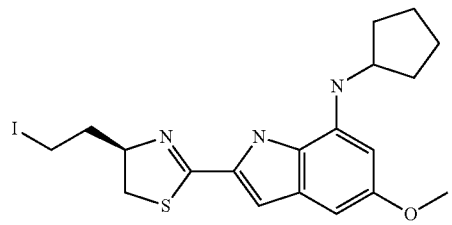

Cyclopentyl-{2-[(R)-4-(2-iodo-ethyl)-4,5-dihydro-thiazol-2-yl]-5-methoxy-1H-indol-7-yl}-amine The compound (1.20 g, 3.34 mmol) prepared in Preparation 60 was reacted according to the same procedure as Preparation 50 to give the title compound (1.23 g, Yield 78%).

Example 146

Synthesis of 1-(4-{2-[(R)-2-(7-cyclopentylamino-5-methoxy-1H-indol-2-yl)-4,5-dihydro-thiazol-4-yl]-ethyl}-piperazin-1-yl)-2-hydroxy-ethanone

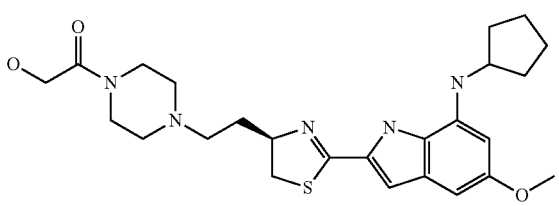

1-(4-{2-[(R)-2-(7-Cyclopentylamino-5-methoxy-1H-indol-2-yl)-4,5-dihydro-thiazol-4-yl]ethyl}-piperazin-1-yl)-2-hydroxy-ethanone The compound (500 mg, 1.07 mmol) prepared in Preparation 61 was reacted according to the same procedures as Example 96 and Example 97 to give the title compound (20 mg, Yield 4%).

¹H-NMR (400 HMz, CDCl₃); δ 11.13 (br s, 1H), 6.98 (s, 1H), 6.42 (s, 1H), 6.13 (d, 1H), 4.85 (m, 1H), 4.07 (s, 2H), 3.81 (m, 8H), 3.55 (m, 2H), 3.39 (m, 1H), 3.13 (m, 1H), 2.96 (m, 1H), 2.90 (m, 1H), 2.35 (m, 3H), 2.10 (m, 2H), 1.99 (m, 3H), 1.84 (m, 1H), 1.75 (m, 1H), 1.62 (m, 4H), 1.44 (m, 1H), 1.35 (m, 1H)

Preparation 62

Synthesis of 2-{(R)-2-[5-methoxy-7-(tetrahydro-pyran-4-ylamino)-1H-indol-2-yl]-4,5-dihydro-thiazol-4-yl}-ethanol

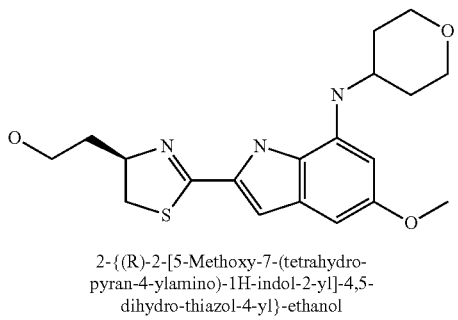

2-{(R)-2-[5-Methoxy-7-(tetrahydro-pyran-4-ylamino)-1H-indol-2-yl]-4,5-dihydro-thiazol-4-yl}-ethanol The compound (4.00 g, 9.91 mmol) prepared in Example 50 was reacted according to the same procedure as Example 70 to give the title compound (2.80 g, Yield 75%).

Preparation 63

Synthesis of {2-[(R)-4-(2-iodo-ethyl)-4,5-dihydro-thiazol-2-yl]-5-methoxy-1H-indol-7-yl}(tetrahydro-pyran-4-yl)-amine

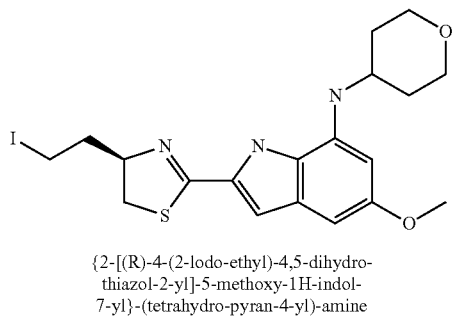

{2-[(R)-4-(2-Iodo-ethyl)-4,5-dihydro-thiazol-2-yl]-5-methoxy-1H-indol-7-yl}-(tetrahydro-pyran-4-yl)-amine The compound (2.80 g, 7.46 mmol) prepared in Preparation 62 was reacted according to the same procedure as Preparation 50 to give the title compound (2.65 g, Yield 73%).

Example 147

Synthesis of 2-hydroxy-1-[4-(2-{(R)-2-[5-methoxy-7-(tetrahydro-pyran-4-ylamino)-1H-indol-2-yl]-4,5-dihydro-thiazol-4-yl}-ethyl)-piperazin-1-yl]ethanone

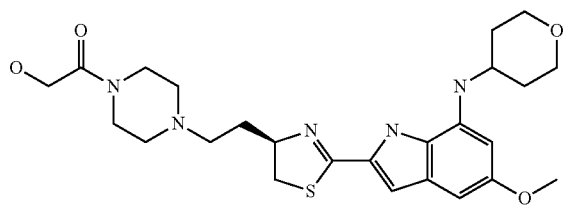

2-Hydroxy-1-[4-(2-{(R)-2-[5-methoxy-7-(tetrahydro-pyran-4-ylamino)-1H-indol-2-yl]-4,5-dihydro-thiazol-4-yl}-ethyl)-piperazin-1-yl]-ethanone The compound (500 mg, 1.03 mmol) prepared in Preparation 63 was reacted according to the same procedures as Example 96 and Example 97 to give the title compound (50 mg, Yield 10%).

¹H-NMR (400 HMz, CDCl₃); δ 11.13 (br s, 1H), 6.91 (s, 1H), 6.47 (s, 1H), 6.17 (s, 1H), 4.86 (m, 1H), 4.13 (m, 2H), 3.97 (m, 3H), 3.84 (m, 3H), 3.62 (m, 2H), 3.47 (m, 4H), 3.03 (m, 3H), 2.43 (m, 3H), 2.17 (m, 5H), 1.98 (m, 3H), 1.44 (m, 2H)

Preparation 64

Synthesis of 3-[(R)-2-(7-amino-5-chloro-1H-indol-2-yl)-4,5-dihydro-thiazol-4-yl]propionic acid ethyl ester

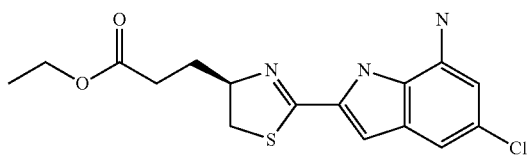

3-[(R)-2-(7-Amino-5-chloro-1H-indol-2-yl)-4,5-dihydro-thiazol-4-yl]-propionic acid ethyl ester The acid compound (2.0 g, 8.3 mmol) prepared in Preparation 33 and the compound (R)-4-amino-5-(4-methoxy-benzylsulfanyl)-pentanoic acid ethyl ester hydrochloride (3.4 g, 10.2 mmol) prepared in Preparation 17 were reacted according to the same procedure as Preparation 34 to give the title compound (0.76 g, Yield: 26%).

¹H-NMR (400 HMz, CDCl₃); δ 10.00 (br s, 1H), 7.08 (s, 1H), 6.80 (s, 1H), 6.57 (s, 1H), 4.71 (m, 1H), 4.07 (m, 2H), 3.88 (br s, 2H), 3.55 (m, 1H), 3.11 (m, 1H), 2.50 (t, 2H), 2.05 (m, 2H), 1.22 (t, 3H)

Example 148

Synthesis of 3-[(R)-2-(5-chloro-7-cyclopentylamino-1H-indol-2-yl)-4,5-dihydro-thiazol-4-yl]propionic acid ethyl ester

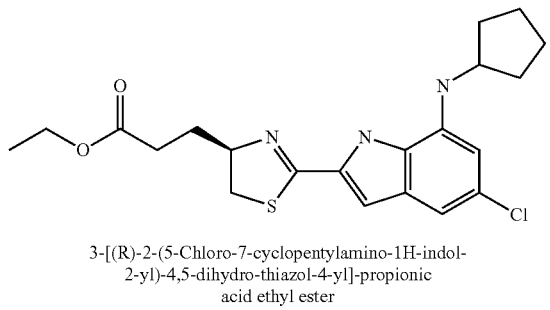

3-[(R)-2-(5-Chloro-7-cyclopentylamino-1H-indol-2-yl)-4,5-dihydro-thiazol-4-yl]-propionic acid ethyl ester The compound (760 mg, 2.1 mmol) prepared in Preparation 64 was reacted according to the same procedure as Example 26 to give the title compound (450 mg, Yield 51%).

Preparation 65

Synthesis of (R)-4-amino-5-(4-methoxy-benzylsulfanyl)-pentanoic acid cyclohexyl ester hydrochloride

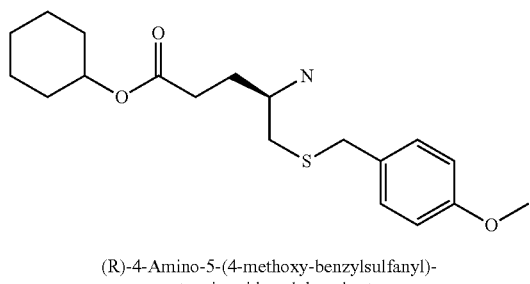

(R)-4-Amino-5-(4-methoxy-benzylsulfanyl)-pentanoic acid cyclohexyl ester (R)-4-t-butoxycarbonylamino-5-hydroxy-pentanoic acid cyclohexyl ester (6.5 g, 20.6 mmol) was reacted according to the same procedure as Preparation 17 to give the title compound (7.5 g, Yield 97%).

Preparation 66

Synthesis of 3-[(R)-2-(7-amino-5-chloro-1H-indol-2-yl)-4,5-dihydro-thiazol-4-yl]propionic acid cyclohexyl ester

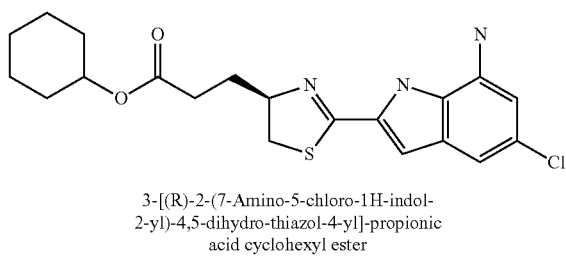

3-[(R)-2-(7-Amino-5-chloro-1H-indol-2-yl)-4,5-dihydro-thiazol-4-yl]-propionic acid cyclohexyl ester The compound (3.9 g, 16.2 mmol) prepared in Preparation 33 and the compound (7.5 g, 19.5 mmol) prepared in Preparation 65 were reacted according to the same procedure as Preparation 34 to give the title compound (2.6 g, Yield 40%).

Preparation 67

Synthesis of 3-[(R)-2-(5-chloro-7-cyclopentylamino-1H-indol-2-yl)-4,5-dihydro-thiazol-4-yl]-propionic acid cyclohexyl ester

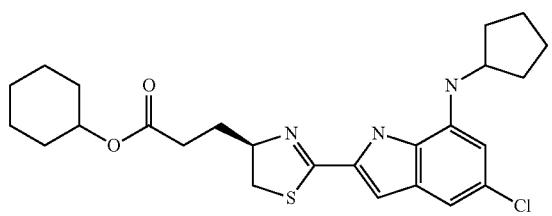

3-[(R)-2-(5-Chloro-7-cyclopentylamino 1H-indol-2-yl)-4,5-dihydro-thiazol-4-yl]-propionic acid cyclohexyl ester The compound (1.30 g, 3.20 mmol) prepared in Preparation 66 was reacted according to the same procedure as Example 29 to give the title compound (1.15 g, Yield 76%).

Example 149

Synthesis of 3-[(R)-2-(5-chloro-7-cyclopentylamino-1H-indol-2-yl)-4,5-dihydro-thiazol-4-yl]-propionic acid

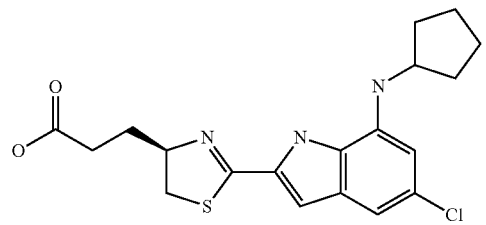

3-[(R)-2-(5-Chloro-7-cyclopentylamino 1H-indol-2-yl)-4,5-dihydro-thiazol-4-yl]-propionic acid The ester compound (500 mg, 1.05 mmol) prepared in Preparation 67 was reacted according to the same procedure as Example 27 to give the title compound (400 mg, Yield 97%).

$^1$H-NMR (400 HMz, DMSO-$d_6$, Na salt); δ 11.69 (br s, 1H), 6.82 (d, J=4.0 Hz, 1H), 6.68 (s, 1H), 6.27 (s, 1H), 6.18 (s, 1H), 4.63 (m, 1H), 3.83 (m, 1H), 3.50 (m, 1H), 3.13 (m, 1H), 2.08~1.96 (m, 6H), 1.72 (m, 2H), 1.58 (m, 4H)

Example 150

Synthesis of 3-[(R)-2-(5-chloro-7-cyclopentylamino-1H-indol-2-yl)-4,5-dihydro-thiazol-4-yl]-propan-1-ol

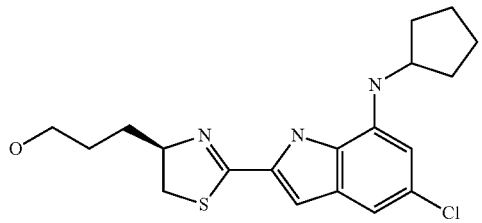

3-[(R)-2-(5-Chloro-7-cyclopentylamino-1H-indol-2-yl)-4,5-dihydro-thiazol-4-yl]-propan-1-ol The compound (650 mg, 1.37 mmol) prepared in Preparation 67 was reacted according to the same procedure as Example 70 to give the title compound (210 mg, Yield 41%).
$^1$H-NMR (400 HMz, CDCl$_3$); δ 10.42 (br s, 1H), 6.94 (s, 1H), 6.82 (s, 1H), 6.37 (s, 1H), 4.58 (m, 1H), 4.56 (m, 1H), 3.75 (m, 2H), 3.65 (m, 1H), 1.95 (m, 7H), 1.51 (m, 4H), 1.31 (m, 2H)

Preparation 68

Synthesis of 3-{(R)-2-[5-chloro-7-(tetrahydro-pyran-4-ylamino)-1H-indol-2-yl]-4,5-dihydro-thiazol-4-yl}-propionic acid cyclohexyl ester

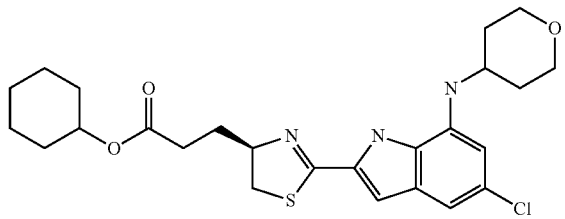

3-{(R)-2-[5-Chloro-7-(tetrahydro-pyran-4-ylamino)-1H-indol-2-yl]-4,5-dihydro-thiazol-4-yl}-propionic acid cyclohexyl ester The compound (1.30 g, 3.20 mmol) prepared in Preparation 66 was reacted according to the same procedure as Example 30 to give the title compound (1.24 g, Yield 79%).

Example 151

Synthesis of 3-{(R)-2-[5-chloro-7-(tetrahydro-pyran-4-ylamino)-1H-indol-2-yl]-4,5-dihydro-thiazol-4-yl}-propionic acid

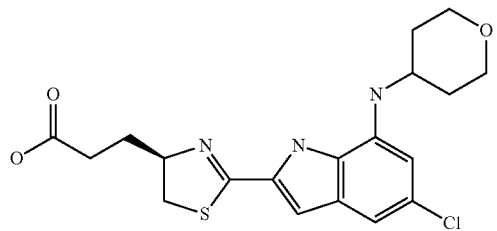

3-{(R)-2-[5-Chloro-7-(tetrahydro-pyran-4-ylamino)-1H-indol-2-yl]-4,5-dihydro-thiazol-4-yl}-propionic acid The ester compound (500 mg, 1.05 mmol) prepared in Preparation 68 was reacted according to the same procedure as Example 27 to give the title compound (250 mg, Yield 59%).
$^1$H-NMR (400 HMz, DMSO-d$_6$, Na salt); δ 11.53 (br s, 1H), 6.86 (s, 1H), 6.76 (s, 1H), 6.34 (s, 1H), 4.67 (m, 1H), 3.91 (m, 2H), 3.49 (m, 4H), 3.21 (m, 1H), 2.50 (m, 2H), 2.01 (m, 4H), 1.43 (m, 2H)

Example 152

Synthesis of 3-{(R)-2-[5-chloro-7-(tetrahydro-pyran-4-ylamino)-1H-indol-2-yl]-4,5-dihydro-thiazol-4-yl}-propan-1-ol

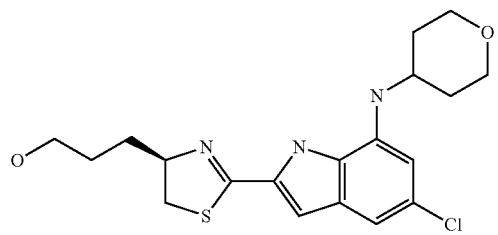

3-{(R)-2-[5-Chloro-7-(tetrahydro-pyran-4-ylamino)-1H-indol-2-yl]-4,5-dihydro-thiazol-4-yl}-propan-1-ol The compound (650 mg, 1.33 mmol) prepared in Preparation 68 was reacted according to the same procedure as Example 70 to give the title compound (150 mg, Yield 29%).
$^1$H-NMR (400 HMz, CDCl$_3$); δ 11.00 (br s, 1H), 6.93 (s, 1H), 6.82 (s, 1H), 6.31 (s, 1H), 4.89 (br s, 1H), 4.56 (m, 1H), 3.95 (m, 1H), 3.85 (m, 1H), 3.77 (m, 1H), 3.65 (m, 1H), 3.51 (m, 4H), 3.10 (m, 1H), 1.97 (m, 2H), 1.83 (m, 3H), 1.74 (m, 1H), 1.44 (m, 1H), 1.40 (m, 1H)

Example 153

Synthesis of 3-[(R)-2-(5-chloro-7-cyclopentylamino-1H-indol-2-yl)-4,5-dihydro-thiazol-4-yl]-N-(2-morpholin-4-yl-ethyl)-propionamide

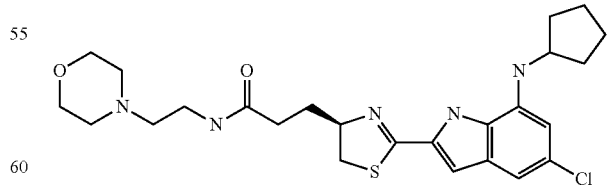

3-[(R)-2-(5-Chloro-7-cyclopentylamino-1H-indol-2-yl)-4,5-dihydro-thiazol-4-yl]-N-(2-morpholin-4-yl-ethyl)-propionamide The compound (150 mg, 0.38 mmol) prepared in Example 149 and 4-(2-aminoethyl)morpholine instead of morpholine were reacted according to the same procedure as Example 70 to give the title compound (50 mg, Yield 26%).

$^1$H-NMR (400 HMz, CDCl$_3$); δ 11.13 (br s, 1H), 7.06 (br s, 1H), 6.93 (s, 1H), 6.82 (s, 1H), 6.39 (s, 1H), 4.61 (m, 1H), 3.88 (m, 2H), 3.77 (s, 4H), 3.45 (m, 2H), 3.07 (m, 1H), 2.70 (m, 6H), 2.44 (m, 2H), 2.10 (m, 3H), 1.95 (m, 1H), 1.71 (m, 2H), 1.64 (m, 2H), 1.54 (m, 2H)

Example 154

Synthesis of 3-[(R)-2-(5-chloro-7-cyclopentylamino-1H-indol-2-yl)-4,5-dihydro-thiazol-4-yl]-1-(4-methyl-piperazin-1-yl)-propan-1-one

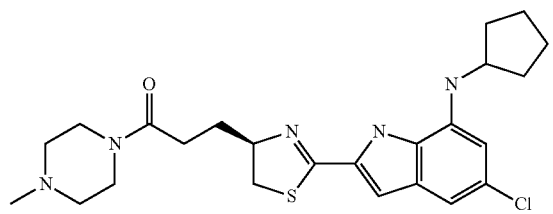

3-[(R)-2-(5-Chloro-7-cyclopentylamino-1H-indol-2-yl)-4,5-dihydro-thiazol-4-yl]-1-(4-methyl-piperazin-1-yl)-propan-1-one The compound (150 mg, 0.38 mmol) prepared in Example 149 and 1-methylpiperazine instead of morpholine were reacted according to the same procedure as Example 73 to give the title compound (50 mg, Yield 28%).

$^1$H-NMR (400 HMz, CDCl$_3$); δ 11.26 (br s, 1H), 6.93 (s, 1H), 6.85 (s, 1H), 6.38 (s, 1H), 4.73 (m, 1H), 3.83 (m, 1H), 3.59 (m, 3H), 3.30 (m, 2H), 3.14 (m, 1H), 2.45 (m, 4H), 2.30 (m, 5H), 2.04 (m, 4H), 1.70 (m, 4H), 1.52 (m, 2H)

Preparation 69

Synthesis of methanesulfonic acid 3-[(R)-2-(5-chloro-7-cyclopentylamino-1H-indol-2-yl)-4,5-dihydro-thiazol-4-yl]-propyl ester

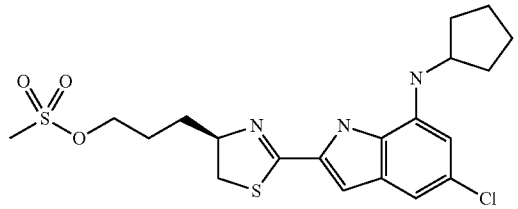

Methanesulfonic acid 3-[(R)-2-(5-chloro-7-cyclopentylamino-1H-indol-2-yl)-4,5-dihydro-thiazol-4-yl]-propyl ester The compound (140 mg, 0.37 mmol) prepared in Example 154 was reacted according to the same procedure as Preparation 22 to give the title compound (120 mg, Yield 71%).

Example 155

Synthesis of 1-(4-{3-[(R)-2-(5-chloro-7-cyclopentylamino-1H-indol-2-yl)-4,5-dihydro-thiazol-4-yl]-propyl}-piperazin-1-yl)-ethanone

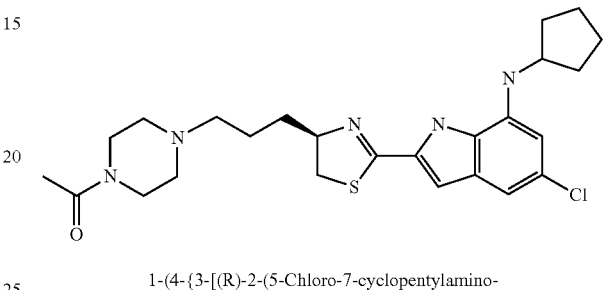

1-(4-{3-[(R)-2-(5-Chloro-7-cyclopentylamino-1H-indol-2-yl)-4,5-dihydro-thiazol-4-yl]-propyl}-piperazin-1-yl)-ethanone The compound (100 mg, 0.22 mmol) prepared in Preparation 69 was reacted according to the same procedure as Example 125 to give the title compound (49 mg, Yield 46%).

$^1$H-NMR (400 HMz, CDCl$_3$); δ 10.33 (br s, 1H), 6.97 (s, 1H), 6.81 (s, 1H), 6.42 (s, 1H), 4.64 (m, 1H), 3.85 (m, 1H), 3.65 (m, 2H), 3.56 (m, 1H), 3.45 (m, 2H), 3.13 (m, 1H), 2.43 (m, 6H), 2.04 (m, 2H), 1.72 (m, 8H), 1.54 (m, 2H)

Example 156

Synthesis of {5-chloro-2-[(R)-4-(3-morpholin-4-yl-propyl)-4,5-dihydro-thiazol-2-yl]-1H-indol-7-yl}-cyclopentyl-amine

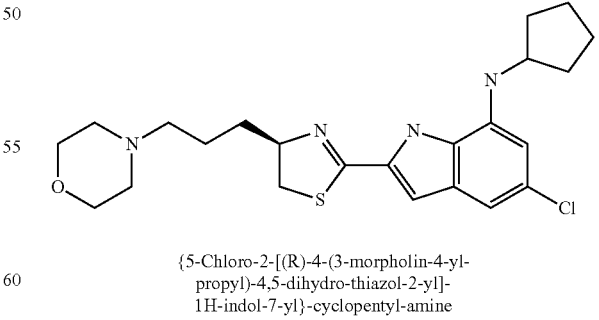

{5-Chloro-2-[(R)-4-(3-morpholin-4-yl-propyl)-4,5-dihydro-thiazol-2-yl]-1H-indol-7-yl}-cyclopentyl-amine The compound (100 mg, 0.22 mmol) prepared in Preparation 69 and morpholine instead of 1-acetylpiperazine were reacted according to the same procedure as Example 125 to give the title compound (43 mg, Yield 44%).

¹H-NMR (400 HMz, CDCl₃); δ 11.07 (br s, 1H), 6.90 (s, 1H), 6.74 (s, 1H), 6.36 (s, 1H), 4.61 (m, 1H), 3.94 (m, 4H), 3.55 (m, 1H), 3.04 (m, 3H), 2.04 (m, 7H), 1.71 (m, 3H), 1.61 (m, 4H), 1.26 (m, 3H)

Example 157

Synthesis of 3-[(R)-2-(7-cyclopentylamino-5-methyl-1H-indol-2-yl)-4,5-dihydro-thiazol-4-yl]-propionic acid ethyl ester

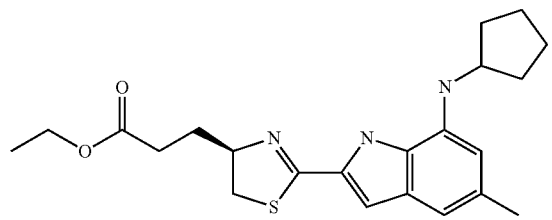

3-[(R)-2-(7-Cyclopentylamino-5-methyl-1H-indol-2-yl)-4,5-dihydro-thiazol-4-yl]-propionic acid ethyl ester The compound (2.0 g, 8.6 mmol) prepared in Preparation 7 and the compound (3.4 g, 10.2 mmol) prepared in Preparation 17 were reacted according to the same procedures as Preparation 33, Preparation 34 and Example 26 in the order to give the title compound (500 mg, Yield 15%).

¹H-NMR (400 HMz, CDCl₃); δ 10.75 (br s, 1H), 6.82 (d, 2H), 6.32 (s, 1H), 4.71 (m, 1H), 4.01 (q, 2H), 3.83 (m, 1H), 3.53 (m, 1H), 3.11 (m, 1H), 2.44 (m, 2H), 2.37 (s, 3H), 2.01 (m, 4H), 1.64 (m, 4H), 1.40 (m, 2H)

Example 158

Synthesis of 3-[(R)-2-(7-cyclopentylamino-5-methyl-1H-indol-2-yl)-4,5-dihydro-thiazol-4-yl]-propionic acid

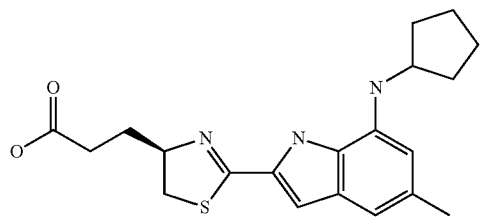

3-[(R)-2-(7-Cyclopentylamino-5-methyl-1H-indol-2-yl)-4,5-dihydro-thiazol-4-yl]-propionic acid The compound (300 mg, 0.75 mmol) prepared in Example 157 was dissolved in tetrahydrofuran (25 ml) and methanol (25 ml). 1N aqueous sodium hydroxide solution (4.0 ml, 4 mmol) was added thereto, and the mixture was stirred for 3 h at room temperature. After completion of the reaction, 1N hydrochloric acid was added. The mixture was extracted with ethyl acetate, dried over anhydrous magnesium sulfate, and filtered. The filtrate was distilled under reduced pressure, and purified by column chromatography to give the title compound (235 mg, Yield 84%).

¹H-NMR (400 HMz, CDCl₃); δ 11.34 (br s, 1H), 6.56 (s, 1H), 6.54 (s, 1H), 6.06 (s, 1H), 5.05 (br d, 1H), 4.60 (m, 1H), 3.81 (m, 1H), 3.45 (m, 1H), 3.06 (m, 1H), 2.28 (s, 3H), 2.09~1.93 (m, 5H), 1.78~1.54 (m, 7H)

Preparation 70

Synthesis of 3-[(R)-2-(7-cyclopentylamino-5-phenoxy-1H-indol-2-yl)-4,5-dihydro-thiazol-4-yl]-propionic acid ethyl ester

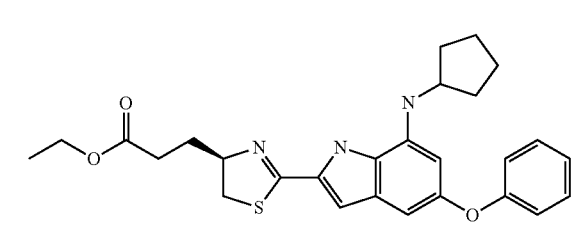

3-[(R)-2-(7-Cyclopentylamino-5-phenoxy-1H-indol-2-yl)-4,5-dihydro-thiazol-4-yl]-propionic acid ethyl ester The compound (2.6 g, 8.4 mmol) prepared in Preparation 12 and the compound (3.4 g, 10.2 mmol) prepared in Preparation 17 were reacted according to the same procedures as Preparation 33, Preparation 34 and Example 26 in the order to give the title compound (1.0 g, Yield 25%).

Example 159

Synthesis of 3-[(R)-2-(7-cyclopentylamino-5-phenoxy-1H-indol-2-yl)-4,5-dihydro-thiazol-4-yl]-propionic acid

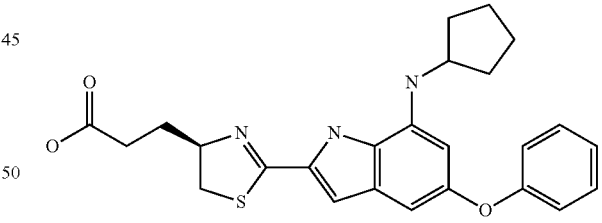

3-[(R)-2-(7-Cyclopentylamino-5-phenoxy-1H-indol-2-yl)-4,5-dihydro-thiazol-4-yl]-propionic acid The compound (600 mg, 1.26 mmol) prepared in Preparation 70 was reacted according to the same procedure as Example 158 to give the title compound (430 mg, Yield 76%).

¹H-NMR (400 HMz, DMSO-d₆); δ 11.59 (br s, 1H), 7.29 (m, 2H), 7.01 (m, 1H), 6.92 (m, 2H), 6.67 (s, 1H), 6.40 (d, 1H), 6.21 (d, 1H), 5.99 (d, 1H), 4.63 (m, 1H), 3.75 (m, 1H), 3.50 (m, 1H), 3.11 (m, 1H), 2.08 (m, 2H), 2.03 (m, 1H), 1.90 (m, 2H), 1.81 (m, 1H), 1.71 (m, 2H), 1.56 (m, 4H)

Example 160

Synthesis of 3-[(R)-2-(7-cyclopentylamino-5-fluoro-1H-indol-2-yl)-4,5-dihydro-thiazol-4-yl]-propionic acid ethyl ester

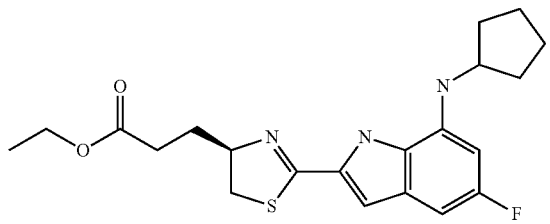

3-[(R)-2-(7-Cyclopentylamino-5-fluoro-1H-indol-2-yl)-4,5-dihydro-thiazol-4-yl]-propionic acid ethyl ester The compound (2.2 g, 8.9 mmol) prepared in Preparation 2 and the compound (3.6 g, 10.7 mmol) prepared in Preparation 17 were reacted according to the same procedures as Preparation 33, Preparation 34 and Example 26 in the order to give the title compound (1.1 g, Yield 31%).

$^1$H-NMR (400 HMz, CDCl$_3$); δ 10.48 (br s, 1H), 6.91 (s, 1H), 6.69 (m, 1H), 6.30 (m, 1H), 4.77 (m, 1H), 4.19~4.02 (m, 3H), 3.84 (m, 1H), 3.60 (m, 1H), 3.18 (m, 1H), 2.51 (m, 2H), 2.07 (m, 4H), 1.74~1.46 (m, 6H), 1.21 (m, 3H)

Example 161

Synthesis of 3-[(R)-2-(7-cyclopentylamino-5-fluoro-1H-indol-2-yl)-4,5-dihydro-thiazol-4-yl]-propionic acid

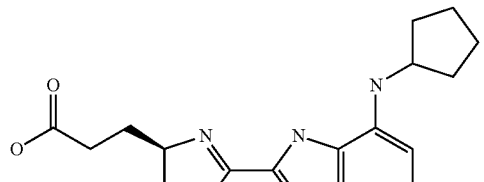

3-[(R)-2-(7-Cyclopentylamino-5-fluoro-1H-indol-2-yl)-4,5-dihydro-thiazol-4-yl]-propionic acid The compound (1.0 g, 2.48 mmol) prepared in Example 160 was reacted according to the same procedure as Example 158 to give the title compound (430 mg, Yield 46%).

$^1$H-NMR (400 HMz, DMSO-d$_6$); δ 11.63 (br s, 1H), 6.49 (m, 1H), 6.33 (m, 1H), 6.09 (m, 1H), 6.66 (m, 1H), 4.61 (m, 1H), 3.85 (m, 1H), 3.52 (m, 1H), 3.11 (m, 1H), 2.09~1.74 (m, 12H),

Example 162

Synthesis of 3-[(R)-2-(5-bromo-7-cyclopentylamino-1H-indol-2-yl)-4,5-dihydro-thiazol-4-yl]-propionic acid ethyl ester

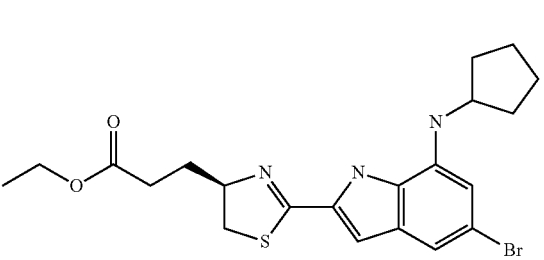

3-[(R)-2-(5-Bromo-7-cyclopentylamino-1H-indol-2-yl)-4,5-dihydro-thiazol-4-yl]-propionic acid ethyl ester The compound (2.1 g, 7.01 mmol) prepared in Preparation 6 and the compound (2.3 g, 6.89 mmol) prepared in Preparation 17 were reacted according to the same procedures as Preparation 33, Preparation 34 and Example 26 in the order to give the title compound (530 mg, Yield 16%).

$^1$H-NMR (400 HMz, CDCl$_3$); δ 10.02 (br s, 1H), 7.16 (s, 1H), 6.81 (s, 1H), 6.57 (s, 1H), 4.74 (m, 1H), 4.11 (m, 2H), 4.02 (m, 2H), 3.59 (q, 1H), 3.16 (q, 1H), 2.52 (m, 2H), 2.06 (m, 4H), 1.72 (m, 3H), 1.49 (m, 2H), 1.19 (t, 3H)

Example 163

Synthesis of 3-[(R)-2-(5-bromo-7-cyclopentylamino-1H-indol-2-yl)-4,5-dihydro-thiazol-4-yl]-propionic acid

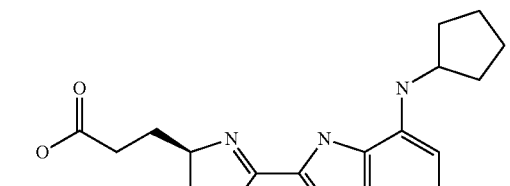

3-[(R)-2-(5-Bromo-7-cyclopentylamino-1H-indol-2-yl)-4,5-dihydro-thiazol-4-yl]-propionic acid The compound (420 mg, 0.88 mmol) prepared in Example 162 was reacted according to the same procedure as Example 158 to give the title compound (350 mg, Yield 91%).

$^1$H-NMR (400 HMz, DMSO-d$_6$); δ 11.77 (br s, 1H), 6.96 (s, 1H), 6.68 (s, 1H), 6.31 (m, 1H), 6.29 (s, 1H), 4.64 (m, 1H), 3.82 (m, 1H), 3.53 (m, 1H), 3.13 (m, 1H), 2.05 (m, 2H), 1.97 (m, 2H), 1.77 (m, 3H), 1.58 (m, 4H)

Hz, 1H), 4.65 (m, 1H), 3.86 (m, 1H), 3.52 (m, 1H), 3.11 (m, 1H), 2.05 (m, 2H), 1.97 (m, 3H), 1.78 (m, 3H), 1.56 (m, 4H)

Preparation 71

Synthesis of 3-[(R)-2-(7-cyclopentylamino-1H-indol-2-yl)-4,5-dihydro-thiazol-4-yl]-propionic acid ethyl ester

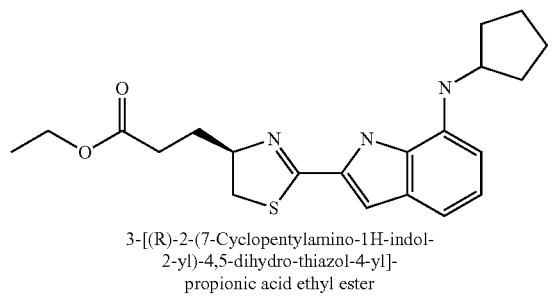

3-[(R)-2-(7-Cyclopentylamino-1H-indol-2-yl)-4,5-dihydro-thiazol-4-yl]-propionic acid ethyl ester The compound (1.64 g, 7.49 mmol) prepared in Preparation 8 and the compound (3.50 g, 10.46 mmol) prepared in Preparation 17 were reacted according to the same procedures as Preparation 33, Preparation 34 and Example 26 in the order to give the title compound (1.23 g, Yield 43%).

Preparation 72

Synthesis of 3-[(R)-2-(7-cyclopentylamino-5-methoxy-1H-indol-2-yl)-4,5-dihydro-thiazol-4-yl]propionic acid ethyl ester

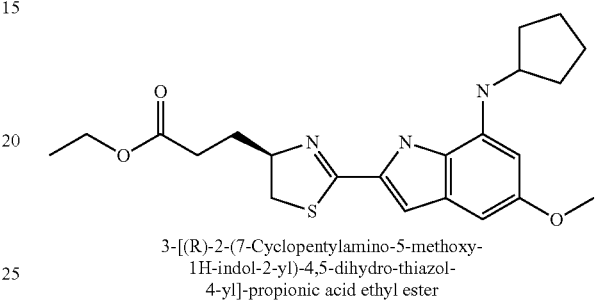

3-[(R)-2-(7-Cyclopentylamino-5-methoxy-1H-indol-2-yl)-4,5-dihydro-thiazol-4-yl]-propionic acid ethyl ester The compound (2.1 g, 8.5 mmol) prepared in Preparation 9 and the compound (3.4 g, 10.2 mmol) prepared in Preparation 17 were reacted according to the same procedures as Preparation 33, Preparation 34 and Example 26 in the order to give the title compound (700 mg, Yield 20%).

Example 164

Synthesis of 3-[(R)-2-(7-cyclopentylamino-1H-indol-2-yl)-4,5-dihydro-thiazol-4-yl]-propionic acid

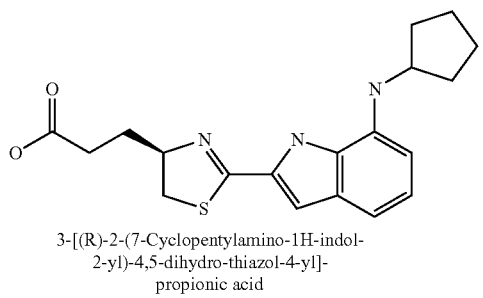

3-[(R)-2-(7-Cyclopentylamino-1H-indol-2-yl)-4,5-dihydro-thiazol-4-yl]-propionic acid The compound (1.0 g, 2.59 mmol) prepared in Preparation 71 was reacted according to the same procedure as Example 158 to give the title compound (560 mg, Yield 60%).

$^1$H-NMR (400 HMz, DMSO-$d_6$); δ 11.46 (br s, 1H), 6.85 (m, 2H), 6.70 (s, 1H), 6.27 (d, J=4.0 Hz, 1H), 5.94 (d, J=8.0

Example 165

Synthesis of 3-[(R)-2-(7-cyclopentylamino-5-methoxy-1H-indol-2-yl)-4,5-dihydro-thiazol-4-yl]-propionic acid

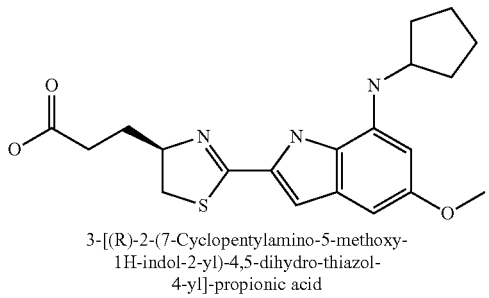

3-[(R)-2-(7-Cyclopentylamino-5-methoxy-1H-indol-2-yl)-4,5-dihydro-thiazol-4-yl]-propionic acid The compound (700 mg, 1.69 mmol) prepared in Preparation 72 was reacted according to the same procedure as Example 158 to give the title compound (430 mg, Yield 66%).

$^1$H-NMR (400 HMz, DMSO-$d_6$); δ 11.28 (br s, 1H), 6.61 (s, 1H), 6.27 (s, 1H), 5.97 (m, 1H), 5.88 (s, 1H), 4.59 (m, 1H), 3.75 (m, 1H), 3.68 (s, 3H), 3.48 (m, 2H), 3.08 (m, 1H), 2.00 (m, 5H), 1.75 (m, 3H), 1.57 (m, 4H)

Example 166

Synthesis of 3-[(R)-2-(7-cyclopentylamino-5-ethoxy-1H-indol-2-yl)-4,5-dihydro-thiazol-4-yl]-propionic acid ethyl ester

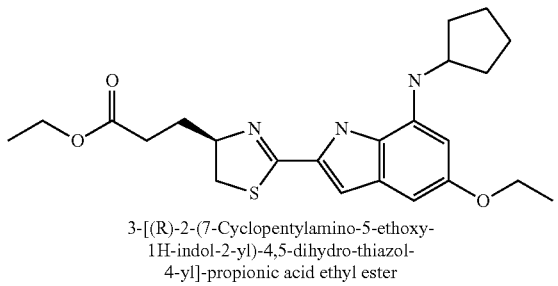

3-[(R)-2-(7-Cyclopentylamino-5-ethoxy-1H-indol-2-yl)-4,5-dihydro-thiazol-4-yl]-propionic acid ethyl ester The compound (2.4 g, 9.0 mmol) prepared in Preparation 11 and the compound (3.0 g, 8.98 mmol) preared in Preparation 17 were reacted according to the same procedures as Preparation 33, Preparation 34 and Example 26 in the order to give the title compound (600 mg, Yield 16%).

$^1$H-NMR (500 HMz, CDCl$_3$); δ 9.79 (br s, 1H), 6.80 (s, 1H), 6.44 (s, 1H), 6.19 (s, 1H), 4.69 (m, 1H), 4.11 (q, 2H), 4.03 (q, 2H), 3.83 (m, 1H), 3.54 (m, 1H), 3.11 (m, 1H), 2.49 (m, 2H), 2.02 (m, 4H), 1.69 (m, 2H), 1.60 (m, 2H), 1.48 (m, 2H), 1.25 (t, 3H), 1.19 (t, 3H)

Example 167

Synthesis of 3-[(R)-2-(7-cyclopentylamino-5-ethoxy-1H-indol-2-yl)-4,5-dihydro-thiazol-4-yl]-propionic acid

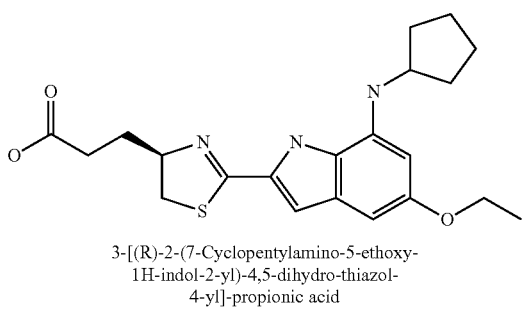

3-[(R)-2-(7-Cyclopentylamino-5-ethoxy-1H-indol-2-yl)-4,5-dihydro-thiazol-4-yl]-propionic acid The compound (300 mg, 0.70 mmol) prepared in Example 166 was reacted according to the same procedure as Example 158 to give the title compound (210 mg, Yield 71%).

$^1$H-NMR (400 HMz, DMSO-d$_6$); δ 11.37 (br s, 1H), 6.78 (s, 1H), 6.30 (s, 1H), 5.94 (s, 1H), 4.64 (m, 1H), 3.93 (q, 2H), 3.82 (m, 1H), 3.60 (m, 1H), 3.21 (m, 1H), 2.44 (m, 2H), 1.97 (m, 4H), 1.71 (m, 2H), 1.57 (m, 4H), 1.32 (t, 3H)

Preparation 73

Synthesis of 7-nitro-5-trifluoromethoxy-1H-indole-carboxylic acid methyl ester

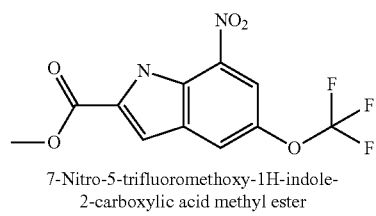

7-Nitro-5-trifluoromethoxy-1H-indole-2-carboxylic acid methyl ester

4-Trifluoromethoxy-2-nitroaniline (10.0 g, 45.0 mmol) was reacted according to the same procedures as Preparations 3 to 5 to give the title compound (3.0 g, Yield 22%).

Example 168

Synthesis of 3-[(R)-2-(7-cyclopentylamino-5-trifluoromethoxy-1H-indol-2-yl)-4,5-dihydro-thiazol-4-yl]-propionic acid ethyl ester

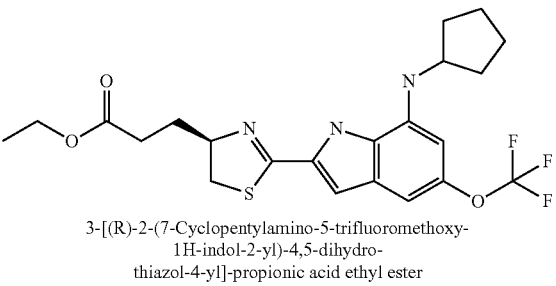

3-[(R)-2-(7-Cyclopentylamino-5-trifluoromethoxy-1H-indol-2-yl)-4,5-dihydro-thiazol-4-yl]-propionic acid ethyl ester The compound (2.7 g, 8.96 mmol) prepared in Preparation 73 and the compound (3.0 g, 8.98 mmol) prepared in Preparation 17 were reacted according to the same procedures as Preparation 33, Preparation 34 and Example 26 in the order to give the title compound (900 mg, Yield 21%).

$^1$H-NMR (500 HMz, CDCl$_3$); δ 10.97 (br s, 1H), 6.93 (s, 1H), 6.86 (s, 1H), 6.30 (s, 1H), 4.76 (m, 1H), 4.05-3.89 (m, 3H), 3.78 (m, 1H), 3.57 (m, 1H), 3.16 (m, 2H), 2.42 (m, 2H), 2.00 (m, 4H), 1.63 (m, 2H), 1.45 (m, 1H), 1.34 (m, 1H)

Example 169

Synthesis of 3-[(R)-2-(7-cyclopentylamino-5-trifluoromethoxy-1H-indol-2-yl)-4,5-dihydro-thiazol-4-yl]-propionic acid

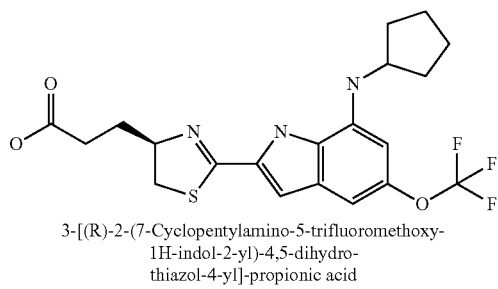

3-[(R)-2-(7-Cyclopentylamino-5-trifluoromethoxy-1H-indol-2-yl)-4,5-dihydro-thiazol-4-yl]-propionic acid The compound (750 mg, 1.60 mmol) prepared in Example 168 was reacted according to the same procedure as Example 158 to give the title compound (600 mg, Yield 5%).

$^1$H-NMR (40 HMz, DMSO-$d_6$) 11.61 (br s, 1H), 6.85 (d, 1H), 6.77 (s, 1H), 6.16 (s, 1H), 4.66 (m, 1H), 3.85 (m, 1H), 3.60 (m, 2H), 3.20 (m, 1H), 2.42 (m, 2H), 1.99 (m, 4H), 1.71 (m, 2H), 1.58 (m, 4H)

Example 170

Synthesis of [(R)-2-(7-cyclopentylamino-5-fluoro-1H-indol-2-yl)-4,5-dihydro-thiazol-4-ylmethoxy]-acetic acid ethyl ester

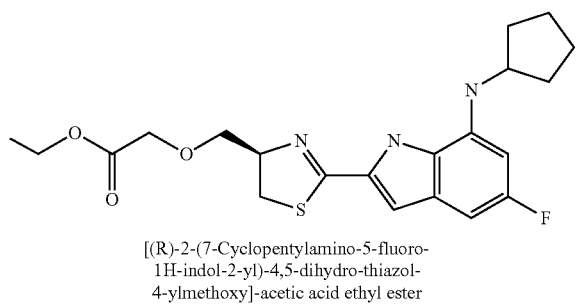

[(R)-2-(7-Cyclopentylamino-5-fluoro-1H-indol-2-yl)-4,5-dihydro-thiazol-4-ylmethoxy]-acetic acid ethyl ester The compound (50 mg, 0.15 mmol) prepared in Example 5 was dissolved in tetrahydrofuran (5 ml). Bromoacetic acid ethyl ester (30 mg, 0.18 mmol) and sodium hydride (8 mg, 0.18 mmol) were added thereto, and the mixture was stirred for 3 h at room temperature. After completion of the reaction, 1N hydrochloric acid was added. The mixture was extracted with ethyl acetate, dried over anhydrous magnesium sulfate, and filtered. The filtrate was distilled under reduced pressure, and purified by column chromatography to give the title compound (15 mg, Yield 24%) and the acid compound (40 mg, Yield 68%) of Example 171.

$^1$H-NMR (400 HMz, CDCl$_3$); δ 10.16 (br s, 1H), 6.87 (s, 1H), 6.66 (dd, J=2.4, 9.2 Hz, 1H), 6.30 (dd, J=2.4, 11.8 Hz, 1H), 4.94 (m, 1H), 4.25 (q, 2H), 4.13 (d, J=5.6 Hz, 2H), 3.87 (m, 1H), 3.76 (d, J=6.4 Hz, 2H), 3.56 (m, 1H), 3.44 (m, 1H), 2.07 (m, 2H), 1.67 (m, 4H), 1.51 (m, 2H), 1.30 (t, 3H)

Example 171

Synthesis of [(R)-2-(7-cyclopentylamino-5-fluoro-1H-indol-2-yl)-4,5-dihydro-thiazol-4-ylmethoxy]-acetic acid

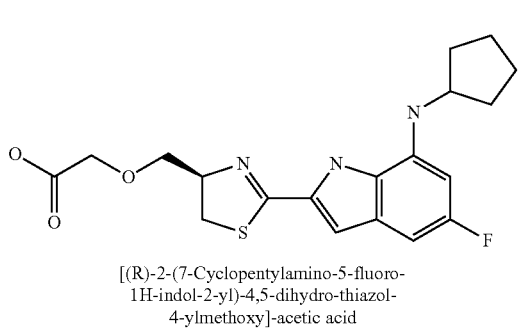

[(R)-2-(7-Cyclopentylamino-5-fluoro-1H-indol-2-yl)-4,5-dihydro-thiazol-4-ylmethoxy]-acetic acid The title compound was additionally obtained in the process of Example 170.

$^1$H-NMR (400 HMz, DMSO-$d_6$); δ 12.70 (br s, 1H), 7.07 (s, 1H), 6.57 (d, J=8.8 Hz, 1H), 6.23 (d, J=12 Hz, 1H), 5.13 (m, 1H), 4.34 (m, 1H), 4.07 (m, 2H), 3.89 (m, 1H), 3.63 (m, 3H), 2.03 (m, 2H), 1.58 (m, 6H)

Example 172

Synthesis of cyclopentyl-{2-[(R)-4-(3-cyclopentyl-[1,2,4]oxadiazol-5-ylmethyl)-4,5-dihydro-thiazol-2-yl]-1H-indol-7-yl}-amine

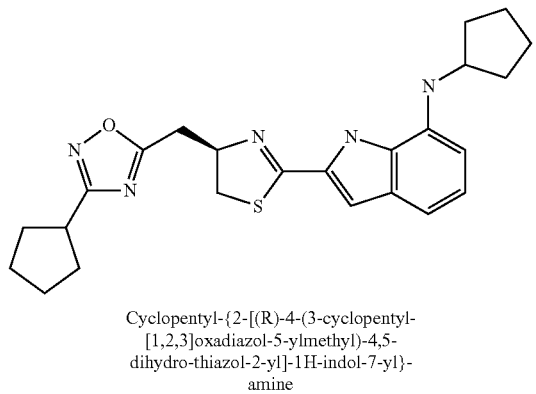

Cyclopentyl-{2-[(R)-4-(3-cyclopentyl-[1,2,3]oxadiazol-5-ylmethyl)-4,5-dihydro-thiazol-2-yl]-1H-indol-7-yl}-amine The compound (140 mg, 0.41 mmol) prepared in Example 42 was dissolved in N,N-dimethylformamide (5 ml). 1,1'-Dicarbonyldiimidazole (73 mg, 0.45 mmol) was added thereto, and the mixture was stirred for 30 min at room temperature. N-hydroxy-cyclopentanecarboxamidine (260 mg, 2.03 mmol) was added thereto, and the mixture was stirred for 5 h at 80° C. After completion of the reaction, water was added. The mixture was extracted with ethyl acetate, dried over anhydrous magnesium sulfate, and filtered. The filtrate was distilled under reduced pressure, and purified by column chromatography to give the title compound (100 mg, Yield 56%).

¹H-NMR (400 HMz, CDCl₃); δ 10.62 (br s, 1H), 7.04 (d, 1H), 6.97 (t, 1H), 6.92 (d, 1H), 6.49 (d, 1H), 5.20 (m, 1H), 3.83 (m, 2H), 3.64 (m, 1H), 3.39 (m, 1H), 3.31 (m, 1H), 3.17 (m, 1H), 3.01 (m, 1H), 1.97 (m, 4H), 1.73 (m, 4H), 1.60 (m, 6H), 1.46 (m, 2H), 1.34 (m, 2H)

Example 173

Synthesis of cyclopentyl-{2-[(R)-4-(3-piperidin-1-yl-[1,2,4]oxadiazol-5-ylmethyl)-4,5-dihydro-thiazol-2-yl]-1H-indol-7-yl}-amine

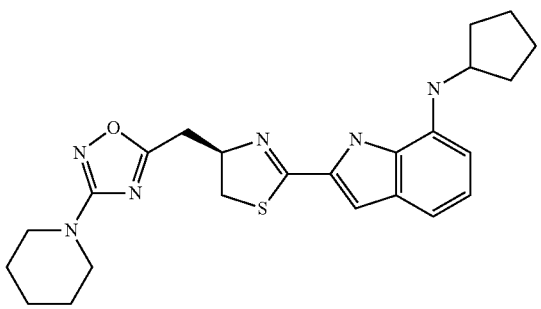

Cyclopentyl-{2-[(R)-4-(3-piperdin-1-yl-[1,2,4]oxadiazol-5-ylmethyl)-4,5-dihydro-thiazol-2-yl]-1H-indol-7-yl}-amine The compound (140 mg, 0.41 mmol) prepared in Example 42 and N-hydroxypiperidinecarboxamidine instead of N-hydroxycyclopentanecarboxamidine were reacted according to the same procedure as Example 172 to give the title compound (100 mg, Yield 54%).

¹H-NMR (400 HMz, CDCl₃); δ 10.56 (br s, 1H), 7.01 (d, 1H), 6.96 (t, 1H), 6.90 (d, 1H), 6.46 (d, 1H), 5.23 (m, 1H), 3.83 (m, 2H), 3.64 (m, 1H), 3.36 (m, 1H), 3.31 (m, 1H), 3.17 (m, 2H), 3.01 (m, 1H), 1.95 (m, 2H), 1.68-1.43 (m, 11H), 1.35 (m, 1H)

Preparation 74

Synthesis of 7-phenoxy-1H-indole-2-carboxylic acid methyl ester

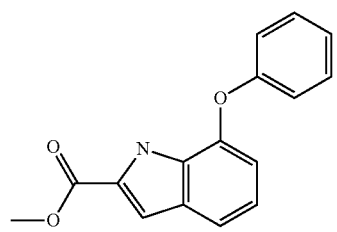

7-Phenoxy-1H-indole-2-carboxylic acid methyl ester (Step 1)

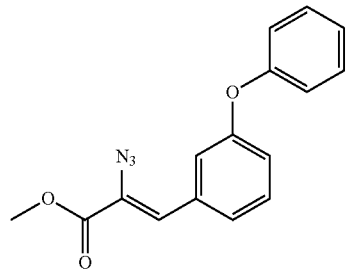

(Z)-2-Azido-3-(3-phenoxy-phenyl)-acrylic acid methyl ester

3-Phenoxy-benzaldehyde (16.1 g, 81.3 mmol) was dissolved in methanol (300 ml). Sodium methoxide (70.3 g, 25%, 325.3 mmol) and methyl azidoacetate (42.0 g, 325.3 mmol) were added thereto, and the mixture was stirred for 5 h at −10° C. After completion of the reaction, water was added. The mixture was extracted with ethyl acetate, dried over anhydrous magnesium sulfate, and filtered. The filtrate was distilled under reduced pressure, and purified by column chromatography to give an azido compound (18.5 g, Yield 77%).

(Step 2)

The compound (18.5 g, 62.6 mmol) prepared in Step 1 was dissolved in xylene (100 ml), and stirred for 4 h at 120° C. After completion of the reaction, and reaction solution was distilled under reduced pressure, and purified by column chromatography to give the title compound (4.9 g, Yield 29%).

Preparation 75

Synthesis of (R)-3-amino-4-tritylsulfanyl-butyric acid methyl ester hydrochloride

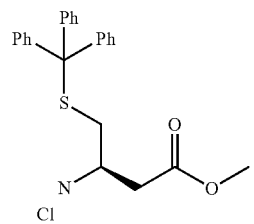

(R)-3-Amino-4-tritylsulfanyl-butyric acid methyl ester (Step 1)

L-cysteine hydrochloride (50 g, 284.7 mmol) was dissolved in N,N-dimethylformamide (200 ml). Trityl chloride (119 g, 427.0 mmol) was added thereto, and the mixture was stirred for 48 h at room temperature. After completion of the reaction, 10% sodium acetate (1.5 L) was added. The mixture was filtered to give a solid, which was then added to acetone (1.5 L), and stirred for 30 min at 50° C. The insoluble solid was filtered, and dried to give a trityl compound (80 g, Yield 78%).

(Step 2)

The compound (34 g, 154 mmol) prepared in Step 1 was reacted according to the same procedures as Steps 2~5 of Preparation 15 to give the title compound (26 g, Yield 39%).

Preparation 76

Synthesis of [(R)-2-(7-phenoxy-1H-indol-2-yl)-4,5-dihydro-thiazol-4-yl]acetic acid methyl ester

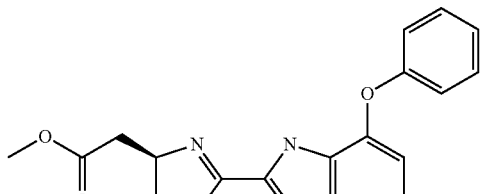

[(R)-2-(7-Phenoxy-1H-indol-2-yl)-4,5-dihydro-thiazol-4-yl]-acetic acid methyl ester The compound (4.9 g, 18.3 mmol) prepared in Preparation 74 and the compound (10.4 g, 24.3 mmol) prepared in Preparation 75 were reacted according to the same procedures as Preparation 33, Preparation 34 and Example 26 in the order to give the title compound (4.48 g, Yield 57%).

Example 174

Synthesis of [(R)-2-(7-phenoxy-1H-indol-2-yl)-4,5-dihydro-thiazol-4-yl]-acetic acid

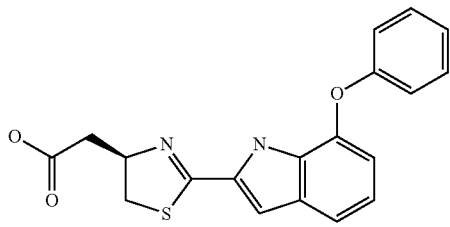

[(R)-2-(7-Phenoxy-1H-indol-2-yl)-4,5-dihydro-thiazol-4-yl]-acetic acid

The compound (500 mg, 1.36 mmol) prepared in Preparation 76 was reacted according to the same procedure as Example 27 to give the title compound (300 mg, Yield 63%).
$^1$H-NMR (400 HMz, DMSO-$d_6$); δ 12.17 (br s, 1H), 7.51 (d, J=8.0 Hz, 1H), 7.41 (t, 1H), 7.28 (br s, 1H), 7.16 (m, 2H), 7.08 (m, 2H), 6.84 (d, J=8.0 Hz, 1H), 4.95 (m, 1H), 3.77 (m, 1H), 3.37 (m, 1H), 2.86 (m, 1H), 2.75 (m, 1H)

Preparation 77

Synthesis of 2-[(R)-2-(7-phenoxy-1H-indol-2-yl)-4,5-dihydro-thiazol-4-yl]ethanol

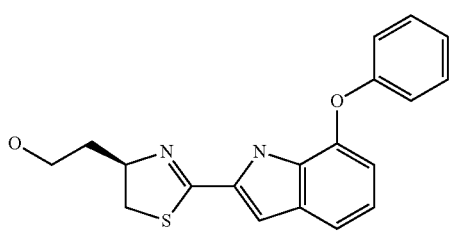

2-[(R)-2-(7-Phenoxy-1H-indol-2-yl)-4,5-dihydro-thiazol-4-yl]-ethanol

The compound (2.56 g, 6.99 mmol) prepared in Preparation 76 was dissolved in tetrahydrofuran (20 ml). Lithium borohydride (7 ml, 2.0M in THF, 14.0 mmol) was added thereto, and the mixture was stirred for 4 h at 0° C. After completion of the reaction, water was added. The mixture was extracted with ethyl acetate, washed with saturated sodium chloride solution, dried over anhydrous magnesium sulfate, and filtered. The filtrate was distilled under reduced pressure, and purified by column chromatography to give the title compound (2.20 g, Yield 93%).

Preparation 78

Synthesis of 2-[(R)-4-(2-iodo-ethyl)-4,5-dihydro-thiazol-2-yl]-7-phenoxy-1H-indole

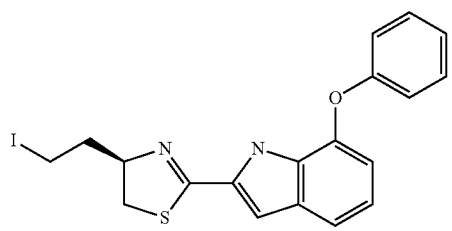

2-[(R)-4-(2-Iodo-ethyl)-4,5-dihydro-thiazol-2-yl]-7-phenoxy-1H-indole

The compound (2.20 g, 6.50 mmol) prepared in Preparation 77 was reacted according to the same procedure as Preparation 50 to give the title compound (1.80 g, Yield 62%).

Example 175

Synthesis of 1-(4-{2-[(R)-2-(7-phenoxy-1H-indol-2-yl)-4,5-dihydro-thiazol-4-yl]-ethyl}-piperazin-1-yl)-ethanone

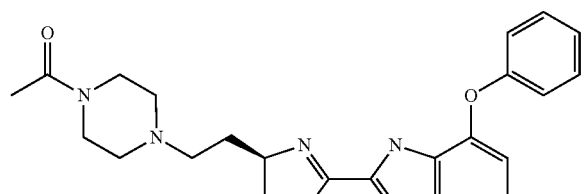

1-(4-{2-[(R)-2-(7-Phenoxy-1H-indol-2-yl)-4,5-dihydro-thiazol-4-yl]-ethyl}-piperazin-1-yl)-ethanone The compound (100 mg, 0.22 mmol) prepared in Preparation 78 was dissolved in acetonitrile (3 ml). 1-Acetylpiperazine (29 mg, 2.2 mmol) and potassium carbonate (93 mg, 0.67 mmol) were added thereto, and the mixture was stirred for 8 h at 80° C. After completion of the reaction, water was added. The mixture was extracted with ethyl acetate, washed with saturated sodium chloride solution, dried over anhydrous magnesium sulfate, and filtered. The filtrate was distilled under reduced pressure, and purified by column chromatography to give the title compound (40 mg, Yield 41%).
$^1$H-NMR (400 HMz, CDCl$_3$); δ 9.73 (br s, 1H), 7.55 (d, J=8.0 Hz, 1H), 7.41 (m, 2H), 7.11 (t, 1H), 7.07 (m, 3H), 6.91 (s, 1H), 6.78 (d, J=8.0 Hz, 2H), 4.71 (m, 1H), 3.58 (m, 2H), 3.48 (m, 1H), 3.38 (m, 2H), 3.11 (t, 1H), 2.56 (m, 2H), 2.50 (m, 4H), 2.06 (s, 3H), 1.98 (m, 1H), 1.82 (m, 1H)

Example 176

Synthesis of 2-[(R)-4-(2-morpholin-4-yl-ethyl)-4,5-dihydro-thiazol-2-yl]-7-phenoxy-1H-indole

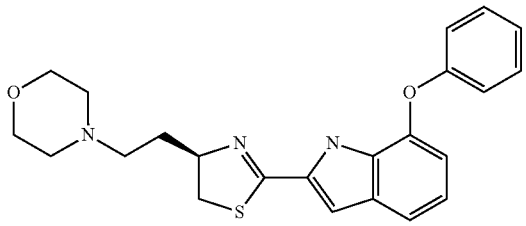

2-[(R)-4-(2-Morpholin-4-yl-ethyl)-4,5-dihydro-thiazol-2-yl]-7-phenoxy-1H-indole

The compound (100 mg, 0.22 mmol) prepared in Preparation 78 and morpholine instead of 1-acetylpiperazine were reacted according to the same procedure as Example 175 to give the title compound (40 mg, Yield 45%).

$^1$H-NMR (400 HMz, CDCl$_3$); δ 9.17 (br s, 1H), 7.42 (d, J=8.0 Hz, 1H), 7.34 (t, 2H), 7.13 (t, 1H), 7.05 (m, 3H), 6.93 (s, 1H), 6.80 (d, J=8.0 Hz, 2H), 4.68 (m, 1H), 3.72 (m, 4H), 3.70 (t, 1H), 3.14 (t, 1H), 2.62 (m, 2H), 2.51 (m, 4H), 2.07 (m, 1H), 1.85 (m, 1H)

Example 177

Synthesis of 7-phenoxy-2-[(R)-4-(2-pyrrolidin-1-yl-ethyl)-4,5-dihydro-thiazol-2-yl]-1H-indole

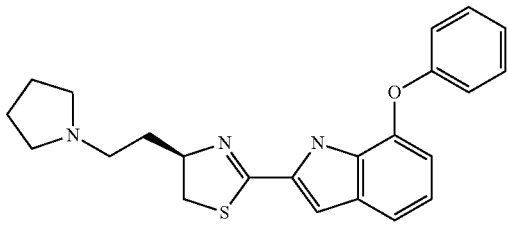

7-Phenoxy-2-[(R)-4-(2-pyrrolidin-1-yl-ethyl)-4,5-dihydro-thiazol-2-yl]-1H-indole The compound (100 mg, 0.22 mmol) prepared in Preparation 78 and pyrrolidine instead of 1-acetylpiperazine were reacted according to the same procedure as Example 175 to give the title compound (80 mg, Yield 93%).

$^1$H-NMR (400 HMz, CDCl$_3$); δ 9.37 (br s, 1H), 7.41 (d, J=8.0 Hz, 1H), 7.34 (t, 2H), 7.10 (t, 1H), 7.05 (m, 3H), 6.92 (s, 1H), 6.80 (d, J=8.0 Hz, 2H), 4.67 (m, 1H), 3.54 (t, 1H), 3.14 (t, 1H), 2.57 (m, 2H), 2.51 (m, 4H), 2.07 (m, 1H), 1.89 (m, 1H), 1.77 (m, 4H)

Example 178

Synthesis of dimethyl-{2-[(R)-2-(7-phenoxy-1H-indol-2-yl)-4,5-dihydro-thiazol-4-yl]ethyl}-amine

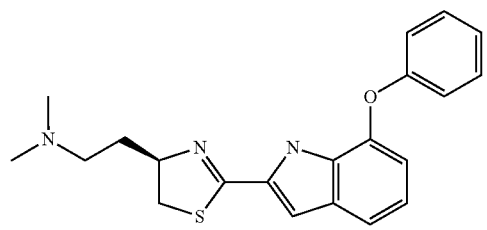

Dimethyl-{2-[(R)-2-(7-phenoxy-1H-indol-2-yl)-4,5-dihydro-thiazol-4-yl]-ethyl}-amine The compound (100 mg, 0.22 mmol) prepared in Preparation 78 and dimethylamine instead of 1-acetylpiperazine were reacted according to the same procedure as Example 175 to give the title compound (70 mg, Yield 87%).

$^1$H-NMR (400 HMz, CDCl$_3$); δ 9.31 (br s, 1H), 7.41 (d, J=8.0 Hz, 1H), 7.43 (t, 2H), 7.10 (t, 1H), 7.05 (m, 3H), 6.92 (s, 1H), 6.80 (d, J=8.0 Hz, 2H), 4.65 (m, 1H), 3.54 (t, 1H), 3.14 (t, 1H), 2.57 (m, 2H), 2.27 (s, 6H), 2.04 (m, 1H), 1.85 (m, 1H)

Preparation 79

Synthesis of (S)-3-amino-4-(4-methoxy-benzylsulfanyl)-butyric acid isopropyl ester

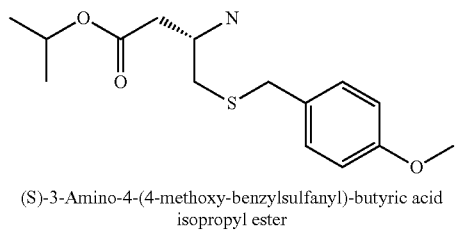

(S)-3-Amino-4-(4-methoxy-benzylsulfanyl)-butyric acid isopropyl ester (Step 1)

The commercially available (S)-2-BOC-amino-succinic acid 1-methyl ester (2.4 g, 10 mmol) was dissolved in DCM (30 ml), and triethylamine (2.8 ml, 20 mmol) was added thereto. Isopropanol (660 mg, 11 mmol), EDC (2.5 g, 26 mmol) and HOBt (2.3 g, 30 mmol) were added, and the mixture was stirred for 4 h at room temperature. The reaction was quenched by saturated aqueous NaHCO$_3$ solution. The organic material was extracted with EtOAc, washed with saturated aqueous sodium chloride solution, and dried over anhydrous magnesium sulfate. The solvent was removed under reduced pressure, and the residue was purified by column chromatography to give a compound (2.5 g, Yield 87%).

(Step 2)

The compound (57.8 g, 200 mmol) prepared in Step 1 was dissolved in methanol (200 ml). LiBH$_4$ (1N THF solution, 400 ml) was added thereto, and the mixture was stirred for 2 h while maintaining the temperature at 10° C. or less. After completion of the reaction, the reaction solution was cooled to 0° C. Water was slowly added to quench the reaction, and methanol was removed under reduced pressure. The residue was diluted with saturated aqueous NaHCO$_3$ solution. The organic material was extracted with EtOAc, and dried over MgSO$_4$. The solvent was removed under reduced pressure, and the residue was purified by column chromatography to give a compound (39 g, Yield 75%).

(Step 3)

The compound (36 g, 137.8 mmol) prepared in Step 2 and triethylamine (38.4 ml, 275.5 mmol) were dissolved in dichloromethane (200 ml). Methanesulfonyl chloride (11.7 ml, 151.5 mmol) was added in drops thereto, and the mixture was stirred for 1 h at 0° C.~room temperature. After completion of the reaction, 1N hydrochloric acid solution was added. The organic material was extracted with ethyl acetate, washed with saturated aqueous sodium chloride solution, and dried over anhydrous magnesium sulfate to give a compound.

171

(Step 4)

Sodium hydride (5.5 g, 137.8 mmol) and 4-methoxybenzylmercaptan (15.4 ml, 110.2 mmol) were dissolved in N,N-dimethylformamide (150 ml), and the mixture was stirred for 10 min at 0° C. To the resulting solution was added in drops the compound (46.7 g, 137.8 mmol) prepared in Step 3, and the mixture was stirred for 4 h at 0° C. Water was added thereto to quench the reaction. The organic material was extracted with ethyl acetate, washed with saturated aqueous sodium chloride solution, and dried over anhydrous magnesium sulfate. The solvent was removed under reduced pressure, and the residue was purified by column chromatography to give a compound.

(Step 5)

The compound (24 g, 62.7 mmol) prepared in Step 4 was dissolved in dichloromethane (200 ml). 4N hydrochloric acid/ethyl acetate solution (20 ml) was added thereto, and the mixture was stirred for 2 h at room temperature. After completion of the reaction, the solvent was thoroughly removed under reduced pressure. The residue was recrystallized from diethylether (150 ml), and dried to give the title compound (20 g, Yield 96%).

Examples 179 to 196

Indole carboxylic acids prepared in Preparations 5, 7, 8 and 12 and the amine compound prepared in Preparation 79 were reacted according to the same procedure as Preparation 34 to give indole derivatives, which were then reacted with commercially available carbonyl compounds according to the same procedures as Examples 26 and 27 in the order to give the Example compounds as shown in the following table.

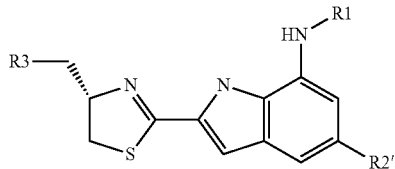

| Example | R3 | R2' | R1 |
|---|---|---|---|
| | H¹ NMR data | | |
| 179 | carboxyl | chloro | cyclopentyl |
| | (400 mhz, DMSO-d₆, ppm); δ 12.51(br s, 1H), 11.51(s, 1H), 6.79 (s, 1H), 6.79(s, 1H), 6.16(s, 1H), 6.14(d, 1H), 4.87(m, 1H), 3.80 (m, 1H), 3.61(m, 1H), 3.19(m, 1H), 2.72(m, 1H), 2.64(m, 1H), 1.93(m, 2H), 1.69(m, 2H), 1.56(m, 4H) | | |
| 180 | carboxyl | methyl | 1-(trifluoroacetyl)piperidin-4-yl |
| | (400 MHz, CDCl₃); δ 11.94 (brs, 1H), 6.98 (s, 1H), 6.78 (s, 1H), 6.25 (s, 1H), 5.33 (m, 1H), 4.13 (m, 1H), 3.76-3.68 (m, 5H), 3.47-3.41 (m, 3H), 2.74-2.63 (m, 2H), 2.36 (s, 3H), 2.04 (m, 2H), 1.56 (m, 2H) | | |
| 181 | carboxyl | H | (tetrahydropyran-2-yl)methyl |
| | (400 MHz, CDCl₃); δ 11.68 (brs, 1H), 7.06-6.98 (m, 3H), 6.45 (s, 1H), 5.32 (m, 1H), 3.96 (m, 1H), 3.77-3.61 (m, 2H), 3.43 (m, 1H), 3.28-3.21 (m, 3H), 2.80 (m, 1H), 2.65 (m, 1H), 1.83 (m, 1H), 1.71 (m, 1H), 1.62-1.42 (m, 4H) | | |
| 182 | carboxyl | H | tetrahydropyran-4-yl |
| | (400 MHz, CDCl₃); δ 11.87 (brs, 1H), 7.15 (s, 1H), 7.03 (m, 2H), 6.50 (m, 1H), 5.39 (m, 1H), 4.06 (m, 2H), 3.80-3.62 (m, 2H), 3.57 (m, 2H), 3.29 (m, 1H), 2.83 (m, 1H), 2.69 (m, 1H), 2.11 (m, 2H), 1.64 (m, 2H) | | |
| 183 | carboxyl | H | (tetrahydropyran-4-yl)methyl |
| | (400 MHz, CDCl₃); δ 11.89 (brs, 1H), 7.13 (s, 1H), 7.04 (m, 2H), 6.44 (m 1H), 5.39 (m, 1H), 3.98 (m, 2H), 3.77 (m, 1H), 3.41 (m, 2H), 3.25 (m, 2H), 3.13 (m, 2H), 2.78 (m, 1H), 2.64 (m, 1H), 2.00 (m, 1H), 1.79 (m, 2H), 1.44 (m, 2H) | | |
| 184 | carboxyl | methyl | 1-acetyl-pyrrolidin-3-yl |
| | (400 MHz, CDCl₃); δ 10.13 (brs, 1H), 6.93 (s, 1H), 6.82 (s, 1H), 6.38 (s, 1H), 5.09 (m, 1H), 4.16 (m, 1H), 3.67 (m, 2H), 3.52 (m, 2H), 3.38 (m, 1H), 3.25 (m, 1H), 2.91 (m, 1H), 2.66 (m, 1H), 2.48 (s, 3H), 2.23 (m, 1H), 2.00 (m, 1H) | | |
| 185 | carboxyl | H | cyclopentyl |
| | (400 MHz, CDCl₃); δ 11.74 (brs, 1H), 7.06 (s, 1H), 6.99 (m, 2H), 6.45 (s, 1H), 5.48 (m, 1H), 3.90 (m, 1H), 3.71 (m, 1H), 3.23 (m, 1H), 2.75 (m, 1H), 2.67 (m, 1H), 2.04 (m, 2H), 1.75 (m, 2H), 1.61-1.48 (m, 4H) | | |
| 186 | carboxyl | phenoxy | (tetrahydropyran-4-yl)methyl |
| | (400 MHz, CDCl₃); δ 11.95 (brs, 1H), 7.28 (m, 2H), 7.06-6.96 (m, 4H), 6.58 (s, 1H), 6.24 (s, 1H), 5.33 (m, 1H), 3.98 (m, 2H), 3.75 (m, 1H), 3.58-3.47 (m, 3H), 2.23 (m, 1H), 2.78-2.62 (m, 2H), 2.04 (m, 2H), 1.26 (m, 2H) | | |
| 187 | carboxyl | phenoxy | tetrahydropyran-4-yl |
| | (400 MHz, CDCl₃); δ 11.94 (brs, 1H), 7.00 (s, 1H), 6.78 (s, 1H), 6.26 (s, 1H), 5.35 (m, 1H), 3.71 (m, 1H), 3.63 (m, 1H), 3.22 (m, 1H), 2.75 (m, 1H), 2.62 (m, 1H), 2.37 (s, 3H), 2.25 (m, 1H), 2.09-1.73 (m, 7H) | | |
| 188 | carboxyl | chloro | tetrahydropyran-4-yl |
| | (400 MHz, CDCl₃); δ 11.21(br s, 1H), 6.66(s, 1H), 6.61(s, 1H), 6.00(s, 1H), 4.89(br s, 1H), 3.95(m, 1H), 3.63(m, 1H), 3.35(m, 2H), 2.67(m, 2H), 2.50(s, 3H), 2.42(m, 2H), 1.80(m, 4H) | | |
| 189 | carboxyl | methyl | cyclobutyl |
| | (400 MHz, CDCl₃); δ 11.829 d, 1H), 6.95(s, 1H), 6.79(s, 1H), 6.20(d, 1H), 5.30(br s, 1H), 4.15(m, 1H), 4.05~3.75(m, 5H), 3.66(m, 1H), 3.19(s, 1H), 2.79~2.61(m, 2H), 2.37(s, 3H), 2.23 (m, 1H), 1.98(m, 1H) | | |
| 190 | carboxyl | methyl | tetrahydrofuran-3-yl |
| | (400 MHz, CDCl₃/MeOH-d₄); δ 11.24(br s, 1H), 6.84(s, 1H), 6.77(s, 1H), 6.25(s, 1H), 5.05(m, 1H), 3.56(m, 1H), 3.15(m, 2H), 3.03(m, 2H), 2.78(m, 1H), 2.63(m, 1H), 2.34(s, 3H), 1.23(m, 1H), 1.18(m, 1H), 0.52(m, 2H), 0.24(m, 2H) | | |
| 191 | carboxyl | methyl | cyclopropylmethyl |
| | (400 MHz, CDCl₃); δ 11.92(br s, 1H), 6.98(s, 1H), 6.77(s, 1H), 6.22(s, 1H), 6.29(br s, 1H), 3.96(m, 2H), 3.70(m, 1H), 3.37(m, 2H), 3.18(m, 1H), 3.08(m, 2H), 2.729 m, 1H), 2.56(m, 1H), 2.37 (s, 3H), 1.91(m, 1H), 1.75(m, 2H), 1.41(m, 2H) | | |
| 192 | carboxyl | methyl | (tetrahydropyran-4-yl)methyl |
| | (400 MHz, DMSO-d₆); δ 11.35(br s, 1H), 6.67(s, 1H), 6.61(s, 1H), 6.09(s, 1H), 5.81(br s, 1H), 4.90(m, 1H), 3.64(m, 1H), 3.21 (m, 1H), 3.05(m, 2H), 2.77~2.69(m, 2H), 2.28(s, 3H), s.23(m, 1H), 1.85(m, 2H), 1.65~1.58(m, 4H), 1.32(m, 2H) | | |
| 193 | carboxyl | methyl | tetrahydropyran-4-yl |
| | (400 MHz, DMSO-d₆); δ 11.88(br s, !H), b7.09(s, 1H), 7.04(s, 1H), 6.74(s, 1H), 4.94(m, 1H), 3.98(m, 1H), 3.73(m, 1H), 3.47 (m, 1H), 2.87~2.70(m, 2H), 2.51(s, 3H) 1.93(m, 2H), 1.76~1.56 (m, 6H) | | |
| 194 | MeO₂C— | methyl | cyclopentyl |
| | (400 MHz, CDCl₃); δ 10.66(br s, 1H), 6.82(s, 1H), 6.41(s, 1H), 6.17(s, 1H), 5.08(m, 1H), 4.01(m, 2H), 3.80(m, 1H), 3.67(m, 1H), 3.49(s, 3H), 3.20(dd, 1H), 2.85(dd, 1H), 2.65(dd, 1H), 2.02 (m, 1H), 1.66~1.53(m, 4H), 1.45~1.33(m, 5H) | | |
| 195 | carboxyl | phenoxy | cyclopentyl |
| | (400 MHz, DMSO-d₆, Na salt); δ 11.85(br s, 1H), 7.31(t, 2H), 7.01(t, 1H), 6.93(d, J = 8 Hz, 2H), 6.64(s, 1H), 6.48(d, J = 4 Hz, 1H), 6.39(s, 1H), 5.97 (s, 1H), 4.93(m, 1H), 3.75(m, 1H), 3.55(t, 1H), 3.20(q, 1H), 2.62(dd, 1H), 2.15(q, 1H), 1.90(m, 2H), 1.72(m, 2H), 1.60(m, 4H) | | |
| 196 | carboxyl | methyl | 4,4-difluorocyclohexyl-1-yl |
| | (400 MHz, CDCl₃); δ 11.94 (brs, 1H), 7.00 (s, 1H), 6.78 (s, 1H), 6.26 (s, 1H), 5.35 (m, 1H), 3.71 (m, 1H), 3.63 (m, 1H), 3.22 (m, 1H), 2.75 (m, 1H), 2.62 (m, 1H), 2.37 (s, 3H), 2.25 (m, 1H), 2.09-1.73 (m, 7H) | | |

Examples 197 to 222

The intermediate esters for preparing the compounds of Examples 179, 185, 186, 192, 193, 195 and 196 and commercially available amine compounds were reacted according to the same procedures as Example 129, Preparation 50 and Example 71 in the order to give the Example compounds as shown in the following table.

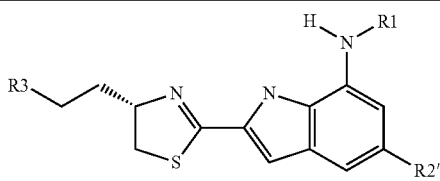

| Example | R3 | R2' | R1 |
|---|---|---|---|
| | H¹ NMR data | | |
| 197 | (3S)-3-(amino)pyrrolidin-1-yl | chloro | cyclopentyl |
| | (400 MHz, MeOD); δ 7.51(s, 1H), 7.28(s, 1H), 7.06(s, 1H), 4.27(m, 1H), 4.15(m, 1H), 3.95-3.8(m, 5H), 3.67(m, 3H), 3.44(dd, 1H), 2.70 (m, 1H), 2.40-2.25(m, 3H), 2.10(m, 2H), 1.91(m, 4H), 1.71(m, 2H) | | |
| 198 | (3S)-3-(dimethylaminophenyl) ethylaminopyrrolidin-1-yl | chloro | cyclopentyl |
| | (500 Hz, CDCl₃); δ 7.16(t, 1H), 6.89(s, 1H), 6.74(s, 1H), 6.61(m, 3H), 6.34(s, 1H), 4.64(m, 1H), 3.86(m, 1H), 3.66(m, 2H), 3.51(m, 2H), 3.45-3.25(br s, 2H), 3.25-3.05(br s, 2H), 3.03(t, 1H), 3.05-2.95(br s, 1H), 2.92(s, 6H), 2.38(br s, 1H), 2.05-1.85(m, 5H), 1.80-1.65(m, 4H), 1.58(m, 1H) | | |
| 199 | 1-(acetyl)piperazin-4-yl | chloro | cyclopentyl |
| | (500 Hz, CDCl₃); δ 10.17(br s, 1H), 7.00(s, 1H), 6.83(s, 1H), 6.43 (s, 1H), 4.75(m, 1H), 3.83(m, 2H), 3.58(m, 1H), 3.56(dd, 1H), 3.48 (m, 1H), 3.32(m, 1H), 3.25(m, 1H), 3.15(dd, 1H), 2.46(m, 2H), 2.36(m, 1H), 2.26(m, 2H), 2.20(m, 1H), 2.05(s, 3H), 2.04(m, 2H), 1.96(m, 1H), 1.80(m, 1H), 1.66(m, 3H), 1.48(m, 2H) | | |
| 200 | 1-(acetyl)piperazin-4-yl | chloro | H |
| | (500 Hz, DMSO); δ 11.70(br s, 1H), 10.41(s, 1H), 7.91(s, 1H), 7.78(d, 1H), 7.58(s, 1H), 7.46(s, 2H), 7.36(m, 3H), 7.09(t, 1H), 7.05(s, 1H), 6.97(d, 2H), 3.86(s, 2H), 2.90(br s, 2H) | | |
| 201 | 2-oxopiperazin-4-yl | methyl | tetrahydropyran-4-yl |
| | (500 MHz, CDCl₃); δ 11.05 (s, 1H), 7.72 (s, 1H), 6.82 (s, 1H), 6.78 (s, 1H), 6.27 (s, 1H), 4.71-4.67 (m, 1H), 4.03-4.01 (m, 2H), 3.62-3.47 (m, 4H), 3.30-3.20 (m, 2H), 3.15 (d, 2H), 3.11-3.08 (m, 1H), 2.59-2.53 (m, 4H), 2.42-2.36 (m, 3H), 2.09-2.04 (m, 2H), 1.95-1.92 (m, 1H), 1.84-1.81 (m, 1H), 1.59-1.51 (m, 2H) | | |
| 202 | morpholin-4-yl | methyl | tetrahydropyran-4-yl |
| | 400 MHz, CDCl₃); δ 10.91(s, 1H), 6.85(s, 1H), 6.83(s, 1H), 6.28 (s, 1H), 4.81(m, 1H), 3.96(m, 2H), 3.60~3.41(m, 7H), 3.17(, 1H), 2.40(m, 2H), 2.36(s, 3H), 2.29(m, 2H), 2.18(m, 2H), 2.04~1.79 (m, 4H), 1.39(m, 2H) | | |
| 203 | 1-(hydroxymethylcarbonyl) piperazin-4-yl | phenoxy | cyclopentyl |
| | (400 MHz, CDCl₃); δ 10.7 (1H, brs), 7.30-7.27 (2H, m), 7.04-6.97 (3H, m), 6.86 (1H, s), 6.62 (1H, d, J = 2.0 Hz), 6.28 (1H, d, J = 2.5 Hz), 4.87-4.80 (1H, m), 3.80-3.75 (1H, m), 3.59-3.55 (2H, m), 3.49-3.45 (1H, m), 3.18-3.08 (2H, m), 3.03-3.01 (1H, m), 2.47-2.38 (3H, m), 2.24-2.14 (3H, m), 2.05-1.88 (4H, m), 1.84-1.55 (8H, m), 1.49-1.39 (2H, m) | | |
| 204 | piperazin-1-yl | phenoxy | cyclopentyl |
| | (400 MHz, CDCl₃); δ 7.40-7.36 (4H, m), 7.16-7.12 (1H, m), 7.04-7.02 (2H, m), 6.94 (1H, s), 4.20-4.15 (1H, m), 3.99-3.94 (1H, m), 3.91-3.80 (5H, m), 3.75-3.63 (6H, m), 3.58-3.48 (1H, m), 2.44-2.40 (2H, m), 2.09-2.07 (2H, m), 1.91-1.89 (4H, m), 1.71-1.69 (2H, m) | | |
| 205 | 1-BOC-piperazin-4-yl | phenoxy | cyclopentyl |
| | (400 MHz, CDCl₃); δ 10.7(1H, s), 7.30-7.26 (2H, m), 7.03-6.98 (3H, m), 6.85 (1H, s), 6.62 (1H, d, J = 2.0 Hz), 6.26 (1H, d, J = 2.4 Hz), 4.82-4.77 (1H, m), 3.87 (1H, brs), 3.78-3.74 (1H, m), 3.59-3.54 (1H, m), 3.31 (4H, brs), 3.19-3.14 (2H, m), 2.48-2.35 (2H, m), 2.26 (1H, brs), 2.17 (1H, brs), 2.03-1.91 (4H, m), 1.84-1.75 (1H, m), 1.67-1.53 (4H, m), 1.45 (9H, s), 1.42-1.35 (1H, m) | | |

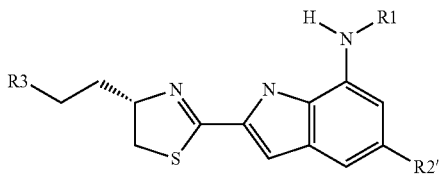

| Example | R3 | R2' | R1 |
|---|---|---|---|
| | H¹ NMR data | | |
| 206 | CF₃ | phenoxy | cyclopentyl |
| | (400 MHz, CDCl₃); δ 10.9 (1H, brs), 7.32-7.28 (2H, m), 7.05-6.99 (3H, m), 6.90 (1H, s), 6.59 (1H, d, J = 1.6 Hz), 6.29 (1H, d, J = 2.0 Hz), 4.77-4.74 (1H, m), 4.06-3.99 (1H, m), 3.95-3.82 (4H, m), 3.62-3.57 (1H, m), 3.18-3.14 (1H, m), 2.87-2.80 (3H, m), 2.77-2.74 (1H, m), 2.00-1.98 (4H, m), 1.69 (2H, brs), 1.60-1.56 (6H, m) | | |
| 207 | 2-oxopiperazin-4-yl | phenoxy | cyclopentyl |
| | (400 MHz, CDCl₃); δ 10.7 (1H, brs), 7.30-7.26 (2H, m), 7.03-7.00 (3H, m), 6.82 (1H, s), 6.60 (1H, d, J = 2.0 Hz), 6.25 (1H, d, J = 2.0 Hz), 4.74-4.71 (2H, m), 3.83 (1H, brs), 3.56-3.52 (1H, m), 3.50-3.26 (2H, m), 3.20-3.10 (2H, m), 2.68-2.61 (4H, m), 2.01-1.86 (4H, m), 1.73-1.58 (8H, m) | | |
| 208 | 1-[(tetrahydrofuran-2-yl)carbonyl]piperazin-4-yl | phenoxy | cyclopentyl |
| | (400 MHz, CDCl₃); δ 10.67-10.58 (1H, m), 7.30-7.27 (2H, m), 7.04-6.98 (m, 3H), 6.85 (1H, d, J = 1.2 Hz), 6.62 (1H, d, J = 2.0 Hz), 6.27 (1H, brs), 4.84-4.78 (1H, m), 4.58-4.54 (m, 1H), 3.96-3.91 (1H, m), 3.87-3.71 (3H, m), 3.59-3.42 (3H, m), 3.19-3.14 (1H, m), 2.47-2.37 (2H, m), 2.33-2.16 (4H, m), 2.07-1.87 (6H, m), 1.83-1.75 (4H, m), 1.68-1.56 (1H, m), 1.49-1.40 (2H, m) | | |
| 209 | 1-(pyridin-2-yl)piperazin-4-yl | phenoxy | cyclopentyl |
| | (400 MHz, CDCl₃); δ 10.3 (1H, s), 8.19-8.18 (1H, m), 7.49-7.45 (1H, m), 7.29-7.25 (2H, m), 7.03-6.98 (3H, m), 6.85 (1H, s), 6.64-6.60 (1H, m), 6.28 (1H, d, J = 2.4 Hz), 4.82-4.78 (1H, m), 3.79 (1H, brs), 3.60-3.55 (1H, m), 3.49-3.45 (4H, m), 3.21-3.17 (1H, m), 2.55-2.41 (6H, m), 1.99 (3H, brs), 1.88-1.86 (1H, m), 1.70 (3H, brs), 1.61-1.47 (3H, m) | | |
| 210 | 1-(2-fluorophenyl) piperazin-4-yl | phenoxy | cyclopentyl |
| | (400 MHz, CDCl₃); δ 10.7 (1H, s), 7.29-7.25 (2H, m), 7.07-6.98 (5H, m), 6.95-6.88 (2H, m), 6.86 (1H, s), 6.23 (1H, d, J = 1.6 Hz), 6.28 (1H, d, J = 1.6 Hz), 4.88-4.81 (1H, m), 3.89 (1H, brs), 3.60-3.56 (1H, m), 3.23-3.18 (1H, m), 2.99 (4H, brs), 2.54-2.43 (5H, m), 2.04-1.94 (3H, m), 1.98-1.82 (2H, m), 1.68-1.37 (6H, m) | | |
| 211 | 1-(acetyl)piperazin-4-yl | phenoxy | cyclopentyl |
| | (400 MHz, CDCl₃); δ 10.6 (1H, s), 7.31-7.27 (2H, m), 7.04-6.98 (3H, m), 6.84 (1H, s), 6.60 (1H, d, J = 2.0 Hz), 6.27 (1H, d, J = 1.6 Hz), 4.77-4.72 (1H, m), 4.30 (1H, brs), 3.81 (1H, brs), 3.74 (1H, brs), 3.64-3.55 (2H, m), 3.41 (1H, brs), 3.17-3.10 (2H, m), 2.89 (1H, brs), 2.68-2.63 (3H, m), 2.56-2.48 (2H, m), 2.06 (3H, s), 2.03-1.90 (4H, m), 1.72 (2H, brs), 1.60-1.56 (4H, m) | | |
| 212 | (2R)-2-(hydroxymethyl)pyrrolidin-1-yl | methyl | (tetrahydropyran-4-yl)methyl |
| | (CDCl₃, 400 MHz) δ 10.25 (s, 1H), 6.76 (s, 1H), 6.74 (s, 1H), 6.23 (s, 1H), 4.67-4.58 (m, 2H), 4.16-4.09 (m, 1H), 4.00-3.94 (m, 2H), 3.73-3.68 (m, 1H), 3.50-3.36 (m, 2H), 3.11 (d, 2H), 2.99-2.94 (m, 2H), 2.32 (s, 3H), 2.15-2.07 (m, 2H), 2.02-1.92 (m, 3H), 1.76-1.73 (m, 2H), 1.42-1.36 (m, 2H), 1.14-1.08 (m, 2H), 0.86-0.81 (m, 2H), 0.73-0.68 (m, 2H) | | |
| 213 | (3R)-3-(acetylamino) pyrrolidin-1-yl | phenoxy | cyclopentyl |
| | (500 Hz, CDCl₃); δ 11.45(br s, 1H), 8.14(br s, 1H), 6.90(s, 1H), 6.77(s, 1H), 6.37(s, 1H), 4.83(m, 1H), 4.66(m, 1H), 4.05(m, 1H), 3.91(m, 1H), 3.77(m, 1H), 3.62-3.52(m, 2H), 3.13(m, 1H), 3.08-3.00(m, 2H), 2.84(m, 1H), 2.43(m, 1H), 2.23(m, 1H), 2.05(m, 4H), 2.00(s, 3H), 1.80(m, 2H), 1.71(m, 2H), 1.63(m, 2H) | | |

-continued

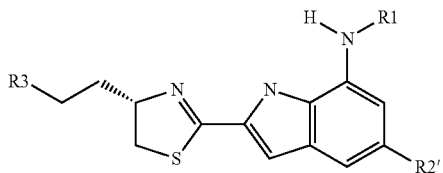

| Example | R3 | R2' | R1 |
|---|---|---|---|
| H¹ NMR data | | | |

214  4-(benzyl)piperazin-1-yl  phenoxy  cyclopentyl
(500 Hz, CDCl₃); δ 7.32-7.24(m, 7H), 7.01(m, 3H), 6.77(s, 1H), 6.59(s, 1H), 6.29(s, 1H), 4.71(m, 1H), 3.87(m, 1H), 3.56(dd, 1H), 3.50(s, 2H), 3.08(dd, 1H), 2.80(br s, 8H), 2.60(br s, 2H), 2.11-1.99 (m, 4H), 1.80(m, 2H), 1.71(m, 2H), 1.61(m, 2H)

215  morpholin-4-yl  methyl  (tetrahydropyran-4-yl)methyl
(500 MHz, CDCl₃); δ 11.13 (s, 1H), 6.84 (s, 1H), 6.81 (s, 1H), 6.24 (s, 1H), 4.81-4.78 (m, 1H), 3.87 (d, 2H), 3.60-3.46 (m, 5H), 3.35-3.30 (m, 2H), 3.19-3.17 (m, 1H), 3.01 (br, 2H), 2.38-2.36 (m, 7H), 2.14 (br, 2H), 1.91-1.88 (m, 1H), 1.75-1.71 (m, 2H), 1.28-1.21 (m, 2H)

216  morpholin-4-yl  phenoxy  (tetrahydropyran-4-yl)methyl
(400 MHz, CDCl₃); δ 10.19 (brs, 1H), 7.29 (m, 2H), 7.01(m, 3H), 6.84(d, 1H), 6.65(d, 1H), 6.27(d, 1H), 4.77(m, 1H), 3.93(m, 2H), 3.83(m, 1H), 3.63-3.55(m, 6H), 3.35(m, 6H), 3.19(m, 1H), 3.04 (m, 2H), 2.46 (m, 2H), 2.34(m, 4H), 2.00(m, 1H), 1.83(m, 2H), 1.60(m, 2H), 1.30(m, 2H)

217  2-oxopiperazin-4-yl  phenoxy  (tetrahydropyran-4-yl)methyl
(400 MHz, CDCl₃); δ 10.7 (brs, 1H), 7.28(m, 2H), 7.00(m, 3H), 6.85(brs, 1H), 6.81(d, 1H), 6.60(d, J = 1.6 Hz, 1H), 6.20(d, J = 2.0 Hz, 1H), 5.03(m, 1H), 4.70(m, 1H), 3.98(m, 2H), 3.56(m, 1H), 3.49-3.36(m, 6H), 3.15-3.06(m, 4H), 2.80 (m, 1H), 2.71(m, 3H), 1.95-1.91(m, 3H), 1.72(m, 2H), 1.42(m, 2H).

218  pyrrolidin-1-yl  phenoxy  cyclopentyl
(500 MHz, CDCl₃); δ 7.31-7.27 (2H, m), 7.03-7.00 (1H, m), 6.96-6.94 (2H, m), 6.50 (1H, d, J = 2.0 Hz), 6.17 (1H, d, J = 2.0 Hz), 4.73-4.66 (1H, m), 3.86 (brs, 1H), 3.74-3.58 (2H, m), 3.46-3.37 (4, m), 3.23-3.19 (1H, m), 2.24-2.10 (6, m), 2.10-1.80 (2H, m), 1.70-1.65 (5H m)

219  morpholin-4-yl  H  4,4-difluorocyclohexyl-1-yl
(400 MHz, CDCl₃); δ 9.67 (brs, 1H), 6.87(s, 1H), 6.82(s, 1H), 6.34 (s, 1H), 4.71 (m, 1H), 3.65( m, 6H), 3.55 (dd, J = 8 Hz, 1H), 3.51(m, 1H), 3.15(dd, J = 8 Hz, 1H), 2.52-2.29(m, 9H), 2.15-2.04(m, 4H), 1.96-1.90(m, 2H), 1.58-1.51(m, 2H)

220  CF₃  phenoxy  (tetrahydropyran-4-yl)methyl

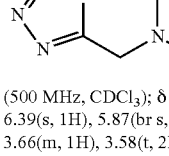

(500 MHz, CDCl₃); δ 9.47(br s, 1H), 6.88(s, 1H), 6.47(s, 1H), 6.39(s, 1H), 5.87(br s, 1H), 4.12-4.00(m, 2H), 3.85(m, 4H), 3.66(m, 1H), 3.58(t, 2H), 3.08(br s, 4H), 2.95(m, 1H), 2.85-2.70(m, 3H), 2.41(s, 3H), 2.10(m, 2H), 1.96(m, 2H), 1.60(m, 2H)

221  2-oxopiperazin-4-yl  phenoxy  (tetrahydropyran-4-yl)methyl
(500 MHz, CDCl₃); δ 11.03(s, 1H), 8.19(br s, 1H), 6.82(s, 1H), 6.79(s, 1H), 6.31(s, 1H), 4.84-4.65(m, 3H), 4.24(m, 1H), 3.91 (m, 2H), 3.82-3.55(m, 4H), 3.31(m, 2H), 3.19(m, 1H), 3.14(m, 2H), 2.95(m, 2H), 2.69(m, 1H), 2.20(m, 1H), 1.98(m, 1H), 1.81(d, 2H), 1.39(m, 2H)

222  2-oxopiperazin-4-yl  phenoxy  4,4-difluorocyclohexyl-1-yl
(400 MHz, CDCl₃); δ 10.14 (brs, 1H), 6.82 (s, 1H), 6.80 (s, 1H), 6.31 (s, 1H), 4.65 (m, 1H), 3.54 (m, 1H), 3.53 (dd, J = 8 Hz, 1H), 3.39 (m, 2H), 3.30 (m, 1H), 3.22-3.08 (m, 4H), 2.78-2.65 (m, 4H), 2.38 (s, 3H), 2.28-2.04 (m, 4H), 1.96-1.86 (m, 2H), 1.73 (m, 2H)

The compounds according to the present invention were tested in the enzyme and animal model experiments in the following Experiments 1 and 2 to evaluate their efficacies.

Experiment 1

Glucokinase Enzymatic Activity Assay

Glucokinase known as hexokinase IV (human GK isoform 1, pancreas form and human GK isoform 2, liver form) was cloned into an expression vector pET15 fx (Novagen Co.), transformed to *E. coli* BL21 (DE3) (Invitrogen Co.) strain, expressed, and purified using a nickel column. Then, the glucokinase obtained from dialysis was used in the following assay.

Glucokinase assay was performed by measuring absorbance according to the conventional manner. Briefly speaking, glucokinase converts the substrate glucose to glucose-6-phosphate under certain conditions, and glucose-6-phosphate dehydrogenase irreversibly converts glucose-6-phosphate to gluconate-6-phosphate. During this procedure, NADH is formed, and its absorbance is measured to calculate the enzymatic activity.

In the measurement of the enzymatic activity, each compound was diluted by two-fold from the maximum to the minimum concentrations, and 2 μl of each solution was added to 96 well UV plate (BD bioscience). 60 μl of the first mixture (final concentrations 25 mM Hepes, 25 mM KCl, 2 mM MgCl₂, 1 mM DTT) was added, and thoroughly mixed. 38 μl of the enzyme mixture (final concentrations 1 mM ATP, 1 mM NAD, 5 mM glucose, 0.85U G6PDH, 37 nM GK) was added (final volume 100 μl), and the mixture was reacted for 10 min at room temperature. The absorbance of NADH was measured at 340 nm using a UV spectrometer (Molecular Device).

The enzyme activating abilities of the compounds according to the present invention are represented as $AC_{1.5}$ (the compound concentration at which the enzymatic activity is increased by 1.5 times, nM), which is in the range of 0.001 uM to 30 uM or less, preferably 0.001 uM to 10 uM, more preferably 0.001 uM to 1 uM. The enzyme activating abilities of the representative compounds are shown in Table 1.

TABLE 1

| Example compound | $AC_{1.5}$ (nM) | Example compound | $AC_{1.5}$ (nM) | Example compound | $AC_{1.5}$ (nM) | Example compound | $AC_{1.5}$ (nM) |
|---|---|---|---|---|---|---|---|
| 1 | 22 | 2 | 41 | 3 | 184 | 4 | 217 |
| 5 | 7 | 6 | 31 | 7 | 7 | 8 | 32 |
| 9 | 24 | 10 | 6 | 11 | 14 | 12 | 25 |
| 13 | 12 | 14 | 8 | 15 | 400 | 16 | 64 |
| 21 | 16 | 22 | 112 | 23 | 19 | 24 | 32 |
| 26 | 7 | 27 | 4 | 28 | 8 | 32 | 22 |
| 30 | 28 | 31 | 16 | 32 | 18 | 36 | 5 |
| 34 | 11 | 35 | 6 | 36 | 12 | 40 | 3 |
| 38 | 18 | 39 | 6 | 40 | 17 | 41 | 17 |
| 46 | 96 | 47 | 27 | 48 | 9 | 49 | 35 |
| 50 | 28 | 51 | 167 | 52 | 20 | 53 | 97 |
| 54 | 18 | 55 | 29 | 56 | 17 | 57 | 21 |
| 58 | 14 | 59 | 28 | 60 | 29 | 61 | 11 |
| 62 | 36 | 63 | 119 | 64 | 17 | 65 | 23 |
| 69 | 64 | 70 | 32 | 71 | 31 | 72 | 51 |
| 73 | 25 | 74 | 14 | 75 | 21 | 76 | 14 |
| 77 | 27 | 78 | 25 | 79 | 19 | 80 | 21 |
| 81 | 6 | 82 | 22 | 83 | 45 | 84 | 27 |
| 85 | 18 | 86 | 23 | 87 | 10 | 88 | 19 |
| 89 | 32 | 90 | 37 | 91 | 72 | 92 | 112 |
| 93 | 239 | 94 | 15 | 95 | 11 | 96 | 5 |
| 97 | 6 | 98 | 7 | 99 | 5 | 100 | 11 |
| 101 | 10 | 102 | 7 | 103 | 16 | 104 | 13 |
| 105 | 6 | 106 | 14 | 107 | 63 | 108 | 15 |
| 109 | 26 | 110 | 30 | 111 | 11 | 112 | 81 |
| 121 | 40 | 122 | 60 | 123 | 62 | 124 | 24 |

TABLE 1-continued

| Example compound | AC$_{1.5}$ (nM) | Example compound | AC$_{1.5}$ (nM) | Example compound | AC$_{1.5}$ (nM) | Example compound | AC$_{1.5}$ (nM) |
|---|---|---|---|---|---|---|---|
| 125 | 23 | 126 | 20 | 127 | 21 | 128 | 16 |
| 129 | 67 | 130 | 14 | 131 | 10 | 132 | 13 |
| 137 | 23 | 138 | 36 | 139 | 38 | 140 | 52 |
| 141 | 24 | 142 | 85 | 143 | 37 | 144 | 122 |
| 145 | 138 | 146 | 29 | 147 | 52 | 148 | 12 |
| 149 | 12 | 150 | 10 | 151 | 14 | 152 | 14 |
| 153 | 12 | 154 | 14 | 155 | 12 | 156 | 22 |
| 157 | 24 | 158 | 16 | 159 | 17 | 160 | 12 |
| 161 | 10 | 162 | 21 | 163 | 5 | 164 | 25 |
| 165 | 12 | 166 | 43 | 167 | 28 | 168 | 15 |
| 169 | 9 | 170 | 12 | 171 | 23 | 176 | 178 |
| 173 | 114 | 178 | 21 | 175 | 71 | 180 | 56 |

Experiment 2

Blood Glucose Lowering Abilities of Glucokinase Activators after their Single Oral Administration in Male C57BL/6 Mouse The glucokinase activators according to the present invention were orally administered in a single dose in the amount of 30 mg/kg body weight to male C57BL/6 mice for 24 h. The media were selected depending on their solubilities from distilled water, pH 1.2 HCl buffer solution, 0.5% methyl cellulose distilled water solution, 10% Gelucire/pH 1.2 HCl buffer solution (1/1). The glucokinase activators were dissolved in the selected media to the medium volume of 0.1 ml/10 g body weight on the basis of the body weight measured on the day of experiment.

Blood glucose was measured by cutting the tail vein before 1 h (time=−1) from the measurement of blood glucose, collecting blood from the tail vein at immediately before the administration of the glucokinase activator (time=0), and at 1, 2, 4, 8, 12, 24 h after administration, loading on the automatic glucometer (Accu-Chek® Active, Roche, USA), dropping 5 μl of the blood to a yellow pad of the Accu-Chek® Active glucose strip, and recording the measured value.

Mice involved in the experiment were divided into groups (n=10, in the case of media group n=4) on one day before the experiment so that each group has uniform average and standard deviation for blood glucose after 4 hour fasting. Mice were fed ad libitum.

Blood glucose-area under the curve (AUC) with respect to the media control was calculated for 24 h after administration of the glucokinase activators. The blood glucose lowering abilities in % of the representative compounds with respect to the 100% of media control were shown in the following Table 2.

TABLE 2

| Example compound | Hypoglycemic ability (% medium) | Medium |
|---|---|---|
| 27 | 75% | Distilled water |
| 33 | 81% | Distilled water |
| 37 | 67% | Distilled water |
| 38 | 71% | 0.5% Methyl cellulose distilled water solution |
| 42 | 57% | Distilled water |
| 52 | 62% | Distilled water |
| 54 | 52% | Distilled water |
| 61 | 54% | Distilled water |
| 96 | 81% | Distilled water |
| 99 | 72% | Distilled water |
| 158 | 66% | Distilled water |
| 159 | 63% | Distilled water |
| 164 | 73% | Distilled water |
| 167 | 64% | Distilled water |
| 174 | 51% | Distilled water |

The invention claimed is:

1. A method for lowering blood glucose level comprising: administering a pharmaceutical composition which comprises an indole compound of the following formula (1), or pharmaceutically acceptable salt or isomers thereof, as an active ingredient together with a pharmaceutically acceptable carrier:

Formula (1)

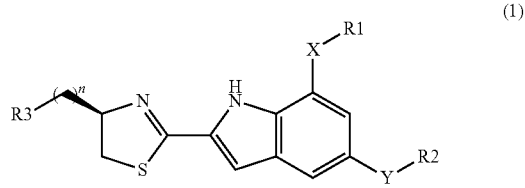

in which
X represents NH,
n denotes a number of 0 to 3,
Y represents a direct bond, —(CH$_2$)$_p$O—, —(CH$_2$)$_q$—, or —(CH$_2$)$_q$SO$_2$—,
p denotes a number of 0 to 2,
q denotes a number of 1 to 3,
R1 represents —(CR4R5)$_p$-A-R6, wherein p is as defined above,
R4 and R5 independently of one another represent hydrogen or C$_1$-C$_5$-alkyl,
A represents 6~12 membered aryl or optionally oxo-containing C$_3$-C$_8$-cycloalkyl, or represents 3~10 membered heterocyclyl or heteroaryl each of which has 1 to 3 hetero atoms selected from O, S, and N,
R6 represents hydrogen, hydroxy, halogen, nitro, C$_1$-C$_6$-alkylcarbonyl, C$_1$-C$_6$-alkylsulfonyl, C$_1$-C$_6$-alkoxycarbonyl or carboxy,
R2 represents nitro, halogen, C$_1$-C$_6$-alkyl or trifluoromethyl, represents 5~12 membered heteroaryl or heterocyclyl each of which has 1 to 3 hetero atoms selected from N and O, or represents optionally C$_1$-C$_6$-alkylsulfonyl-substituted 6~12 membered aryl,
R3 represents R7-X—B—X'—,
B represents a direct bond, or represents 3~10 membered heterocyclyl or heteroaryl each of which optionally contains oxo, is optionally fused, and has 1 to 4 hetero atoms selected from N, O and S,
X and X' independently of one another represent a direct bond, or are selected from the group consisting of —CO—, —(CH$_2$)$_q$—, —NR4C(O)—, —NR4-, —OC(O)—, —O—, —(CH$_2$)$_p$C(O)—, —(CH$_2$)$_p$O—, —(CH$_2$)$_p$NR4-, —C(O)NR4- and —S(O)$_r$—, wherein p and q are as defined above, r denotes a number of 0 to 2, and R4 represents hydrogen or C$_1$-C$_5$-alkyl,
R7 represents hydrogen, hydroxy, C$_1$-C$_6$-alkyl, C$_1$-C$_6$-alkoxy, halogeno-C$_1$-C$_6$-alkyl or C$_3$-C$_6$-cycloalkyl, represents 6~12 membered aryl, or represents 4~8 membered heteroaryl or heterocyclyl each of which has 1 to 4 hetero atoms selected from N and O, where alkyl, alkoxy, aryl, cycloalkyl, heterocyclyl and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, $C_1$-$C_6$-alkyl, halogeno-$C_1$-$C_6$-alkyl, $C_1$-$C_6$-alkylsulfonyl, aryl-$C_1$-$C_6$-alkoxy and oxo.

2. The method of claim 1 wherein in the compound of formula (1), or pharmaceutically acceptable salt or isomer thereof, X represents NH, n denotes a number of 0 to 3, Y represents a direct bond, —$(CH_2)_pO$—, —$(CH_2)_q$—, or —$(CH_2)_qSO_2$—, P denotes a number of 0 to 2, q denotes a number of 1 to 3, R1 represents —$(CR4R5)_p$-A-R6, wherein p is as defined above, R4 and R5 independently of one another represent hydrogen or $C_1$-$C_5$-alkyl, A represents 6~12 membered aryl or optionally oxo-containing $C_3$-$C_7$-cycloalkyl, or represents 4~8 membered heterocyclyl or heteroaryl each of which has 1 to 3 hetero atoms selected from O, S, and N, R6 represents hydrogen, hydroxy, halogen, nitro, $C_1$-$C_6$-alkylcarbonyl, $C_1$-$C_6$-alkylsulfonyl, $C_1$-$C_6$-alkoxycarbonyl or carboxy, R2 represents halogen, $C_1$-$C_6$-alkyl or trifluoromethyl, represents 5~8 membered heteroaryl or heterocyclyl each of which has 1 to 3 hetero atoms selected from N and O, or represents optionally $C_1$-$C_6$-alkylsulfonyl-substituted 6~10 membered aryl, R3 represents R7-X—B—X'—, B represents a direct bond, or represents 4~10 membered heterocyclyl or heteroaryl each of which optionally contains oxo, is optionally fused, and has 1 to 4 hetero atoms selected from N, O and S, X and X' independently of one another represent a direct bond, or are selected from the group consisting of —CO—, —$(CH_2)_q$—, —NR4C(O)—, —NR4-, —OC(O)—, —O—, —$(CH_2)_pC(O)$—, —C(O)NR4- and —S(O)$_r$—, wherein p and q are as defined above, r denotes a number of 0 to 2, and R4 represents hydrogen or $C_1$-$C_5$-alkyl, and R7 represents hydrogen, hydroxy, $C_1$-$C_6$-alkyl, halogeno-$C_1$-$C_6$-alkyl or $C_3$-$C_6$-cycloalkyl, represents 6~12 membered aryl, or represents 4~8 membered heteroaryl or heterocyclyl each of which has 1 to 4 hetero atoms selected from N and O.

3. The method of claim 2 wherein in the compound of formula (1), or pharmaceutically acceptable salt or isomer thereof, R1 represents —$(CH_2)_p$-A-R6, wherein p denotes a number of 0 to 2, R4 and R5 independently of one another represent hydrogen or $C_1$-$C_5$-alkyl, A represents 6~12 membered aryl or optionally oxo-containing $C_3$-$C_6$-cycloalkyl or represents 5~6 membered heterocyclyl which has 1 to 2 hetero atoms selected from O, S, and N, and R6 represents hydrogen, halogen, nitro, $C_1$-$C_6$-alkylcarbonyl, $C_1$-$C_6$-alkylsulfonyl, $C_1$-$C_6$-alkoxycarbonyl or carboxy.

4. The method of claim 3 wherein in the compound of formula (1), or pharmaceutically acceptable salt or isomer thereof, R1 is selected from the group consisting of cyclopropyl, cyclobutyl, cyclopentyl, difluorocyclohexyl, tetrahydrofuran, tetrahydropyran, (tetrahydropyran-4-yl)methyl, tetrahydrothiopyran, 4-oxo-cyclohexyl, (1-methanesulfonyl)pyrrolidine, (1-acetyl)piperidine and 4-nitrophenyl.

5. The method of claim 2 wherein in the compound of formula (1), or pharmaceutically acceptable salt or isomer thereof, Y represents a direct bond, —O—, —$(CH_2)O$—, —$(CH_2)$— or —$(CH_2)SO_2$—.

6. The method of claim 2 wherein in the compound of formula (1), or pharmaceutically acceptable salt or isomer thereof, R2 represents halogen, $C_1$-$C_3$-alkyl or trifluoromethyl, represents 5~6 membered heteroaryl or heterocyclyl each of which has 1 to 3 hetero atoms selected from N and O, or represents optionally methanesulfonyl-substituted 6~10 membered aryl.

7. The method of claim 6 wherein in the compound of formula (1), or pharmaceutically acceptable salt or isomer thereof, R2 is selected from the group consisting of fluoro, chloro, bromo, methyl, ethyl, propyl, phenyl, methanesulfonylphenyl, pyridine, morpholine, 1,2-imidazole, 1,3-imidazole, pyrrolidine and pyrrole.

8. The method of claim 2 wherein in the compound of formula (1), or pharmaceutically acceptable salt or isomer thereof, B represents a direct bond, represents pyrazole, imidazole or oxadiazole each of which is optionally substituted by $C_1$-$C_6$-alkyl, or represents 5~9 membered heterocyclyl which optionally contains oxo, is optionally fused, and has 1 to 4 hetero atoms selected from N, S and O.

9. The method of claim 8 wherein in the compound of formula (1), or pharmaceutically acceptable salt or isomer thereof, B represents a direct bond, or is selected from the following formulae (i) to (xi)

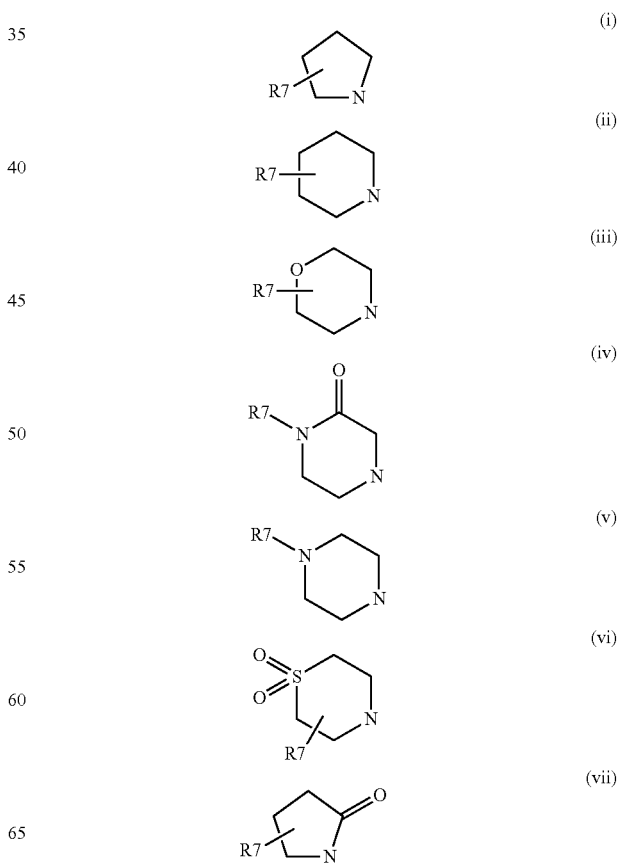

(viii)

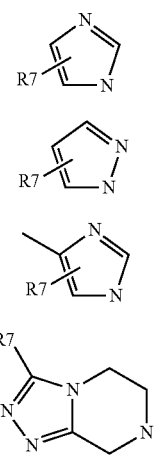

(ix)

(x)

(xi)

in which R7 is as defined in claim 1 or 2.

10. The method of claim 2 wherein in the compound of formula (1), or pharmaceutically acceptable salt or isomer thereof, X' represents a direct bond, or is selected from the group consisting of —CO—, —NR4CO—, —SO$_2$— and —O—.

11. The method of claim 2 wherein in the compound of formula (1), or pharmaceutically acceptable salt or isomer thereof, X represents a direct bond, or is selected from the group consisting of —C(O)NR4-, —NR4-, —OC(O)—, —NR4C(O)—, —(CH$_2$)C(O)—, —S(O)$_2$— and —C(O)—.

12. The method of claim 11 wherein in the compound of formula (1), or pharmaceutically acceptable salt or isomer thereof, X represents a direct bond, or is selected from the group consisting of —C(O)NH—, —C(O)N(Me)-, —NH—, —N(Me)-, —OC(O)—, —N(Me)C(O)—, —(CH$_2$)C(O)—, —S(O)$_2$— and —C(O)—.

13. The method of claim 2 wherein in the compound of formula (1), or pharmaceutically acceptable salt or isomer thereof, R7 represents hydrogen, hydroxy, $C_1$-$C_6$-alkyl, halogeno-$C_1$-$C_6$-alkyl or $C_4$-$C_6$-cycloalkyl, represents optionally halogen-substituted 6~10 membered aryl, or represents 5~6 membered heteroaryl or heterocyclyl each of which has 1 to 4 hetero atoms selected from N and O.

14. The method of claim 13 wherein in the compound of formula (1), or pharmaceutically acceptable salt or isomer thereof, R7 is selected from the group consisting of hydrogen, hydroxy, methyl, trifluoromethyl, ethyl, t-butyl, cyclohexyl, pyrrolidine, phenyl, 2-fluorophenyl, piperidine, pyridine, 1,3-pyrazine, 1,4-pyrazine, furan, trifluoromethyl, 1,2,3,4-tetrazole and tetrahydrofuran.

15. The method of claim 2 wherein the compound of formula (1) is selected from the group consisting of
[(R)-2-(7-cyclopentylamino-5-fluoro-1H-indol-2-yl)-4,5-dihydro-thiazol-4-yl]-methanol;
{(R)-2-[5-fluoro-7-(tetrahydro-pyran-4-ylamino)-1H-indol-2-yl]-4,5-dihydro-thiazol-4-yl}-methanol;
[(R)-2-(5-chloro-7-cyclopentylamino-1H-indol-2-yl)-4,5-dihydro-thiazol-4-yl]-methanol;
{(R)-2-[5-chloro-7-(tetrahydro-pyran-4-ylamino)-1H-indol-2-yl]-4,5-dihydro-thiazol-4-yl}-methanol;
{(R)-2-[5-chloro-7-(tetrahydro-thiopyran-4-ylamino)-1H-indol-2-yl]-4,5-dihydro-thiazol-4-yl}-methanol;
[(R)-2-(5-bromo-7-cyclopentylamino-1H-indol-2-yl)-4,5-dihydro-thiazol-4-yl]-methanol;
{(R)-2-[5-bromo-7-(tetrahydro-pyran-4-ylamino)-1H-indol-2-yl]-4,5-dihydro-thiazol-4-yl}-methanol;
[(R)-2-(7-cyclopentylamino-5-methoxy-1H-indol-2-yl)-4,5-dihydro-thiazol-4-yl]-methanol;
{(R)-2-[7-cyclopentylamino-5-(pyridin-3-yloxy)-1H-indol-2-yl]-4,5-dihydro-thiazol-4-yl}-methanol;
{(R)-2-[5-(pyridin-3-yloxy)-7-(tetrahydro-pyran-4-ylamino)-1H-indol-2-yl]-4,5-dihydro-thiazol-4-yl}-methanol;
{(R)-2-[5-morpholin-4-ylmethyl-7-(tetrahydro-pyran-4-ylamino)-1H-indol-2-yl]-4,5-dihydro-thiazol-4-yl}-methanol;
[(R)-2-(7-cyclopentylamino-5-pyrazol-1-ylmethyl-1H-indol-2-yl]-4,5-dihydro-thiazol-4-yl]-methanol;
[(R)-2-(7-cyclopentylamino-5-imidazol-1-ylmethyl-1H-indol-2-yl]-4,5-dihydro-thiazol-4-yl}-methanol;
{(R)-2-[7-cyclopentylamino-5-(1H-pyrrol-3-ylmethyl)-1H-indol-2-yl]-4,5-dihydro-thiazol-4-yl}-methanol;
[(R)-2-(7-cyclopentylamino-5-methanesulfonylmethyl-1H-indol-2-yl]-4,5-dihydro-thiazol-4-yl]-methanol;
[7-Cyclopentylamino-2-((R)-4-hydroxymethyl-4,5-dihydro-thiazol-2-yl)-1H-indol-5-yl]-methanol;
[(R)-2-(5-chloro-7-cyclopentylamino-1H-indol-2-yl)-4,5-dihydro-thiazol-4-yl]-acetic acid methyl ester;
[(R)-2-(5-chloro-7-cyclopentylamino-1H-indol-2-yl)-4,5-dihydro-thiazol-4-yl]-acetic acid;
[(R)-2-(5-chloro-7-cyclopentylamino-1H-indol-2-yl)-4,5-dihydro-thiazol-4-yl]-acetic acid ethyl ester;
2-[(R)-2-(5-chloro-7-cyclopentylamino-1H-indol-2-yl)-4,5-dihydro-1,3-thiazol-4-yl]-ethanol;
{(R)-2-[5-chloro-7-(tetrahydro-pyran-4-ylamino)-1H-indol-2-yl]-4,5-dihydro-thiazol-4-yl}-acetic acid methyl ester;
{(R)-2-[5-chloro-7-(tetrahydro-pyran-4-ylamino)-1H-indol-2-yl]-4,5-dihydro-thiazol-4-yl}-acetic acid;
2-{(R)-2-[5-chloro-7-(tetrahydro-pyran-4-ylamino)-1H-indol-2-yl]-4,5-dihydro-thiazol-4-yl}-ethanol;
[(R)-2-(5-bromo-7-cyclopentylamino-1H-indol-2-yl)-4,5-dihydro-thiazol-4-yl]-acetic acid;
2-[(R)-2-(5-bromo-7-cyclopentylamino-1H-indol-2-yl)-4,5-dihydro-1,3-thiazol-4-yl]-ethanol;
{(R)-2-[5-bromo-7-(tetrahydro-pyran-4-ylamino)-1H-indol-2-yl]-4,5-dihydro-thiazol-4-yl}-acetic acid;
2-{(R)-2-[5-bromo-7-(tetrahydro-pyran-4-ylamino)-1H-indol-2-yl]-4,5-dihydro-thiazol-4-yl}-ethanol;
[(R)-2-(7-cyclopentylamino-5-fluoro-1H-indol-2-yl)-4,5-dihydro-thiazol-4-yl]-acetic acid;
[(R)-2-(7-cyclopentylamino-5-fluoro-1H-indol-2-yl)-4,5-dihydro-thiazol-4-yl]-acetic acid ethyl ester;
2-[(R)-2-(7-cyclopentylamino-5-fluoro-1H-indol-2-yl)-4,5-dihydro-thiazol-4-yl]-ethanol;
{(R)-2-[5-fluoro-7-(tetrahydro-pyran-4-ylamino)-1H-indol-2-yl]-4,5-dihydro-thiazol-4-yl}-acetic acid;
2-{(R)-2-[5-fluoro-7-(tetrahydro-pyran-4-ylamino)-1H-indol-2-yl]-4,5-dihydro-thiazol-4-yl}-ethanol;
[(R)-2-(7-cyclopentylamino-5-methoxy-1H-indol-2-yl)-4,5-dihydro-thiazol-4-yl]-acetic acid methyl ester;
[(R)-2-(7-cyclopentylamino-5-methoxy-1H-indol-2-yl)-4,5-dihydro-thiazol-4-yl]-acetic acid;
[(R)-2-(7-cyclopentylamino-5-methoxy-1H-indol-2-yl)-4,5-dihydro-thiazol-4-yl]-acetic acid ethyl ester;
{(R)-2-[5-methoxy-7-(tetrahydro-pyran-4-ylamino)-1H-indol-2-yl]-4,5-dihydro-thiazol-4-yl}-acetic acid methyl ester;
{(R)-2-[5-methoxy-7-(tetrahydro-pyran-4-ylamino)-1H-indol-2-yl]-4,5-dihydro-thiazol-4-yl}-acetic acid;

[(R)-2-(7-cyclopentylamino-5-ethoxy-1H-indol-2-yl)-4,5-dihydro-thiazol-4-yl]-acetic acid;
[(R)-2-(7-cyclopentylamino-5-propoxy-1H-indol-2-yl)-4,5-dihydro-thiazol-4-yl]-acetic acid;
[(R)-2-(7-cyclopentylamino-5-phenoxy-1H-indol-2-yl)-4,5-dihydro-thiazol-4-yl]-acetic acid;
{(R)-2-[5-phenoxy-7-(tetrahydro-pyran-4-ylamino)-1H-indol-2-yl]-4,5-dihydro-thiazol-4-yl}-acetic acid;
{(R)-2-[7-cyclopentylamino-5-(pyridin-3-yloxy)-1H-indol-2-yl]-4,5-dihydro-thiazol-4-yl}-acetic acid methyl ester;
{(R)-2-[7-cyclopentylamino-5-(pyridin-3-yloxy)-1H-indol-2-yl]-4,5-dihydro-thiazol-4-yl}-acetic acid;
{(R)-2-[5-(pyridin-3-yloxy)-7-(tetrahydro-pyran-4-ylamino)-1H-indol-2-yl]-4,5-dihydro-thiazol-4-yl}-acetic acid methyl ester;
{(R)-2-[5-(pyridin-3-yloxy)-7-(tetrahydro-pyran-4-ylamino)-1H-indol-2-yl]-4,5-dihydro-thiazol-4-yl}-acetic acid;
[(R)-2-(7-cyclopentylamino-5-methyl-1H-indol-2-yl)-4,5-dihydro-thiazol-4-yl]-acetic acid methyl ester;
[(R)-2-(7-cyclopentylamino-5-methyl-1H-indol-2-yl)-4,5-dihydro-thiazol-4-yl]-acetic acid;
{(R)-2-[5-methyl-7-(tetrahydro-pyran-4-ylamino)-1H-indol-2-yl]-4,5-dihydro-thiazol-4-yl}-acetic acid;
{(R)-2-[5-methyl-7-(4-oxo-cyclohexylamino)-1H-indol-2-yl]-4,5-dihydro-thiazol-4-yl}-acetic acid;
{(R)-2-[7-cyclopentylamino-5-(4-methanesulfonyl-phenoxy)-1H-indol-2-yl]-4,5-dihydro-thiazol-4-yl}-acetic acid;
[(R)-2-(7-cyclopentylamino-5-phenoxymethyl-1H-indol-2-yl)-4,5-dihydro-thiazol-4-yl]-acetic acid methyl ester;
[(R)-2-(7-cyclopentylamino-5-phenoxymethyl-1H-indol-2-yl)-4,5-dihydro-thiazol-4-yl]-acetic acid;
[(R)-2-(7-cyclopentylamino-5-pyrrolidin-1-ylmethyl-1H-indol-2-yl)-4,5-dihydro-thiazol-4-yl]-acetic acid methyl ester;
[(R)-2-(7-cyclopentylamino-5-methanesulfonylmethyl-1H-indol-2-yl)-4,5-dihydro-thiazol-4-yl]-acetic acid methyl ester;
[(R)-2-(7-cyclopentylamino-5-methanesulfonylmethyl-1H-indol-2-yl)-4,5-dihydro-thiazol-4-yl]-acetic acid;
2-[(R)-2-(7-cyclopentylamino-5-methanesulfonylmethyl-1H-indol-2-yl)-4,5-dihydro-thiazol-4-yl]-ethanol;
Cyclopentyl-{5-methanesulfonylmethyl-2-[(R)-4-(2-morpholin-4-yl-ethyl)-4,5-dihydro-thiazol-2-yl]-1H-indol-7-yl}-amine;
1-(4-{2-[(R)-2-(7-cyclopentylamino-5-methanesulfonylmethyl-1H-indol-2-yl)-4,5-dihydro-thiazol-4-yl]-ethyl}-piperazin-1-yl)-ethanone;
2-[(R)-2-(5-chloro-7-cyclopentylamino-1H-indol-2-yl)-4,5-dihydro-thiazol-4-yl]-1-morpholin-4-yl-ethanone;
2-[(R)-2-(5-chloro-7-cyclopentylamino-1H-indol-2-yl)-4,5-dihydro-thiazol-4-yl]-N-(2-morpholin-4-yl-ethyl)-acetamide;
2-[(R)-2-(5-chloro-7-cyclopentylamino-1H-indol-2-yl)-4,5-dihydro-thiazol-4-yl]-N-(3-morpholin-4-yl-propyl)-acetamide;
2-[(R)-2-(5-chloro-7-cyclopentylamino-1H-indol-2-yl)-4,5-dihydro-thiazol-4-yl]-N-methyl-acetamide;
2-[(R)-2-(5-chloro-7-cyclopentylamino-1H-indol-2-yl)-4,5-dihydro-thiazol-4-yl]-N,N-dimethyl-acetamide;
2-[(R)-2-(5-chloro-7-cyclopentylamino-1H-indol-2-yl)-4,5-dihydro-thiazol-4-yl]-1-(4-methyl-piperazin-1-yl)-ethanone;
2-[(R)-2-(5-chloro-7-cyclopentylamino-1H-indol-2-yl)-4,5-dihydro-thiazol-4-yl]-1-(3-dimethylamino-pyrrolidin-1-yl)-ethanone;
2-[(R)-2-(5-chloro-7-cyclopentylamino-1H-indol-2-yl)-4,5-dihydro-thiazol-4-yl]-1-(3-hydroxy-pyrrolidin-1-yl)-ethanone;
2-[(R)-2-(5-chloro-7-cyclopentylamino-1H-indol-2-yl)-4,5-dihydro-thiazol-4-yl]-1-piperidin-1-yl-ethanone;
2-{(R)-2-[5-chloro-7-(tetrahydro-pyran-4-ylamino)-1H-indol-2-yl]-4,5-dihydro-thiazol-4-yl}-N-methyl-acetamide;
2-{(R)-2-[5-chloro-7-(tetrahydro-pyran-4-ylamino)-1H-indol-2-yl]-4,5-dihydro-thiazol-4-yl}-1-morpholin-4-yl-ethanone;
2-[(R)-2-(7-cyclopentylamino-5-fluoro-1H-indol-2-yl)-4,5-dihydro-thiazol-4-yl]-1-(4-methyl-piperazin-1-yl)-ethanone;
2-[(R)-2-(7-cyclopentylamino-5-fluoro-1H-indol-2-yl)-4,5-dihydro-thiazol-4-yl]-N-(2-morpholin-4-yl-ethyl)-acetamide;
1-(4-Acetyl-piperazin-1-yl)-2-[(R)-2-(7-cyclopentylamino-5-fluoro-1H-indol-2-yl)-4,5-dihydro-thiazol-4-yl]-ethanone;
2-[(R)-2-(7-cyclopentylamino-5-methoxy-1H-indol-2-yl)-4,5-dihydro-thiazol-4-yl]-N-methyl-acetamide;
2-[(R)-2-(7-cyclopentylamino-5-methoxy-1H-indol-2-yl)-4,5-dihydro-thiazol-4-yl]-1-morpholin-4-yl-ethanone;
{5-Chloro-2-[(R)-4-(2-dimethylamino-ethyl)-4,5-dihydro-thiazol-2-yl]-1H-indol-7-yl}-cyclopentyl-amine;
{5-Chloro-2-[(R)-4-(2-morpholin-4-yl-ethyl)-4,5-dihydro-thiazol-2-yl]-1H-indol-7-yl}-cyclopentyl-amine;
{5-Chloro-2-[(R)-4-(2-piperazin-1-yl-ethyl)-4,5-dihydro-thiazol-2-yl]-1H-indol-7-yl}-cyclopentyl-amine;
1-(4-{2-[(R)-2-(5-chloro-7-cyclopentylamino-1H-indol-2-yl)-4,5-dihydro-thiazol-4-yl]-ethyl}-piperazin-1-yl)-ethanone;
(5-Chloro-2-{(R)-4-[2-(4-ethanesulfonyl-piperazin-1-yl)-ethyl]-4,5-dihydro-thiazol-2-yl}-1H-indol-7-yl)-cyclopentyl-amine;
1-(4-{2-[(R)-2-(5-chloro-7-cyclopentylamino-1H-indol-2-yl)-4,5-dihydro-thiazol-4-yl]-ethyl}-piperazin-1-yl)-2-hydroxy-ethanone;
(5-Chloro-2-{(R)-4-[2-(4-methyl-piperazin-1-yl)-ethyl]-4,5-dihydro-thiazol-2-yl}-1H-indol-7-yl)-cyclopentyl-amine;
1-{2-[(R)-2-(5-chloro-7-cyclopentylamino-1H-indol-2-yl)-4,5-dihydro-thiazol-4-yl]-ethyl}-piperidin-4-ol;
(4-{2-[(R)-2-(5-chloro-7-cyclopentylamino-1H-indol-2-yl)-4,5-dihydro-thiazol-4-yl]-ethyl}-piperazin-2-one;
(5-Chloro-2-{(R)-4-[2-(3-dimethylamino-pyrrolidin-1-yl)-ethyl]-4,5-dihydro-thiazol-2-yl}-1H-indol-7-yl)-cyclopentyl-amine;
{5-Chloro-2-[(R)-4-(2-piperidin-1-yl-ethyl)-4,5-dihydro-thiazol-2-yl]-1H-indol-7-yl}-cyclopentyl-amine;
(5-Chloro-2-{(R)-4-[2-(1,1-dioxo-thiomorpholin-4-yl)-ethyl]-4,5-dihydro-thiazol-2-yl}-1H-indol-7-yl)-cyclopentyl-amine;
{5-Chloro-2-[(R)-4-(2-pyrazol-1-yl-ethyl)-4,5-dihydro-thiazol-2-yl]-1H-indol-7-yl}-cyclopentyl-amine;
(S)-1-{2-[(R)-2-(5-chloro-7-cyclopentylamino-1H-indol-2-yl)-4,5-dihydro-thiazol-4-yl]-ethyl}-pyrrolidine-2-carboxylic acid;
{5-Chloro-2-[(R)-4-(2-methanesulfonyl-ethyl)-4,5-dihydro-thiazol-2-yl]-1H-indol-7-yl}-cyclopentyl-amine;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid ethyl ester;

3-{2-[(R)-2-(5-chloro-7-cyclopentylamino-1H-indol-2-yl)-4,5-dihydro-thiazol-4-yl]-ethyl}-5-methyl-3H-imidazole-4-carboxylic acid;

1-{2-[(R)-2-(5-chloro-7-cyclopentylamino-1H-indol-2-yl)-4,5-dihydro-thiazol-4-yl]-ethyl}-pyrrolidin-2-one;

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid;

1-(2-{(R)-2-[5-chloro-7-(tetrahydro-pyran-4-ylamino)-1H-indol-2-yl]-4,5-dihydro-thiazol-4-yl}-ethyl)-piperidine-3-carboxylic acid dimethylamide;

[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-carbamic acid t-butyl ester;

(2-{(R)-4-[2-((S)-3-amino-pyrrolidin-1-yl)-ethyl]-4,5-dihydro-thiazol-2-yl}-5-chloro-1H-indol-7-yl)-(tetrahydro-pyran-4-yl)-amine;

N—[(S)-1-(2-{(R)-2-[5-chloro-7-(tetrahydro-pyran-4-ylamino)-1H-indol-2-yl]-4,5-dihydro-thiazol-4-yl}-ethyl)-pyrrolidin-3-yl]-acetamide;

{5-Chloro-2-[(R)-4-(2-piperazin-1-yl-ethyl)-4,5-dihydro-thiazol-2-yl]-1H-indol-7-yl}-(tetrahydro-pyran-4-yl)-amine;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-hydroxy-ethanone;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-2-tetrazol-1-yl-ethanone;

1-[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-3,3,3-trifluoro-propan-1-one;

[4-(2-{(R)-2-[5-chloro-7-(tetrahydro-pyran-4-ylamino)-1H-indol-2-yl]-4,5-dihydro-thiazol-4-yl}-ethyl)-piperazin-1-yl]-furan-2-yl-methanone;

(5-Chloro-2-{(R)-4-[2-(2,3,5,6-tetrahydro-[1,2']bipyrazinyl-4-yl)-ethyl]-4,5-dihydro-thiazol-2-yl}-1H-indol-7-yl)-(tetrahydro-pyran-4-yl)-amine;

(5-Chloro-2-{(R)-4-[2-(4-pyrimidin-2-yl-piperazin-1-yl)-ethyl]-4,5-dihydro-thiazol-2-yl}-1H-indol-7-yl)-(tetrahydro-pyran-4-yl)-amine;

{2-[(R)-4-(2-amino-ethyl)-4,5-dihydro-thiazol-2-yl]-5-fluoro-1H-indol-7-yl}-cyclopentyl-amine;

1-(4-{2-[(R)-2-(7-cyclopentylamino-5-fluoro-1H-indol-2-yl)-4,5-dihydro-thiazol-4-yl]-ethyl}-piperazin-1-yl)-ethanone;

Cyclopentyl-{5-fluoro-2-[(R)-4-(2-morpholin-4-yl-ethyl)-4,5-dihydro-thiazol-2-yl]-1H-indol-7-yl}-amine;

Cyclopentyl-{2-[(R)-4-(2-dimethylamino-ethyl)-4,5-dihydro-thiazol-2-yl]-5-fluoro-1H-indol-7-yl}-amine;

Cyclopentyl-{5-fluoro-2-[(R)-4-(2-pyrrolidin-1-yl-ethyl)-4,5-dihydro-thiazol-2-yl]-1H-indol-7-yl}-amine;

Cyclopentyl-(2-{(R)-4-[2-(1,1-dioxo-thiomorpholin-4-yl)-ethyl]-4,5-dihydro-thiazol-2-yl}-5-fluoro-1H-indol-7-yl)-amine;

4-{2-[(R)-2-(7-cyclopentylamino-5-fluoro-1H-indol-2-yl)-4,5-dihydro-thiazol-4-yl]-ethyl}-piperazin-2-one;

1-(4-{2-[(R)-2-(7-cyclopentylamino-5-fluoro-1H-indol-2-yl)-4,5-dihydro-thiazol-4-yl]-ethyl}-piperazin-1-yl)-2-hydroxy-ethanone;

Cyclopentyl-{5-fluoro-2-[(R)-4-(2-methanesulfonyl-ethyl)-4,5-dihydro-thiazol-2-yl]-1H-indol-7-yl}-amine;

{2-[(R)-4-(2-dimethylamino-ethyl)-4,5-dihydro-thiazol-2-yl]-5-fluoro-1H-indol-7-yl}-(tetrahydro-pyran-4-yl)-amine;

{5-Fluoro-2-[(R)-4-(2-pyrrolidin-1-yl-ethyl)-4,5-dihydro-thiazol-2-yl]-1H-indol-7-yl}-(tetrahydro-pyran-4-yl)-amine;

{5-Fluoro-2-[(R)-4-(2-morpholin-4-yl-ethyl)-4,5-dihydro-thiazol-2-yl]-1H-indol-7-yl}-(tetrahydro-pyran-4-yl)-amine;

1-[4-(2-{(R)-2-[5-fluoro-7-(tetrahydro-pyran-4-ylamino)-1H-indol-2-yl]-4,5-dihydro-thiazol-4-yl}-ethyl-piperazin-1-yl)-ethanone;

(2-{(R)-4-[2-(1,1-dioxo-thiomorpholin-4-yl)-ethyl]-4,5-dihydro-thiazol-2-yl}-5-fluoro-1H-indol-7-yl)-(tetrahydropyran-4-yl)-amine;

(5-Fluoro-2-[(R)-4-(2-methanesulfonyl-ethyl)-4,5-dihydro-thiazol-2-yl]-1H-indol-7-yl)-(tetrahydro-pyran-4-yl)-amine;

4-(2-{(R)-2-[5-fluoro-7-(tetrahydro-pyran-4-ylamino)-1H-indol-2-yl]-4,5-dihydro-thiazol-4-yl}-ethyl)-piperazin-2-one;

1-[4-(2-{(R)-2-[5-fluoro-7-(tetrahydro-pyran-4-ylamino)-1H-indol-2-yl]-4,5-dihydro-thiazol-4-yl}-ethyl)-piperazin-1-yl]-2-hydroxy-ethanone;

1-(4-{2-[(R)-2-(7-cyclopentylamino-5-methoxy-1H-indol-2-yl)-4,5-dihydro-thiazol-4-yl]-ethyl}-piperazin-1-yl)-2-hydroxy-ethanone;

2-Hydroxy-1-[4-(2-{(R)-2-[5-methoxy-7-(tetrahydro-pyran-4-ylamino)-1H-indol-2-yl]-4,5-dihydro-thiazol-4-yl}-ethyl)-piperazin-1-yl]-ethanone;

3-[(R)-2-(5-chloro-7-cyclopentylamino-1H-indol-2-yl)-4,5-dihydro-thiazol-4-yl]-propionic acid ethyl ester;

3-[(R)-2-(5-chloro-7-cyclopentylamino-1H-indol-2-yl)-4,5-dihydro-thiazol-4-yl]-propionic acid;

3-[(R)-2-(5-chloro-7-cyclopentylamino-1H-indol-2-yl)-4,5-dihydro-thiazol-4-yl]-propan-1-ol;

3-{(R)-2-[5-chloro-7-(tetrahydro-pyran-4-ylamino)-1H-indol-2-yl]-4,5-dihydro-thiazol-4-yl}-propionic acid;

3-{(R)-2-[5-chloro-7-(tetrahydro-pyran-4-ylamino)-1H-indol-2-yl]-4,5-dihydro-thiazol-4-yl}-propan-1-ol;

3-[(R)-2-(5-chloro-7-cyclopentylamino-1H-indol-2-yl)-4,5-dihydro-thiazol-4-yl]-N-(2-morpholin-4-yl-ethyl)-propionamide;

3-[(R)-2-(5-chloro-7-cyclopentylamino-1H-indol-2-yl)-4,5-dihydro-thiazol-4-yl]-1-(4-methyl-piperazin-1-yl)-propan-1-one;

1-(4-{3-[(R)-2-(5-chloro-7-cyclopentylamino-1H-indol-2-yl)-4,5-dihydro-thiazol-4-yl]-propyl}-piperazin-1-yl)-ethanone;

{5-Chloro-2-[(R)-4-(3-morpholin-4-yl-propyl)-4,5-dihydro-thiazol-2-yl]-1H-indol-7-yl}-cyclopentyl-amine;

3-[(R)-2-(7-cyclopentylamino-5-methyl-1H-indol-2-yl)-4,5-dihydro-thiazol-4-yl]-propionic acid ethyl ester;

3-[(R)-2-(7-cyclopentylamino-5-methyl-1H-indol-2-yl)-4,5-dihydro-thiazol-4-yl]-propionic acid;

3-[(R)-2-(7-cyclopentylamino-5-phenoxy-1H-indol-2-yl)-4,5-dihydro-thiazol-4-yl]-propionic acid;

3-[(R)-2-(7-cyclopentylamino-5-fluoro-1H-indol-2-yl)-4,5-dihydro-thiazol-4-yl]-propionic acid ethyl ester;

3-[(R)-2-(7-cyclopentylamino-5-fluoro-1H-indol-2-yl)-4,5-dihydro-thiazol-4-yl]-propionic acid;

3-[(R)-2-(5-bromo-7-cyclopentylamino-1H-indol-2-yl)-4,5-dihydro-thiazol-4-yl]-propionic acid ethyl ester;

3-[(R)-2-(5-bromo-7-cyclopentylamino-1H-indol-2-yl)-4,5-dihydro-thiazol-4-yl]-propionic acid;
3-[(R)-2-(7-cyclopentylamino-5-methoxy-1H-indol-2-yl)-4,5-dihydro-thiazol-4-yl]-propionic acid;
3-[(R)-2-(7-cyclopentylamino-5-ethoxy-1H-indol-2-yl)-4,5-dihydro-thiazol-4-yl]-propionic acid ethyl ester;
3-[(R)-2-(7-cyclopentylamino-5-ethoxy-1H-indol-2-yl)-4,5-dihydro-thiazol-4-yl]-propionic acid;
3-[(R)-2-(7-cyclopentylamino-5-trifluoromethoxy-1H-indol-2-yl)-4,5-dihydro-thiazol-4-yl]-propionic acid ethyl ester;
3-[(R)-2-(7-cyclopentylamino-5-trifluoromethoxy-1H-indol-2-yl)-4,5-dihydro-thiazol-4-yl]-propionic acid;
[(R)-2-(7-cyclopentylamino-5-fluoro-1H-indol-2-yl)-4,5-dihydro-thiazol-4-ylmethoxy]-acetic acid ethyl ester;
[(R)-2-(7-cyclopentylamino-5-fluoro-1H-indol-2-yl)-4,5-dihydro-thiazol-4-ylmethoxy]-acetic acid;
[(S)-2-(5-chloro-7-cyclopentylamino-1H-indol-2-yl)-4,5-dihydro-thiazol-4-yl]-acetic acid;
{(S)-2-[7-(1-acetyl-piperidin-4-ylamino)-5-methyl-1H-indol-2-yl]-4,5-dihydro-thiazol-4-yl}-acetic acid;
{(S)-2-[7-(1-acetyl-pyrrolidin-3-ylamino)-5-methyl-1H-indol-2-yl]-4,5-dihydro-thiazol-4-yl}-acetic acid;
((S)-2-{5-phenoxy-7-[(tetrahydro-pyran-4-ylmethyl)-amino]-1H-indol-2-yl}-4,5-dihydro-thiazol-4-yl)-acetic acid;
{(S)-2-[5-phenoxy-7-(tetrahydro-pyran-4-ylamino)-1H-indol-2-yl]-4,5-dihydro-thiazol-4-yl}-acetic acid;
{(S)-2-[5-chloro-7-(tetrahydro-pyran-4-ylamino)-1H-indol-2-yl]-4,5-dihydro-thiazol-4-yl}-acetic acid;
[(S)-2-(7-cyclobutylamino-5-methyl-1H-indol-2-yl)-4,5-dihydro-thiazol-4-yl]-acetic acid;
{(S)-2-[5-methyl-7-(tetrahydro-furan-3-ylamino)-1H-indol-2-yl]-4,5-dihydro-thiazol-4-yl}-acetic acid;
{(S)-2-[7-(cyclopropylmethyl-amino)-5-methyl-1H-indol-2-yl]-4,5-dihydro-thiazol-4-yl}-acetic acid;
((S)-2-{5-methyl-7-[(tetrahydro-pyran-4-ylmethyl)-amino]-1H-indol-2-yl}-4,5-dihydro-thiazol-4-yl)-acetic acid;
{(S)-2-[5-methyl-7-(tetrahydro-pyran-4-ylamino)-1H-indol-2-yl]-4,5-dihydro-thiazol-4-yl}-acetic acid;
[(S)-2-(7-cyclopentylamino-5-methyl-1H-indol-2-yl)-4,5-dihydro-thiazol-4-yl]-acetic acid methylester;
[(S)-2-(7-cyclopentylamino-5-phenoxy-1H-indol-2-yl)-4,5-dihydro-thiazol-4-yl]-acetic acid;
{(S)-2-[7-(4,4-difluoro-cyclohexylamino)-5-methyl-1H-indol-2-yl]-4,5-dihydro-thiazol-4-yl}-acetic acid;
(2-{(S)-4-[2-((R)-3-amino-pyrrolidin-1-yl)-ethyl]-4,5-dihydro-thiazol-2-yl}-5-chloro-1H-indol-7-yl)-cyclopentyl-amine;
(5-Chloro-2-{(S)-4-[2-((R)-3-dimethylamino-pyrrolidin-1-yl)-ethyl]-4,5-dihydro-thiazol-2-yl}-1H-indol-7-yl)-cyclopentyl-amine;
1-(4-{2-[(S)-2-(5-chloro-7-cyclopentylamino-1H-indol-2-yl)-4,5-dihydro-thiazol-4-yl]-ethyl}-piperazin-1-yl)-ethanone;
1-(4-{2-[(S)-2-(5-methyl-7-(tetrahydro-pyran-4-ylamino)-1H-indol-2-yl)-4,5-dihydro-thiazol-4-yl]-ethyl}-piperazin-1-yl)-ethanone;
{5-Methyl-2-[(S)-4-(2-morpholin-4-yl-ethyl)-4,5-dihydro-thiazol-2-yl]-1H-indol-7-yl}-(tetrahydro-pyran-4-yl)-amine;
1-(4-{2-[(S)-2-(7-cyclopentylamino-5-phenoxy-1H-indol-2-yl)-4,5-dihydro-thiazol-4-yl]-ethyl}-piperazin-1-yl)-2-hydroxy-ethanone;
Cyclopentyl-{5-phenoxy-2-[(S)-4-(2-piperazin-1-yl-ethyl)-4,5-dihydro-thiazol-2-yl]-1H-indol-7-yl}-amine;
4-{2-[(S)-2-(7-cyclopentylamino-5-phenoxy-1H-indol-2-yl)-4,5-dihydro-thiazol-4-yl]-ethyl}-piperazine-1-carboxylic acid t-butyl ester;
Cyclopentyl-(2-{(S)-4-[2-(3-methyl-5,6-dihydro-8H-[1,2,4]triazolo[4,3-a]pyrazin-7-yl)-ethyl]-4,5-dihydro-thiazol-2-yl}-5-phenoxy-1H-indol-7-yl)-amine;
4-{2-[(S)-2-(7-cyclopentylamino-5-phenoxy-1H-indol-2-yl)-4,5-dihydro-thiazol-4-yl]-ethyl}-piperazin-2-one;
(4-{2-[(S)-2-(7-cyclopentylamino-5-phenoxy-1H-indol-2-yl)-4,5-dihydro-thiazol-4-yl]-ethyl}-piperazin-1-yl)-(tetrahydro-furan-2-yl)-methanone;
Cyclopentyl-(5-phenoxy-2-{(S)-4-[2-(4-pyridin-2-yl-piperazin-1-yl)-ethyl]-4,5-dihydro-thiazol-2-yl}-1H-indol-7-yl)-amine;
Cyclopentyl-[2-((S)-4-{2-[4-(2-fluoro-phenyl)-piperazin-1-yl]-ethyl}-4,5-dihydro-thiazol-2-yl)-5-phenoxy-1H-indol-7-yl]-amine;
1-(4-{2-[(S)-2-(7-cyclopentylamino-5-phenoxy-1H-indol-2-yl)-4,5-dihydro-thiazol-4-yl]-ethyl}-piperazin-1-yl)-ethanone;
{(R)-1-[2-[(S)-2-{5-methyl-7-[(tetrahydro-pyran-4-ylmethyl)-amino]-1H-indol-2-yl}-4,5-dihydro-thiazol-4-yl]-ethyl]-pyrrolidin-2-yl}-methanol;
N—((R)-1-{2-[(S)-2-(7-cyclopentylamino-5-phenoxy-1H-indol-2-yl)-4,5-dihydro-thiazol-4-yl]-ethyl}-pyrrolidin-3-yl)-acetamide;
(2-{(S)-4-[2-(4-benzyl-piperazin-1-yl)-ethyl]-4,5-dihydro-thiazol-2-yl}-5-phenoxy-1H-indol-7-yl)-cyclopentyl-amine;
4-[2-((S)-2-{5-phenoxy-7-[(tetrahydro-pyran-4-ylmethyl)-amino]-1H-indol-2-yl}-4,5-dihydro-thiazol-4-yl)-ethyl]-piperazin-2-one;
Cyclopentyl-{5-phenoxy-2-[(S)-4-(2-pyrrolidin-1-yl-ethyl)-4,5-dihydro-thiazol-2-yl]-1H-indol-7-yl}-amine;
(4,4-Difluoro-cyclohexyl)-{2-[(S)-4-(2-morpholin-4-yl-ethyl)-4,5-dihydro-thiazol-2-yl]-1H-indol-7-yl}-amine;
(2-{(S)-4-[2-(3-methyl-5,6-dihydro-8H-[1,2,4]triazolo[4,3-pyrazin-7-yl]-ethyl)-4,5-dihydro-thiazol-2-yl}-5-phenoxy-1H-indol-7-yl)-(tetrahydro-pyran-4-ylmethyl)-amine;
4-[2-((S)-2-{5-phenoxy-7-[(tetrahydro-pyran-4-ylmethyl)-amino]-1H-indol-2-yl}-4,5-dihydro-thiazol-4-yl)-ethyl]-piperazin-2-one;
4-(2-{(S)-2-[7-(4,4-difluoro-cyclohexylamino)-5-phenoxy-7-1H-indol-2-yl]-4,5-dihydro-thiazol-4-yl}-ethyl)-piperazin-2-one, and pharmaceutically acceptable salts or isomers thereof.

16. A method for the treatment of type 2 diabetes or obesity comprising:

administering a pharmaceutical composition which comprises an indole compound of the following Formula (1), or pharmaceutically acceptable salt or isomer thereof, as an active ingredient together with a pharmaceutically acceptable carrier:

Formula (1)

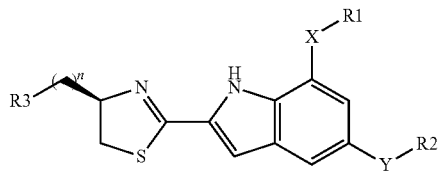

in which
X represents NH,
n denotes a number of 0 to 3,
Y represents a direct bond, —$(CH_2)_pO$—, —$(CH_2)_q$—, or —$(CH_2)_qSO_2$—,
p denotes a number of 0 to 2,
q denotes a number of 1 to 3,
R1 represents —$(CR4R5)_p$-A-R6, wherein p is as defined above,
R4 and R5 independently of one another represent hydrogen or $C_1$-$C_5$-alkyl,
A represents 6~12 membered aryl or optionally oxo-containing $C_3$-$C_8$-cycloalkyl, or represents 3~10 membered heterocyclyl or heteroaryl each of which has 1 to 3 hetero atoms selected from O, S, and N,
R6 represents hydrogen, hydroxy, halogen, nitro, $C_1$-$C_6$-alkylcarbonyl, $C_1$-$C_6$-alkylsulfonyl, $C_1$-$C_6$-alkoxycarbonyl or carboxy,
R2 represents nitro, halogen, $C_1$-$C_6$-alkyl or trifluoromethyl, represents 5~12 membered heteroaryl or heterocyclyl each of which has 1 to 3 hetero atoms selected from N and O, or represents optionally $C_1$-$C_6$-alkylsulfonyl-substituted 6~12 membered aryl,
R3 represents R7-X—B—X'—,
B represents a direct bond, or represents 3~10 membered heterocyclyl or heteroaryl each of which optionally contains oxo, is optionally fused, and has 1 to 4 hetero atoms selected from N, O and S,
X and X' independently of one another represent a direct bond, or are selected from the group consisting of —CO—, —$(CH_2)_q$—, —NR4C(O)—, —NR4-, —OC(O)—, —O—, —$(CH_2)_pC(O)$—, —$(CH_2)_pO$—, —$(CH_2)_pNR4$-, —C(O)NR4- and —$S(O)_r$—, wherein p and q are as defined above, r denotes a number of 0 to 2, and R4 represents hydrogen or $C_1$-$C_5$-alkyl,
R7 represents hydrogen, hydroxy, $C_1$-$C_6$-alkyl, $C_1$-$C_6$-alkoxy, halogeno-$C_1$-$C_6$-alkyl or $C_3$-$C_6$-cycloalkyl, represents 6~12 membered aryl, or represents 4~8 membered heteroaryl or heterocyclyl each of which has 1 to 4 hetero atoms selected from N and O,
where alkyl, alkoxy, aryl, cycloalkyl, heterocyclyl and heteroaryl may be optionally substituted, and the substituents are one or more selected from the group consisting of hydroxy, halogen, nitrile, amino, $C_1$-$C_6$-alkylamino, di($C_1$-$C_6$-alkyl)amino, $C_1$-$C_6$-alkyl, halogeno-$C_1$-$C_6$-alkyl, $C_1$-$C_6$-alkylsulfonyl, aryl-$C_1$-$C_6$-alkoxy and oxo.

17. The method of claim 16 wherein said method is for the treatment of obesity.

18. The method of claim 16 wherein said method is for the treatment of type 2 diabetes.

* * * * *